(12) United States Patent
Ryu et al.

(10) Patent No.: US 11,690,288 B2
(45) Date of Patent: Jun. 27, 2023

(54) COMPOSITION FOR ORGANIC OPTOELECTRONIC DIODE, ORGANIC OPTOELECTRONIC DIODE, AND DISPLAY DEVICE

(71) Applicant: SAMSUNG SDI CO., LTD., Yongin-si (KR)

(72) Inventors: Dong Wan Ryu, Suwon-si (KR); Sangshin Lee, Suwon-si (KR); Seungjae Lee, Suwon-si (KR); Sung-Hyun Jung, Suwon-si (KR); Eun Sun Yu, Suwon-si (KR); Dalho Huh, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 603 days.

(21) Appl. No.: 16/628,119

(22) PCT Filed: Jul. 4, 2018

(86) PCT No.: PCT/KR2018/007580
§ 371 (c)(1),
(2) Date: Jan. 2, 2020

(87) PCT Pub. No.: WO2019/013488
PCT Pub. Date: Jan. 17, 2019

(65) Prior Publication Data
US 2020/0136057 A1  Apr. 30, 2020

(30) Foreign Application Priority Data
Jul. 14, 2017  (KR) ........................ 10-2017-0089716

(51) Int. Cl.
| | | |
|---|---|---|
| H01L 51/00 | (2006.01) |
| H10K 85/60 | (2023.01) |
| C07D 403/10 | (2006.01) |
| C07D 491/048 | (2006.01) |
| C07D 495/04 | (2006.01) |
| C09K 11/02 | (2006.01) |
| H10K 50/11 | (2023.01) |
| H10K 101/10 | (2023.01) |

(52) U.S. Cl.
CPC ......... *H10K 85/654* (2023.02); *C07D 403/10* (2013.01); *C07D 491/048* (2013.01); *C07D 495/04* (2013.01); *C09K 11/025* (2013.01); *H10K 85/657* (2023.02); *H10K 85/6572* (2023.02); *H10K 50/11* (2023.02); *H10K 2101/10* (2023.02)

(58) Field of Classification Search
CPC ............. H01L 51/0067; H01L 51/0071; H01L 51/0072; H01L 51/5016; H01L 51/0085; H01L 2251/5384; H01L 51/0073; H01L 51/0074; H01L 51/5024; C07D 403/10; C07D 491/048; C07D 495/04; C09K 11/025; C09K 11/06; C09K 2211/1033; C09K 2211/1037
USPC ......................................................... 428/690
See application file for complete search history.

(56) References Cited

U.S. PATENT DOCUMENTS

| | | | |
|---|---|---|---|
| 9,478,758 B1 | 10/2016 | Tsai | |
| 9,530,969 B2 | 12/2016 | Mizuki | |
| 2015/0105563 A1* | 4/2015 | Ahn | .............. H01L 51/0072 548/418 |
| 2015/0218441 A1* | 8/2015 | Cho | ............... H01L 51/0094 252/519.21 |
| 2022/0275008 A1* | 9/2022 | Kim | ............... H01L 51/0094 |

FOREIGN PATENT DOCUMENTS

| | | |
|---|---|---|
| JP | 5357150 B2 | 9/2013 |
| KR | 10-2013-0059265 A | 6/2013 |
| KR | 10-2013-0093195 A | 8/2013 |
| KR | 10-2013-0112342 A | 10/2013 |
| KR | 10-2013-0134202 A | 12/2013 |
| KR | 10-2014-0032823 A | 3/2014 |
| KR | 10-1423066 B1 | 7/2014 |
| KR | 10-2014-0096203 A | 8/2014 |
| KR | 10-2014-0105913 A | 9/2014 |
| KR | 10-1486561 B1 | 1/2015 |
| KR | 10-2015-0034333 A | 4/2015 |
| KR | 10-1523124 B1 | 5/2015 |
| KR | 10-2015-0096593 A | 8/2015 |
| KR | 10-2016-0133814 A | 11/2016 |
| KR | 10-2018-0008279 A | 1/2018 |

OTHER PUBLICATIONS

CAS reg. No. 2267278-29-3, Feb. 6, 2019. (Year: 2019).*
CAS reg. No. 57102-62-2, Nov. 16, 1984. (Year: 1984).*
CAS reg. No. 1579302-66-1, Apr. 2, 2014. (Year: 2014).*
Translation of KR 2014/0096203, Aug. 5, 2014. (Year: 2014).*
International Search Report dated Oct. 8, 2018 for PCT/KR2018/007580.
Chinese Search Report dated Jan. 20, 2023.

* cited by examiner

*Primary Examiner* — Douglas J McGinty
(74) *Attorney, Agent, or Firm* — Lee IP Law, P.C.

(57) ABSTRACT

The present invention relates to a composition for an organic optoelectronic diode, comprising a first compound for an organic optoelectronic diode; and a second compound for an organic optoelectronic diode, and an organic optoelectronic diode and a display device including the same.

13 Claims, 2 Drawing Sheets

[Figure 1]
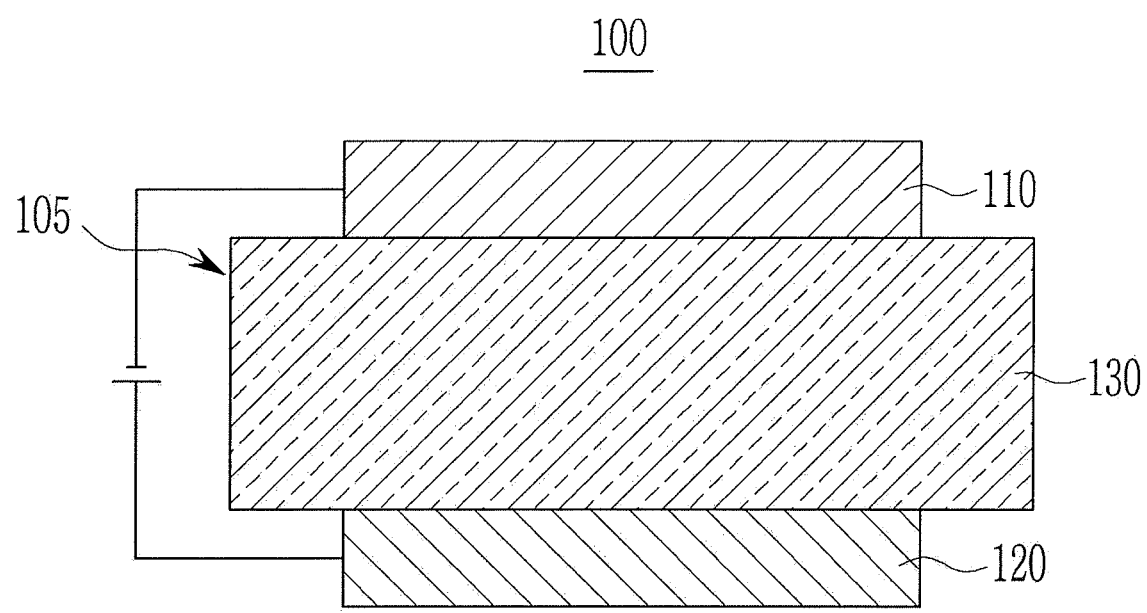

【Figure 2】
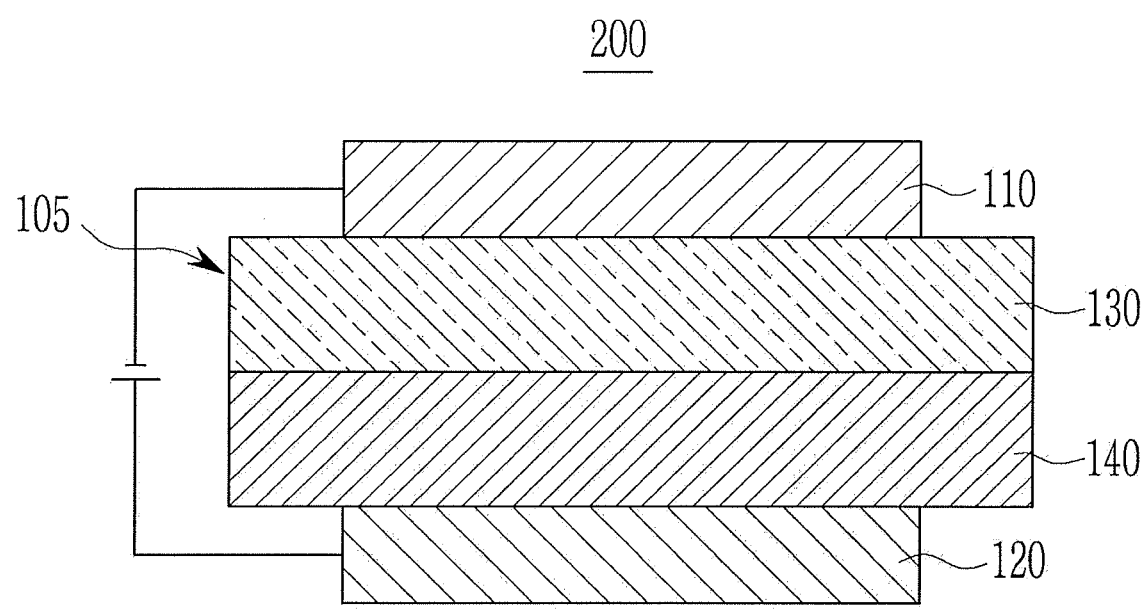

COMPOSITION FOR ORGANIC OPTOELECTRONIC DIODE, ORGANIC OPTOELECTRONIC DIODE, AND DISPLAY DEVICE

CROSS REFERENCE TO RELATED APPLICATIONS

This is the U.S. national phase application based on PCT Application No. PCT/KR2018/007580, filed Jul. 4, 2018, which is based on Korean Patent Application No. 10-2017-0089716, filed Jul. 14, 2017, the entire contents of all of which are hereby incorporated by reference.

TECHNICAL FIELD

A composition for an organic optoelectronic diode, an organic optoelectronic diode, and a display device are disclosed.

BACKGROUND ART

An organic optoelectronic diode is a diode that converts electrical energy into photoenergy, and vice versa.

An organic optoelectronic diode may be classified as follows in accordance with its driving principles. One is a photoelectric diode where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of the organic optoelectronic diode may be an organic photoelectric diode, an organic light emitting diode, an organic solar cell, and an organic photo conductor drum.

Of these, an organic light emitting diode (OLED) has recently drawn attention due to an increase in demand for flat panel displays. The organic light emitting diode is a diode converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material capable of increasing hole and electron mobility and simultaneously increasing electrochemical stability is needed so that the organic light emitting diode may be applied to a large-size flat panel display.

DISCLOSURE

Technical Problem

An embodiment provides a composition for an organic optoelectronic diode capable of realizing an organic optoelectronic diode having high efficiency and long life-span.

Another embodiment provides an organic optoelectronic diode including the composition.

Another embodiment provides a display device including the organic optoelectronic diode.

Another embodiment provides a compound for an organic optoelectronic diode.

Technical Solution

According to an embodiment, a composition for an organic optoelectronic diode includes a first compound for an organic optoelectronic diode represented by Chemical Formula 1; and a second compound for an organic optoelectronic diode represented by Chemical Formula 2.

[Chemical Formula 1]

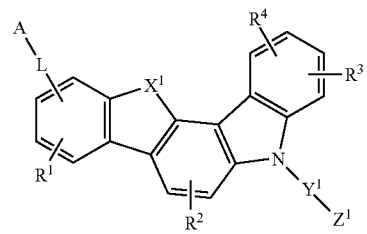

[Chemical Formula 2]

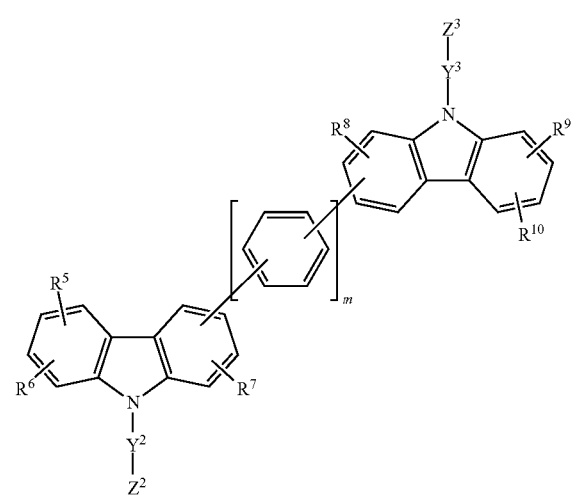

In Chemical Formula 1 and Chemical Formula 2, $X^1$ is O or S,

A is a substituted or unsubstituted pyridinyl group, a substituted or unsubstituted pyrimidinyl group, a substituted or unsubstituted triazinyl group, a substituted or unsubstituted benzimidazolyl group, a substituted or unsubstituted pyrazinyl group, a substituted or unsubstituted quinolinyl group, a substituted or unsubstituted isoquinolinyl group, a substituted or unsubstituted quinoxalinyl group, or a substituted or unsubstituted quinazolinyl group, L and $Y^1$ to $Y^3$ are independently a single bond, a substituted or unsubstituted C6 to C30 arylene group, or a substituted or unsubstituted C2 to C30 heteroarylene group, $Z^1$ to $Z^3$ are independently a substituted or unsubstituted C6 to C30 aryl group, or a substituted or unsubstituted C2 to C30 heterocyclic group, $R^1$ to $R^{10}$ are independently hydrogen, deuterium, a substituted or unsubstituted C1 to C10 alkyl group, a substituted or unsubstituted C6 to C30 aryl group, or a substituted or unsubstituted C2 to C30 heterocyclic group, and m is one of integers of 0 to 2.

According to another embodiment, an organic optoelectronic diode includes an anode and a cathode facing each other and at least one organic layer disposed between the anode and the cathode, wherein the organic layer includes the aforementioned composition for an organic optoelectronic diode.

According to another embodiment, a display device including the organic optoelectronic diode is provided.

According to another embodiment, a compound for an organic optoelectronic diode is provided.

Advantageous Effects

An organic optoelectronic diode having high efficiency and a long life-span may be realized.

DESCRIPTION OF THE DRAWINGS

FIGS. 1 and 2 are cross-sectional views showing organic light emitting diodes according to embodiments.

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heterocyclic group. In addition, in a specific example of the present invention, "substituted" refers to replacement of at least one hydrogen of a substituent or a compound by deuterium, a C1 to C20 alkyl group, a C6 to C30 aryl group, or a C2 to C30 heterocyclic group. In addition, in a specific example of the present invention, "substituted" refers to replacement of at least one hydrogen of a substituent or a compound by deuterium, a C1 to C5 alkyl group, a C6 to C18 aryl group, a dibenzofuranyl group, a dibenzothiophenyl group, or a carbazolyl group. In addition, in a specific example of the present invention, "substituted" refers to replacement of at least one hydrogen of a substituent or a compound by deuterium, a C1 to C5 alkyl group, a C6 to C18 aryl group, a dibenzofuranyl group, or a dibenzothiophenyl group. In addition, in a specific example of the present invention, "substituted" refers to replacement of at least one hydrogen of a substituent or a compound by deuterium, a methyl group, an ethyl group, a propanyl group, a butyl group, a phenyl group, a biphenyl group, a naphthyl group, an anthracenyl group, a phenanthrenyl group, a triphenylenyl group, a fluorenyl group, a dibenzofuranyl group, or a dibenzothiophenyl group.

In the present specification when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, or two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic diode according to an embodiment is described.

A composition for an organic optoelectronic diode according to an embodiment may include a first compound for an organic optoelectronic diode represented by Chemical Formula 1; and a second compound for an organic optoelectronic diode represented by Chemical Formula 2.

[Chemical Formula 1]

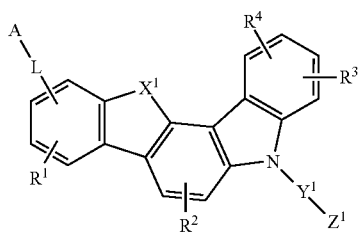

[Chemical Formula 2]

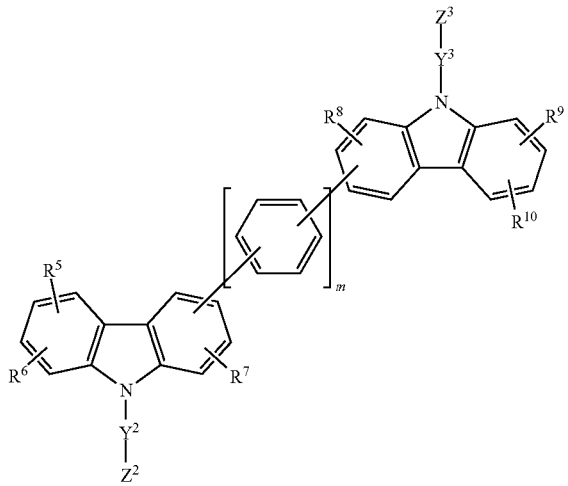

In Chemical Formula 1 and Chemical Formula 2, $X^1$ is O or S,

A is a substituted or unsubstituted pyridinyl group, a substituted or unsubstituted pyrimidinyl group, a substituted or unsubstituted triazinyl group, a substituted or unsubstituted benzimidazolyl group, a substituted or unsubstituted pyrazinyl group, a substituted or unsubstituted quinolinyl group, a substituted or unsubstituted isoquinolinyl group, a substituted or unsubstituted quinoxalinyl group, or a substituted or unsubstituted quinazolinyl group, L and $Y^1$ to $Y^3$ are independently a single bond, a substituted or unsubstituted C6 to C30 arylene group, or a substituted or unsubstituted C2 to C30 heteroarylene group, $Z^1$ to $Z^3$ are independently a substituted or unsubstituted C6 to C30 aryl group, or a substituted or unsubstituted C2 to C30 heterocyclic group, $R^1$ to $R^{10}$ are independently hydrogen, deuterium, a substituted or unsubstituted C1 to C10 alkyl group, a substituted or unsubstituted C6 to C30 aryl group, or a substituted or unsubstituted C2 to C30 heterocyclic group, and m is one of integers of 0 to 2.

"Substituted" of Chemical Formula 1 and Chemical Formula 2 refers to replacement of at least one hydrogen by deuterium, a C1 to C20 alkyl group, a C6 to C30 aryl group, or a C2 to C30 heterocyclic group. In a specific example of the present invention, the "substituted" refers to replacement of at least one hydrogen by deuterium, a C1 to C20 alkyl group, a C6 to C30 aryl group, a dibenzofuranyl group, or a dibenzothiophenyl group.

In one example of the present invention the present invention, the "substituted" refers to replacement of at least one hydrogen by deuterium, a phenyl group, an ortho-biphenyl group, a meta-biphenyl group, a para-biphenyl group, a naphthyl group, an anthracenyl group, a phenanthrenyl group, a triphenylenyl group, a fluorenyl group, a dibenzofuranyl group, or a dibenzothiophenyl group.

The composition for the organic optoelectronic diode according to the present invention uses an electron transporting host having an indolodibenzofuran (or indolodibenzothiophene) structure and a hole transporting host having a structure in which two carbazoles are linked as a phosphorescence light emitting material and thus may reduce a driving voltage and simultaneously, provide an organic optoelectronic diode having a long life-span and high efficiency.

Particularly, since a substituent, A having electron characteristics in the indolodibenzofuran (or indolodibenzothiophene) structure is linked in a dibenzofuran (or dibenzothiophene) moiety direction, and LUMO of the electron transporting substituent expands and more stabilizes injected electrons than a structure of being linked in an N-direction of a carbazole moiety, when applied as an electron transporting light emitting host in OLED, a low drive and a long life-span may be expected.

For example, Chemical Formula 1 of the present invention may be represented by Chemical Formula 1-1, Chemical Formula 1-2, Chemical Formula 1-3, or Chemical Formula 1-4, but is not necessarily limited thereto.

In an example embodiment of the present invention, A of Chemical Formula 1 may be a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinoxalinyl group, or a substituted or unsubstituted quinazolinyl group, and may be for example selected from substituents of Group I.

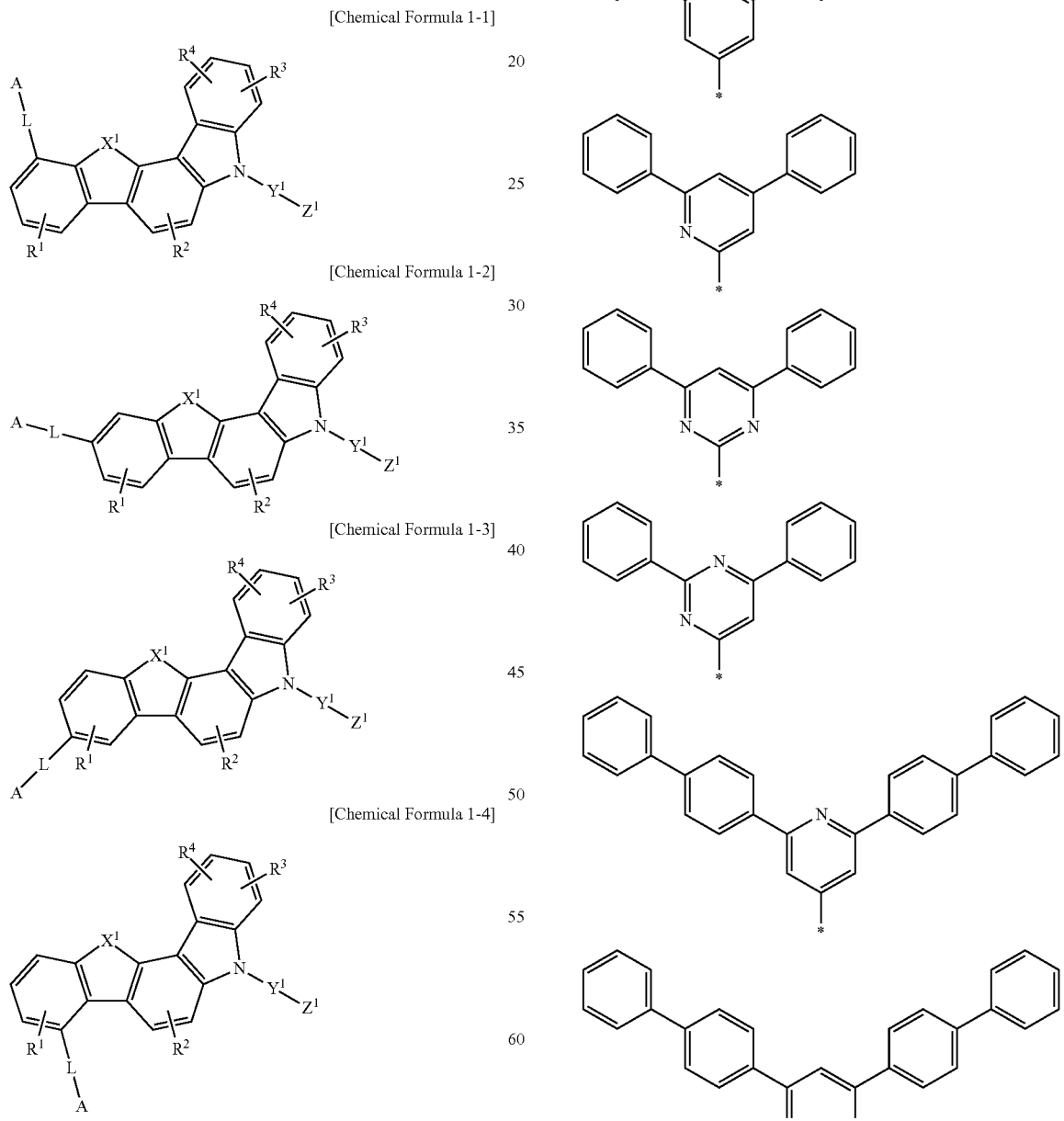

In Chemical Formula 1-1 to Chemical Formula 1-4, $X^1$, A, L, $Y^1$, $Z^1$, and $R^1$ to $R^4$ are the same as defined in Chemical Formula 1.

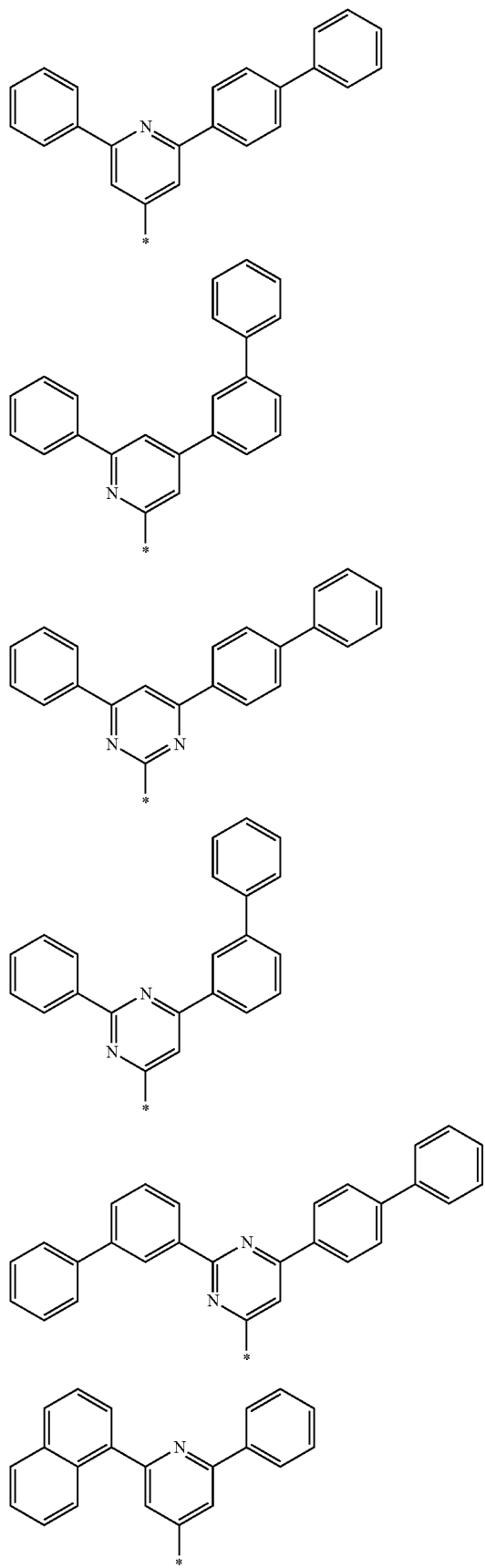
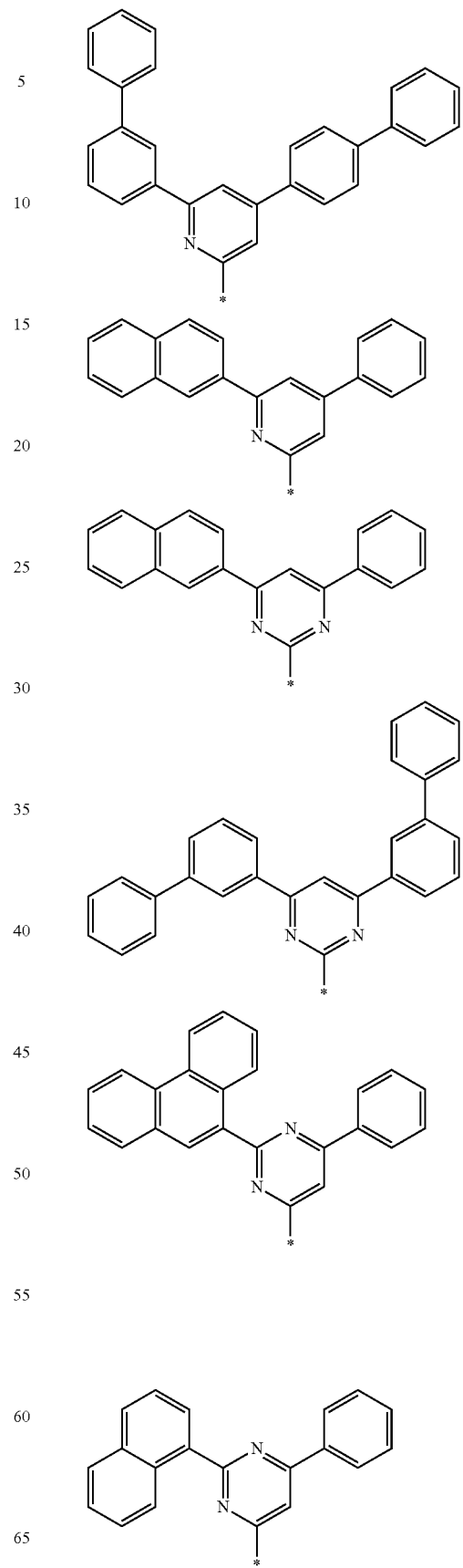

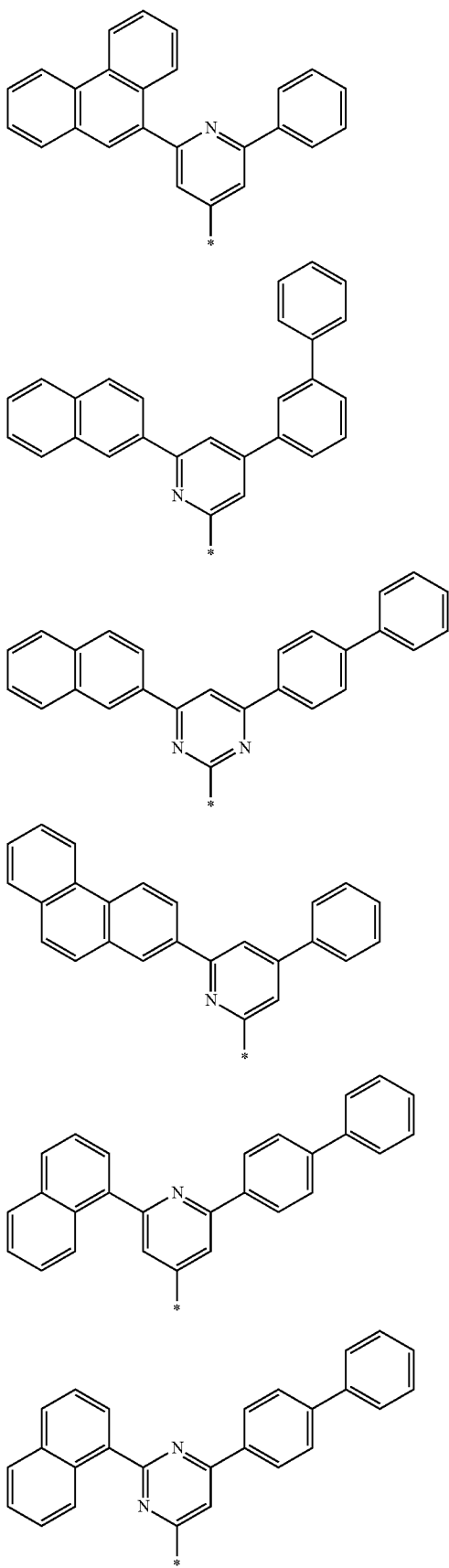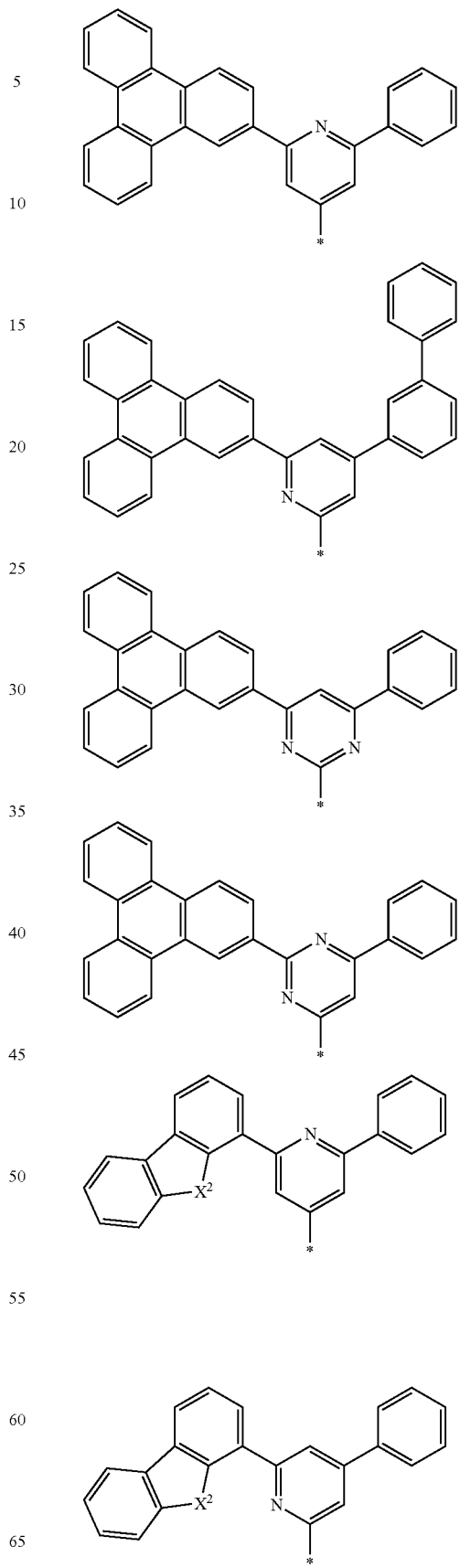

-continued
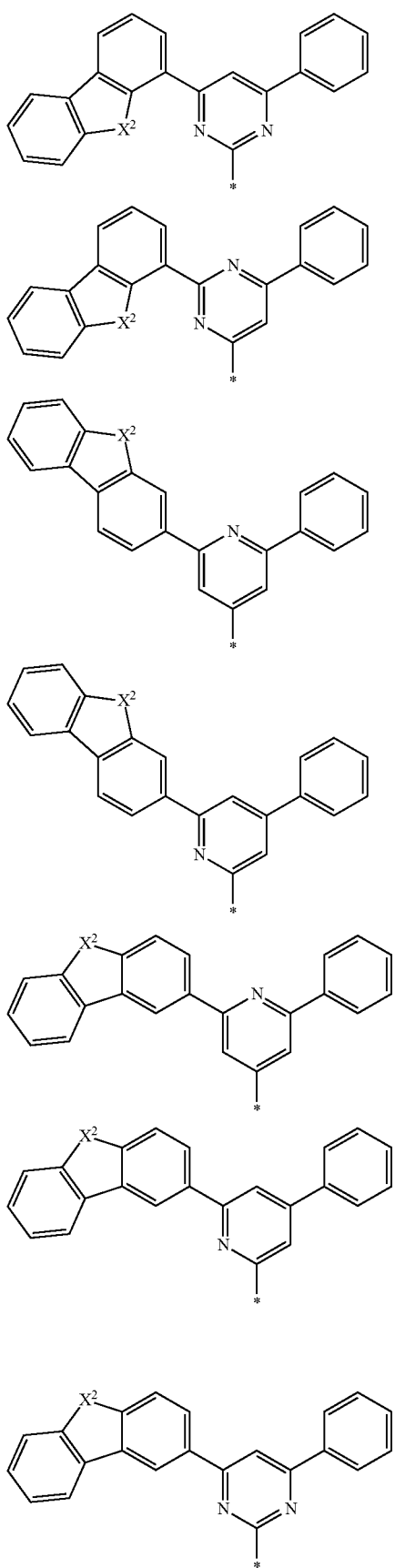
-continued
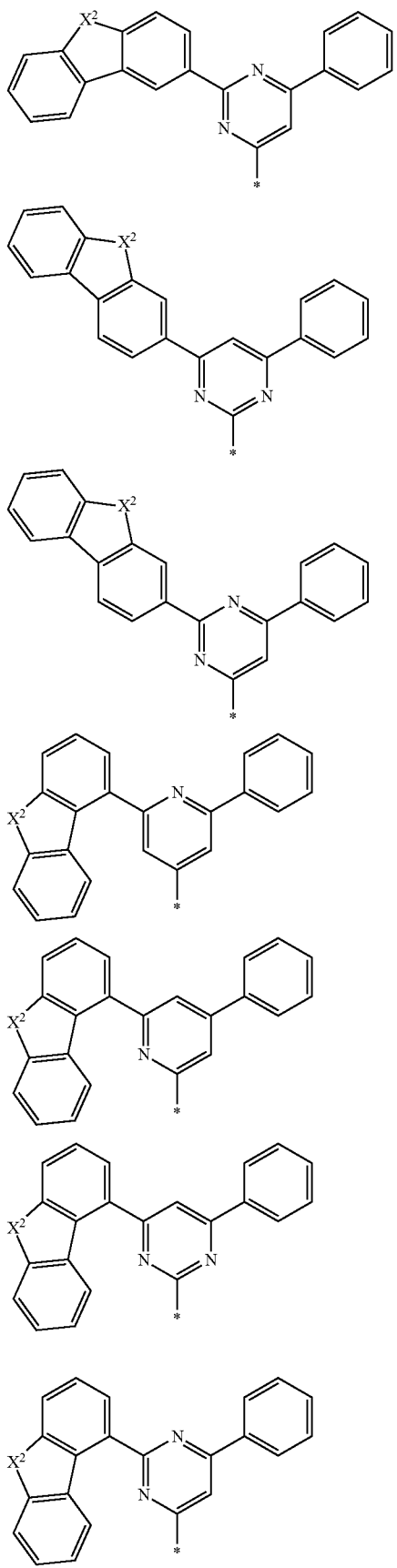

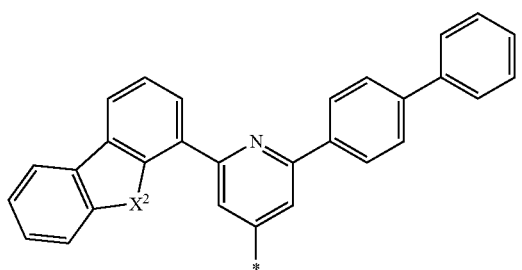
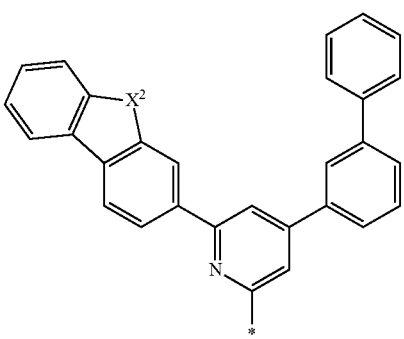
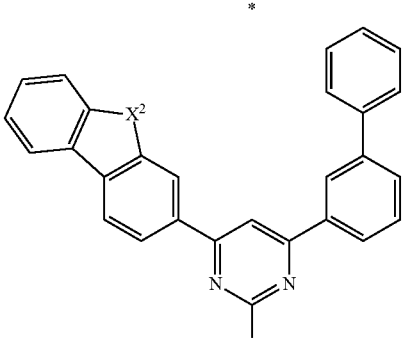
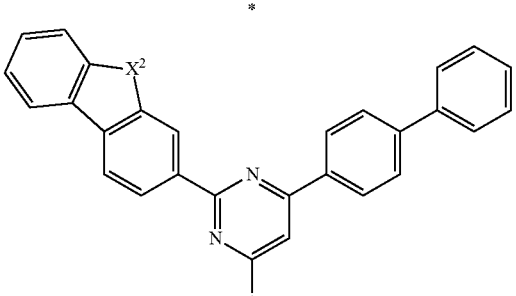
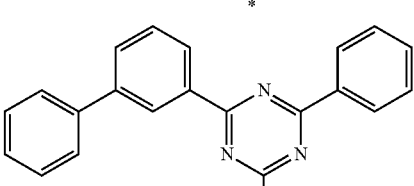
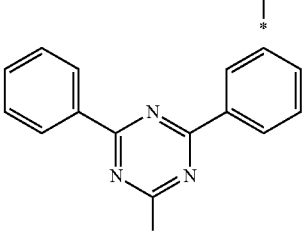
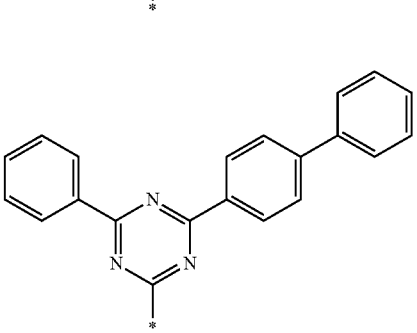

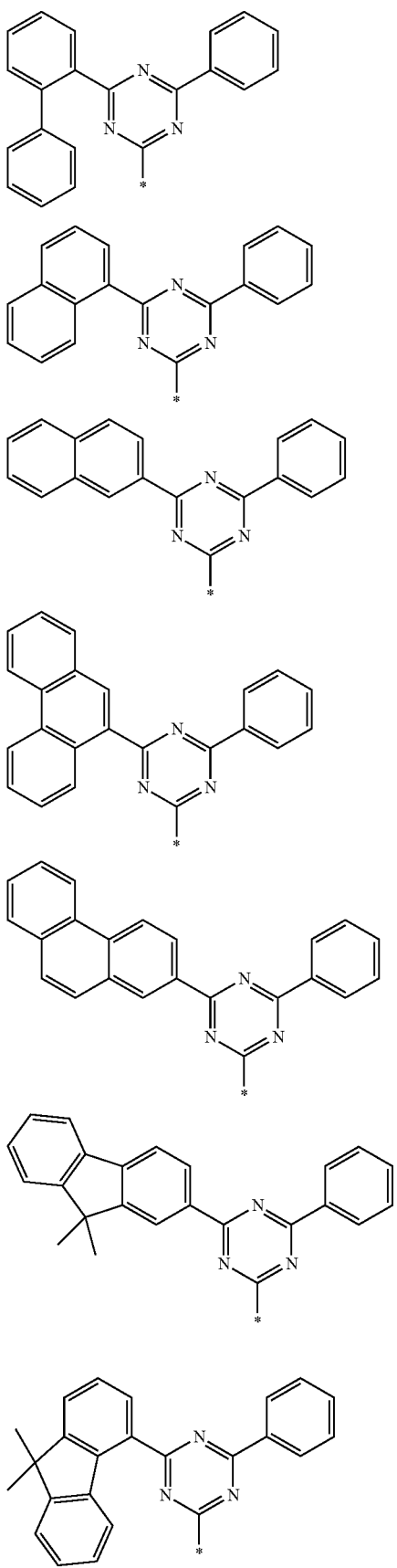
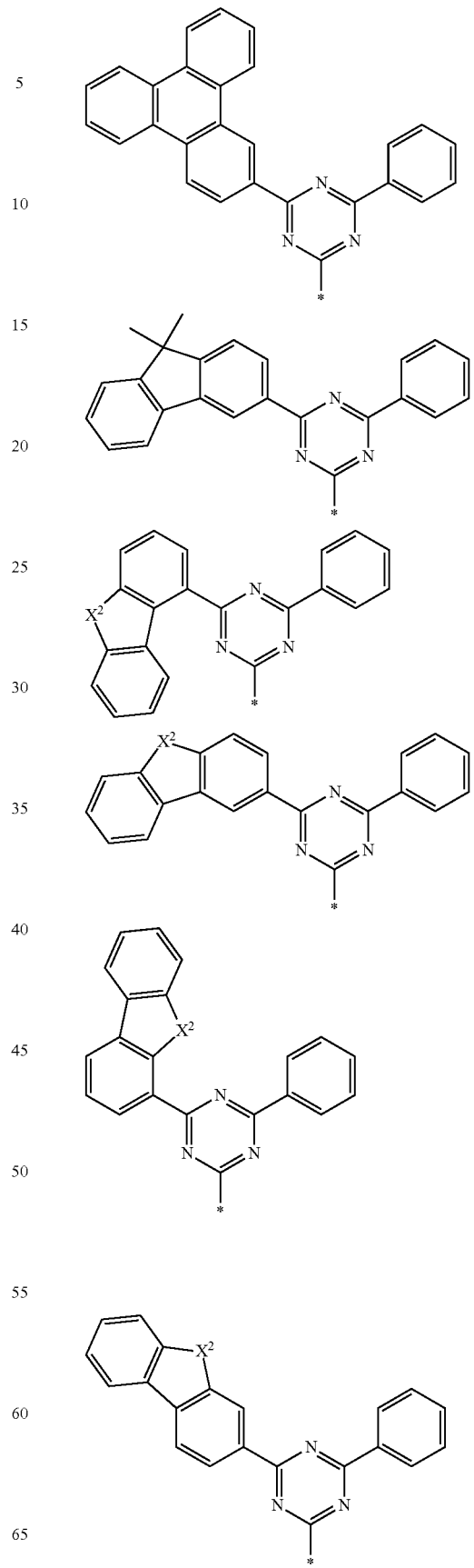

-continued
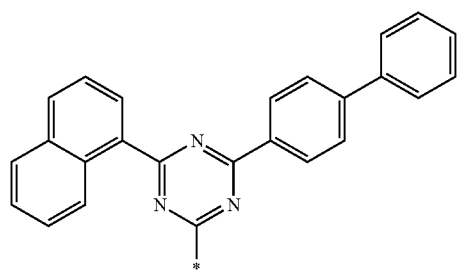
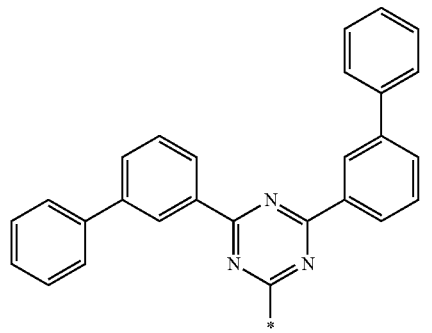
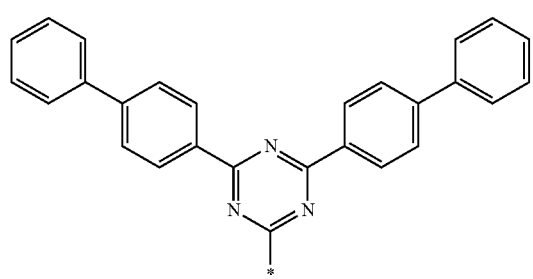
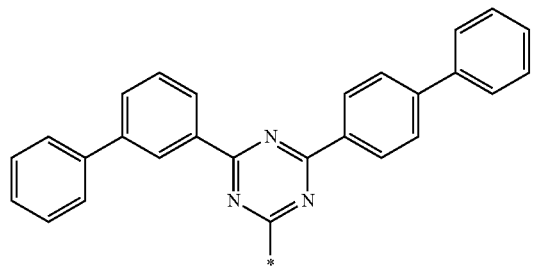
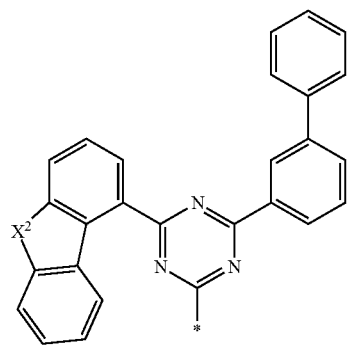
-continued
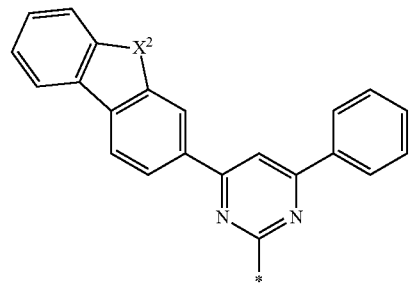
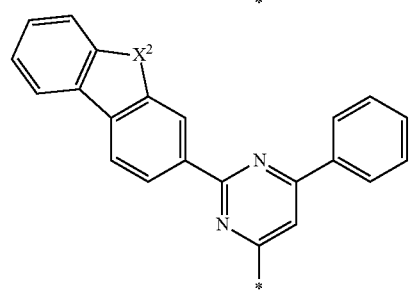
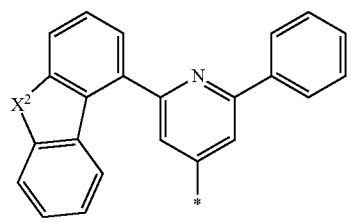
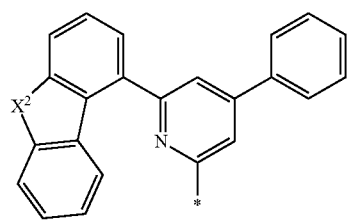
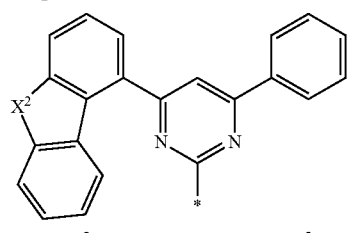
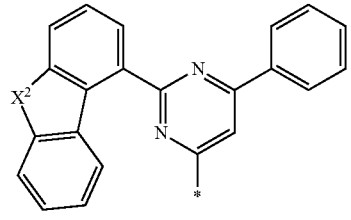
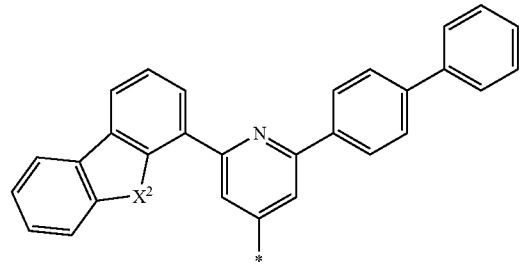

-continued
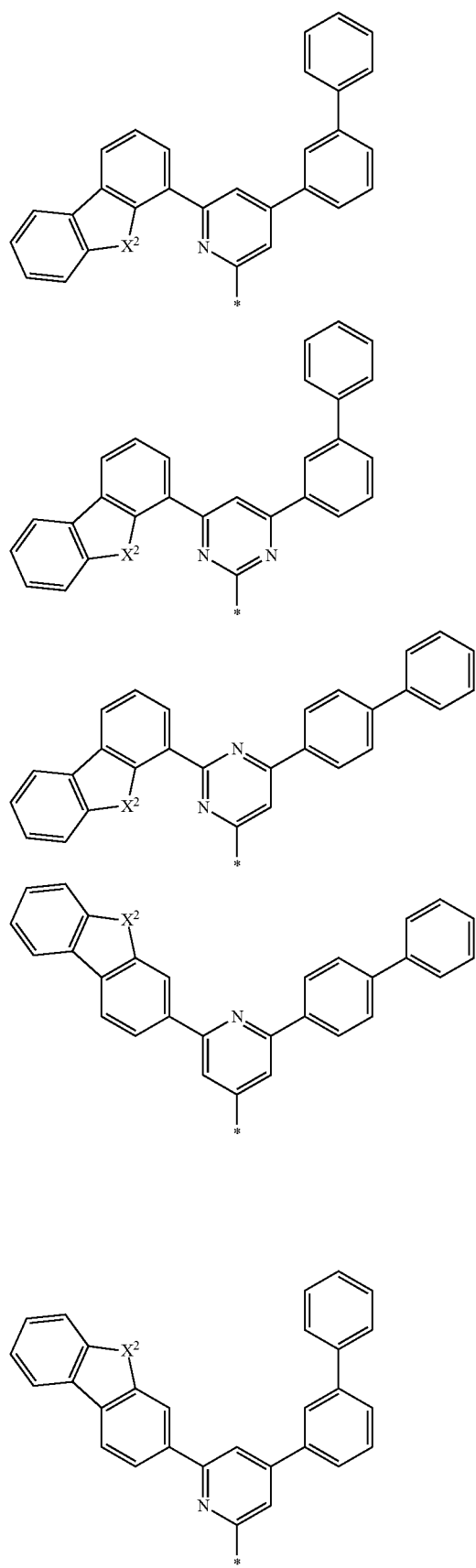
-continued
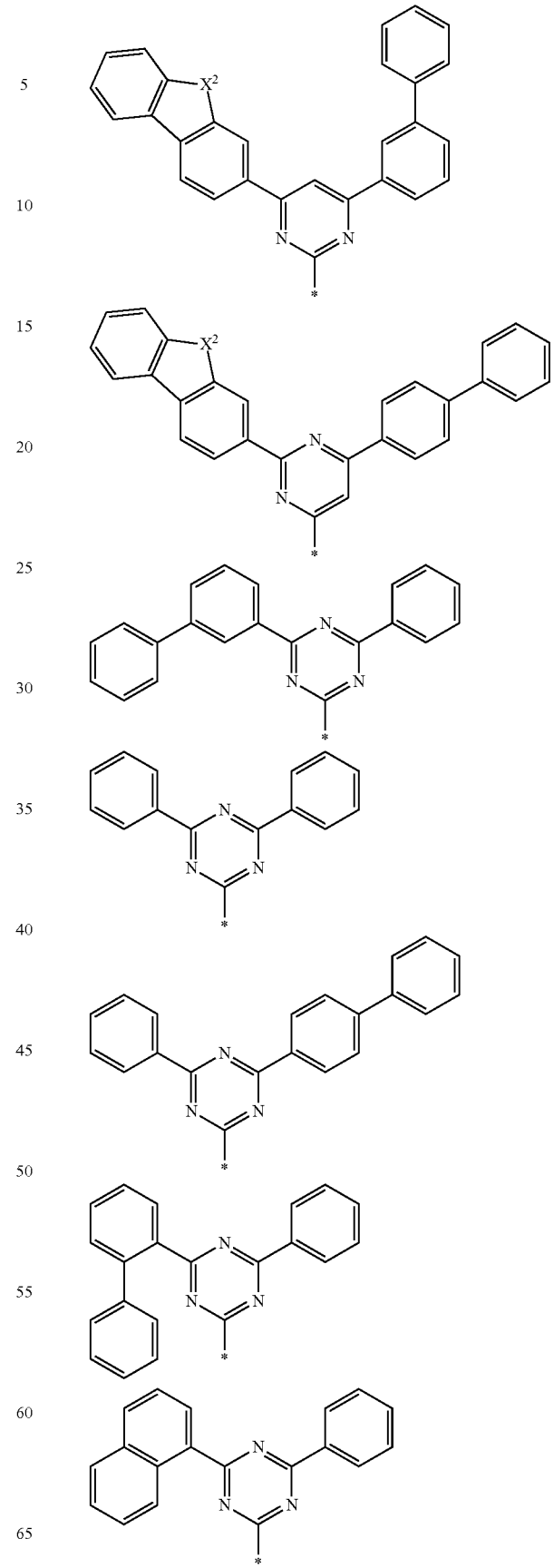

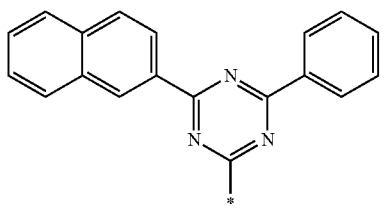
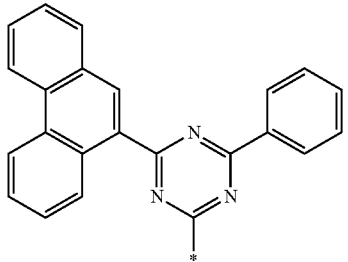
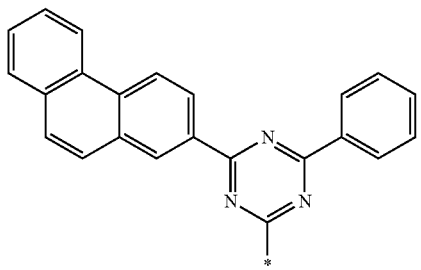
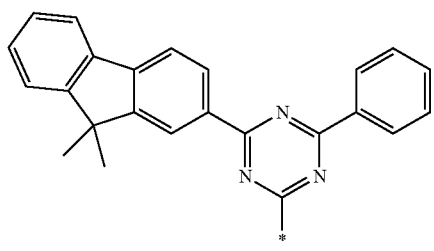
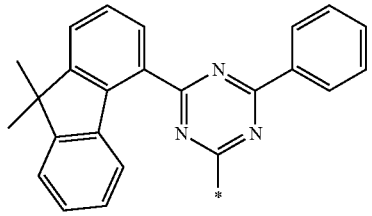
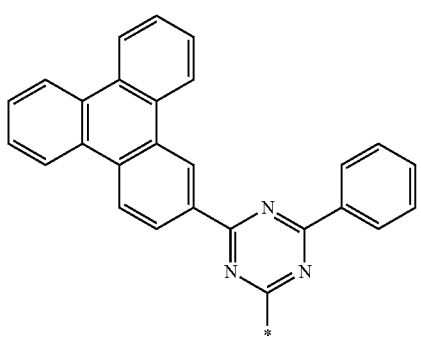
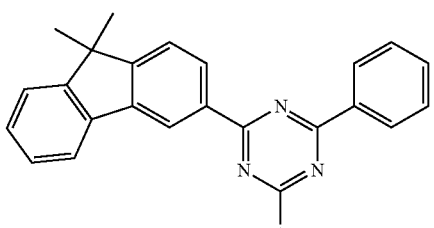
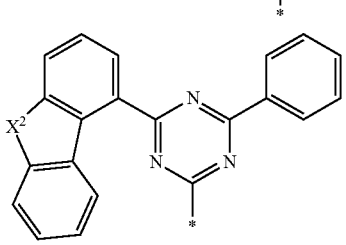
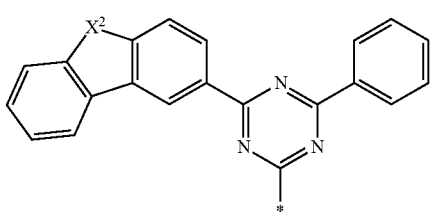
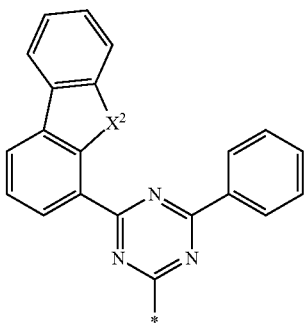
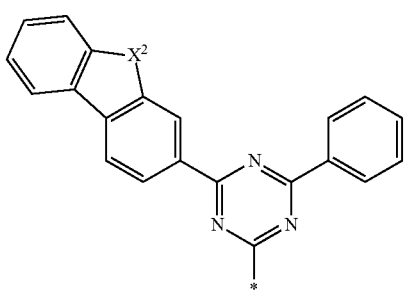
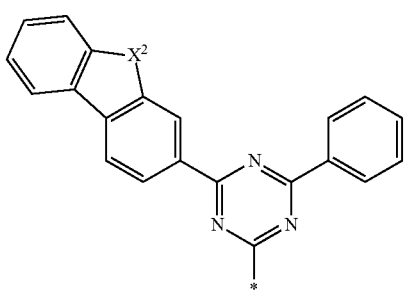
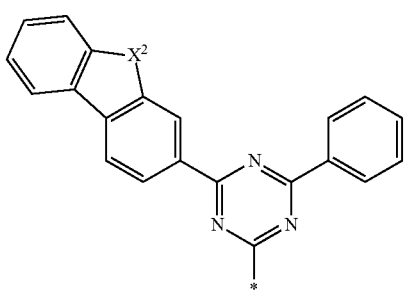

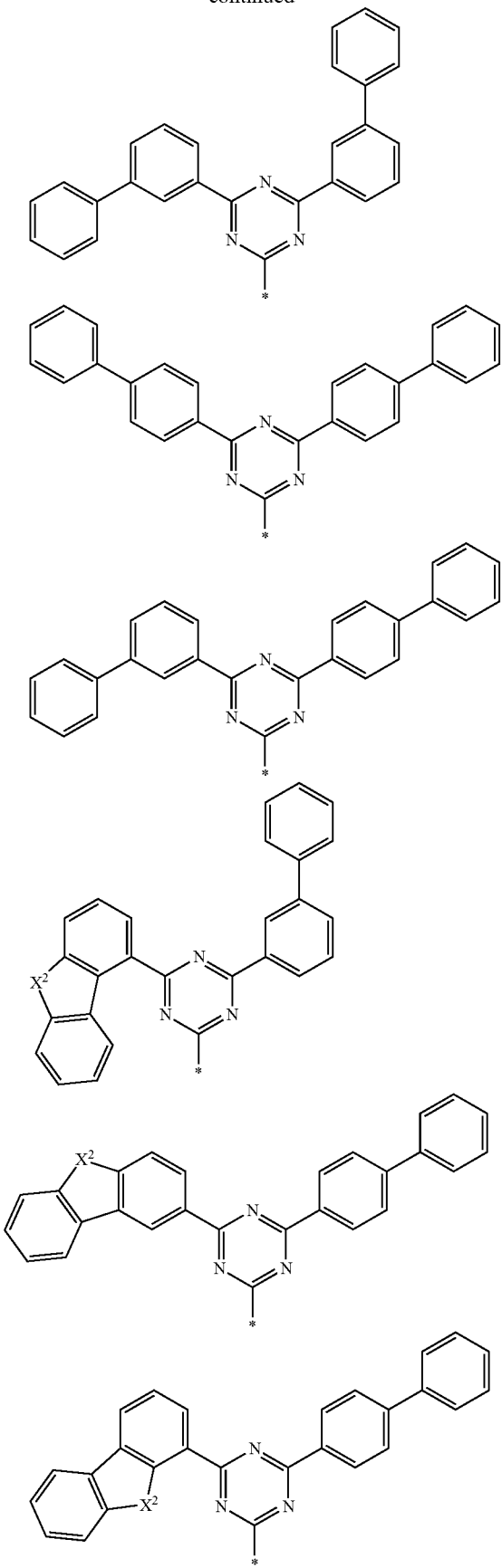
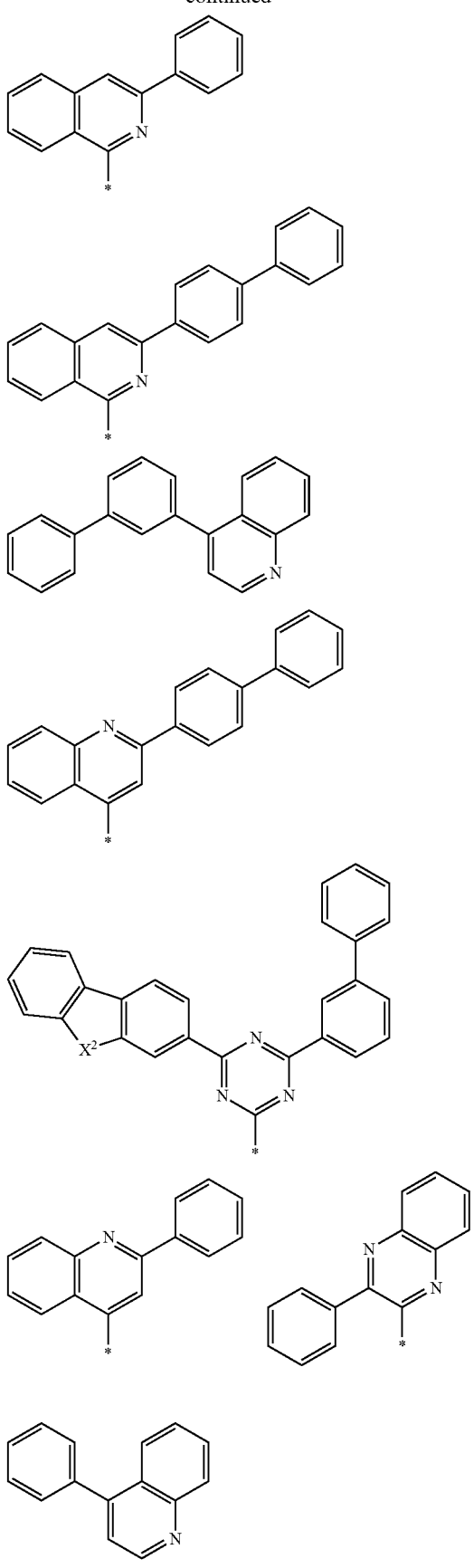

-continued
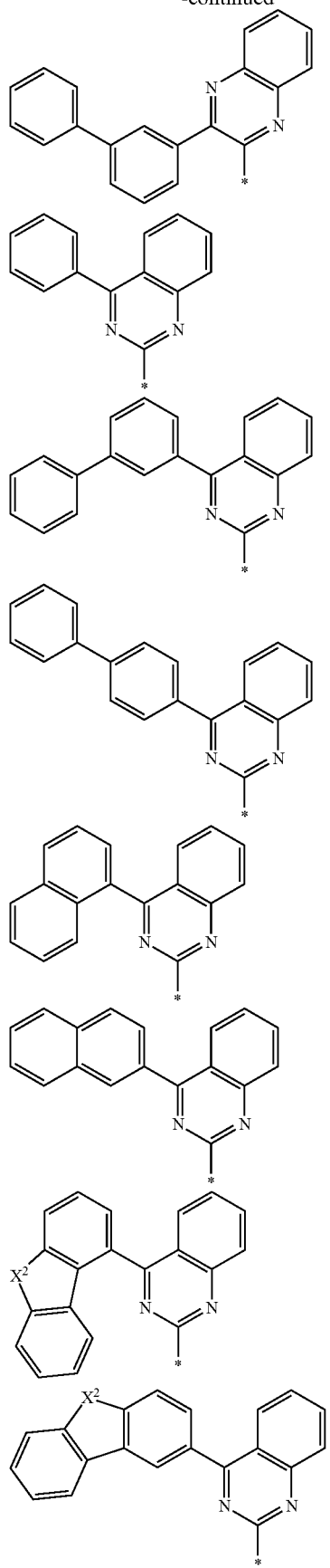
-continued
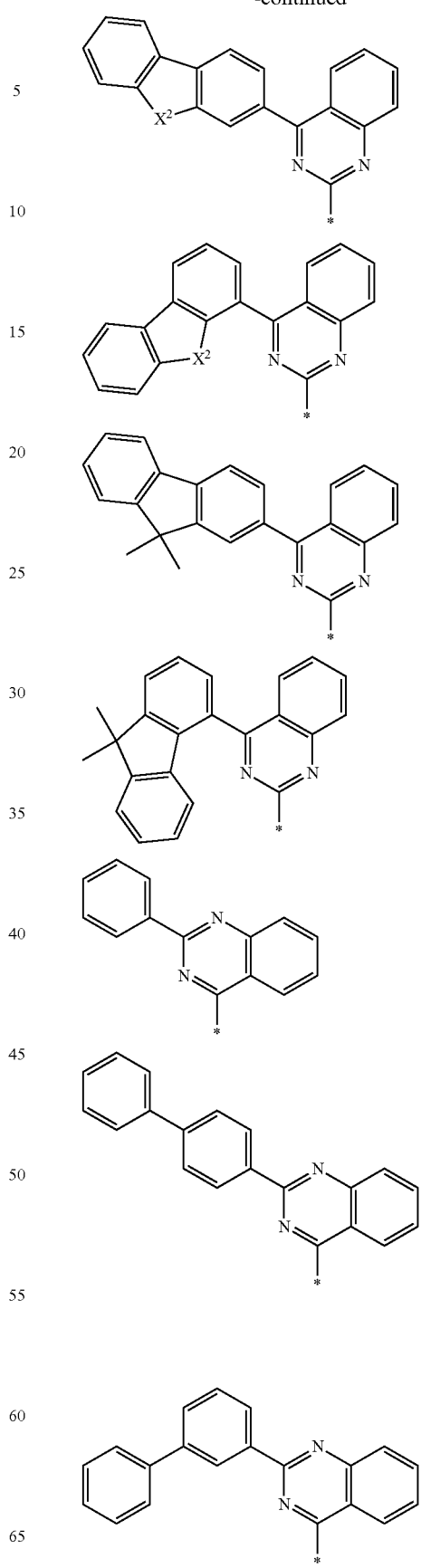

-continued

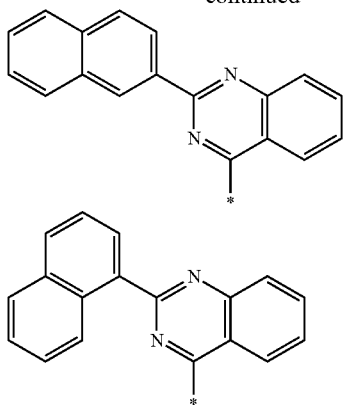

In Group I, $X^2$ may be O or S and * may be a linking point with L.

In a specific example embodiment of the present invention, A of Chemical Formula 1 may be a substituted or unsubstituted pyrimidinyl group, a substituted or unsubstituted triazinyl group, a substituted or unsubstituted quinolinyl group, a substituted or unsubstituted isoquinolinyl group, or a substituted or unsubstituted quinazolinyl group, and more specifically, A of Chemical Formula 1 may be a substituted or unsubstituted triazinyl group, or a substituted or unsubstituted quinazolinyl group.

In an example embodiment of the present invention, $Z^1$ of Chemical Formula 1 may be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted dibenzofuranyl group, or a substituted or unsubstituted dibenzothiophenyl group, and specifically, $Z^1$ of Chemical Formula 1 may be a substituted or unsubstituted C6 to C30 aryl group or a substituted or unsubstituted C2 to C30 heterocyclic group. More specifically, $Z^1$ of Chemical Formula 1 may be a phenyl group, a biphenyl group, a naphthyl group, a terphenyl group, an anthracenyl group, a triphenyl group, a phenanthrenyl group, a fluorenyl group, a dibenzofuranyl group, or a dibenzothiophenyl group. More specifically, $Z^1$ of Chemical Formula 1 may be a phenyl group, a biphenyl group, or a naphthyl group, but is not limited thereto.

In an example embodiment of the present invention, L of Chemical Formula 1 may be a single bond, a phenylene group, a biphenylene group, or a naphthylene group, and more specifically a single bond or a phenylene group, but is not limited thereto.

In an example embodiment of the present invention, $Y^1$ of Chemical Formula 1 may be a single bond, a substituted or unsubstituted phenylene group, a substituted or unsubstituted biphenylene group, or a substituted or unsubstituted naphthylene group, but is not limited thereto.

In an example embodiment of the present invention, $R^1$ to $R^4$ of Chemical Formula 1 may independently be hydrogen, deuterium, a C1 to C4 alkyl group, a phenyl group, a naphthyl group, a biphenyl group, a terphenyl group, a fluorenyl group, a dibenzofuranyl group, or a dibenzothiophenyl group, and more specifically hydrogen, deuterium, a phenyl group, or a naphthyl group, but are not limited thereto.

For example, $Y^1$ of Chemical Formula 1 may specifically be a single bond or a substituted or unsubstituted phenylene group, in an example embodiment of the present invention, $Y^1$ of Chemical Formula 1 may be a single bond, a substituted or unsubstituted para-phenylene group, or a substituted or unsubstituted meta-phenylene group, and $Z^1$ of Chemical Formula 1 may be a substituted or unsubstituted C6 to C30 aryl group.

In addition, $R^1$ to $R^4$ of Chemical Formula 1 may independently be hydrogen, deuterium, a substituted or unsubstituted C6 to C20 aryl group, or a substituted or unsubstituted C2 to C20 heterocyclic group, specifically, hydrogen, deuterium, a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group, and for example $R^1$ to $R^4$ may be all hydrogen or one of $R^1$ to $R^4$ may be a phenyl group, a biphenyl group, a naphthyl group, a dibenzofuranyl group, or a dibenzothiophenyl group.

The first compound for the organic optoelectronic diode represented by Chemical Formula 1 may be for example represented by Chemical Formula 1-1 and an electron transporting group, ET group (A) is bound at an ortho position of $X^1$, for example O or S, and thereby more improved effect may be exhibited.

[Chemical Formula 1-1]

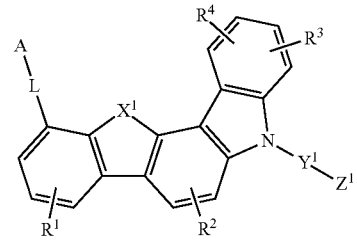

In Chemical Formula 1-1, $X^1$ is O or S,

A is a substituted or unsubstituted pyridinyl group, a substituted or unsubstituted pyrimidinyl group, a substituted or unsubstituted triazinyl group, a substituted or unsubstituted benzimidazolyl group, a substituted or unsubstituted pyrazinyl group, a substituted or unsubstituted quinolinyl group, a substituted or unsubstituted isoquinolinyl group, a substituted or unsubstituted quinoxalinyl group, or a substituted or unsubstituted quinazolinyl group, L is a single bond or a C6 to C30 arylene group, $Y^1$ is a single bond, a substituted or unsubstituted C6 to C30 arylene group, or a substituted or unsubstituted C2 to C30 heteroarylene group, $Z^1$ is a substituted or unsubstituted C6 to C30 aryl group, or a substituted or unsubstituted C2 to C30 heterocyclic group, and $R^1$ to $R^4$ are independently hydrogen, deuterium, C1 to C10 alkyl group, a substituted or unsubstituted C6 to C30 aryl group, or a substituted or unsubstituted C2 to C30 heterocyclic group.

For example, $Y^1$ may be a single bond, a C6 to C30 arylene group, a dibenzothiophenyl group, or a dibenzofuranyl group, $Z^1$ may be a C6 to C30 aryl group, a dibenzothiophenyl group, or a dibenzofuranyl group, and $R^1$ to $R^4$ may independently be hydrogen, deuterium, a C1 to C4 alkyl group, a phenyl group, a naphthyl group, a biphenyl group, a terphenyl group, a fluorenyl group, a dibenzofuranyl group, or a dibenzothiophenyl group, but they are not limited thereto.

In an example embodiment of the present invention, A of Chemical Formula 1-1 may be a substituted or unsubstituted pyrimidinyl group, a substituted or unsubstituted triazinyl group, or a substituted or unsubstituted quinazolinyl group.

In an example embodiment of the present invention, L of Chemical Formula 1-1 may be a single bond, a phenylene group, a biphenylene group, or a naphthylene group, and more specifically a single bond or a phenylene group.

In an example embodiment of the present invention, $Y^1$ of Chemical Formula 1-1 may be a single bond, a phenylene group, a biphenylene group, or a naphthylene group.

In an example embodiment of the present invention, $Z^1$ of Chemical Formula 1-1 may be a phenyl group, a biphenyl group, a naphthyl group, a terphenyl group, an anthracenyl group, a triphenyl group, a phenanthrenyl group, a fluorenyl group, a dibenzofuranyl group, or a dibenzothiophenyl group. More specifically, it may be a phenyl group, a biphenyl group, or a naphthyl group.

In an example embodiment of the present invention, $R^1$ to $R^4$ of Chemical Formula 1 may independently be hydrogen, deuterium, a C1 to C4 alkyl group, a phenyl group, a naphthyl group, a biphenyl group, a terphenyl group, a fluorenyl group, a dibenzofuranyl group, or a dibenzothiophenyl group, and more specifically hydrogen, deuterium, a phenyl group, or a naphthyl group, but are not limited thereto.

For example, in Chemical Formula 1-1, "substituted" refers to replacement of at least one hydrogen by deuterium, a C1 to C4 alkyl group, a C6 to C18 aryl group, a dibenzofuranyl group, or a dibenzothiophenyl group.

The first compound for the organic optoelectronic diode represented by Chemical Formula 1 may be for example selected from compounds of Group 1, but is not limited thereto.

[Group 1]

[A-1]

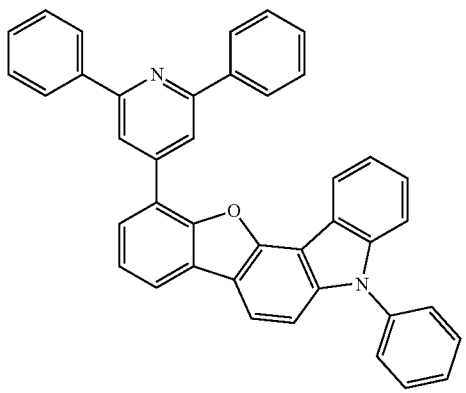

[A-2]

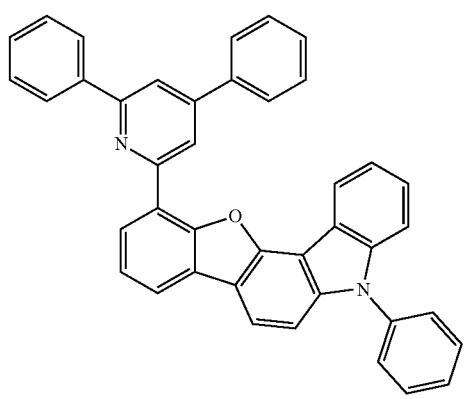

[A-3]

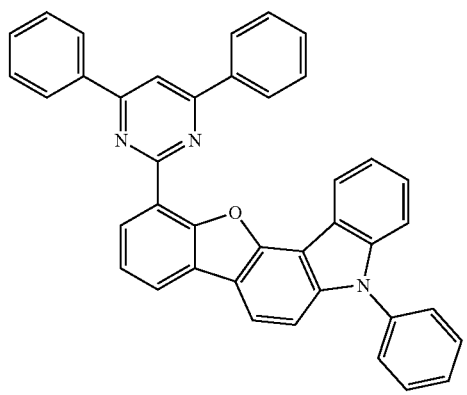

[A-4]

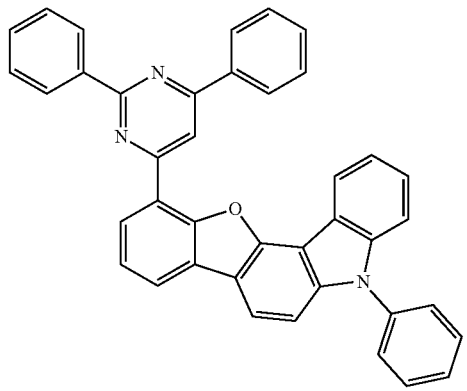

[A-5]

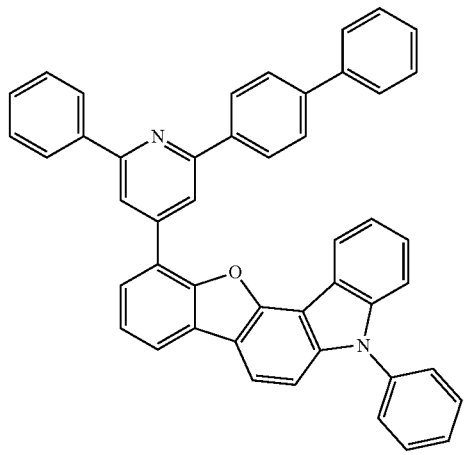

-continued
[A-6]
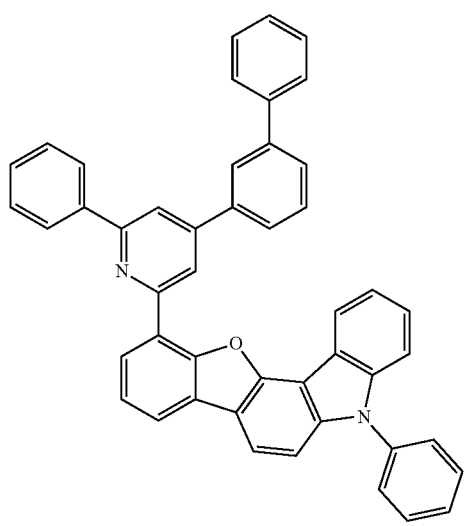
[A-7]
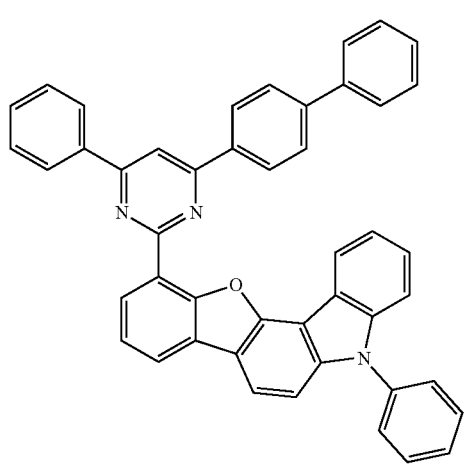
[A-8]
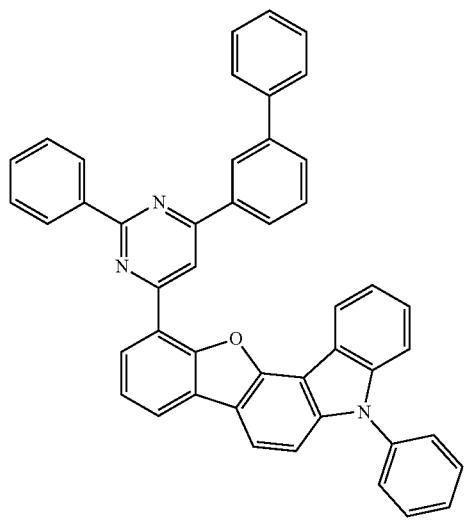
-continued
[A-9]
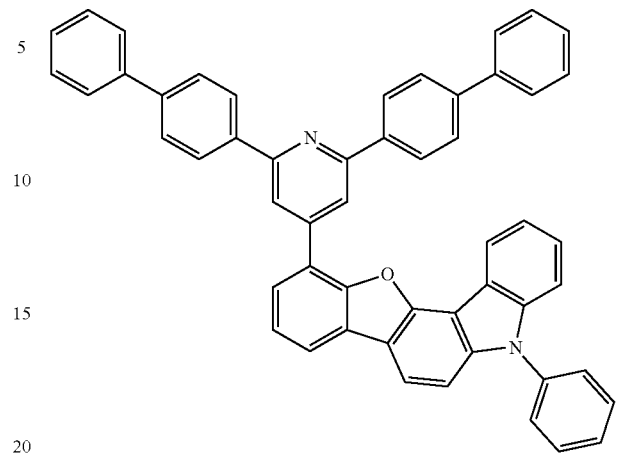
[A-10]
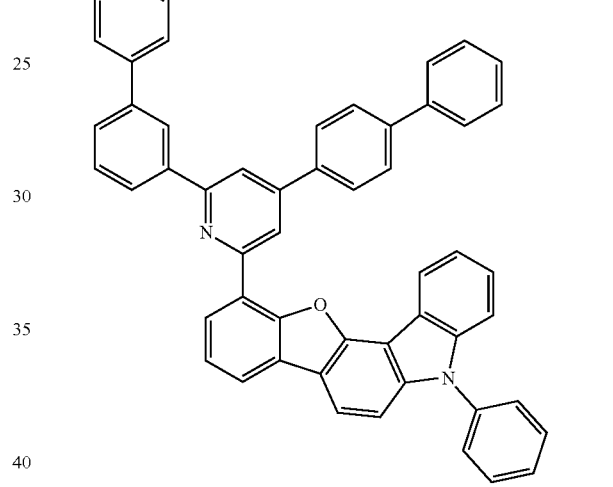
[A-11]
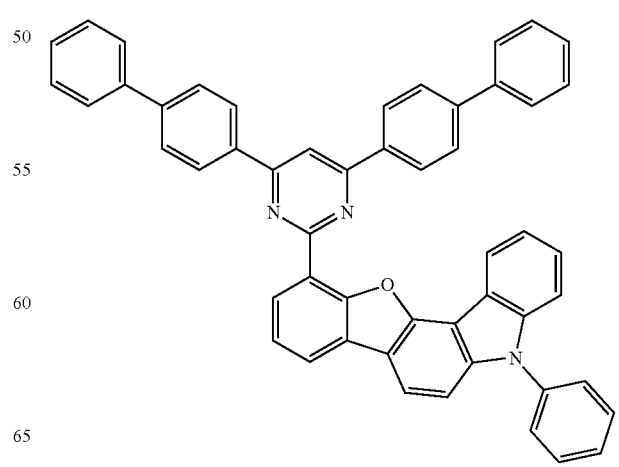

-continued
[A-12]
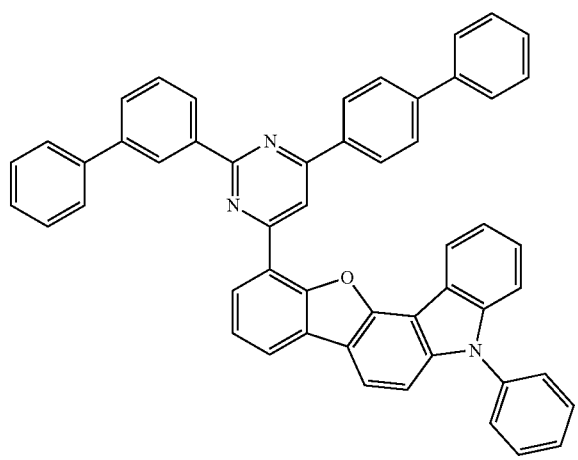
[A-13]
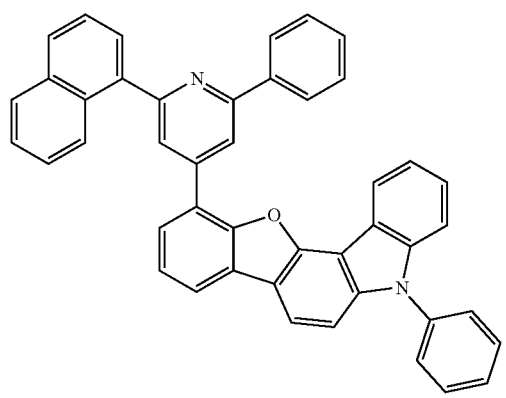
[A-14]
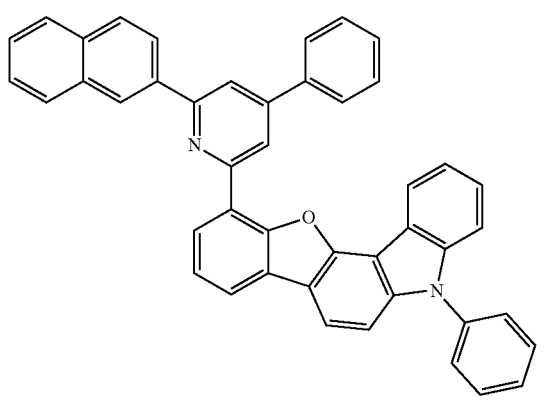
-continued
[A-15]
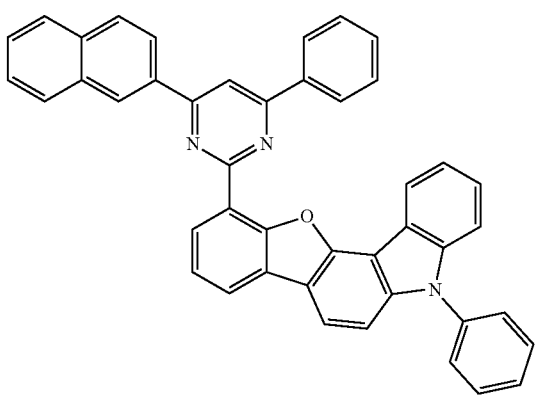
[A-16]
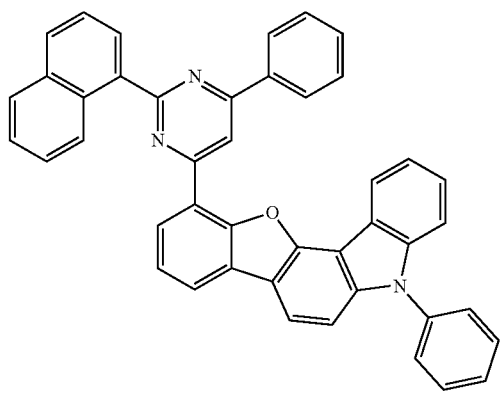
[A-17]
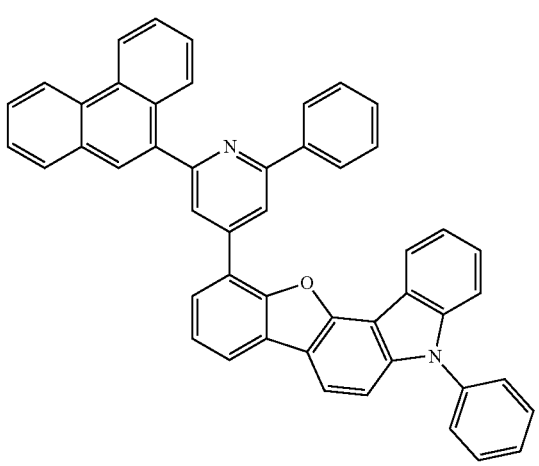

-continued
[A-18]
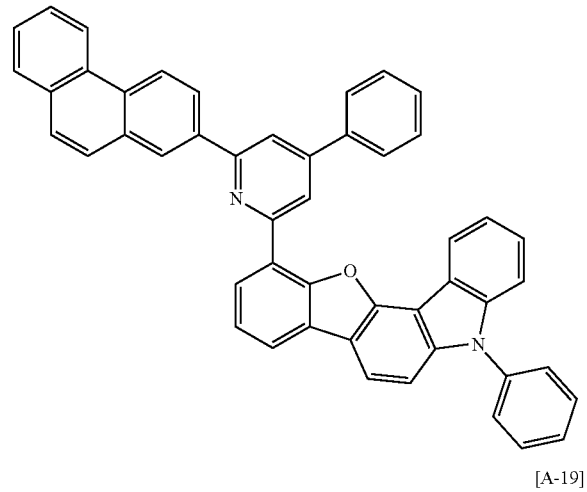
[A-21]
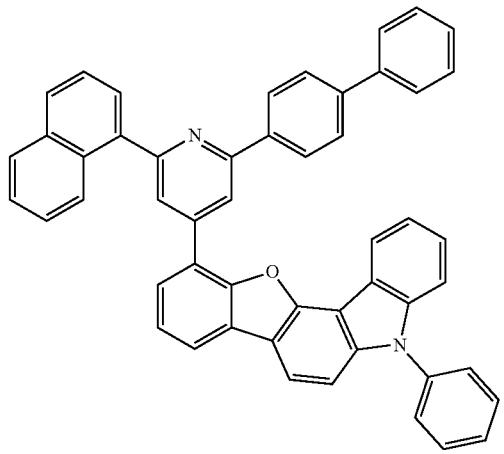
[A-19]
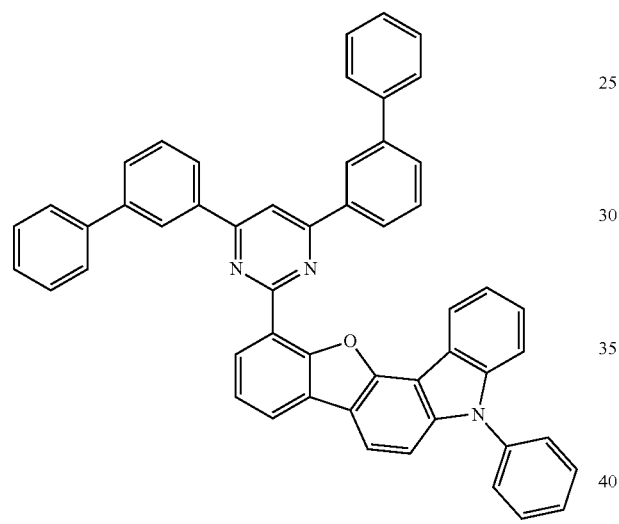
[A-22]
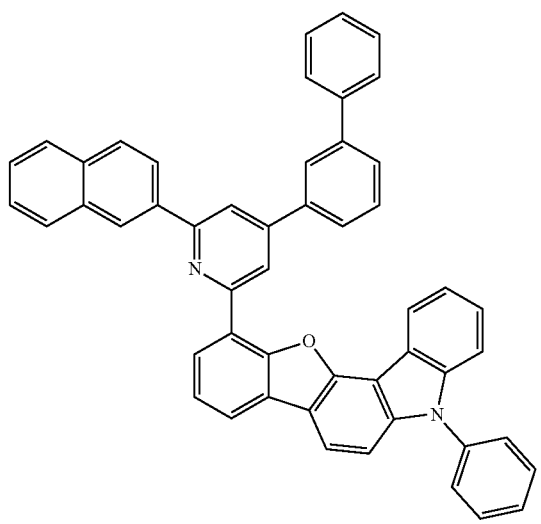
[A-20]
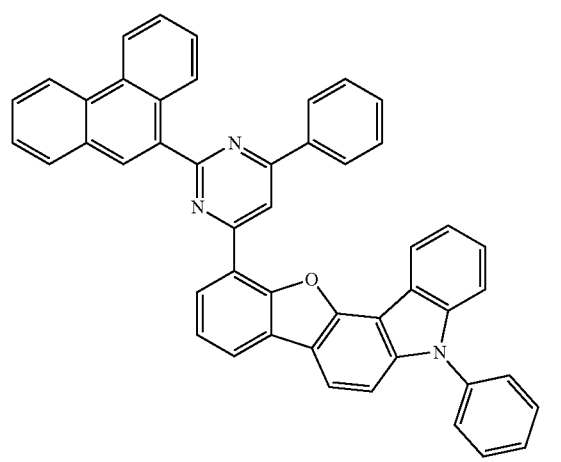
[A-23]
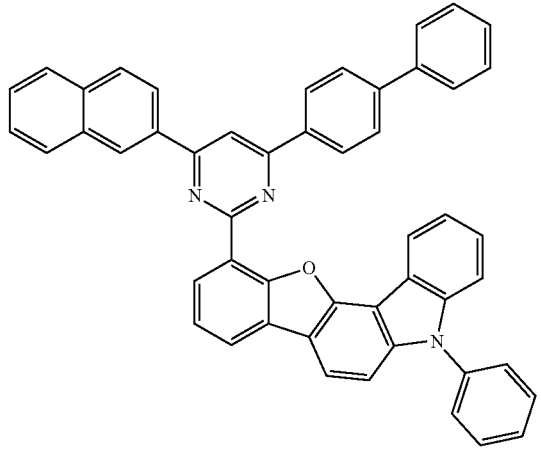

[A-24]
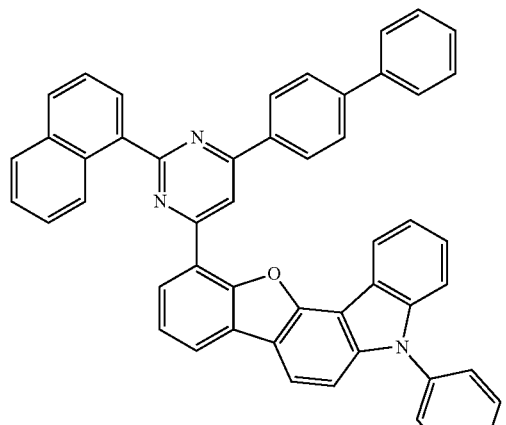
[A-25]
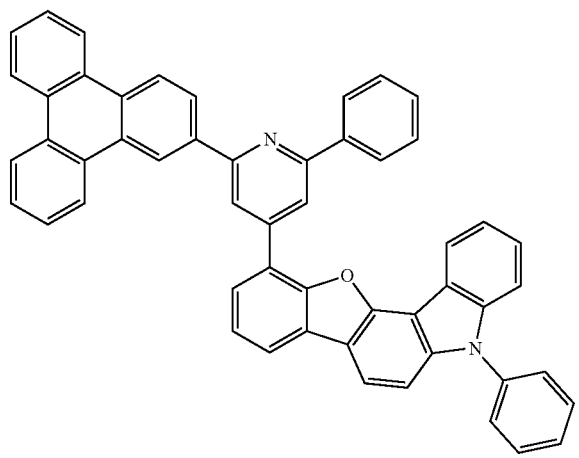
[A-26]
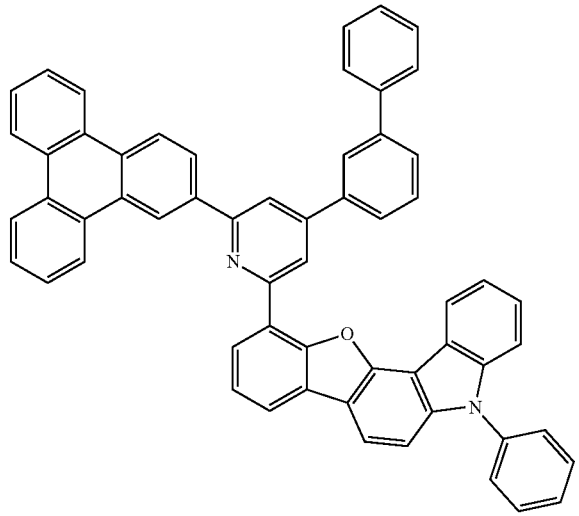
[A-27]
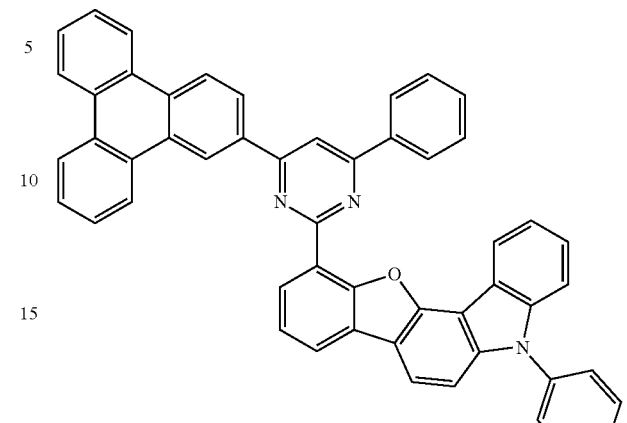
[A-28]
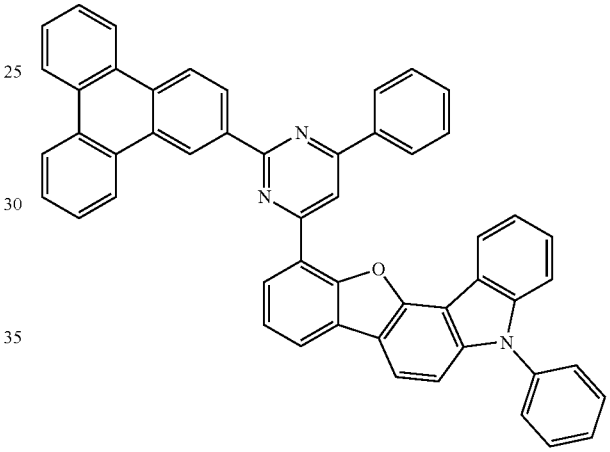
[A-29]
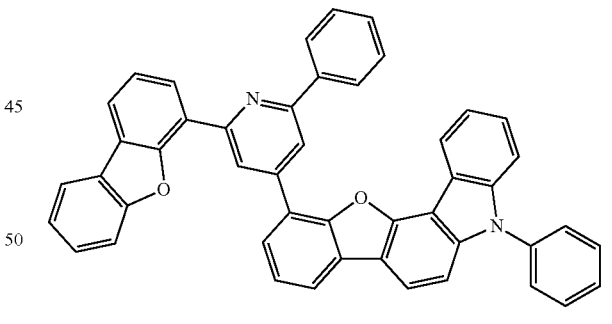
[A-30]
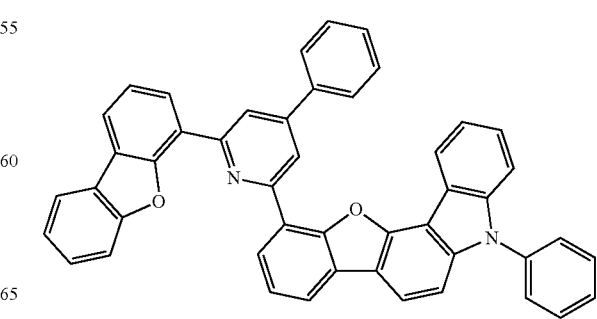

[A-31]
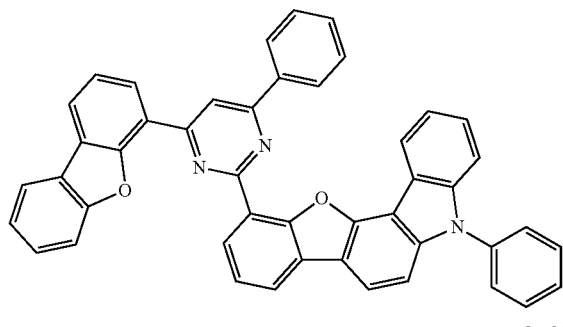
[A-32]
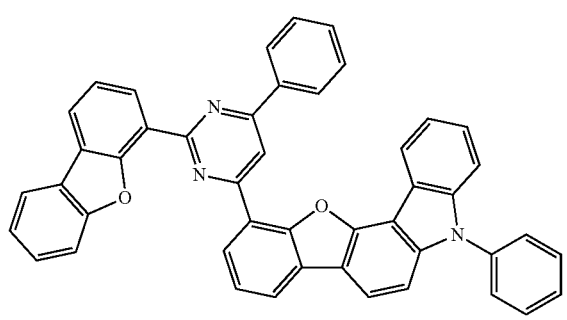
[A-33]
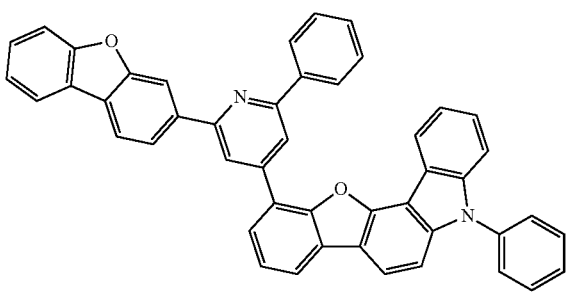
[A-34]
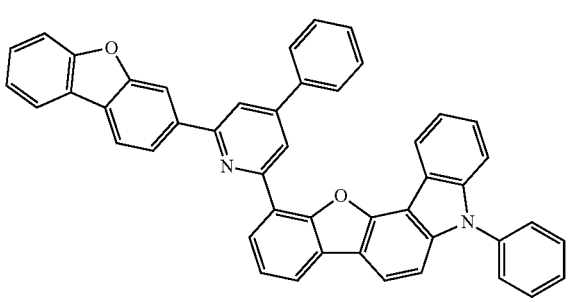
[A-35]
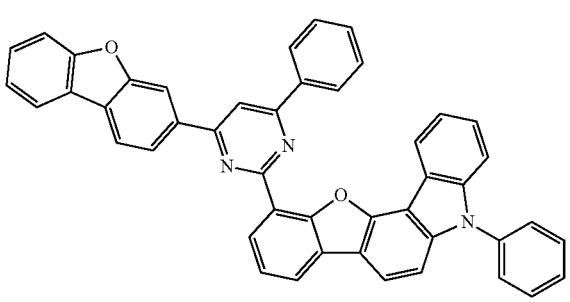
[A-36]
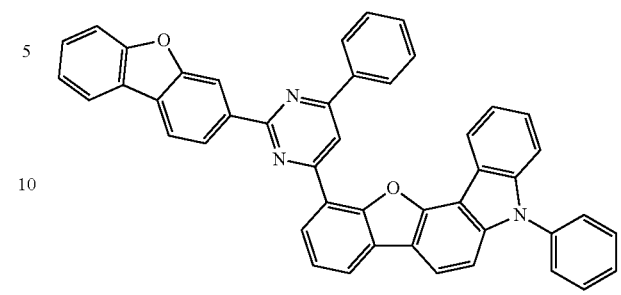
[A-37]
[A-38]
[A-39]
[A-40]

[A-41]
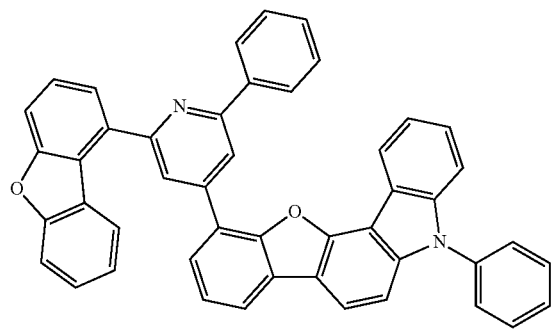
[A-42]
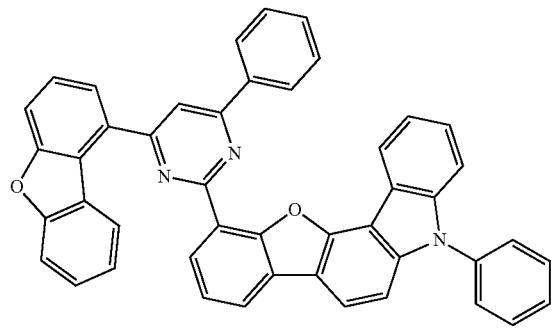
[A-43]
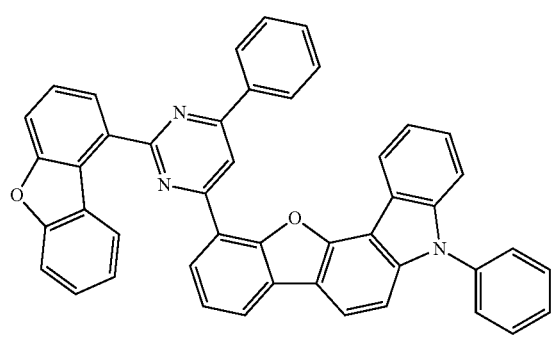
[A-45]
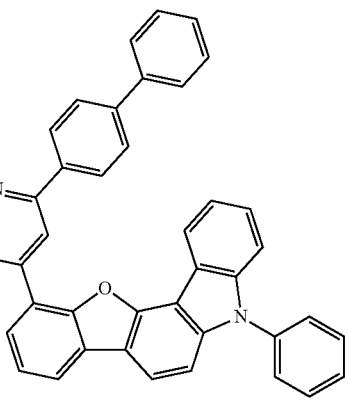
[A-46]
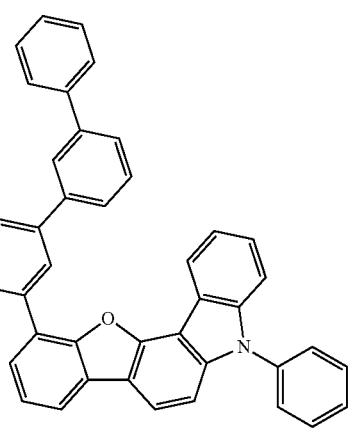
[A-47]
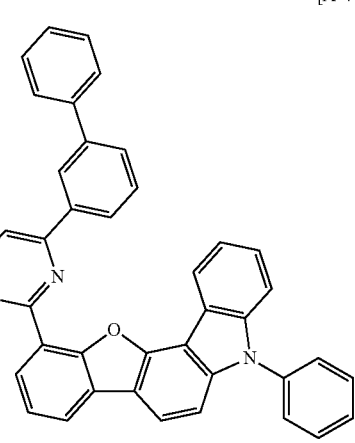
[A-44]

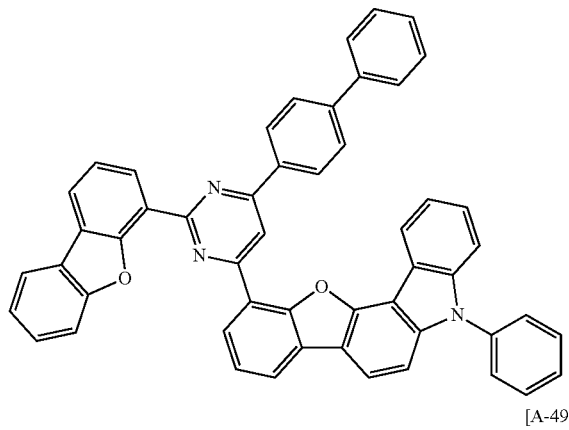
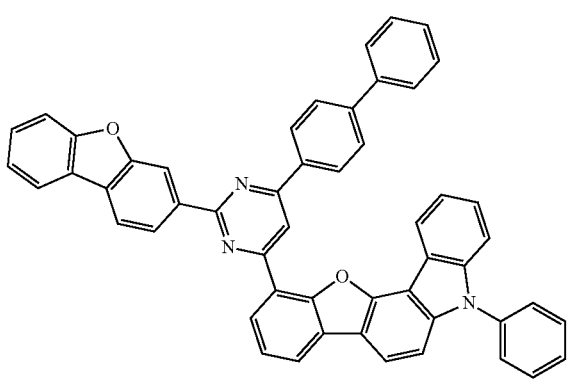
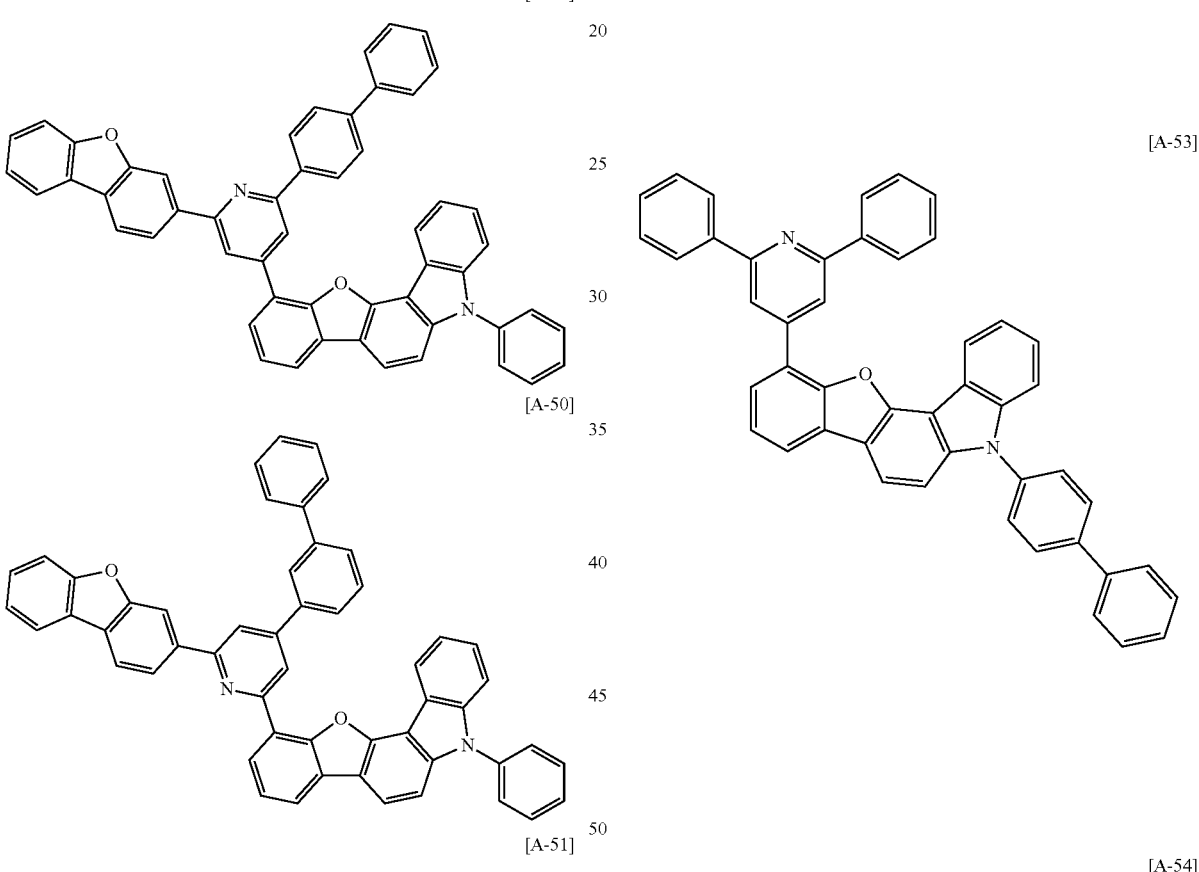
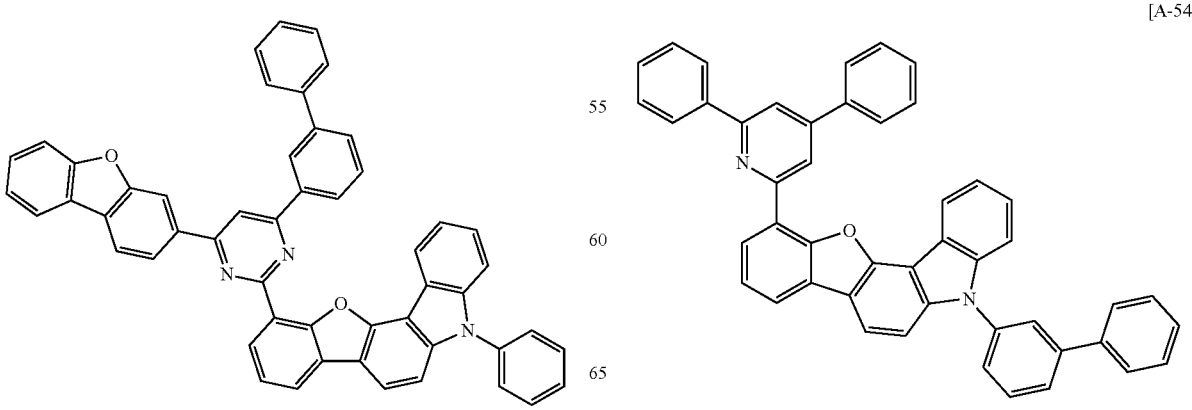

-continued
[A-55]
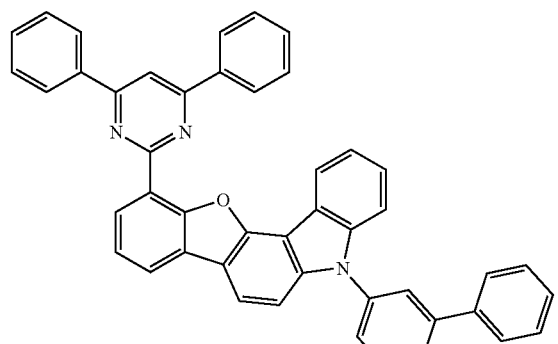
[A-58]
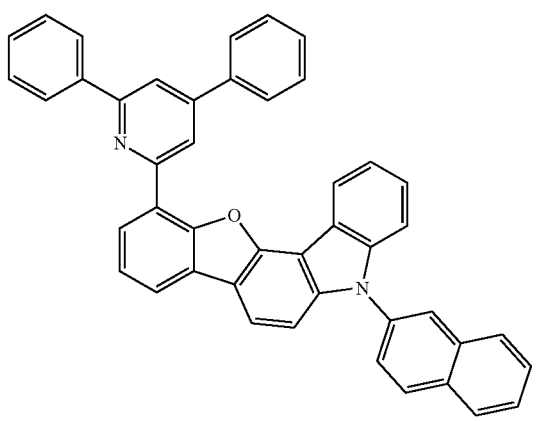
[A-56]
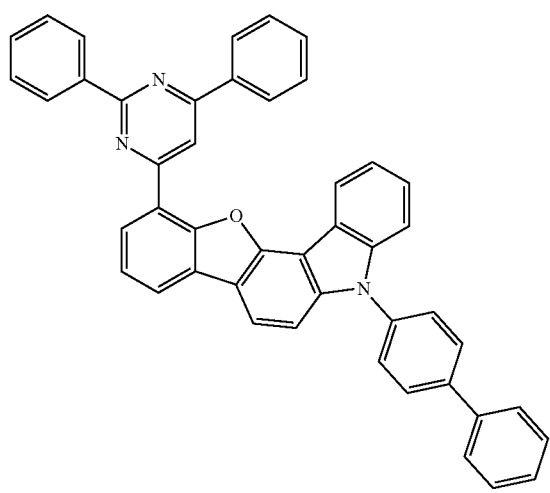
[A-59]
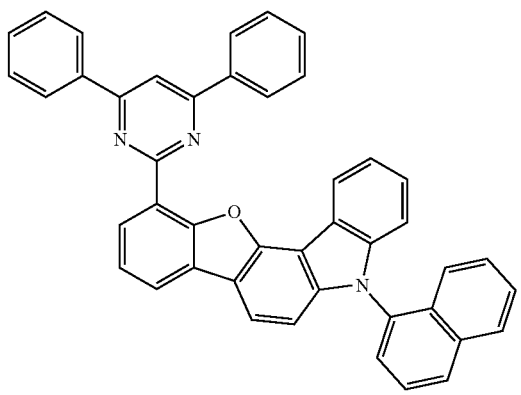
[A-57]
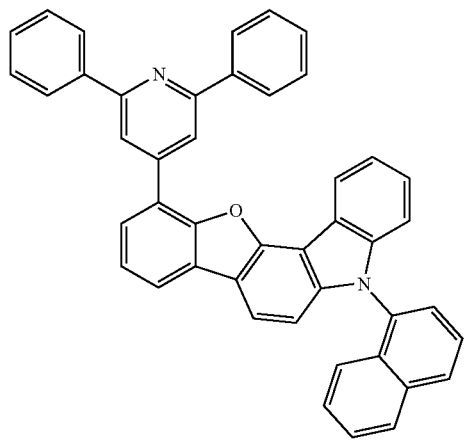
[A-60]
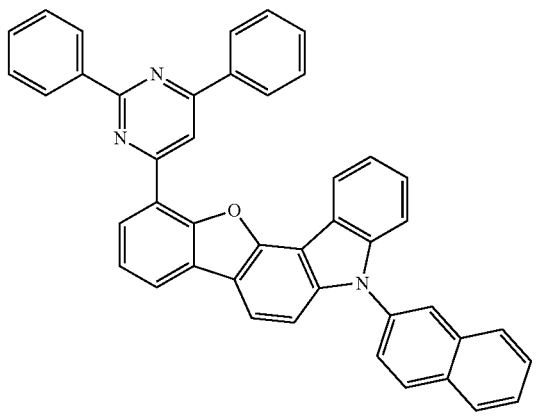

-continued
[A-61]
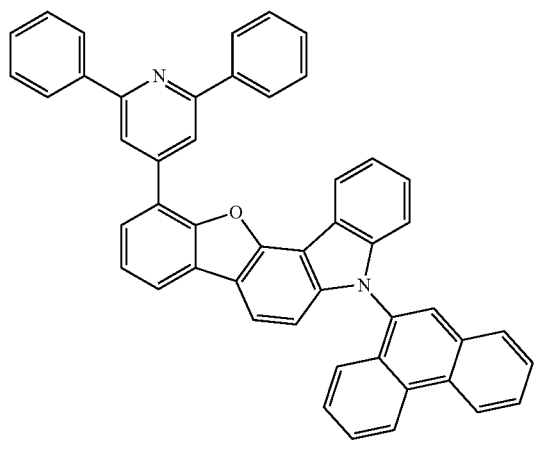
[A-62]
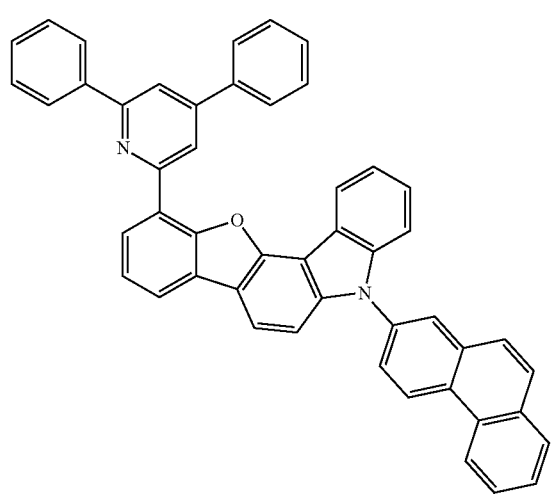
[A-63]
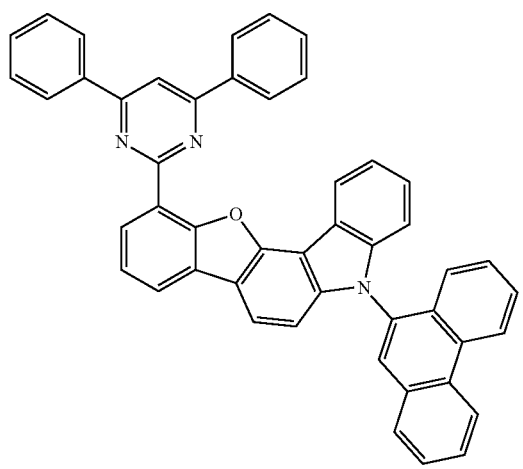
-continued
[A-64]
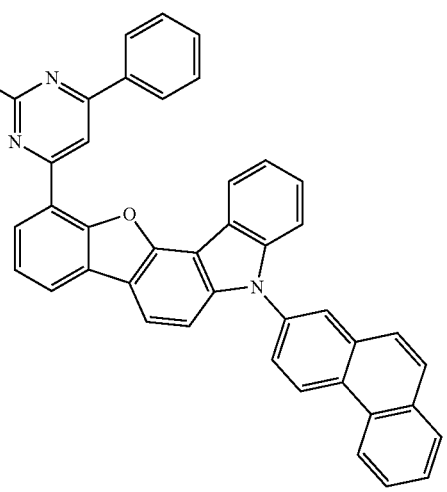
[A-65]
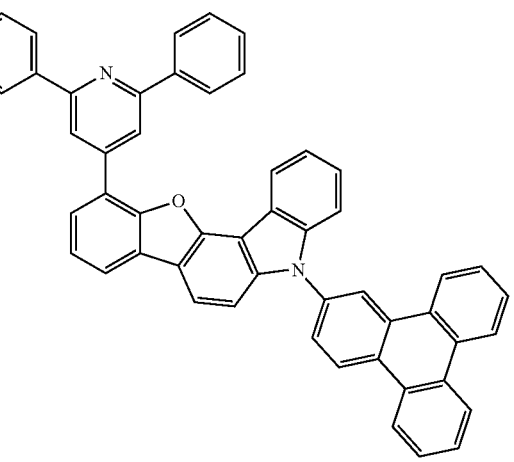
[A-66]
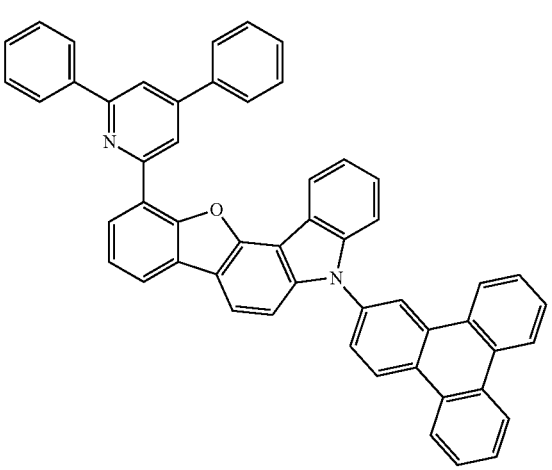

-continued
[A-67]
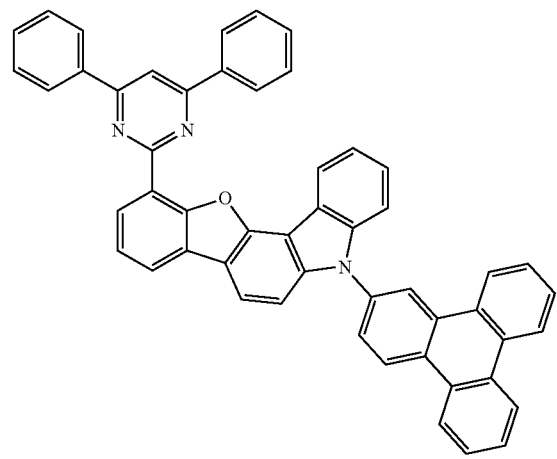
[A-68]
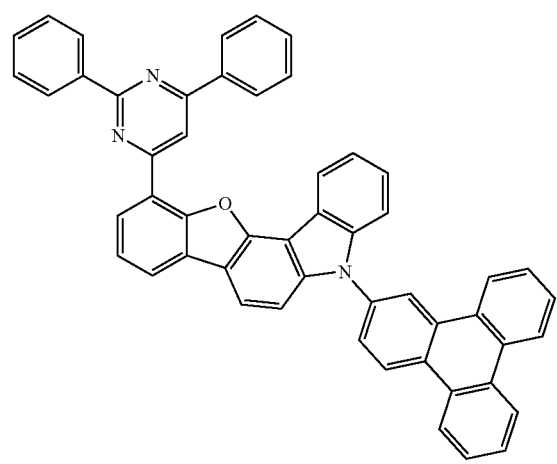
[A-69]
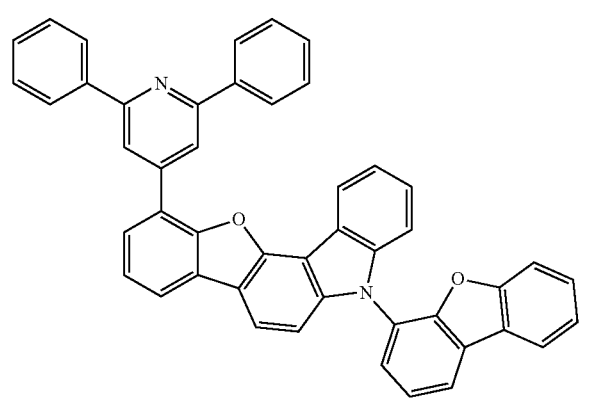
-continued
[A-70]
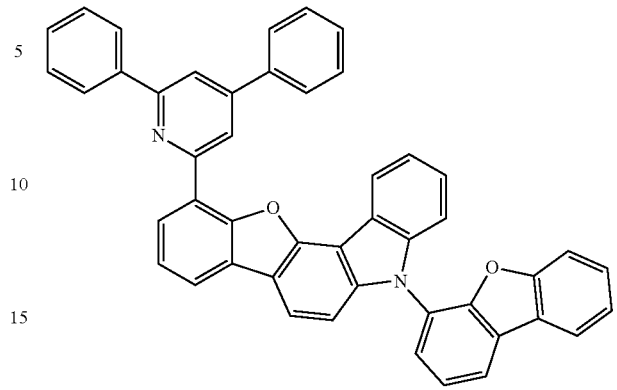
[A-71]
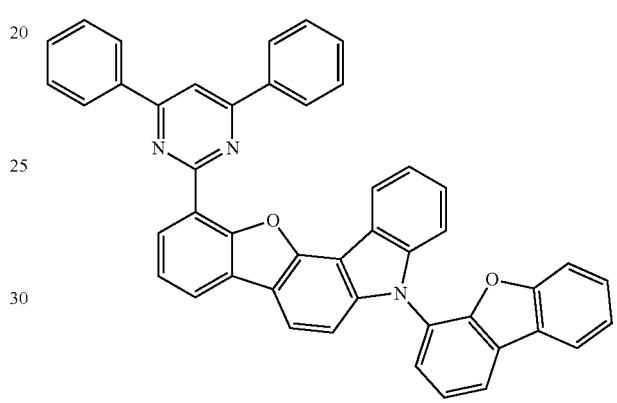
[A-72]
[A-73]
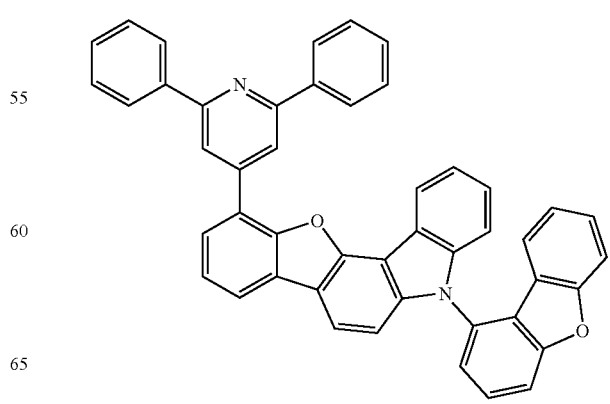

[A-74]
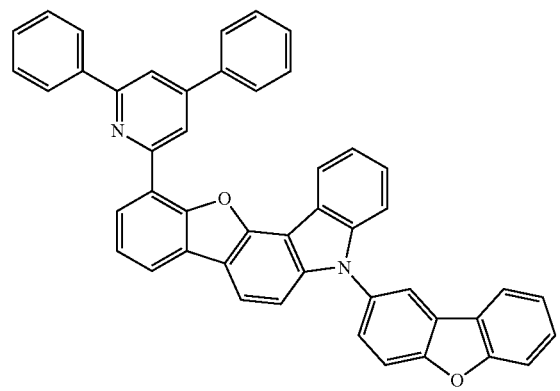
[A-77]
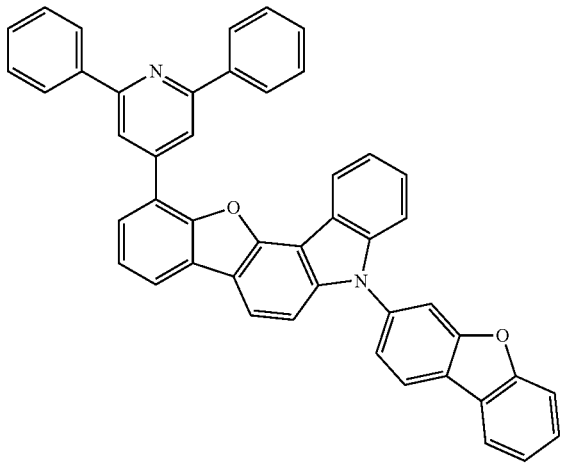
[A-75]
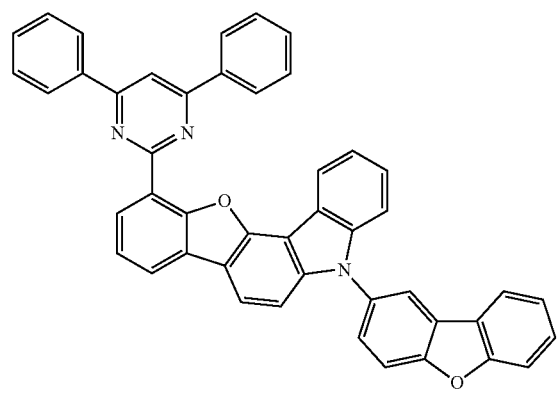
[A-78]
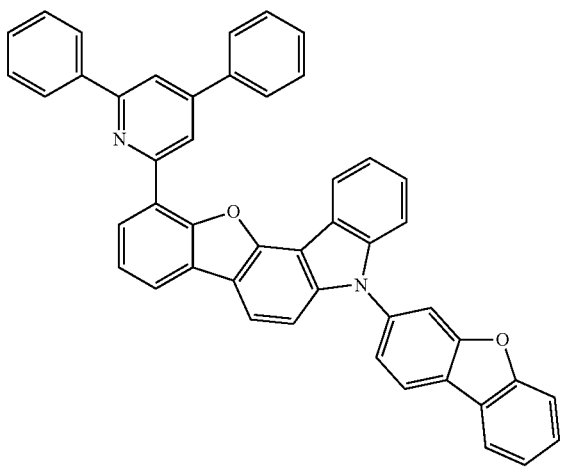
[A-76]
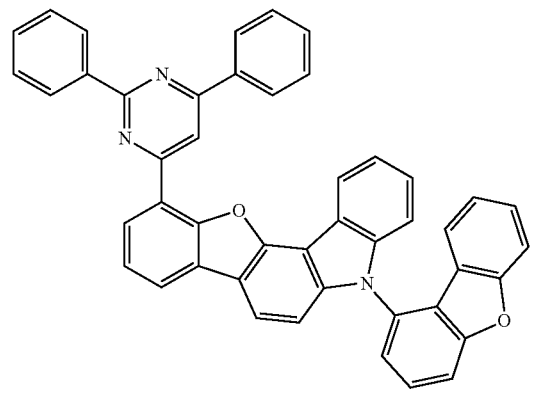
[A-79]
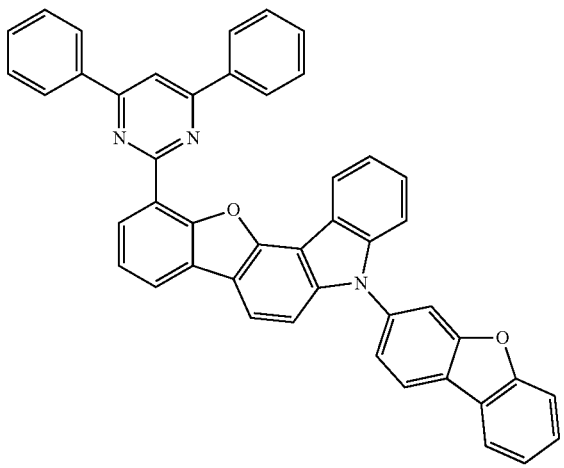

[A-80]
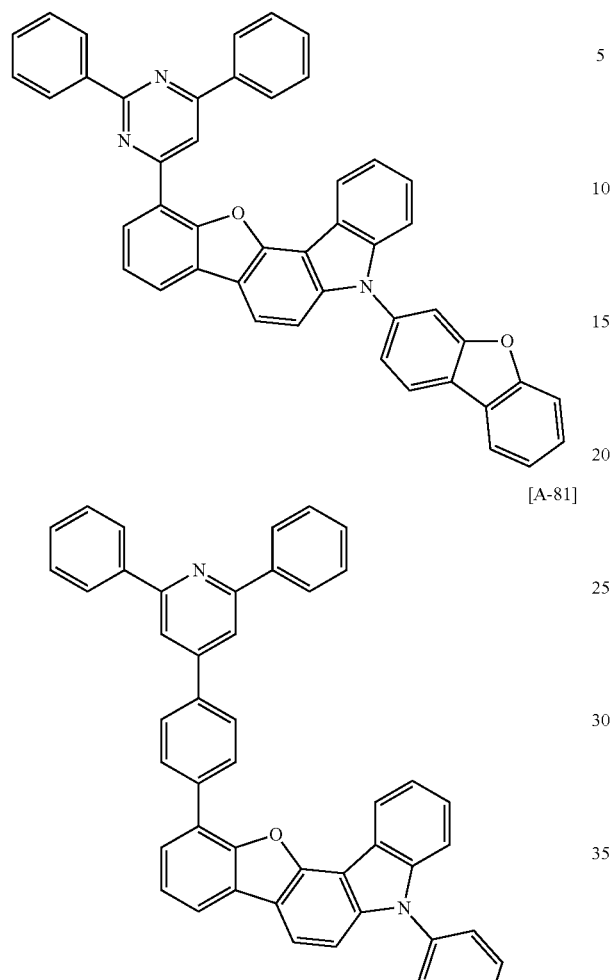
[A-83]
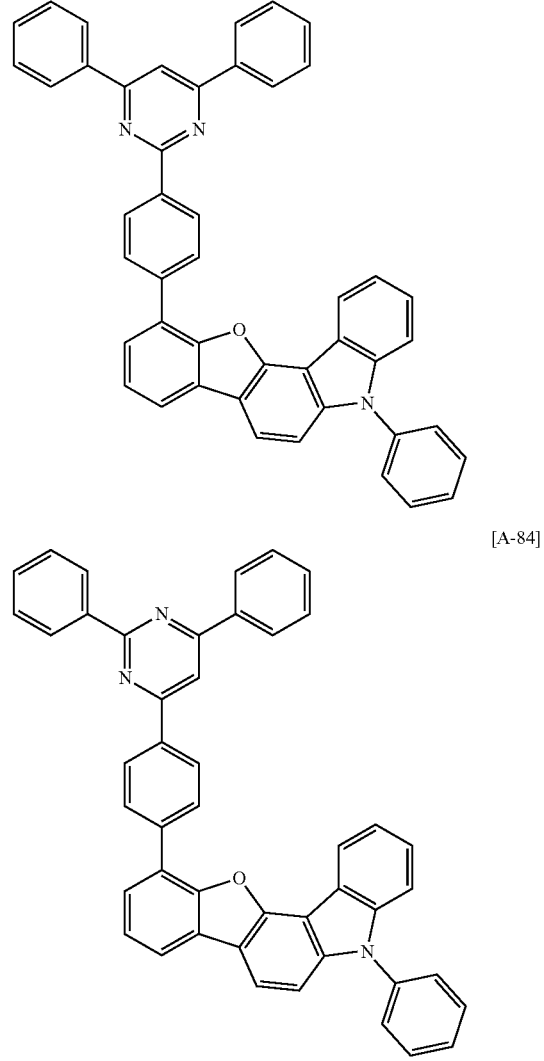
[A-81]
[A-84]
[A-82]
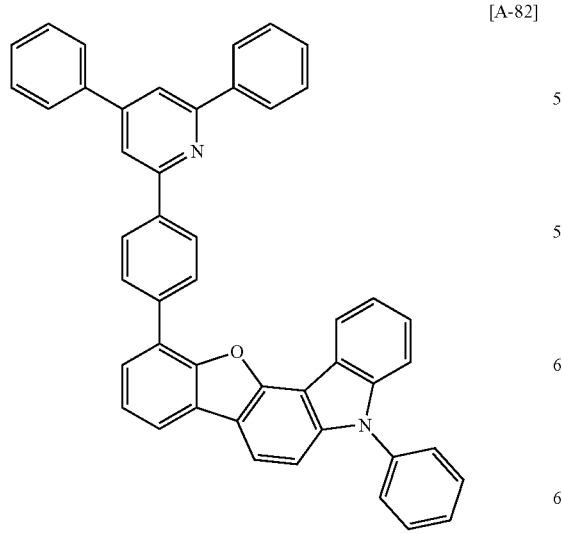
[A-85]
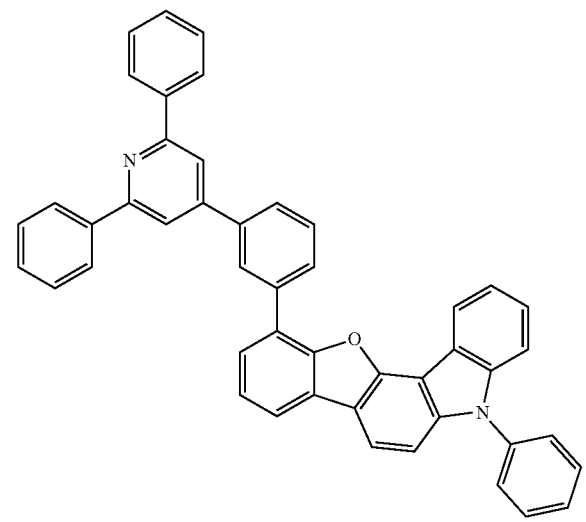

[A-86]
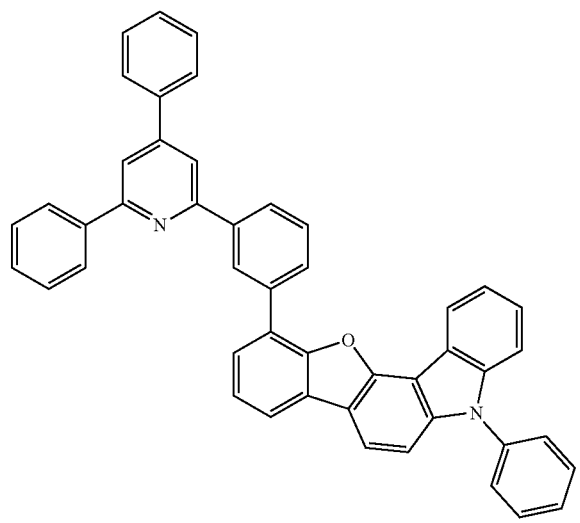
[A-87]
[A-88]
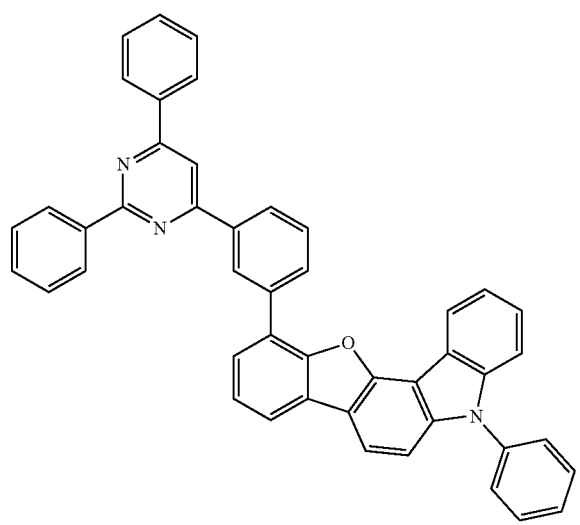
[A-89]
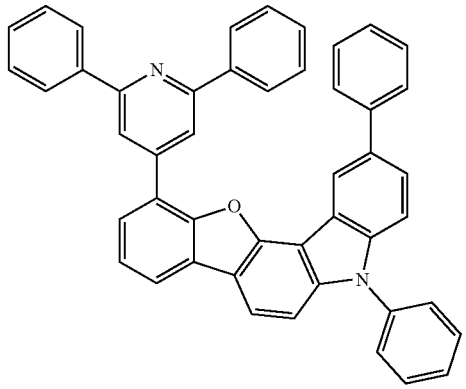
[A-90]
[A-91]
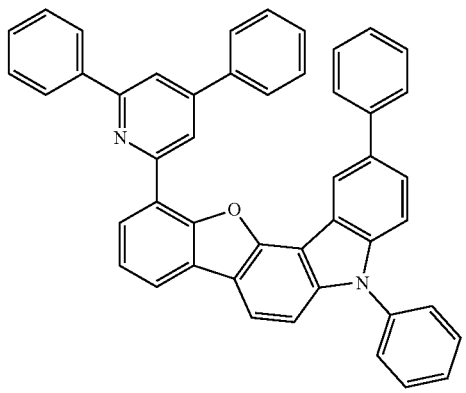
[A-92]
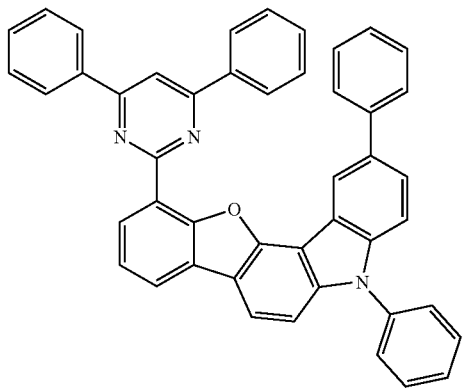

[A-93]
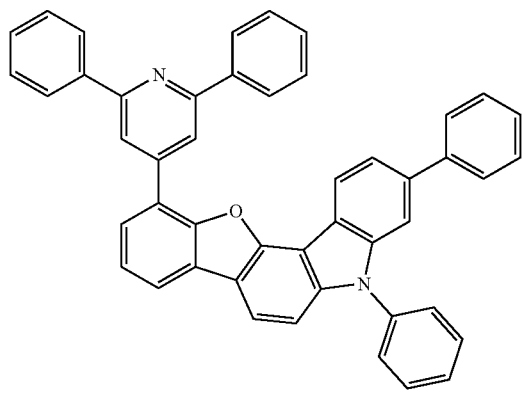
[A-94]
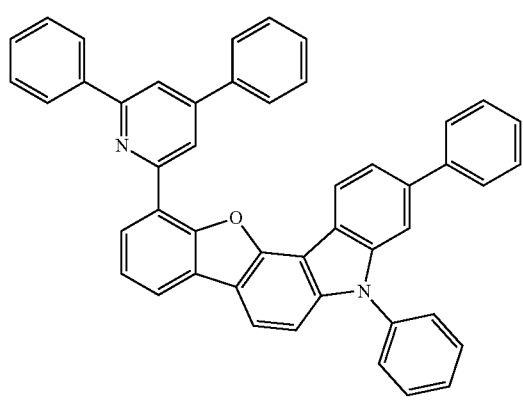
[A-95]
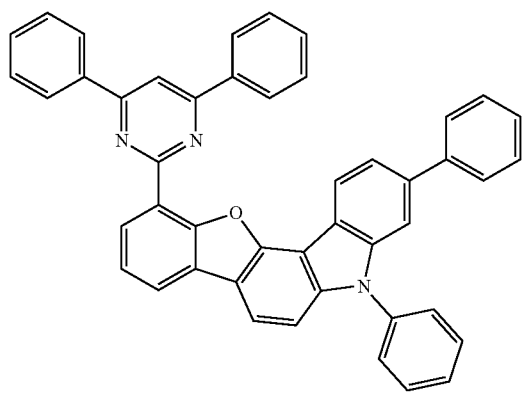
[A-96]
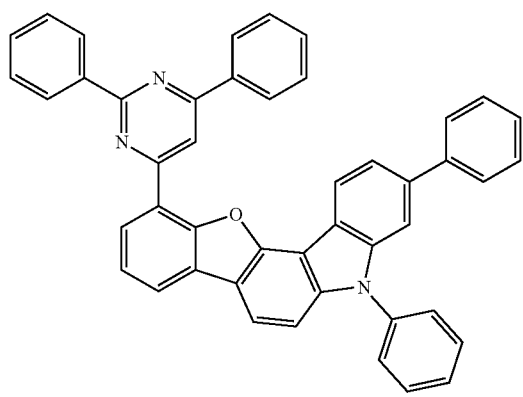
[A-97]
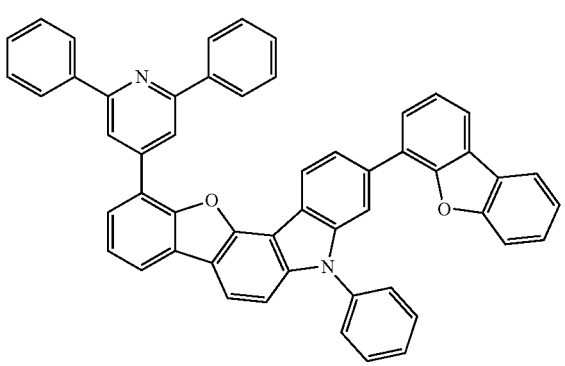
[A-98]
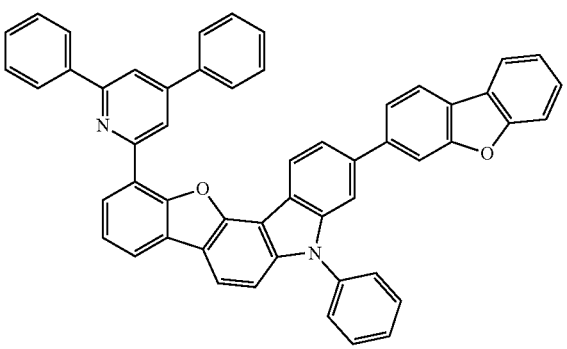
[A-99]
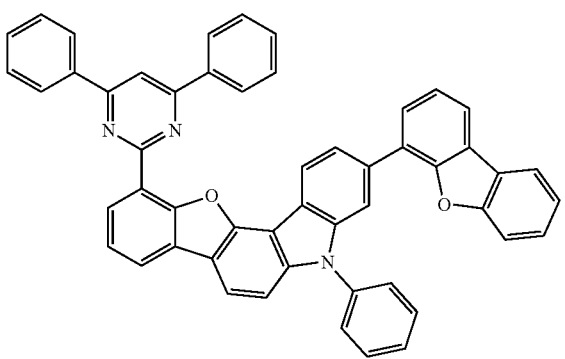
[A-100]
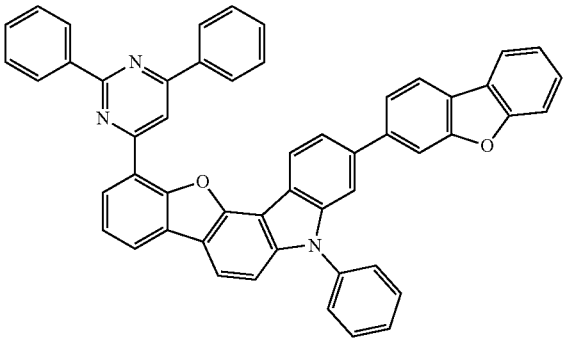

[A-101]
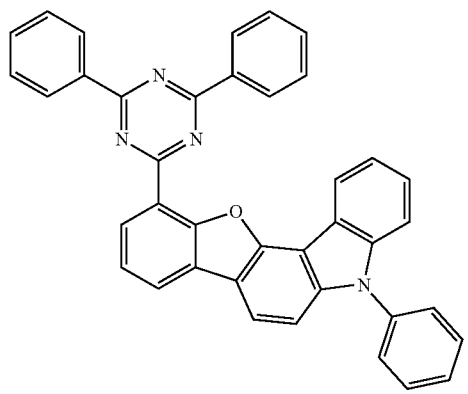
[A-104]
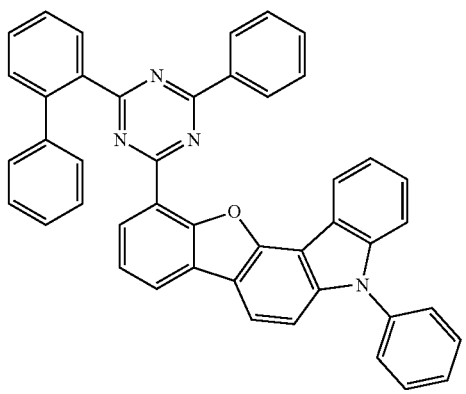
[A-102]
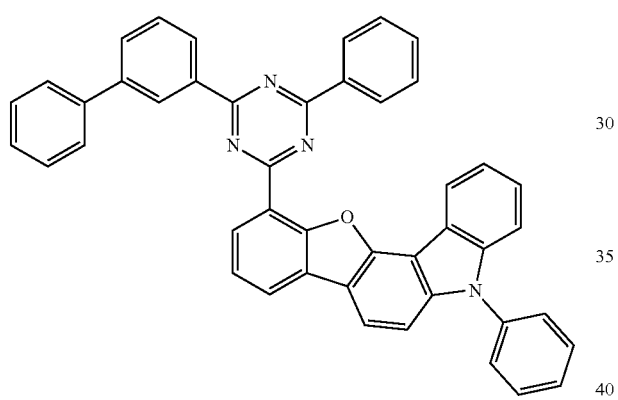
[A-105]
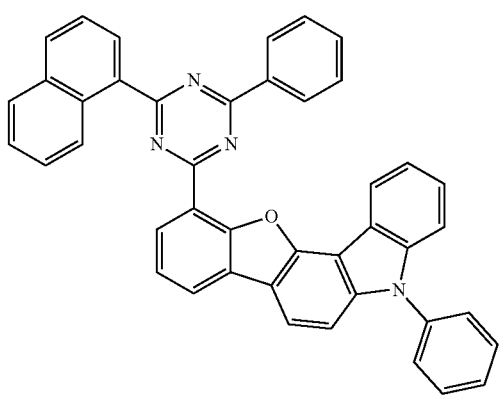
[A-103]
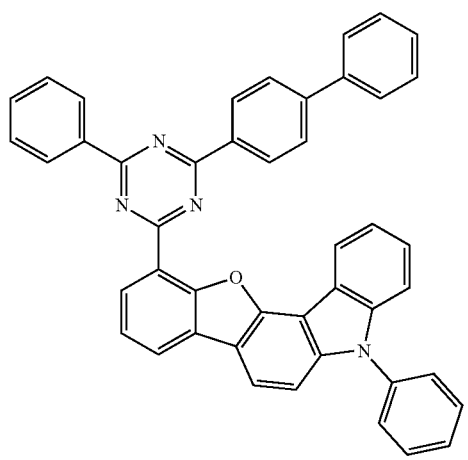
[A-106]
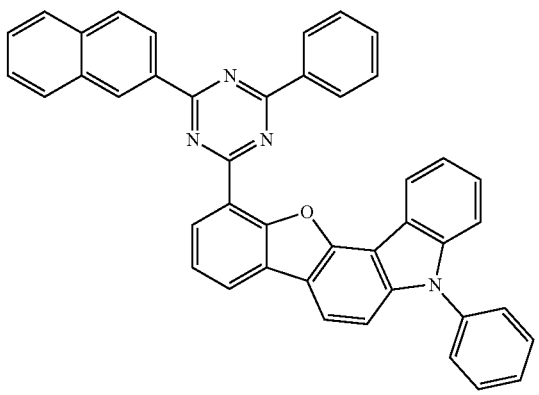

[A-107]
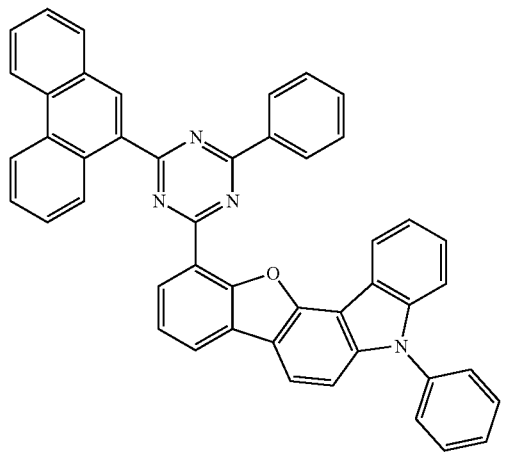
[A-110]
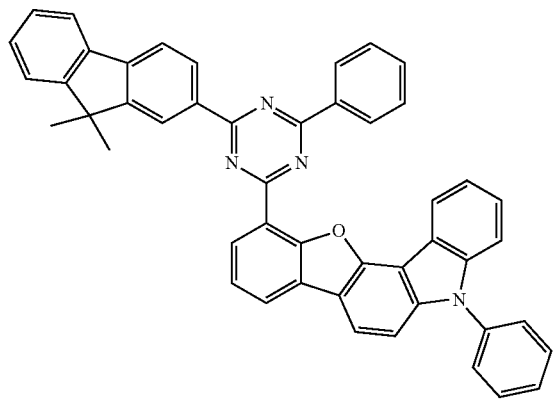
[A-108]
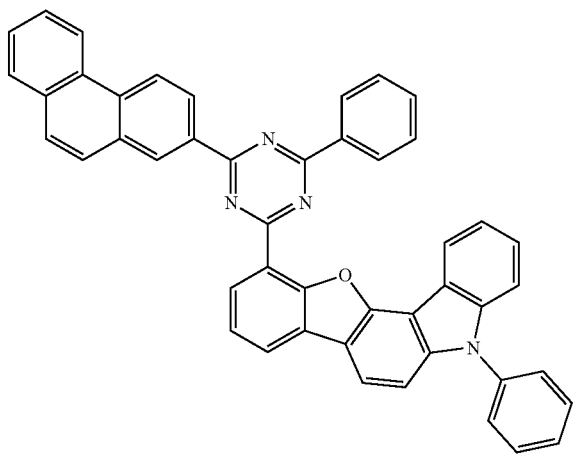
[A-111]
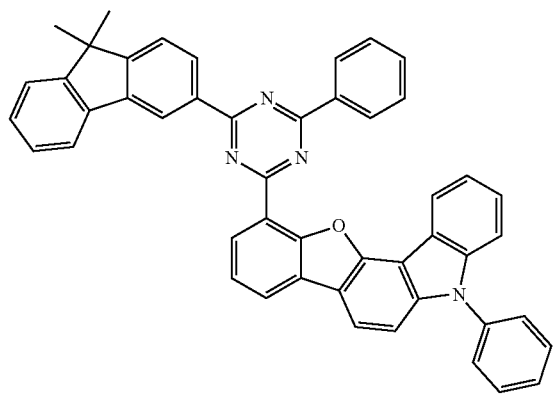
[A-109]
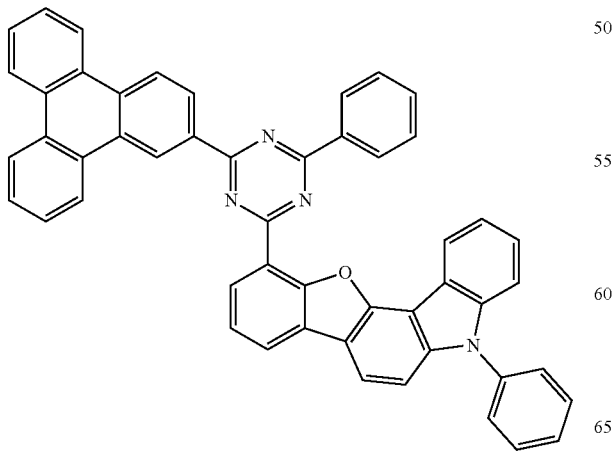
[A-112]
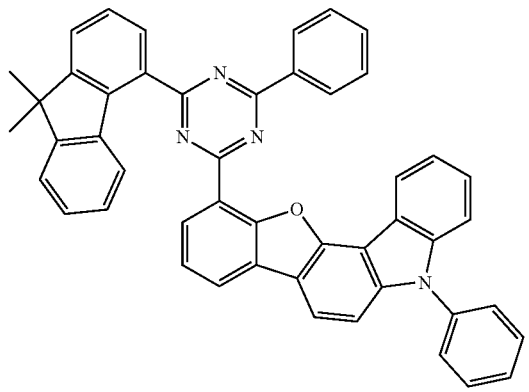

[A-113]
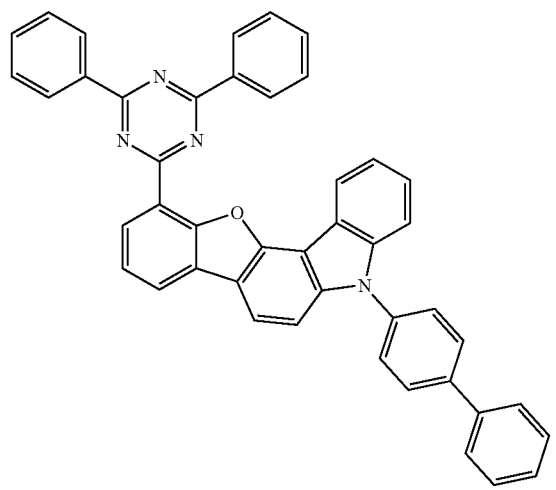
[A-114]
[A-115]
[A-116]
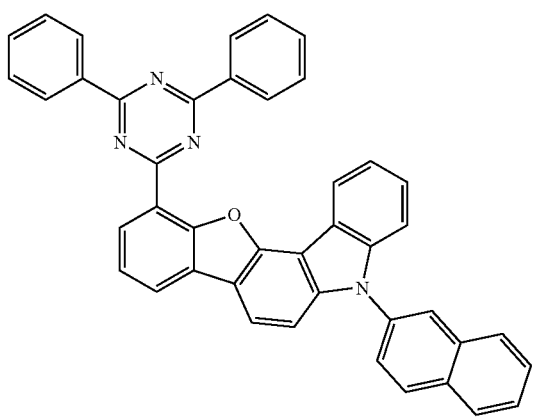
[A-117]
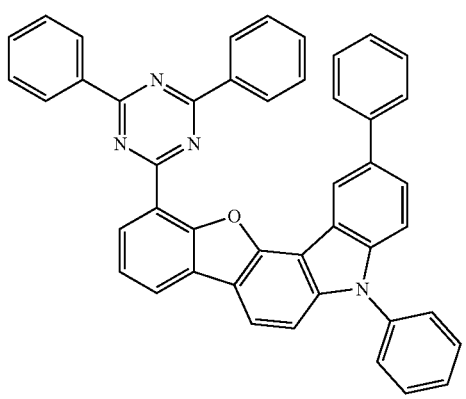
[A-118]
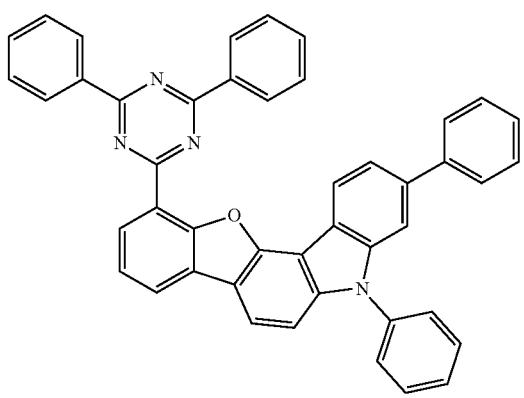

[A-119]
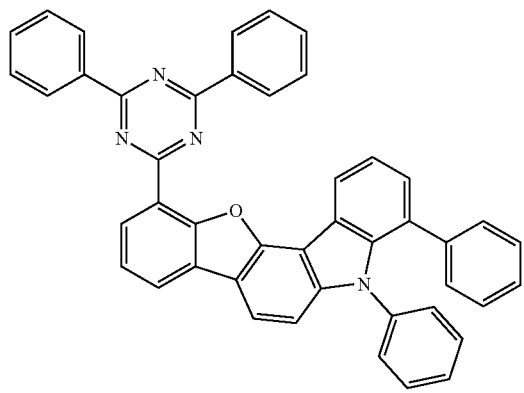
[A-120]
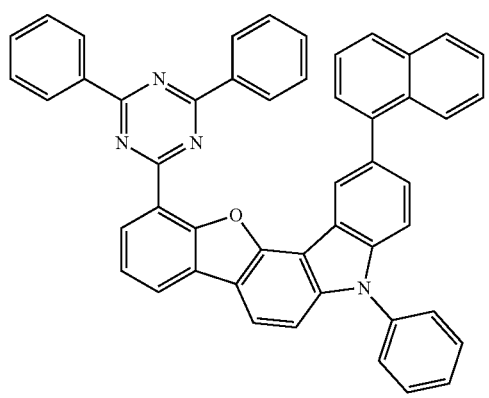
[A-121]
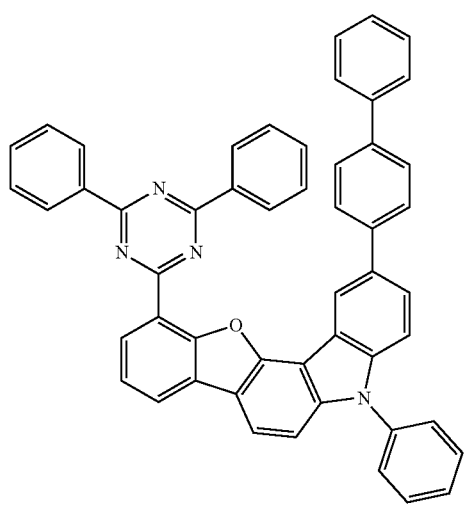
[A-122]
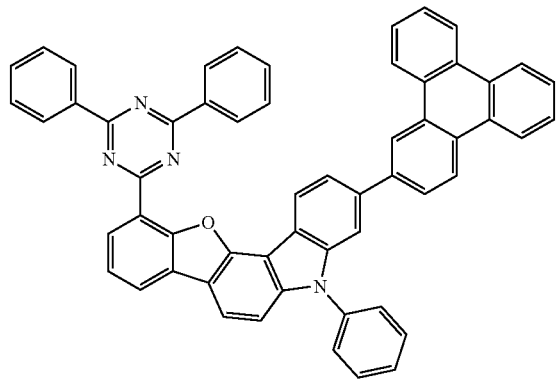
[A-123]
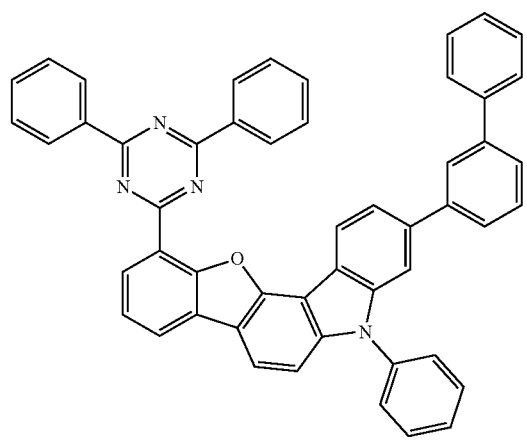
[A-124]
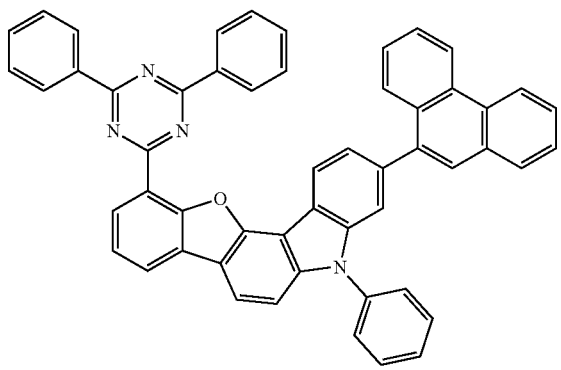
[A-125]
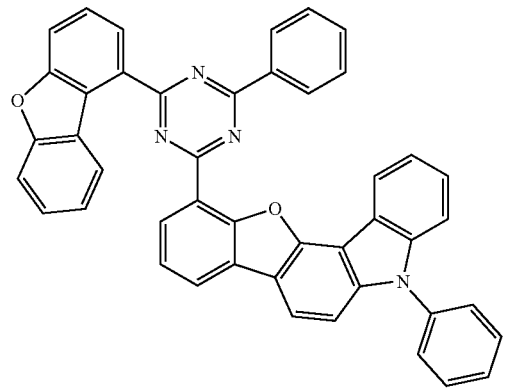

[A-126]
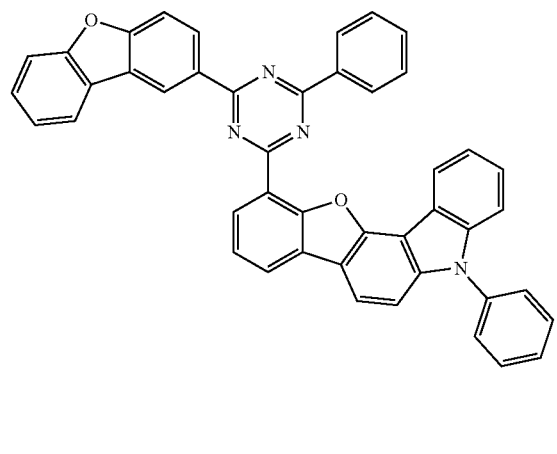
[A-129]
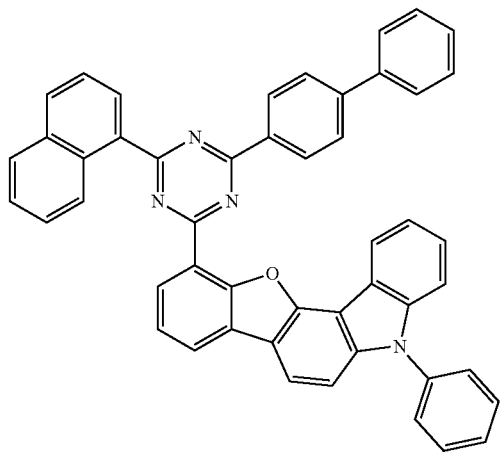
[A-127]
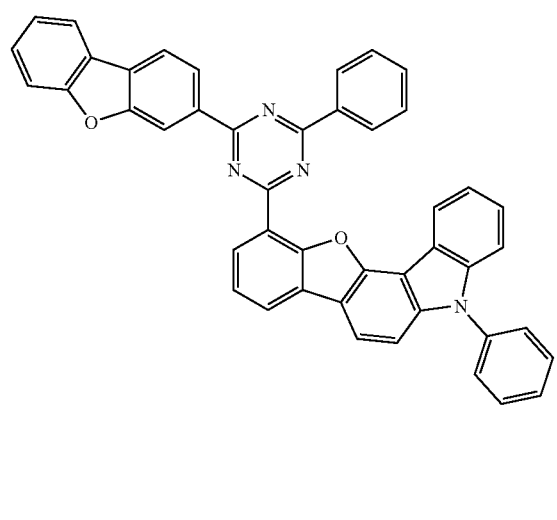
[A-130]
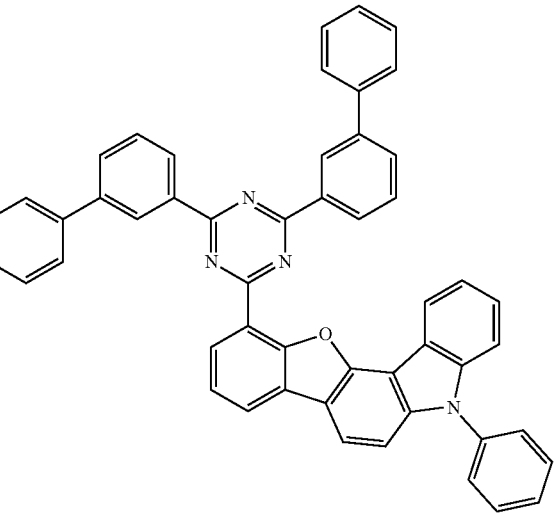
[A-128]
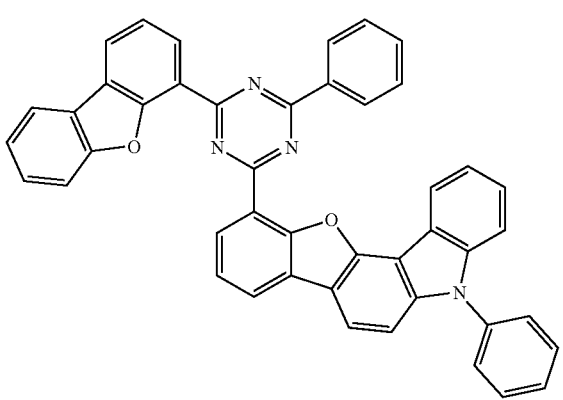
[A-131]
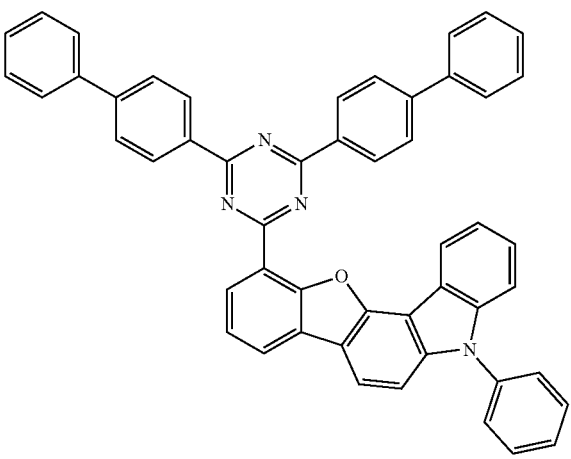

[A-132]
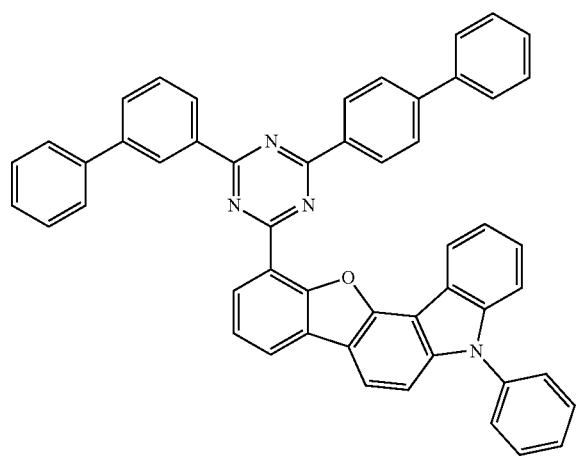
[A-135]
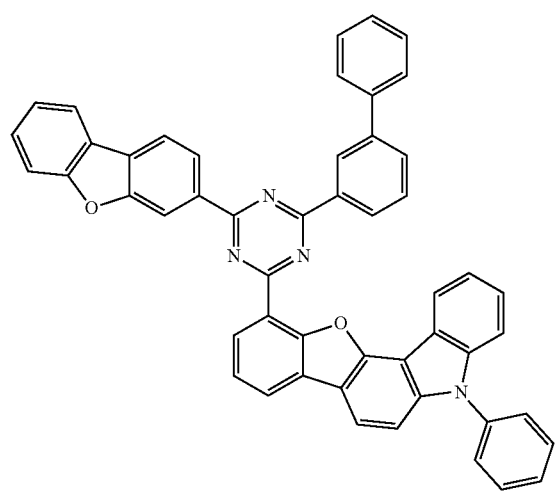
[A-133]
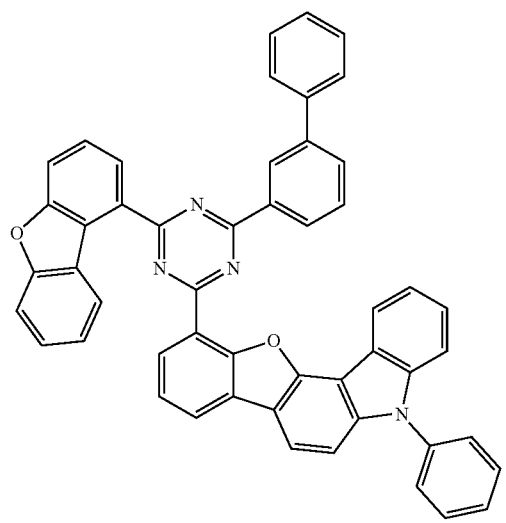
[A-136]
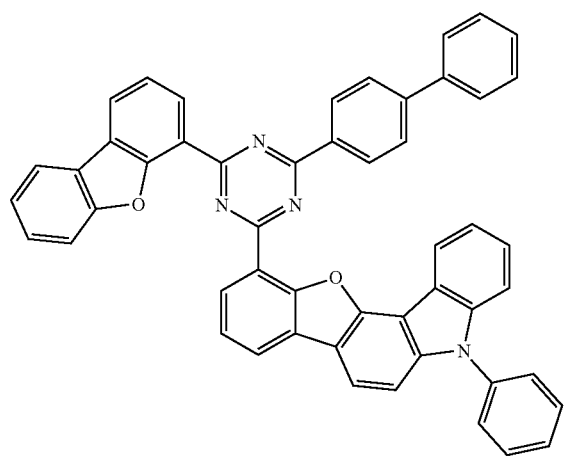
[A-134]
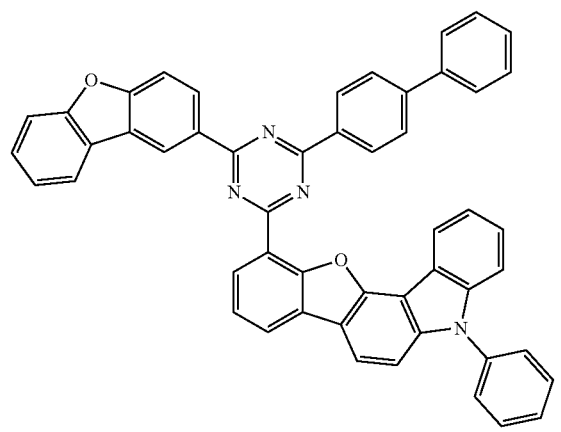
[A-137]
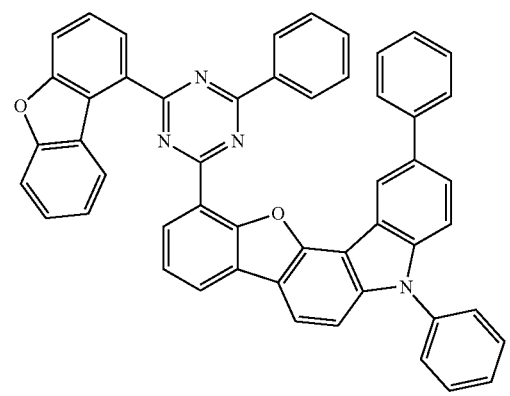

[A-138]
[A-139]
[A-140]
[A-141]
[A-142]
[A-143]
[A-144]
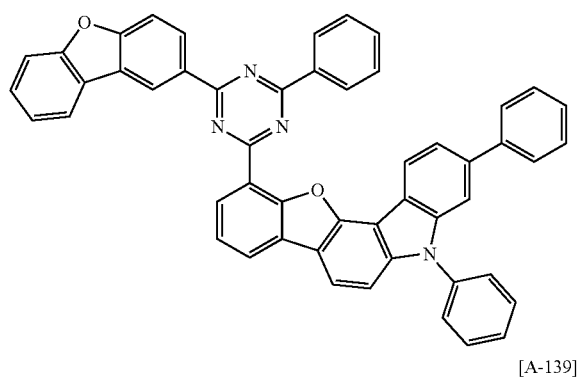
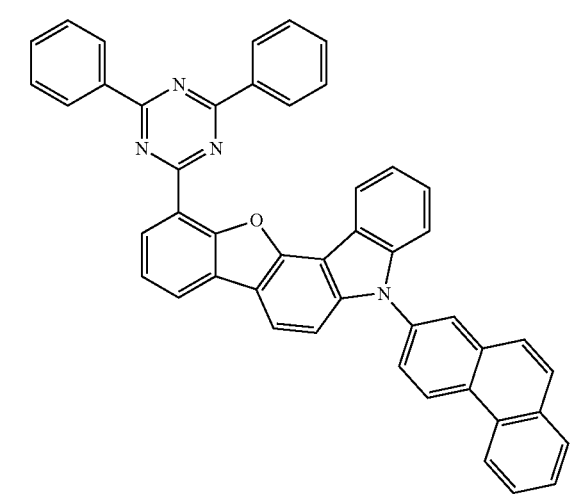
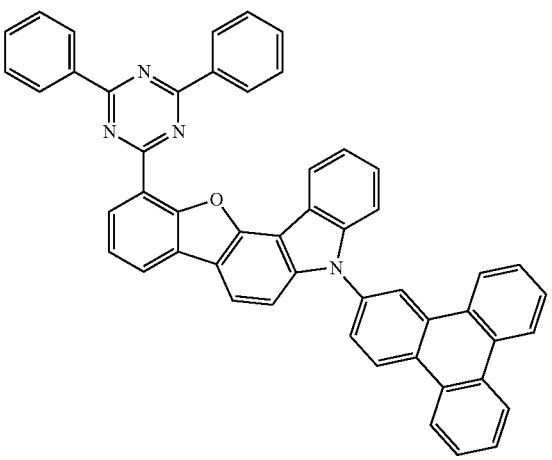
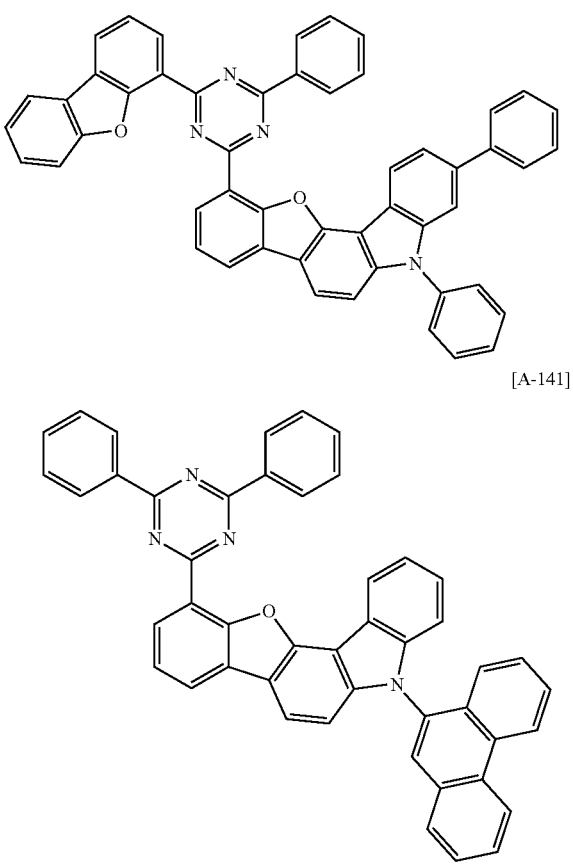
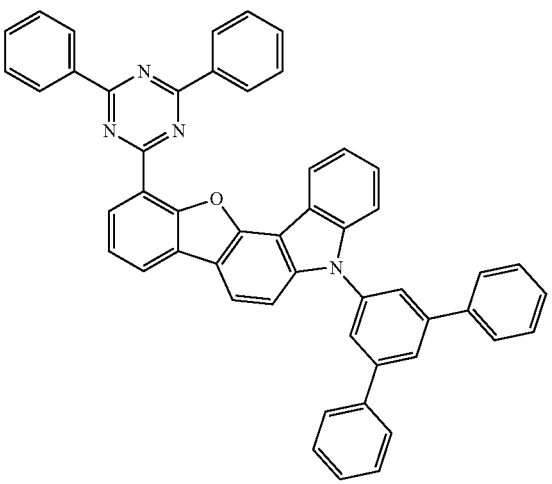

[A-145]
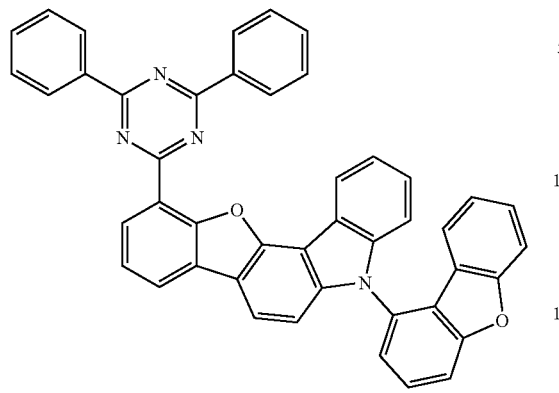
[A-148]
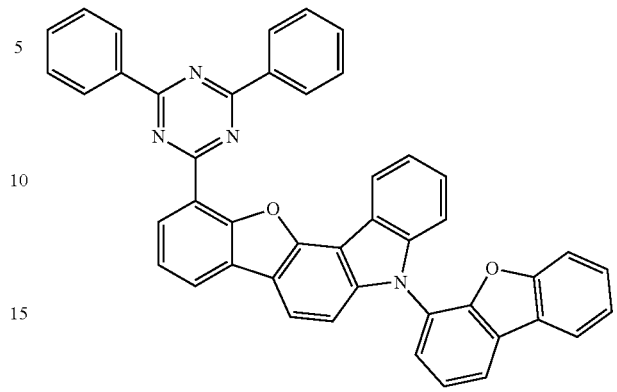
[A-146]
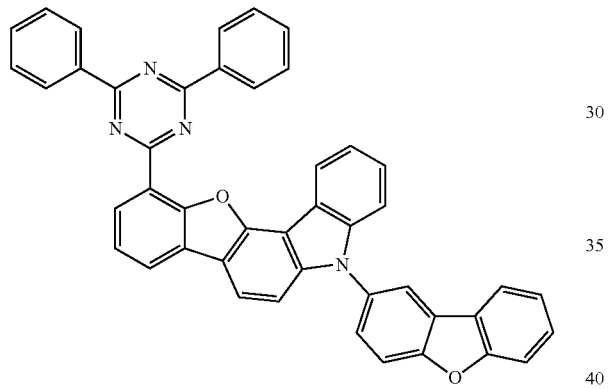
[A-149]
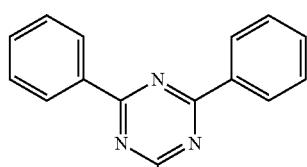
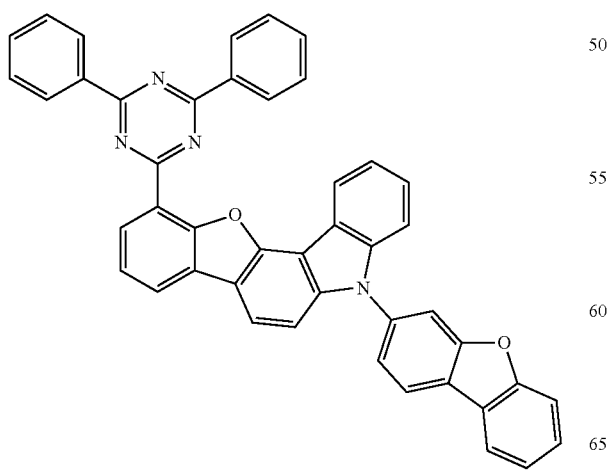
[A-147]
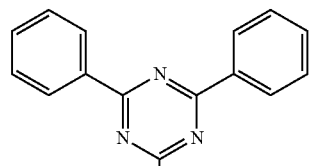
[A-150]
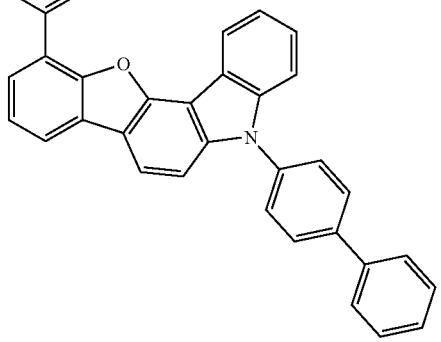

[A-151]
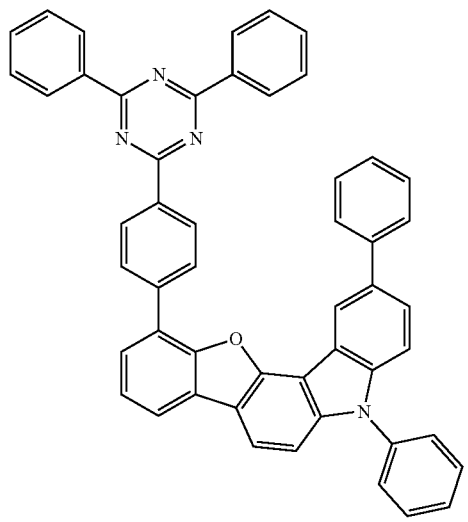
[A-152]
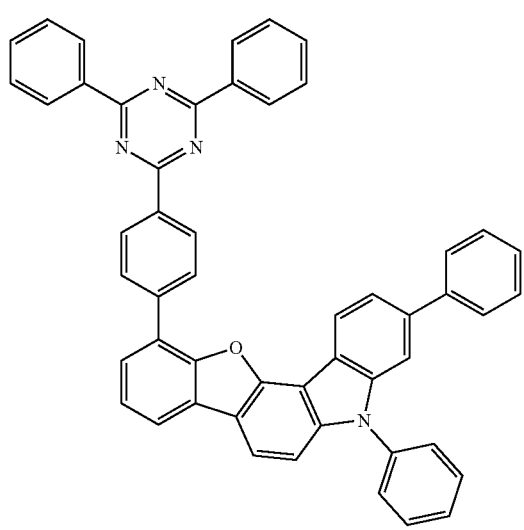
[A-153]
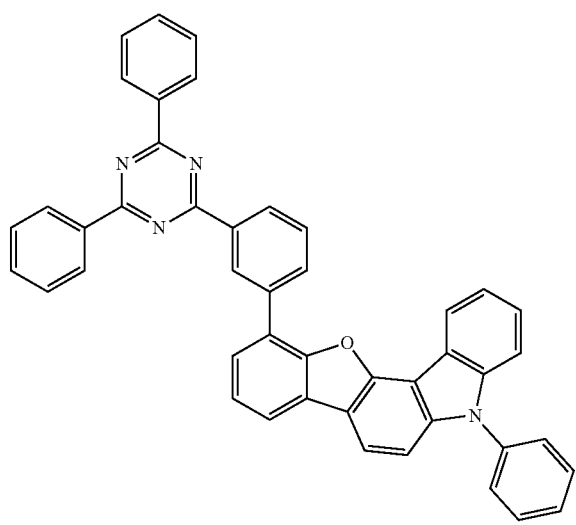
[A-154]
[A-155]
[A-156]
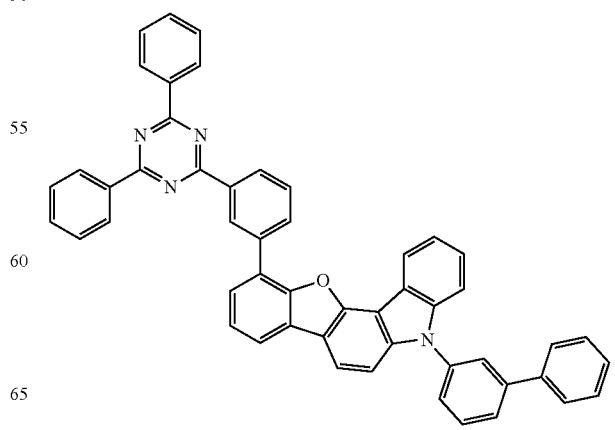

-continued
[A-157]
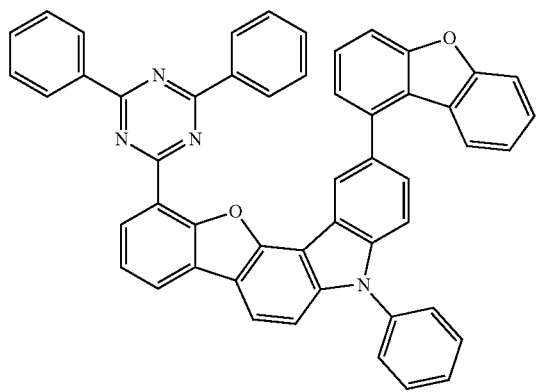
[A-158]
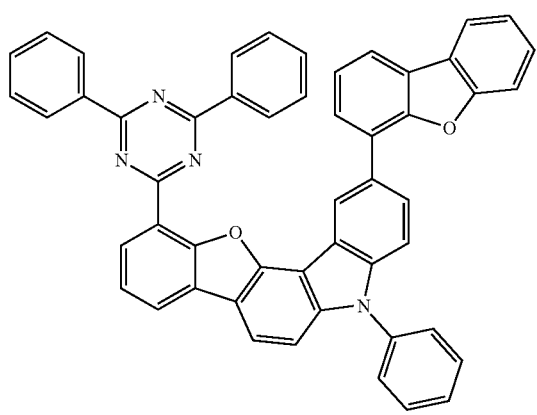
[A-159]
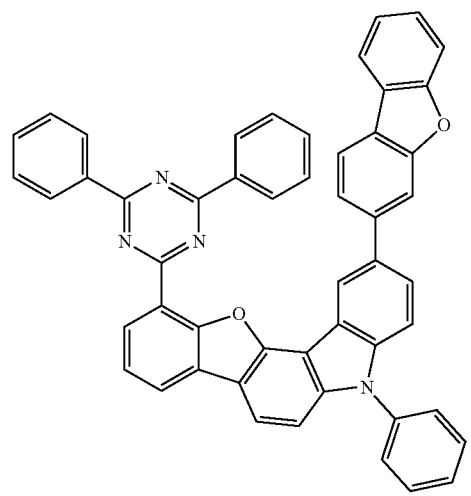
-continued
[A-160]
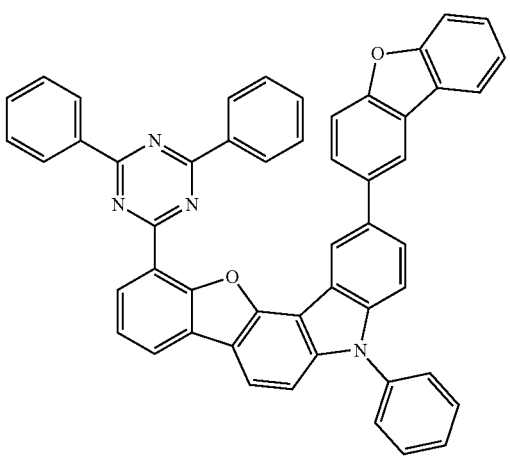
[A-161]
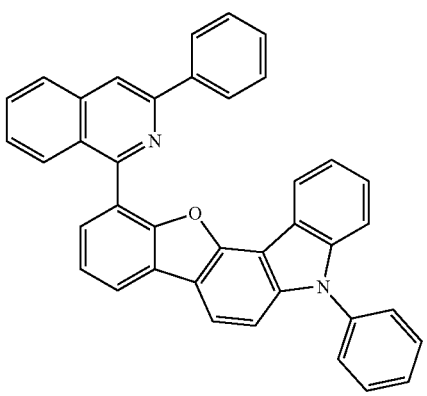
[A-162]
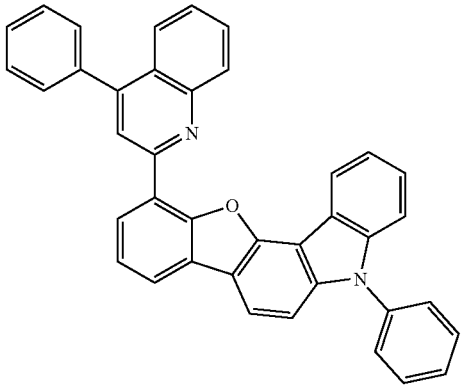

[A-163]
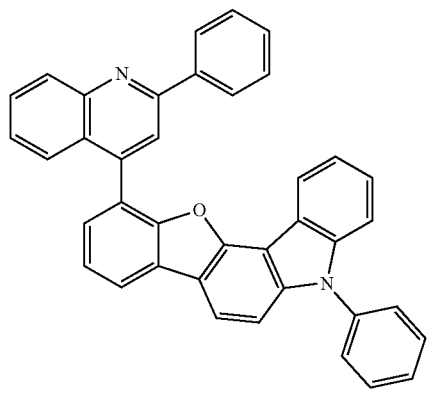
[A-164]
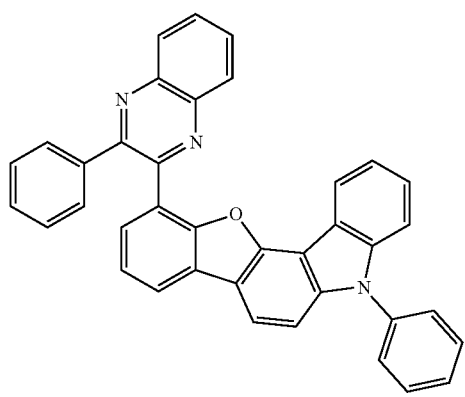
[A-165]
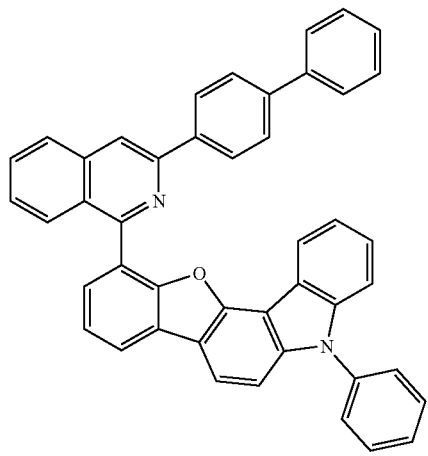
[A-166]
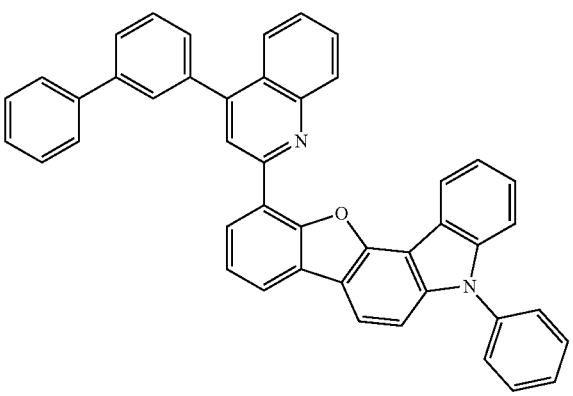
[A-167]
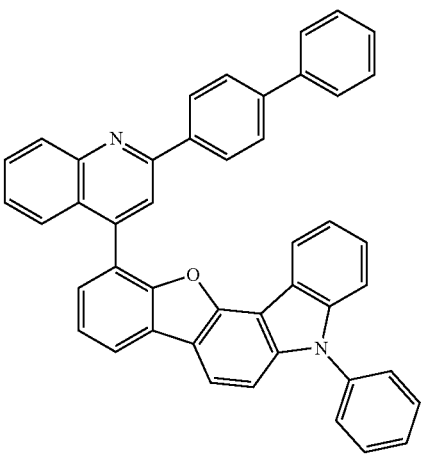
[A-168]
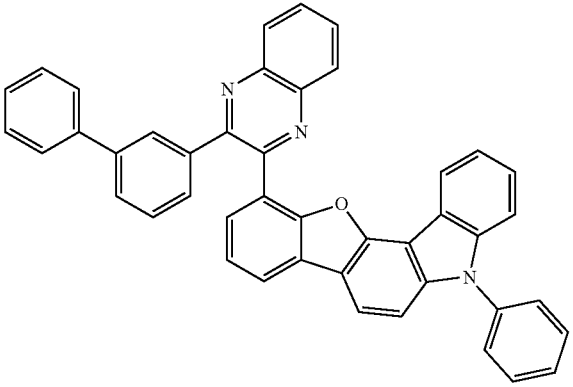

[A-169]
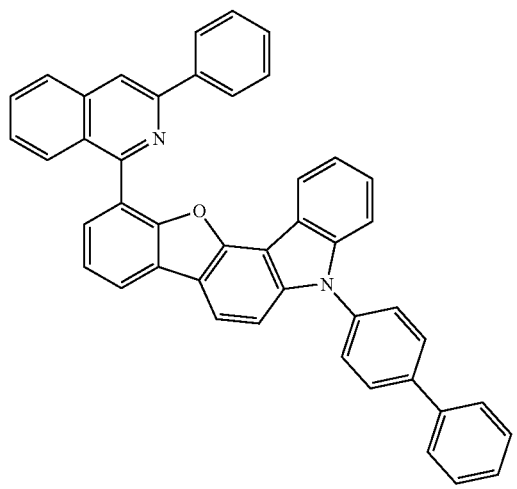
[A-170]
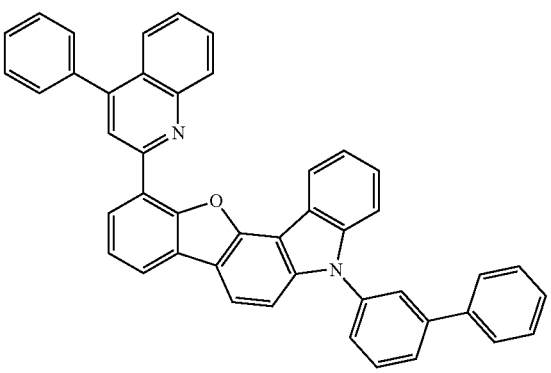
[A-171]
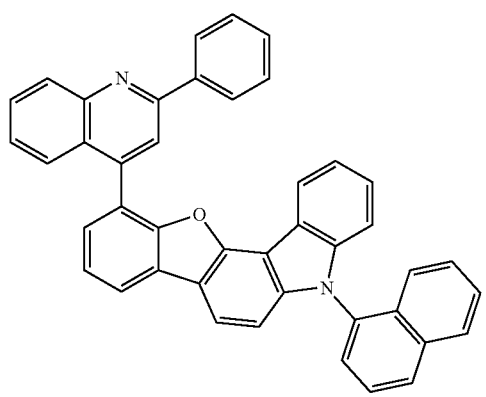
[A-172]
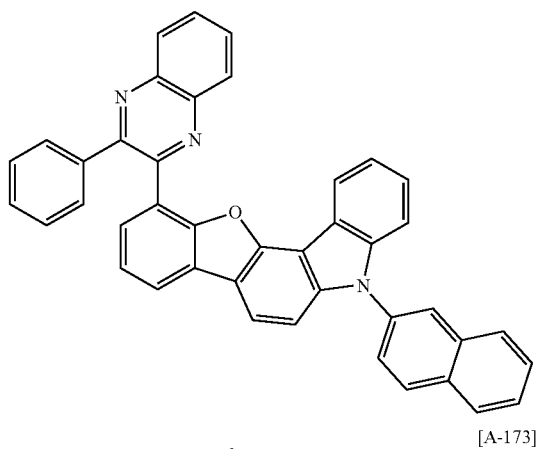
[A-173]
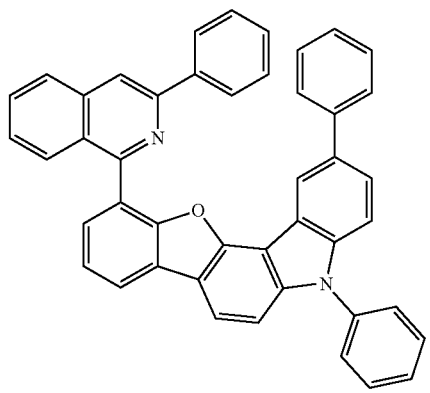
[A-174]
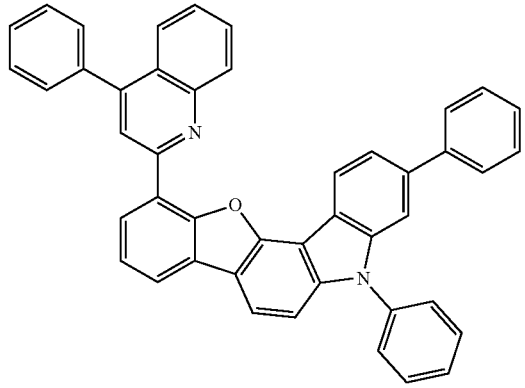
[A-175]
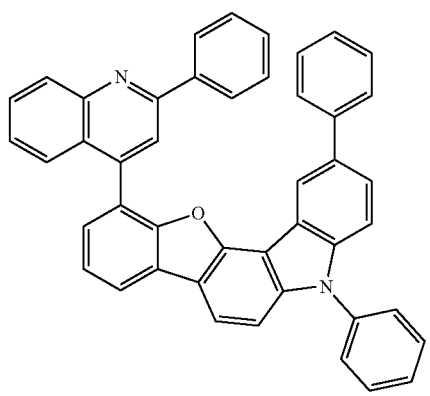

[A-176]
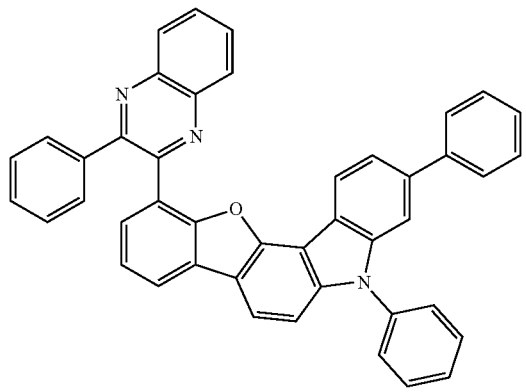
[A-177]
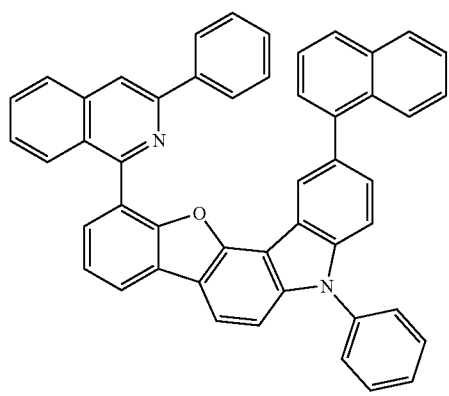
[A-178]
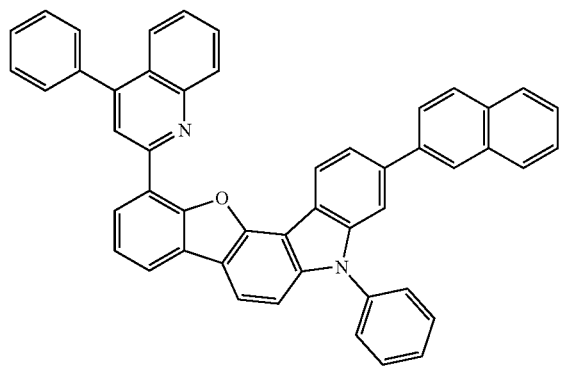
[A-179]
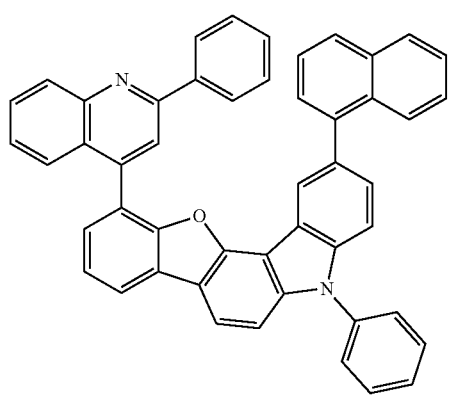
[A-180]
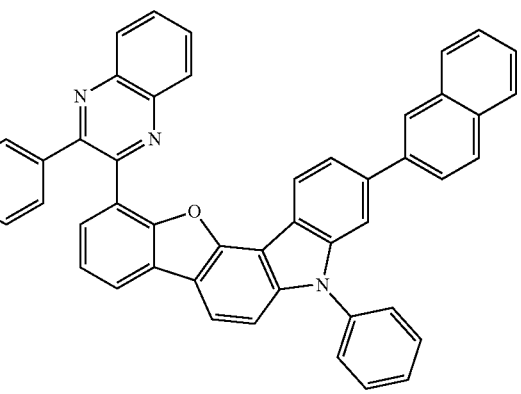
[A-181]
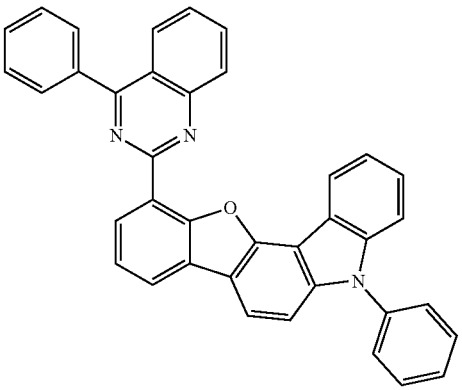
[A-182]
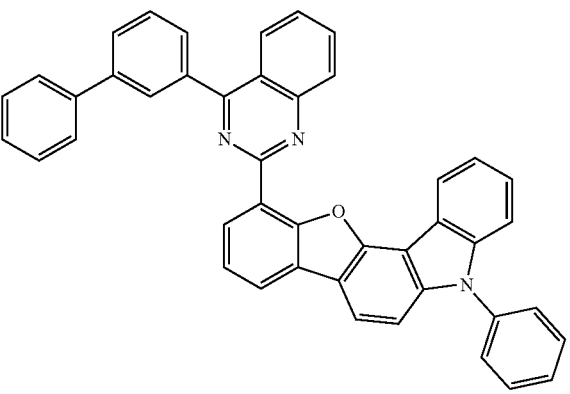

[A-183]
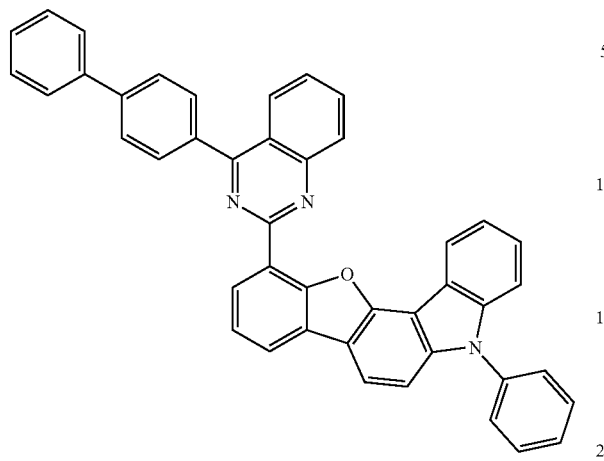
[A-184]
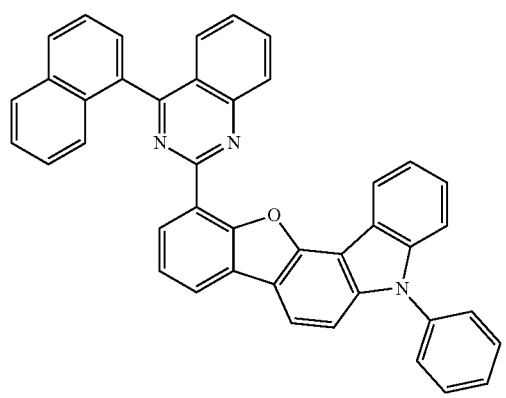
[A-185]
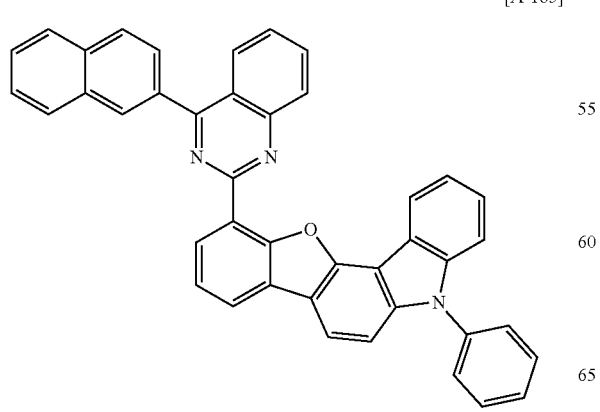
[A-186]
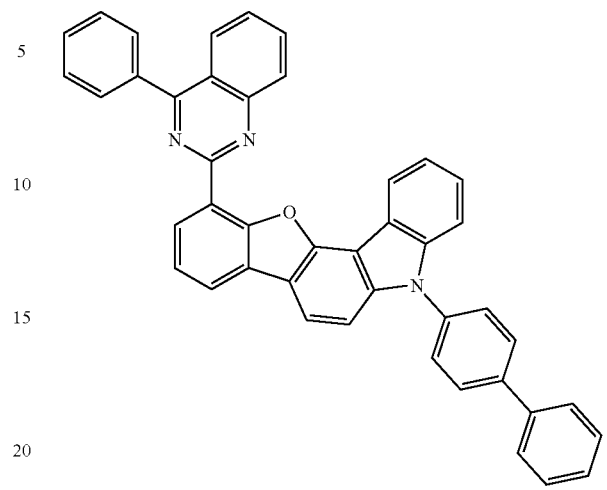
[A-187]
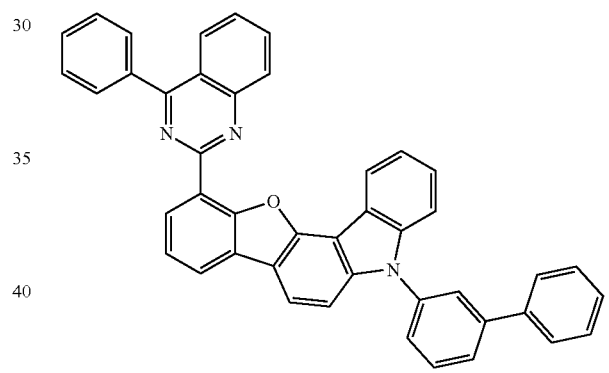
[A-188]
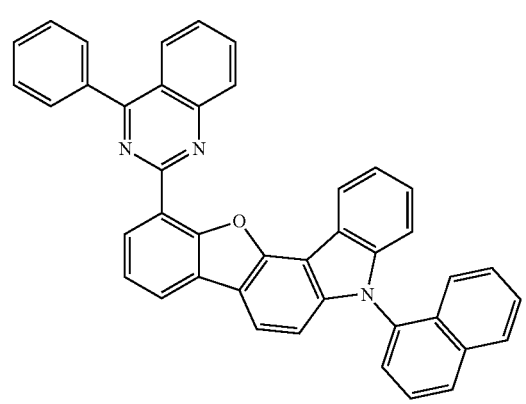

[A-189]
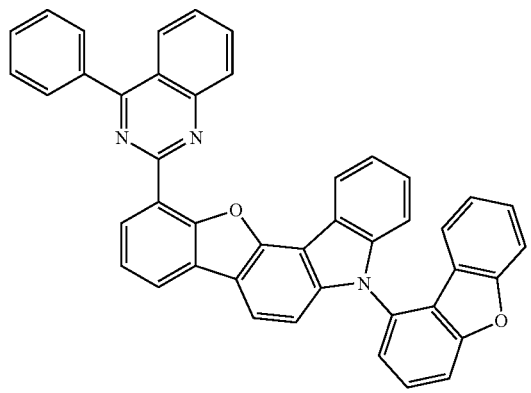
[A-190]
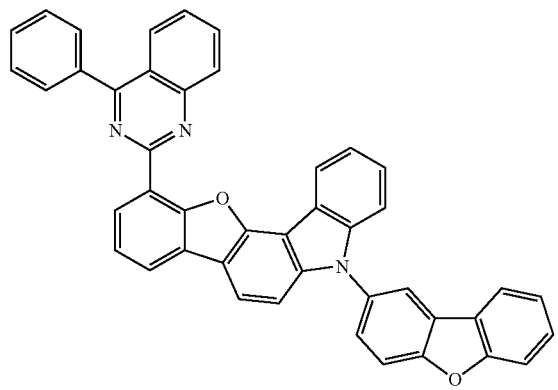
[A-191]
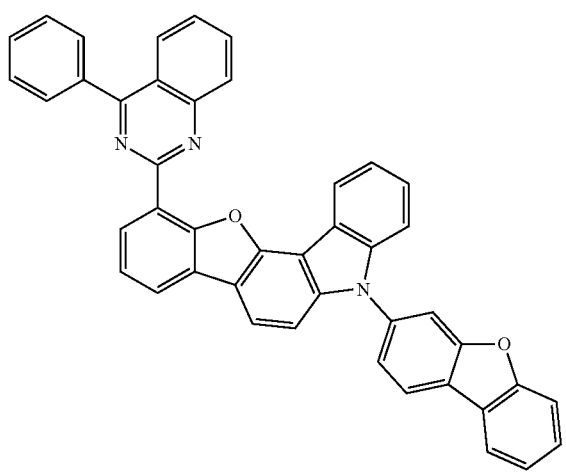
[A-192]
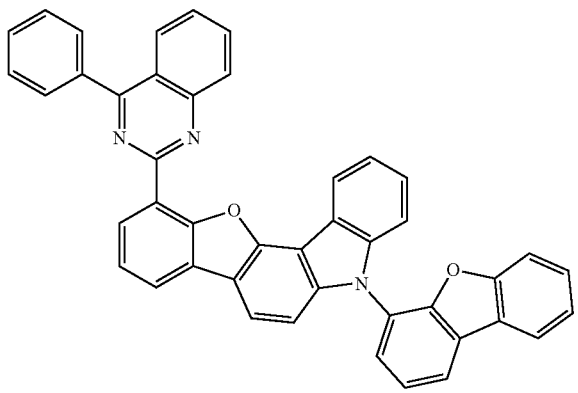
[A-193]
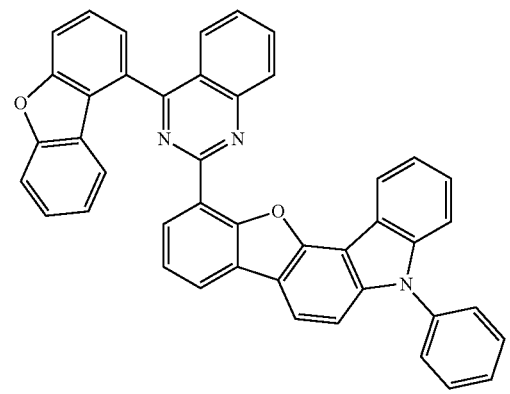
[A-194]
[A-195]
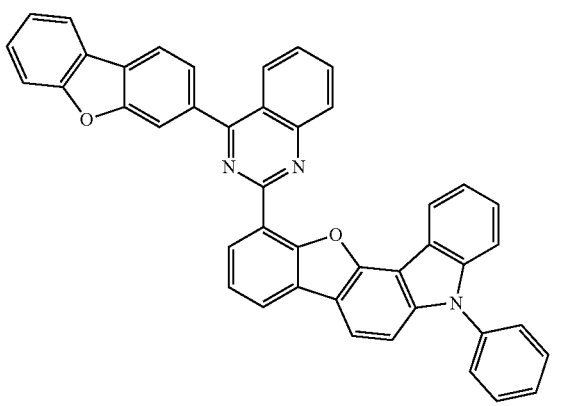

[A-196]
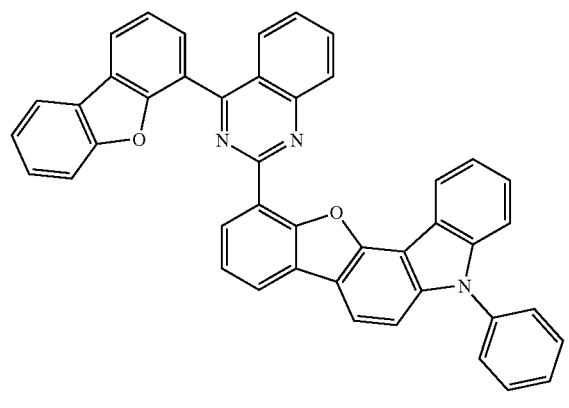
[A-197]
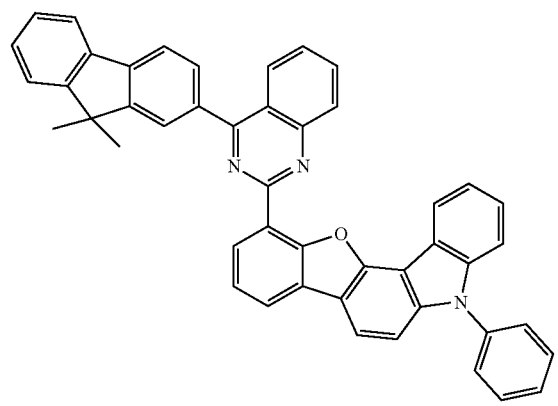
[A-198]
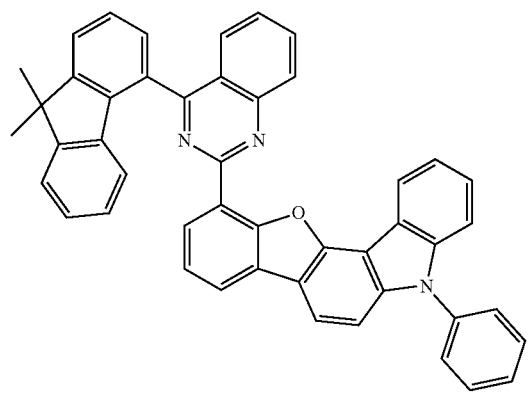
[A-199]
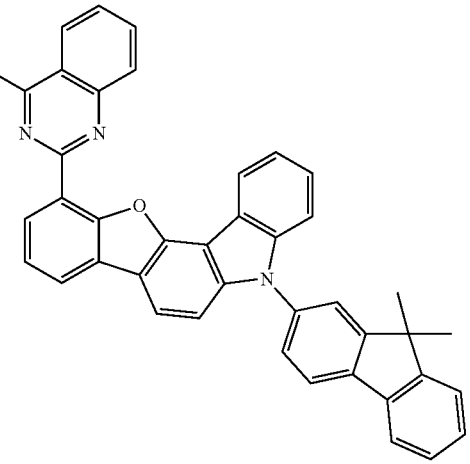
[A-200]
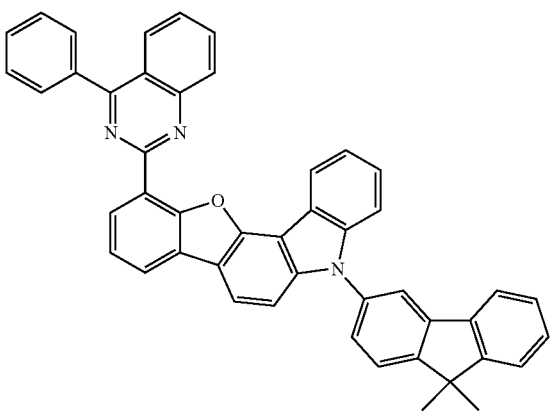
[A-201]
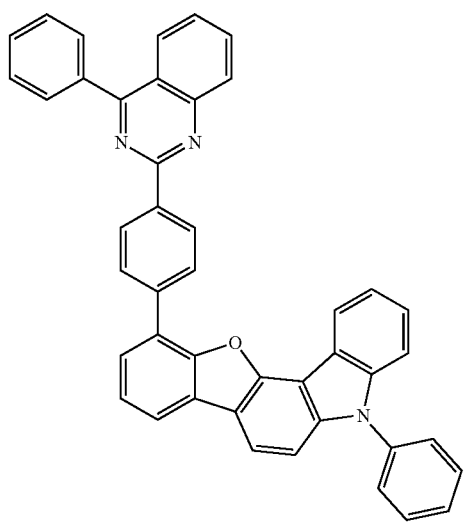

[A-202]
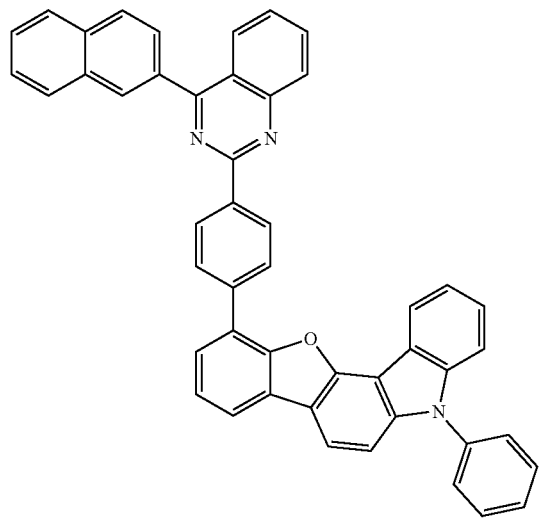
[A-203]
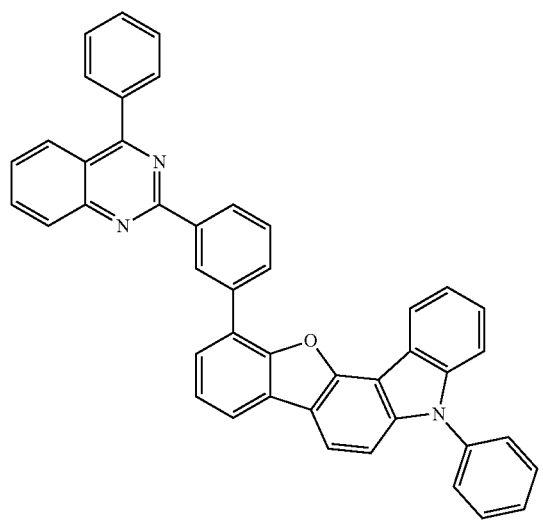
[A-204]
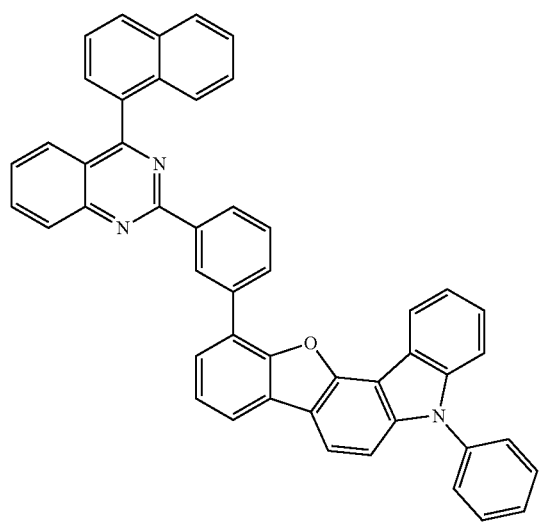
[A-205]
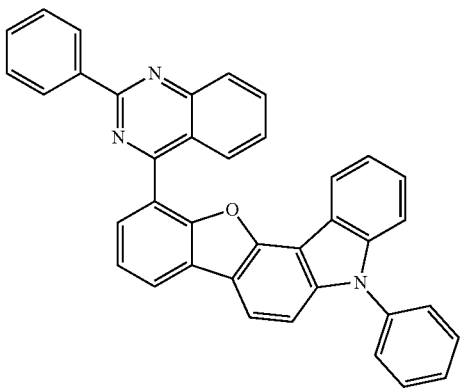
[A-206]
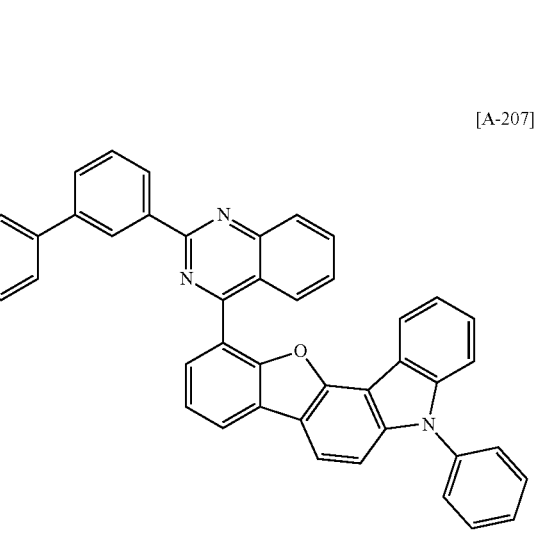
[A-207]

[A-208]
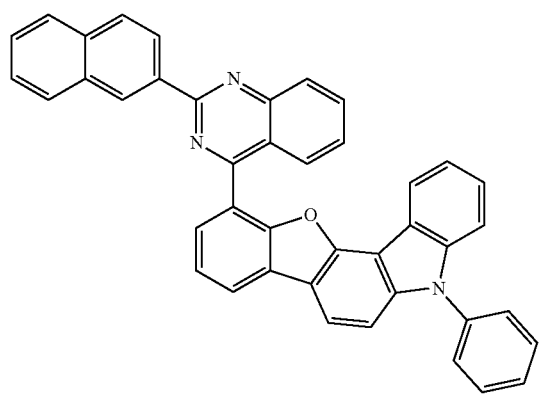
[B-3]
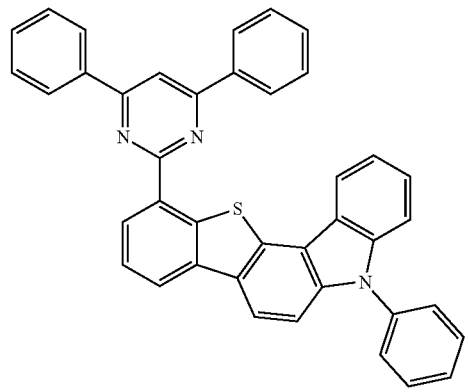
[B-1]
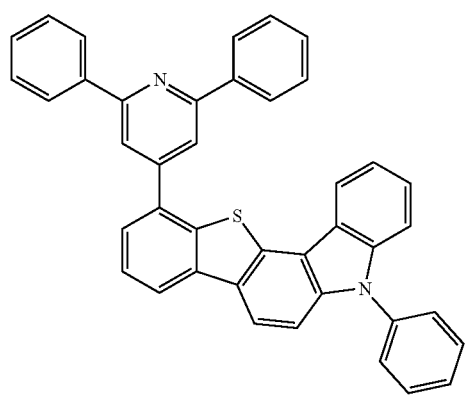
[B-4]
[B-2]
[B-5]
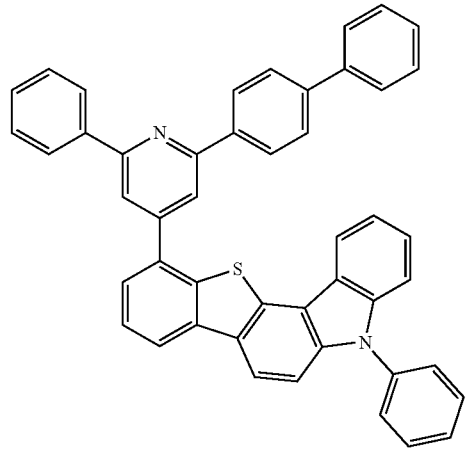

97
-continued
[B-6]
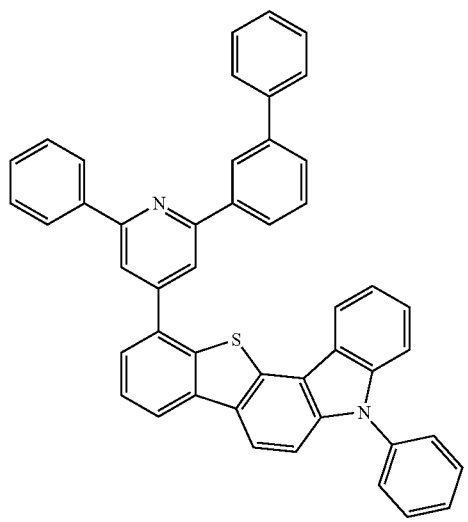
[B-7]
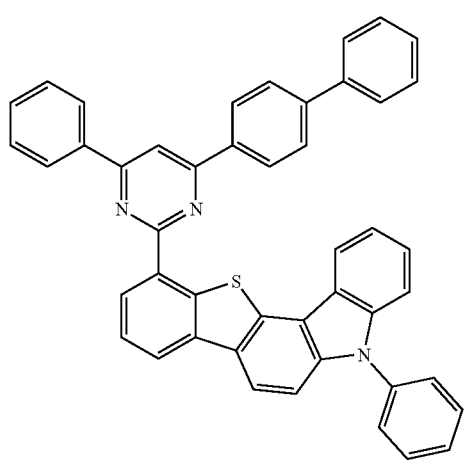
[B-8]
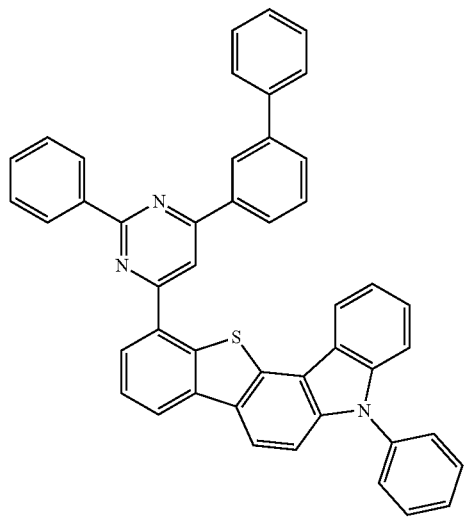
98
-continued
[B-9]
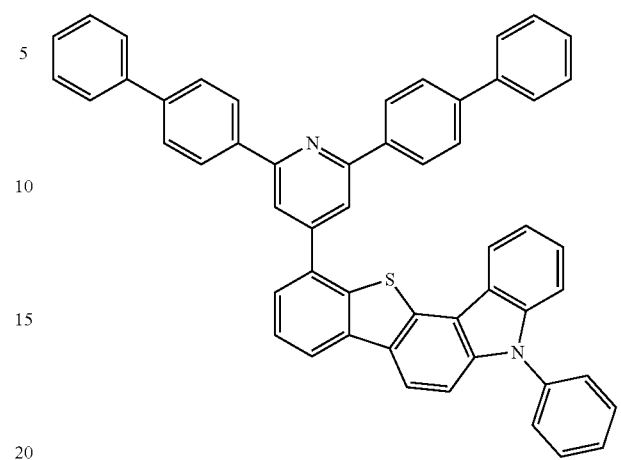
[B-10]
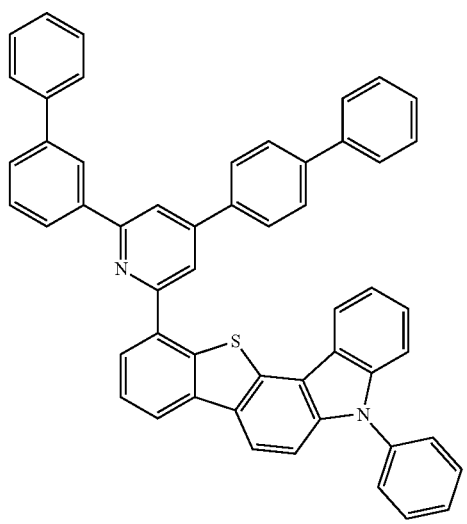
[B-11]
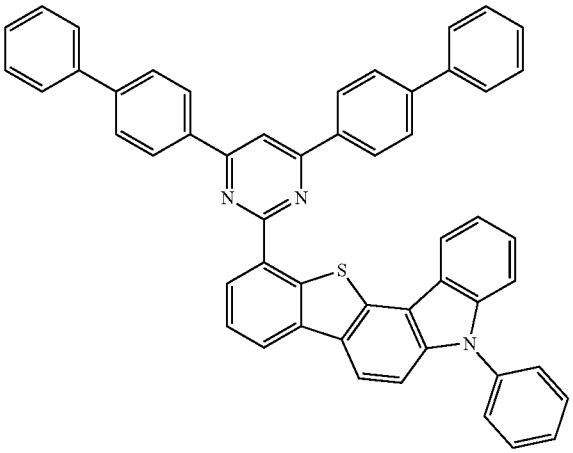

[B-12]
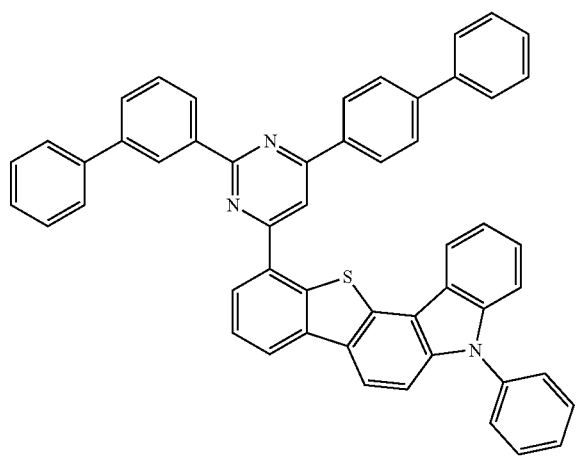
[B-13]
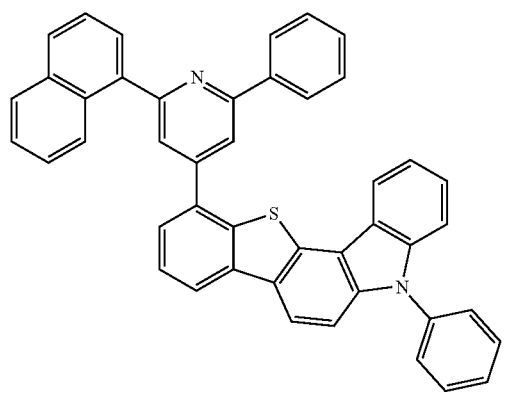
[B-14]
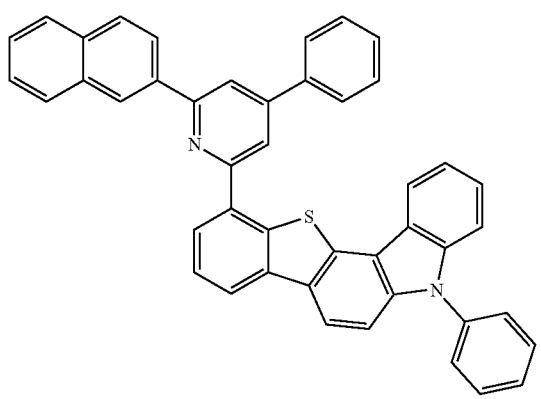
[B-15]
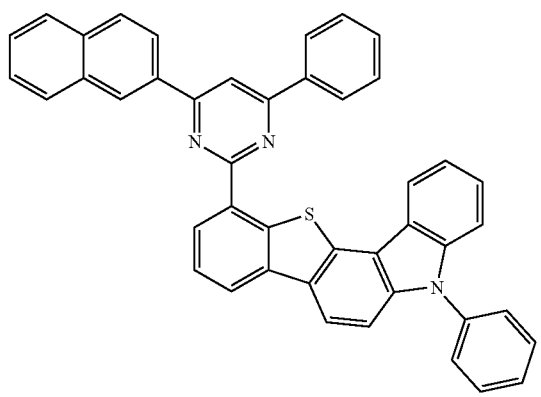
[B-16]
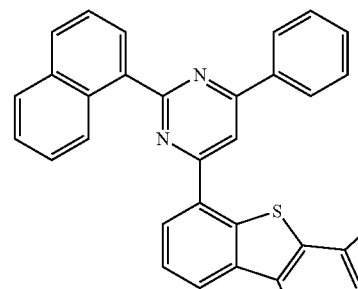
[B-17]
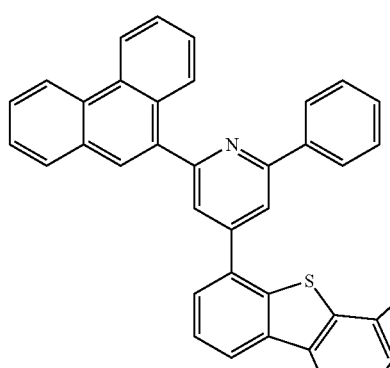

[B-18]
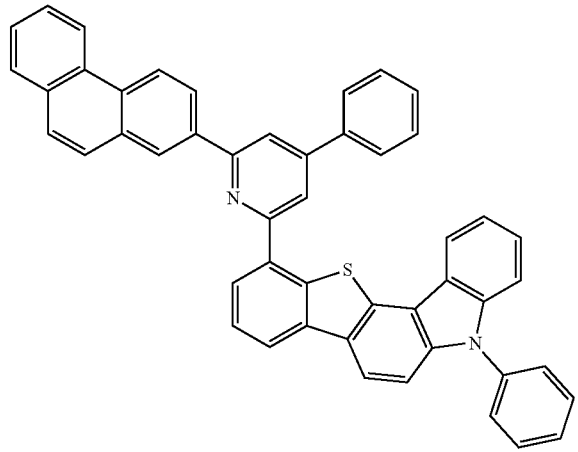
[B-21]
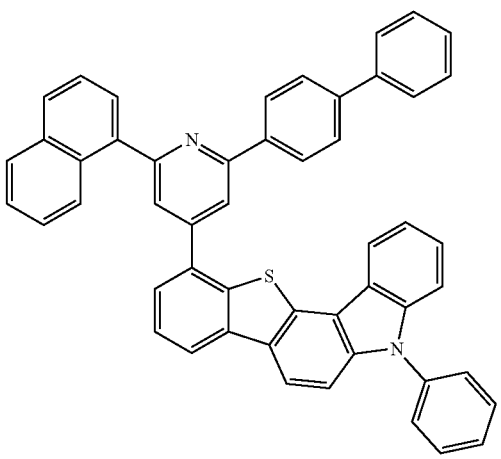
[B-19]
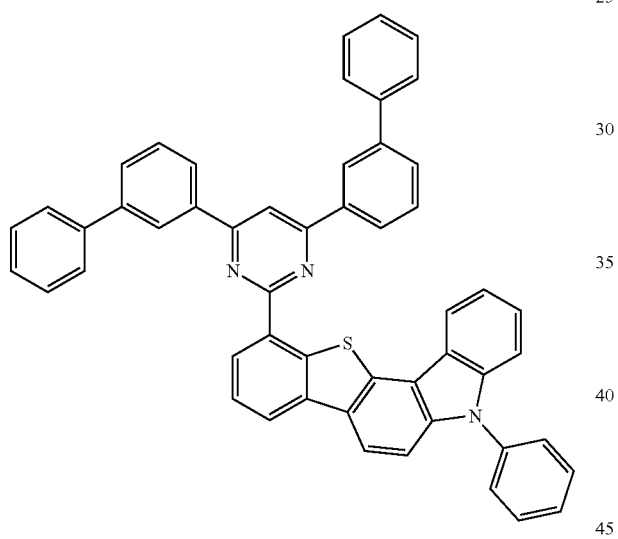
[B-22]
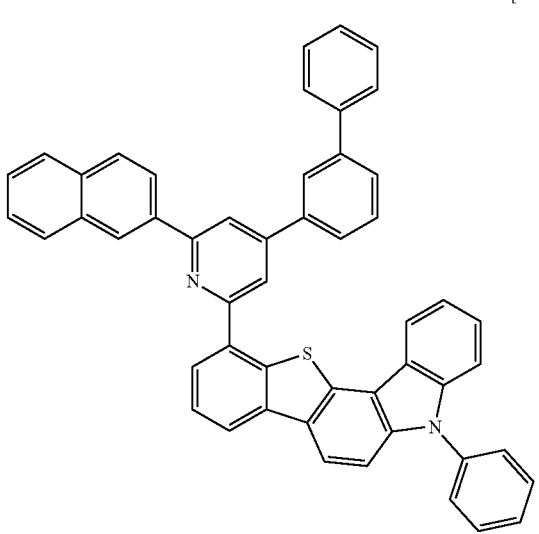
[B-20]
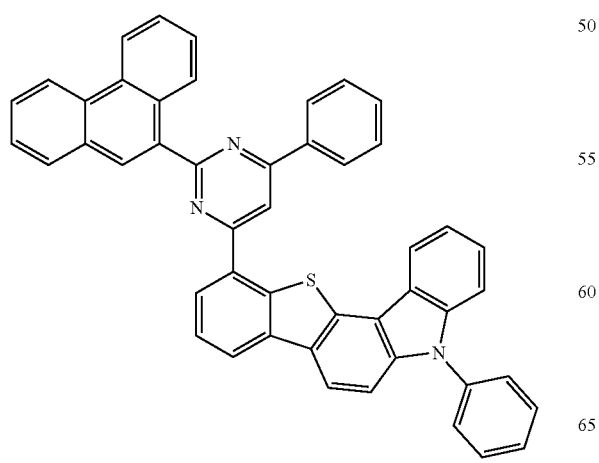
[B-23]
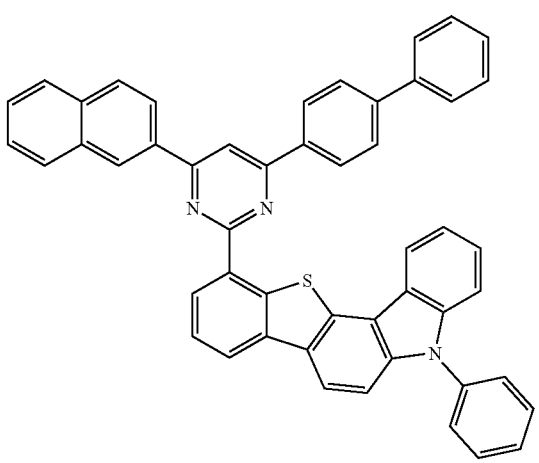

[B-24]
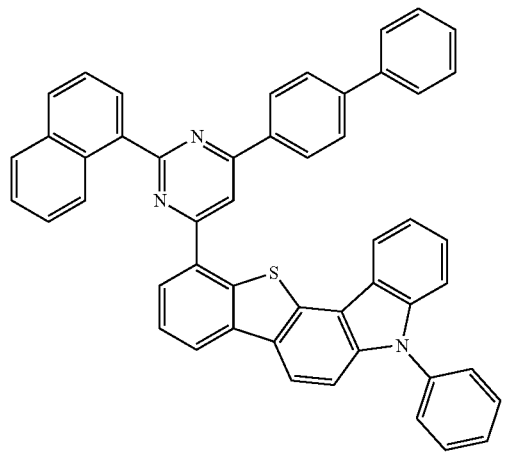
[B-27]
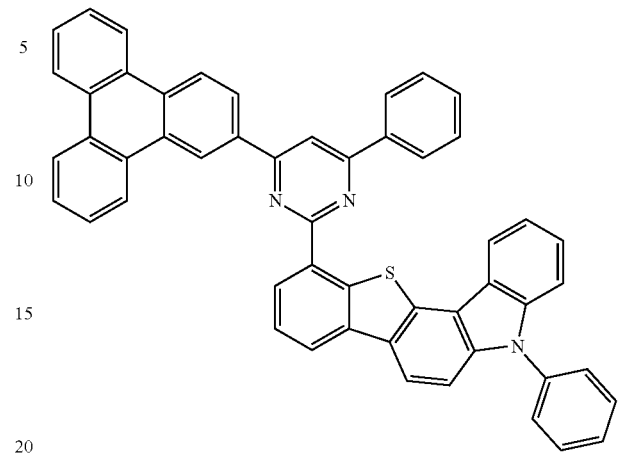
[B-25]
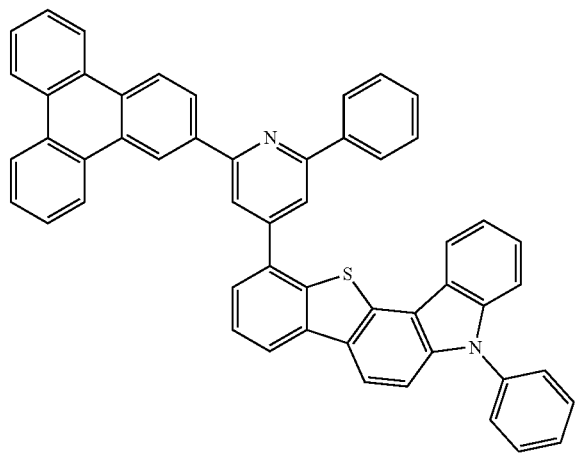
[B-28]
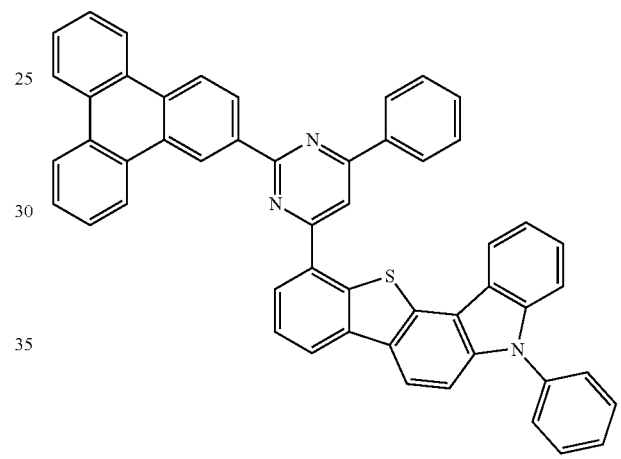
[B-26]
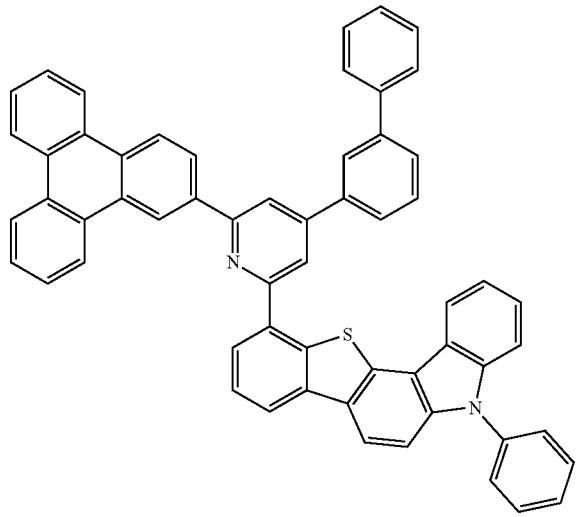
[B-29]
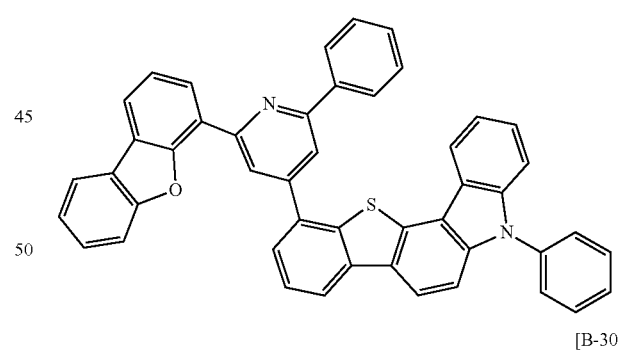
[B-30]
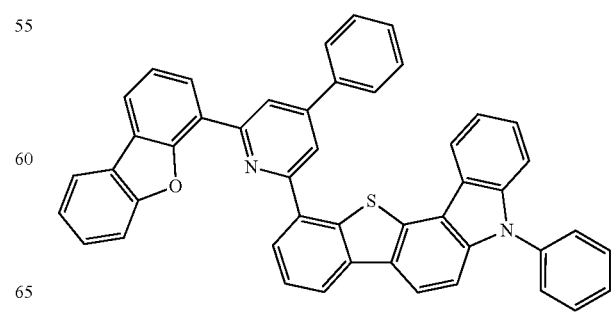

[B-31]
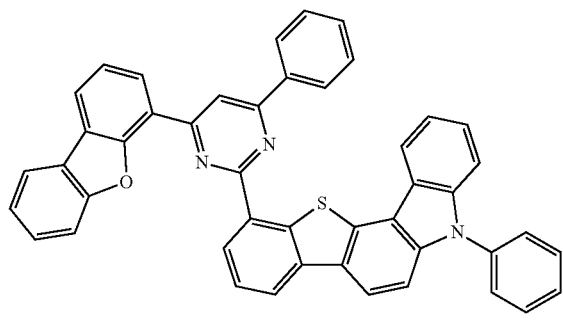
[B-32]
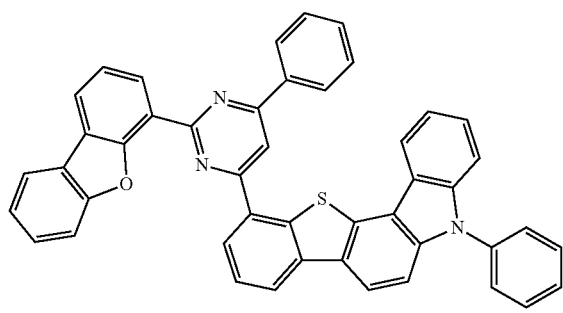
[B-33]
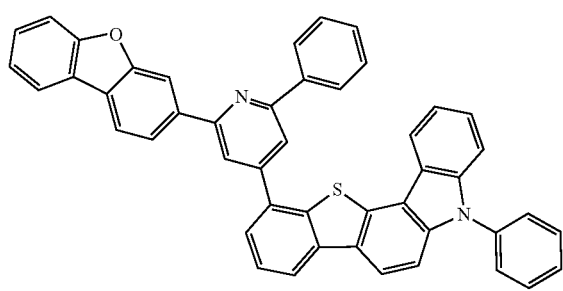
[B-34]
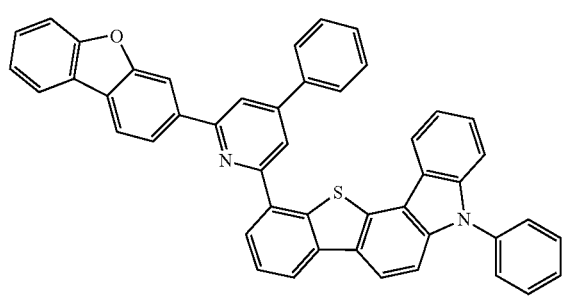
[B-35]
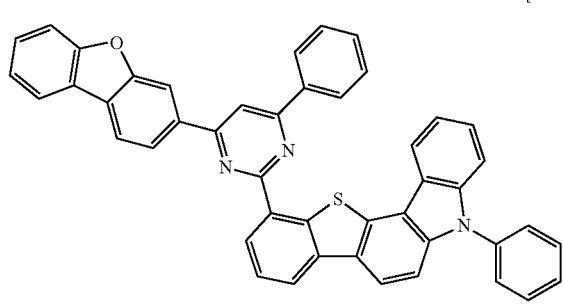
[B-36]
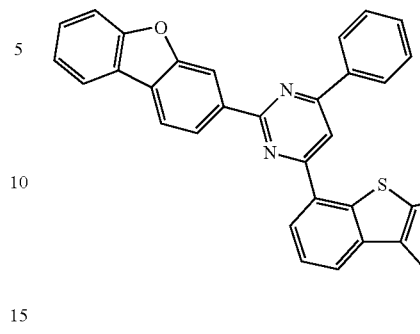
[B-37]
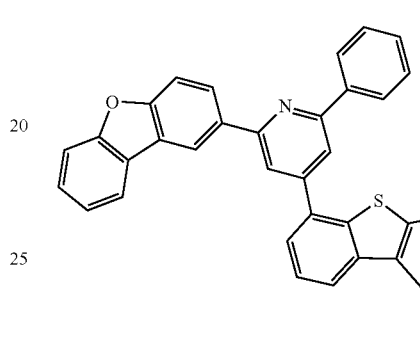
[B-38]
[B-39]
[B-40]
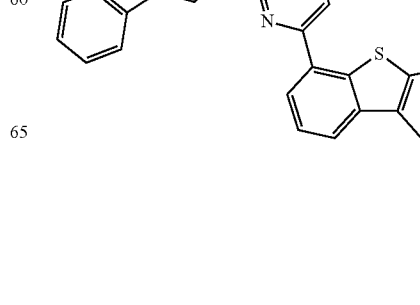

[B-41]
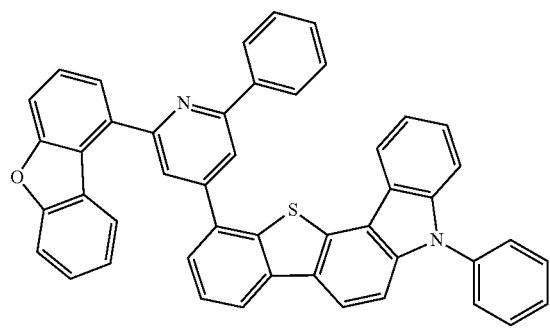
[B-42]
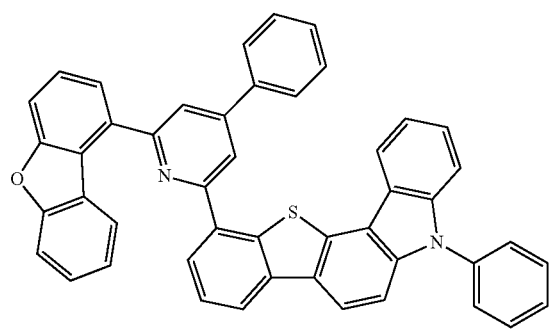
[B-43]
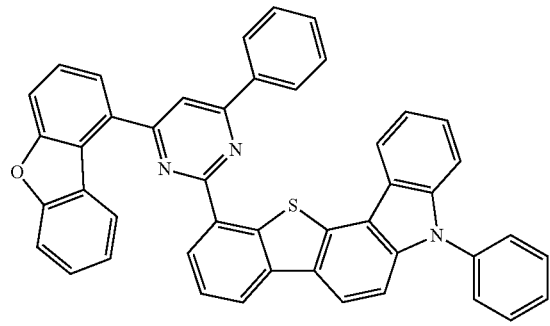
[B-44]
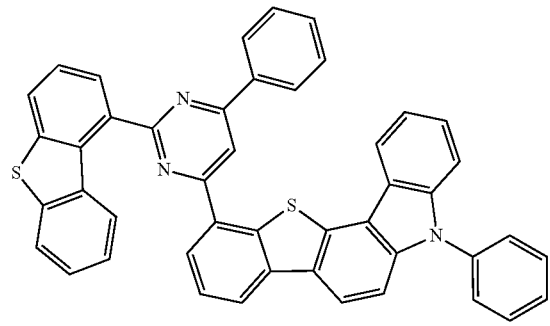
[B-45]
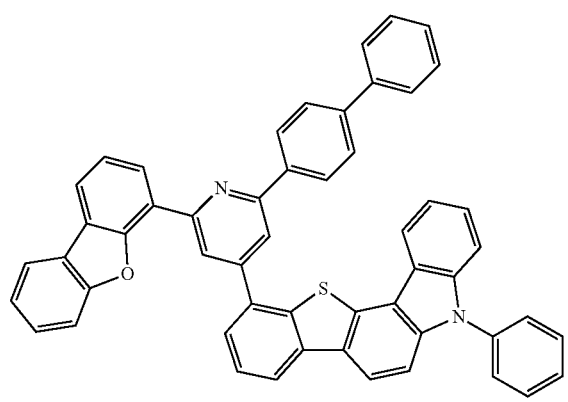
[B-46]
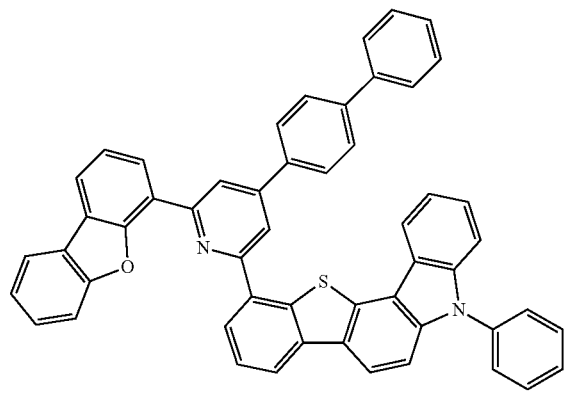
[B-47]
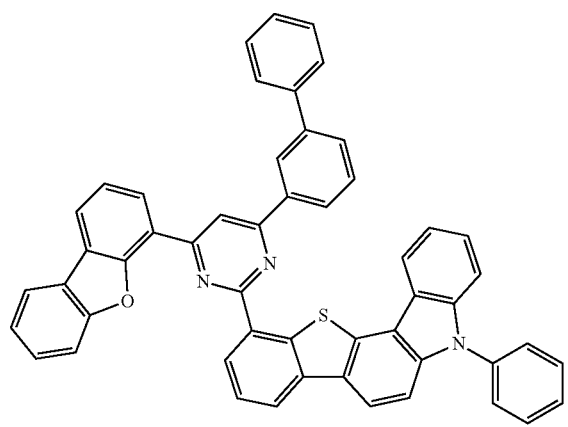

[B-48]
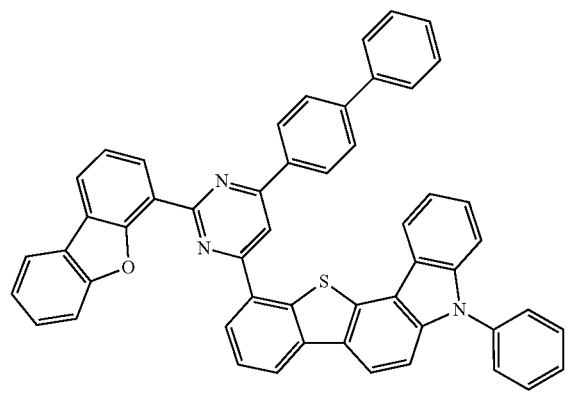
[B-49]
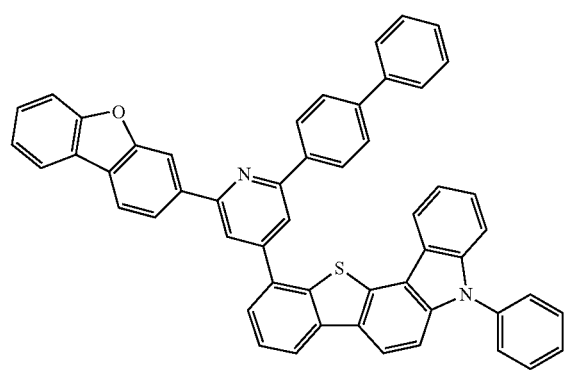
[B-50]
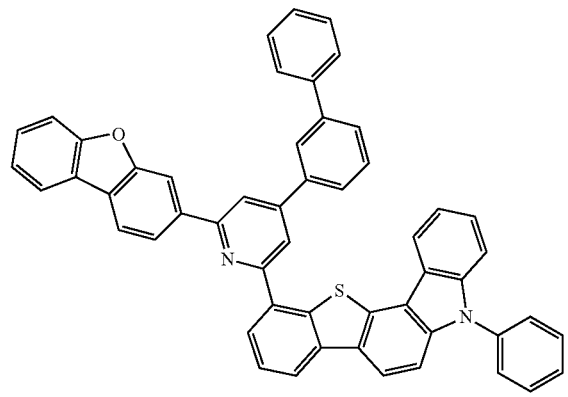
[B-51]
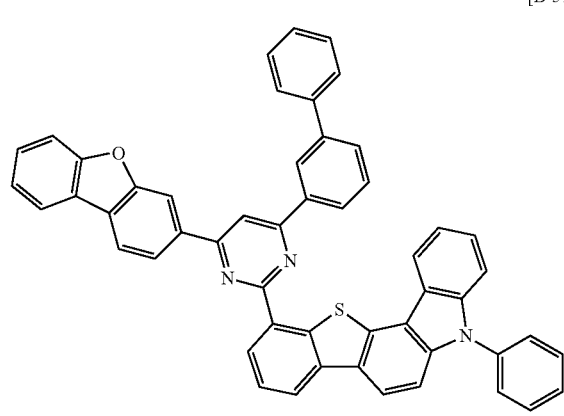
[B-52]
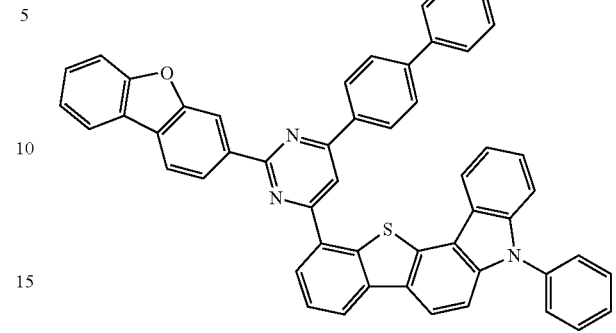
[B-53]
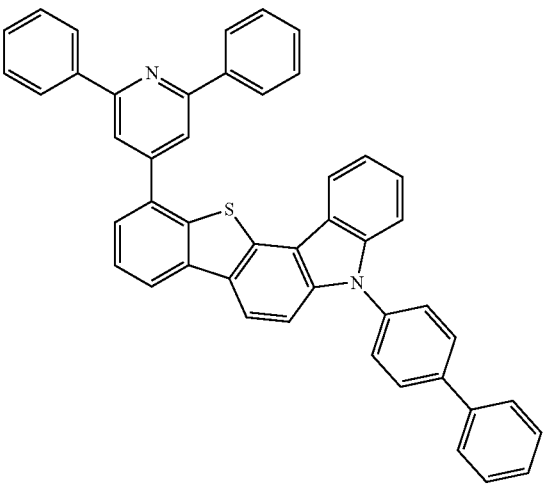
[B-54]
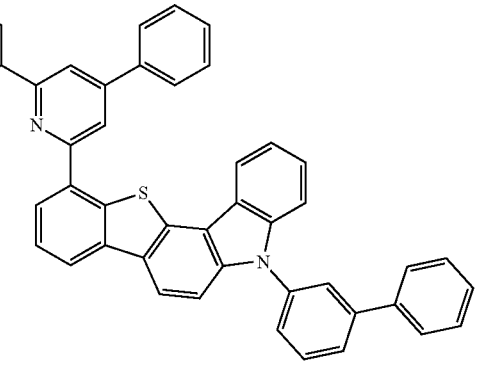

-continued
[B-55]
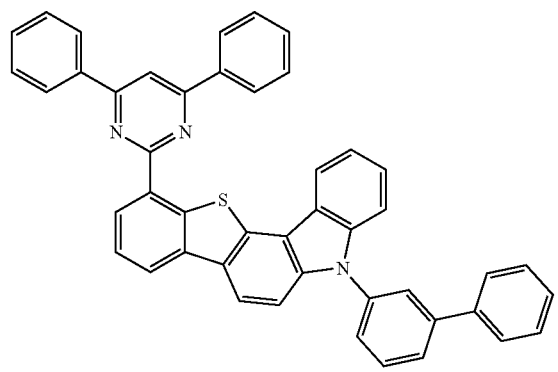
[B-56]
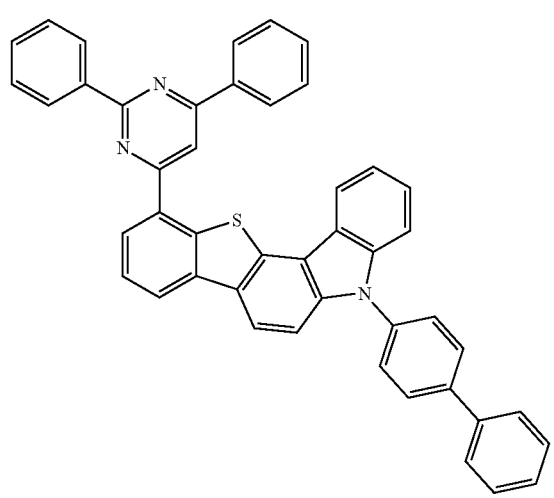
[B-57]
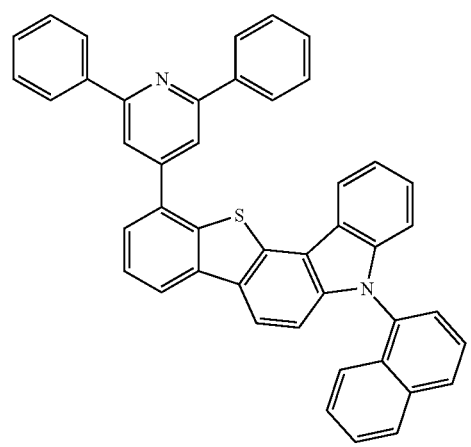
[B-58]
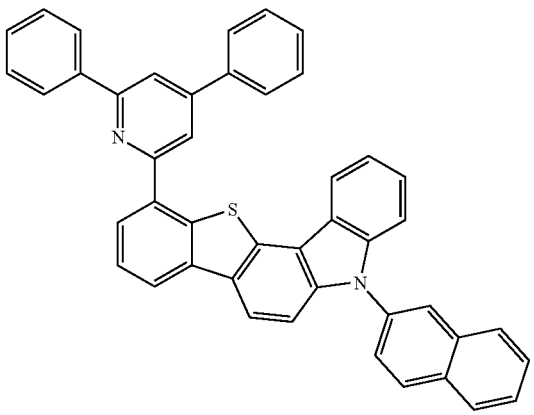
[B-59]
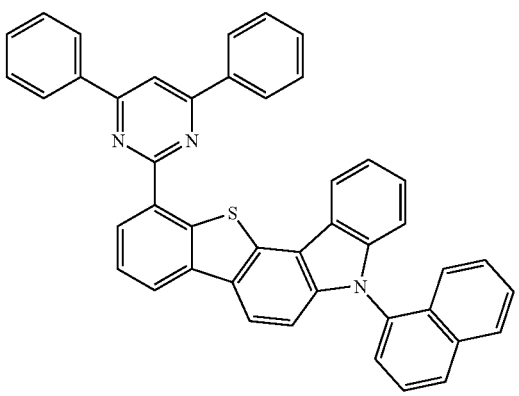
[B-60]
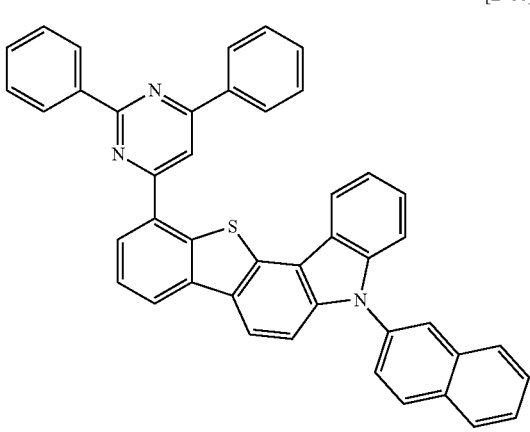

[B-61]
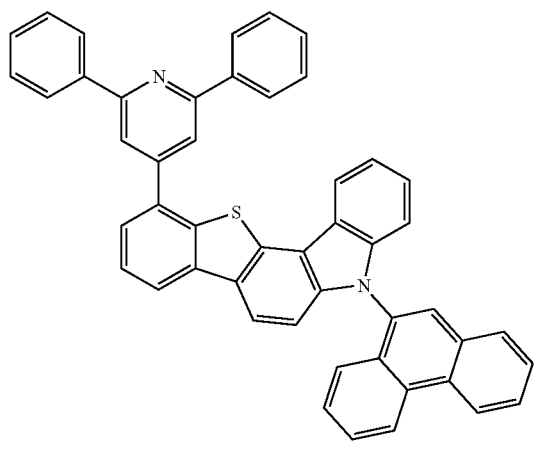
[B-62]
[B-63]
[B-64]
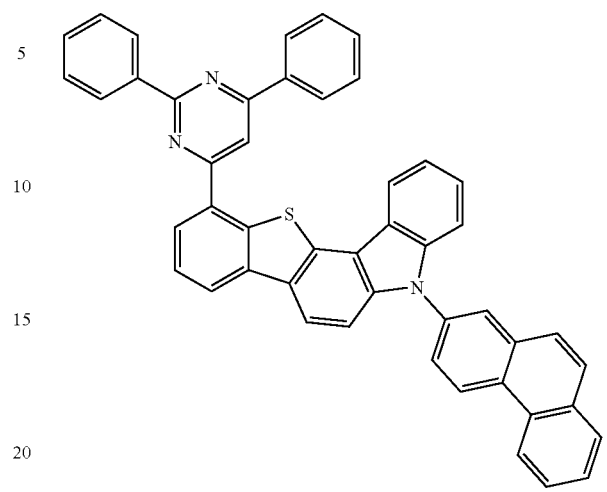
[B-65]
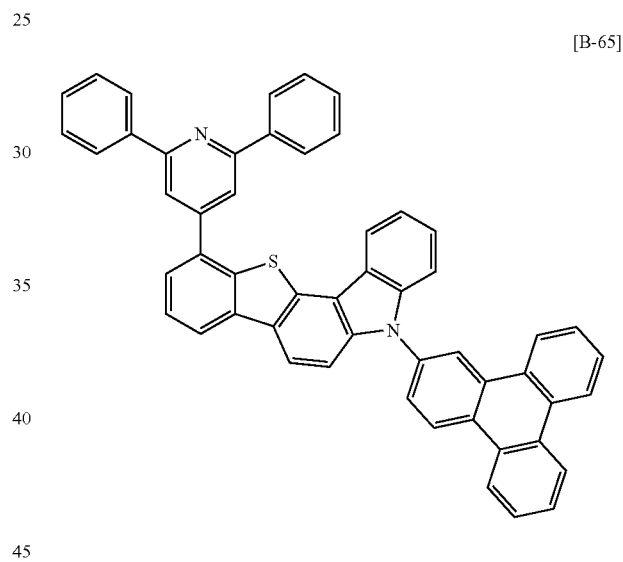
[B-66]
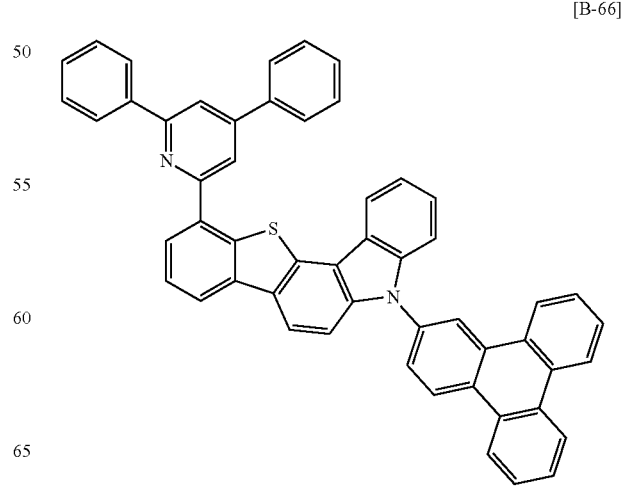

[B-67]
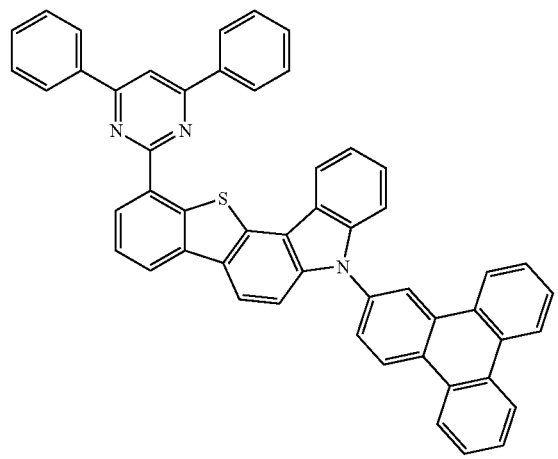
[B-68]
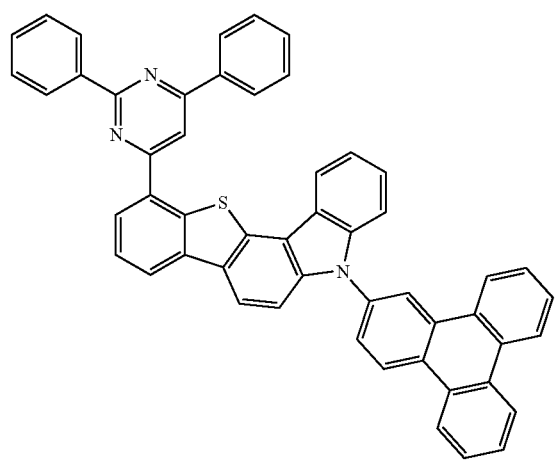
[B-69]
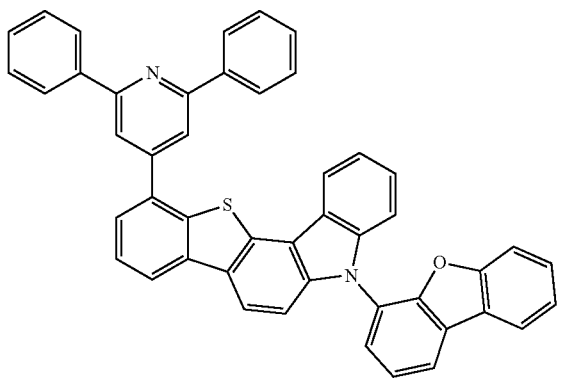
[B-70]
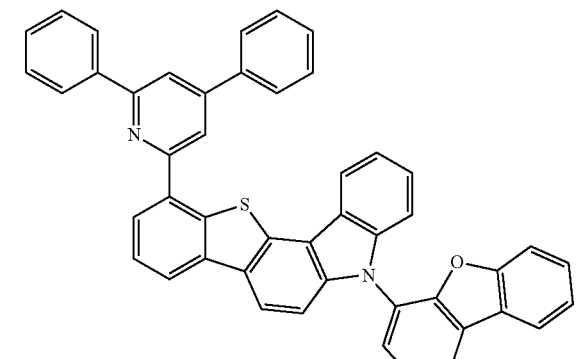
[B-71]
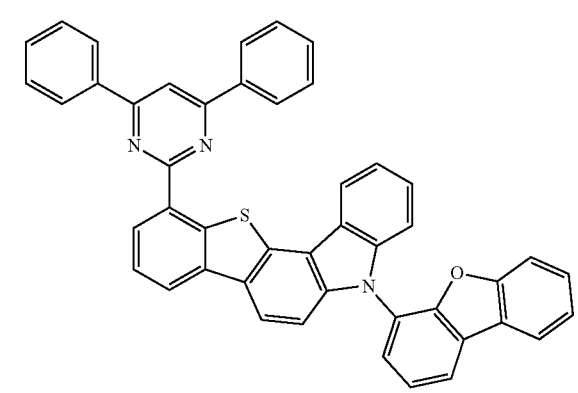
[B-72]
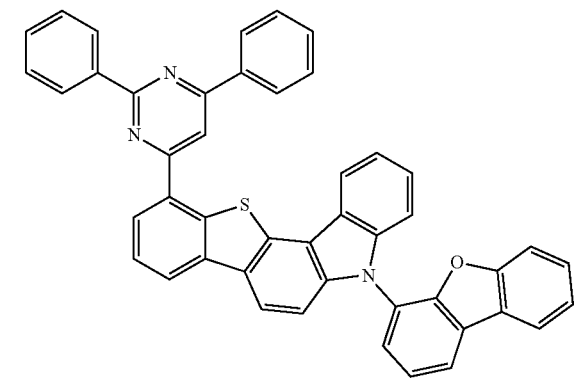
[B-73]
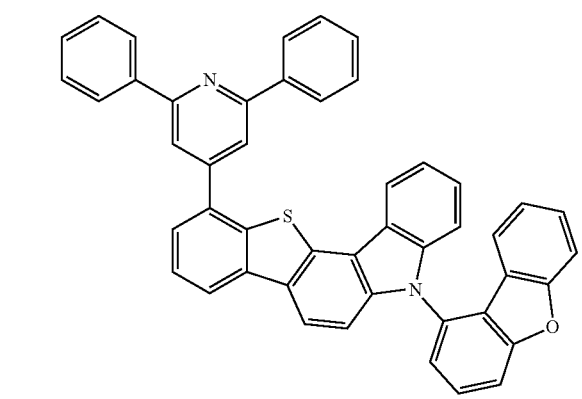

[B-74]
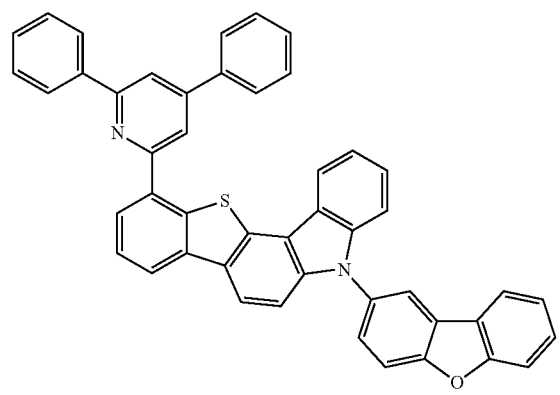
[B-75]
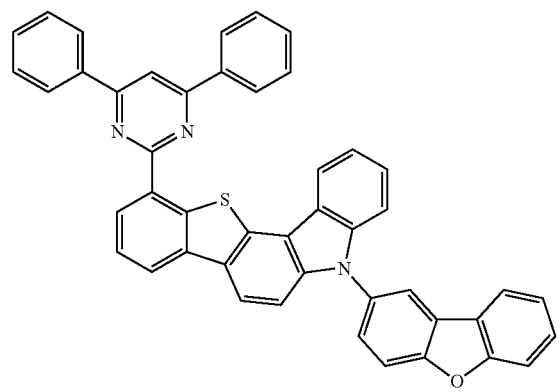
[B-76]
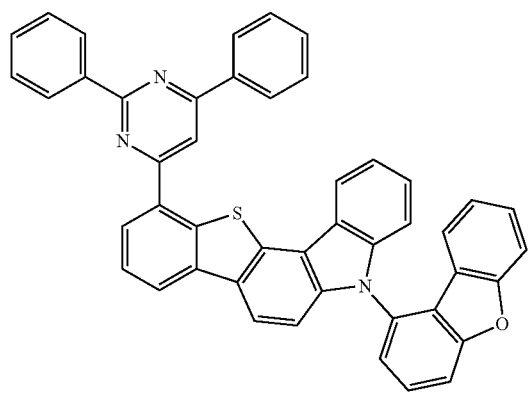
[B-77]
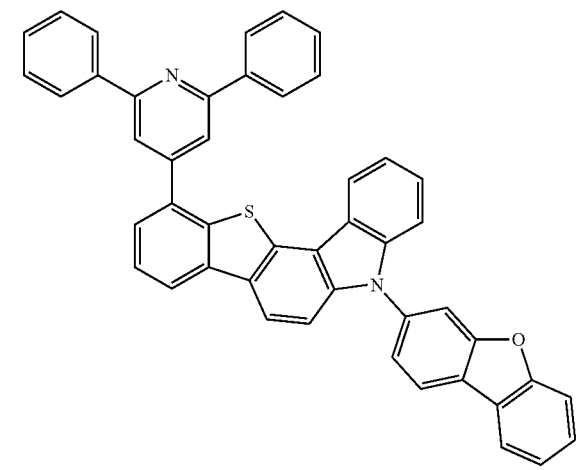
[B-78]
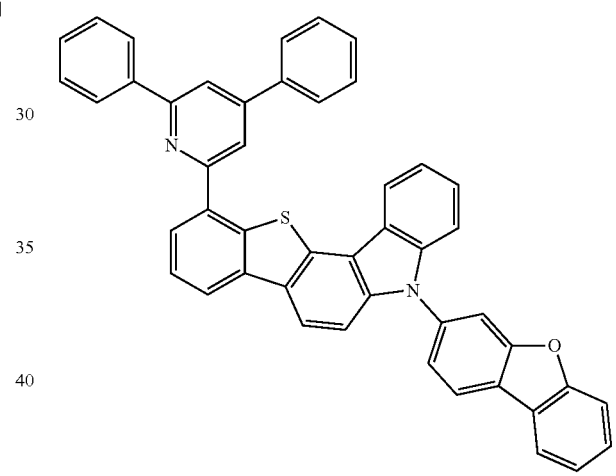
[B-79]
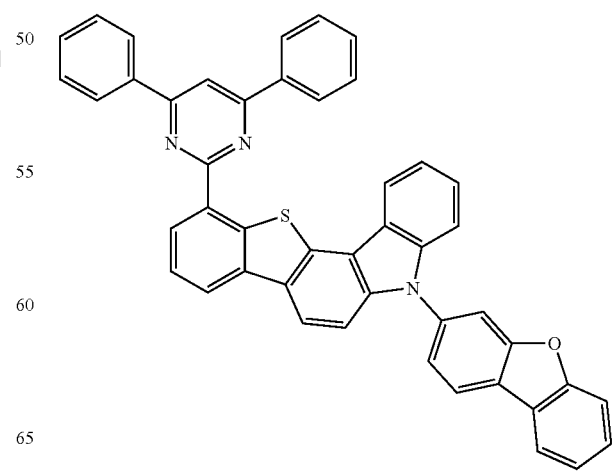

-continued
[B-80]
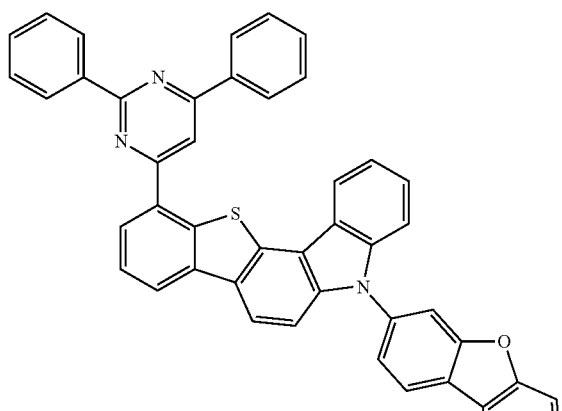
[B-81]
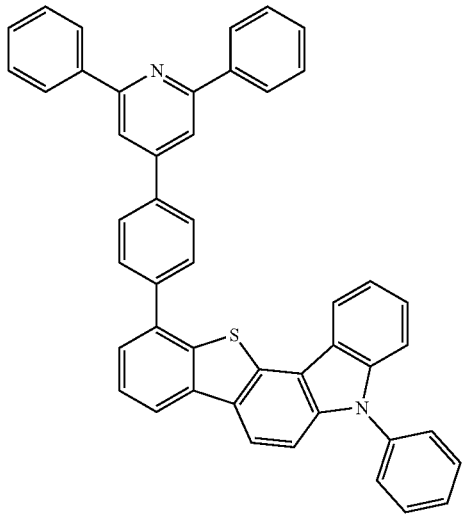
[B-82]
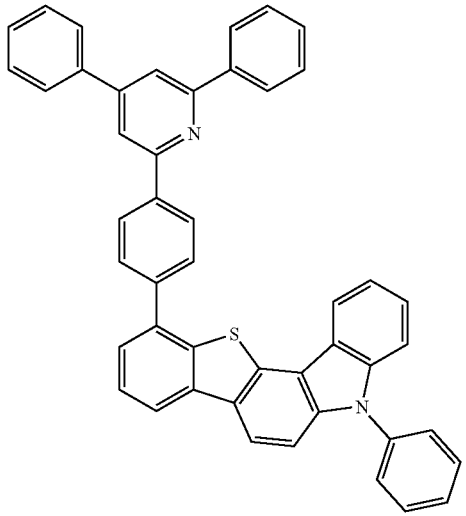
-continued
[B-83]
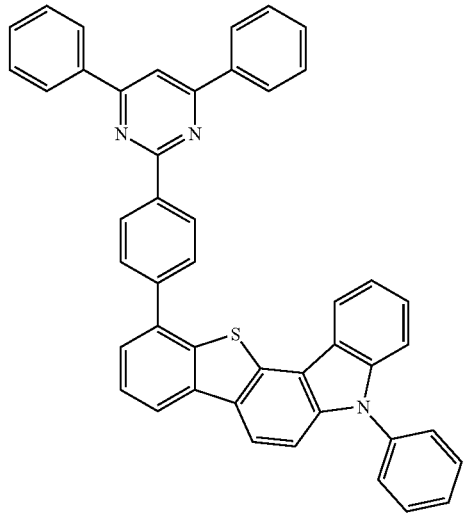
[B-84]
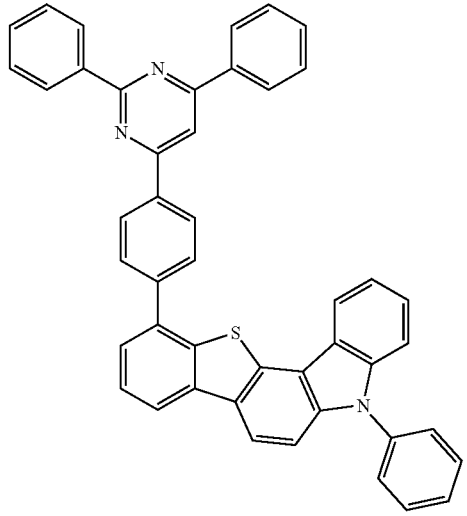
[B-85]
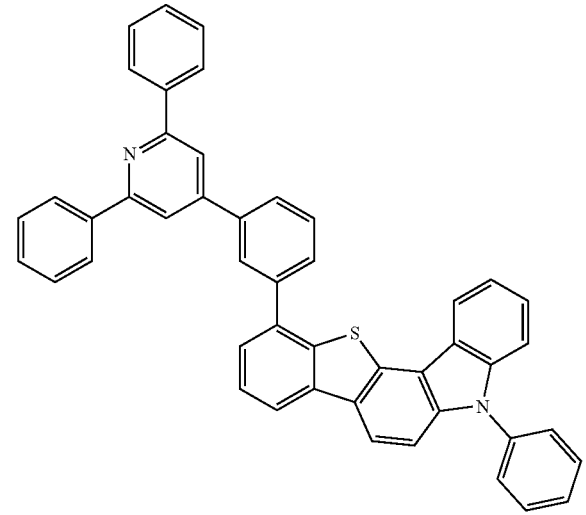

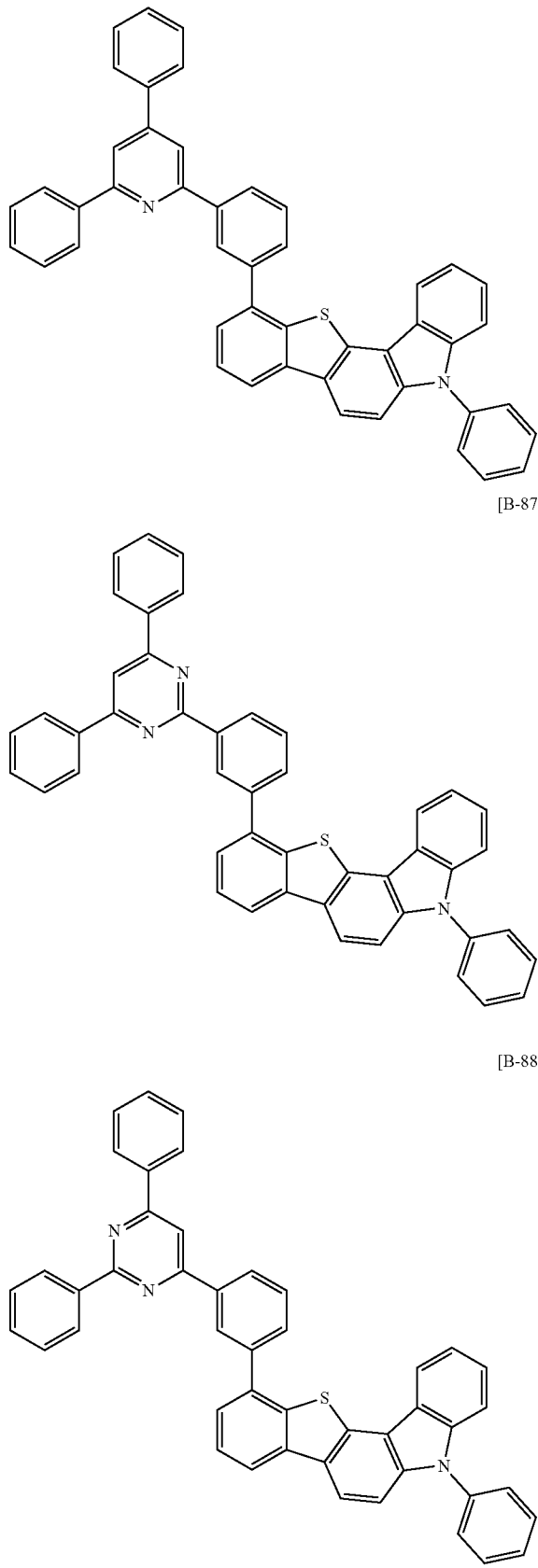
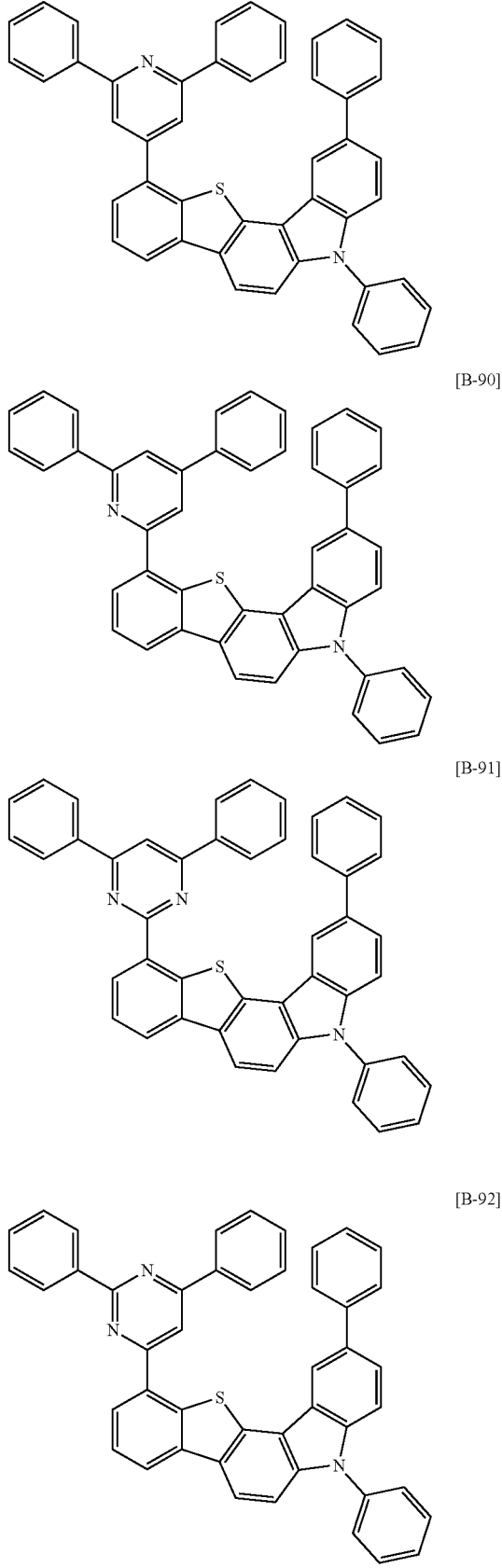

[B-93]
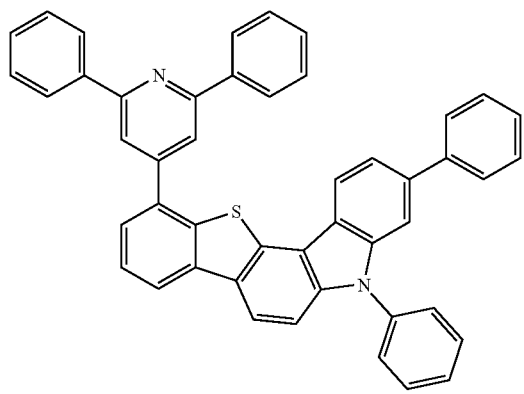
[B-94]
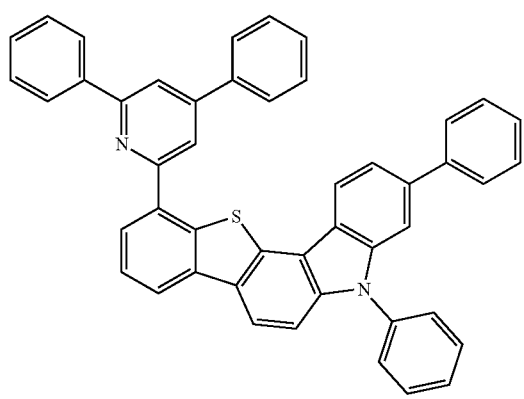
[B-95]
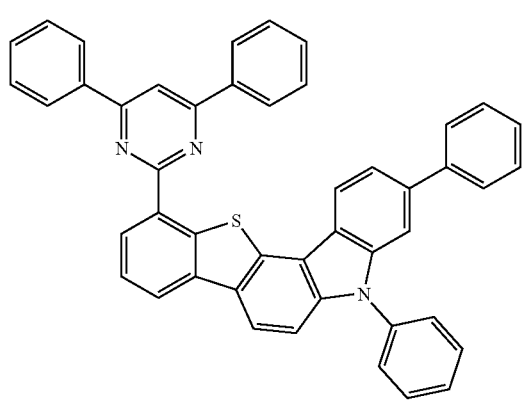
[B-96]
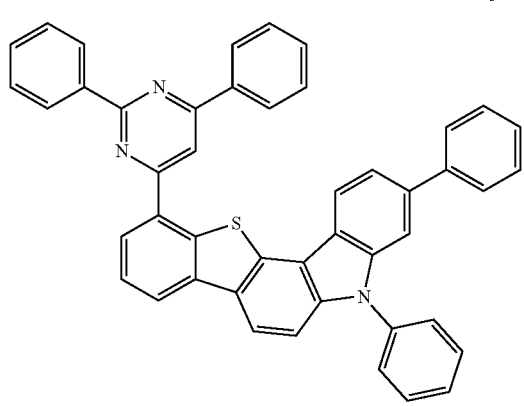
[B-97]
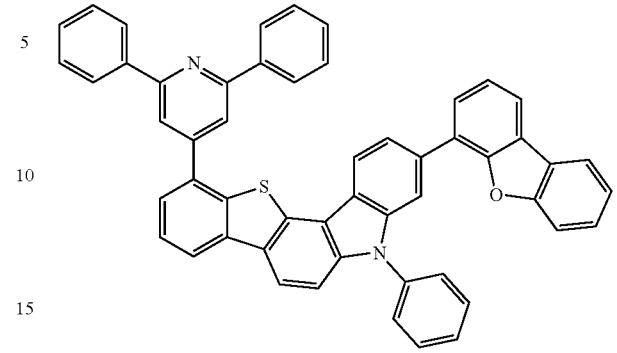
[B-98]
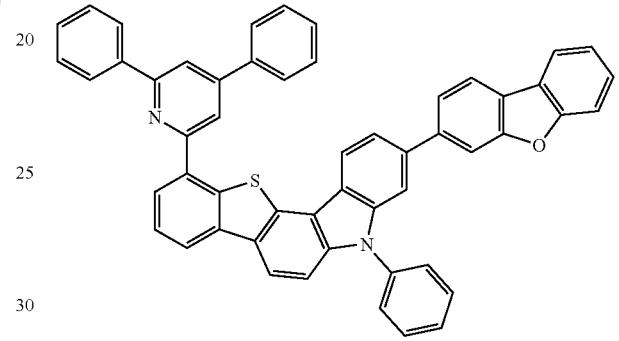
[B-99]
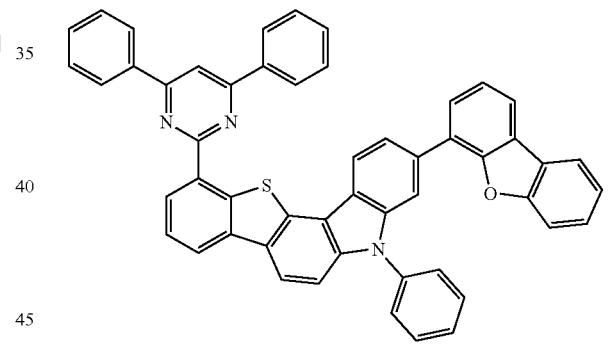
[B-100]
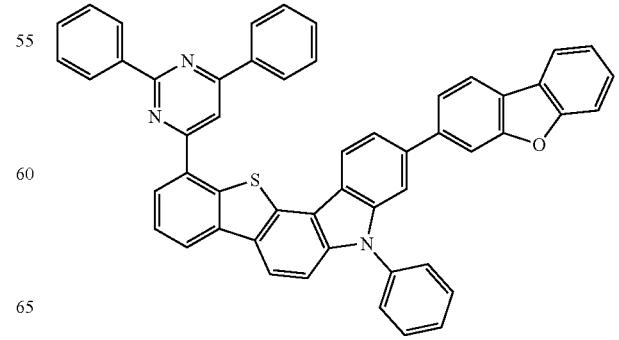

[B-101]
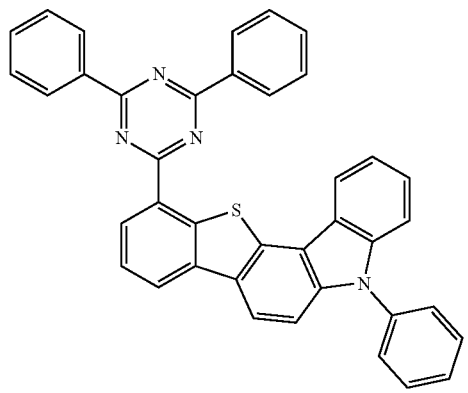
[B-104]
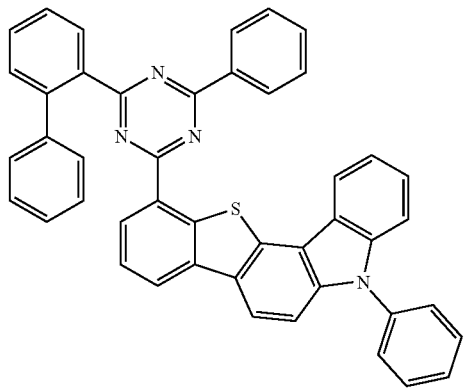
[B-102]
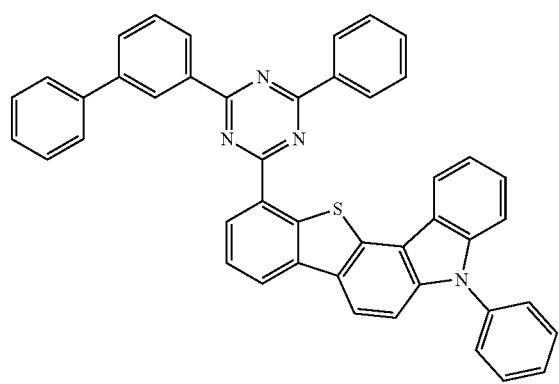
[B-105]
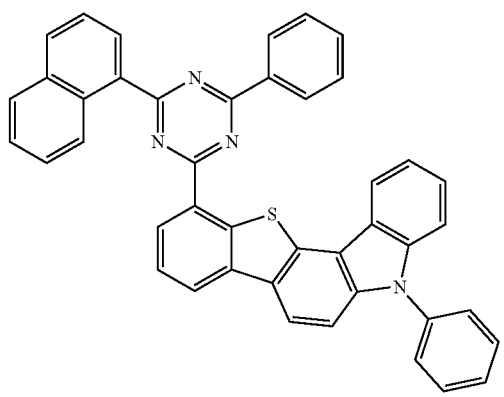
[B-103]
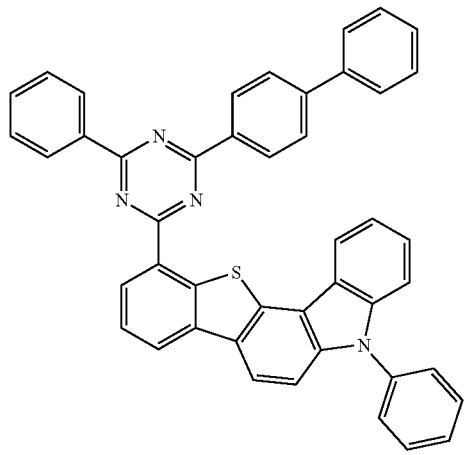
[B-106]
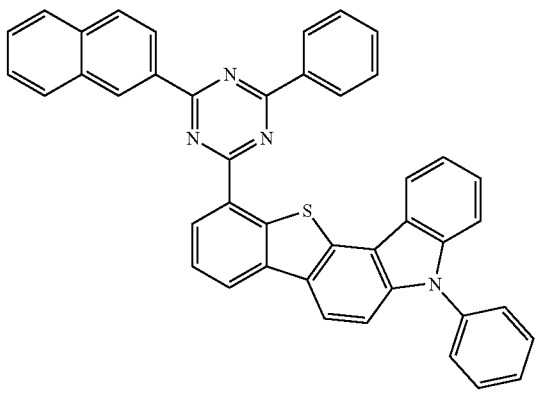

-continued
[B-107]
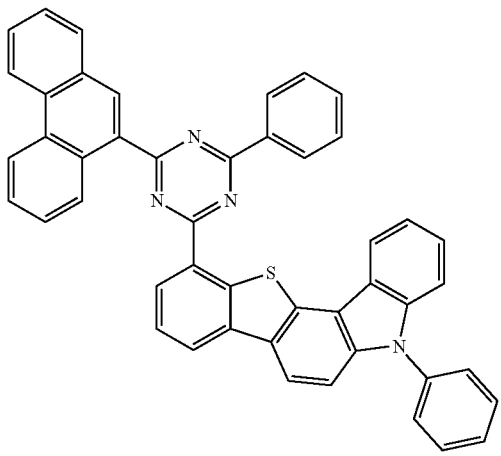
[B-110]
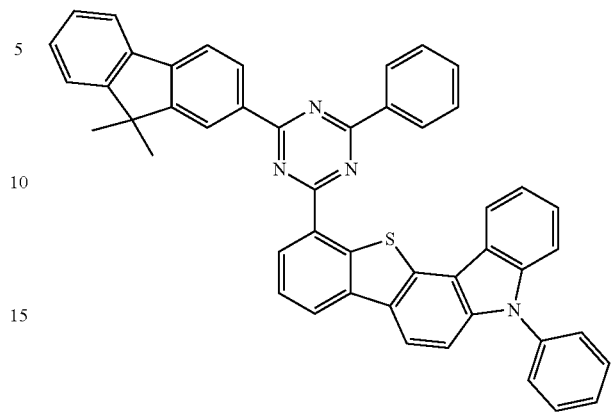
[B-108]
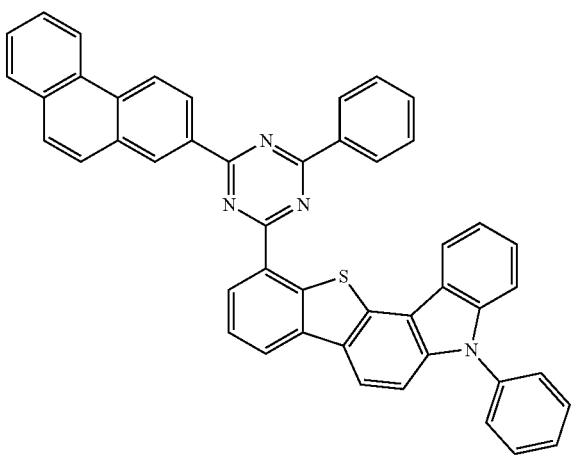
[B-111]
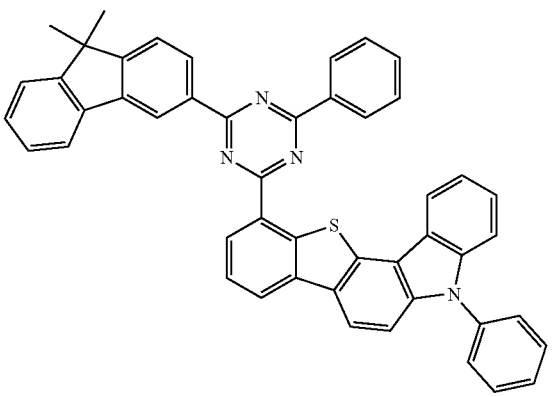
[B-109]
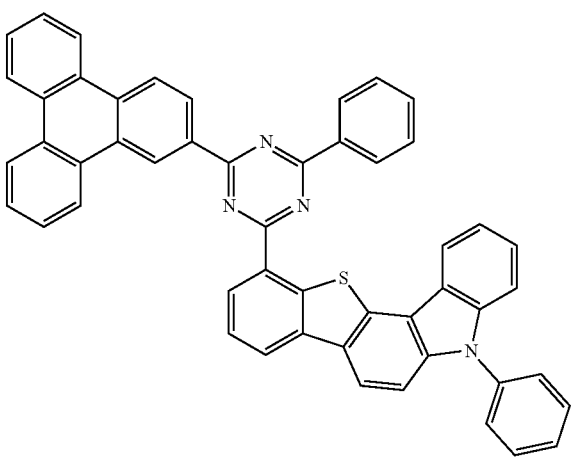
[B-112]
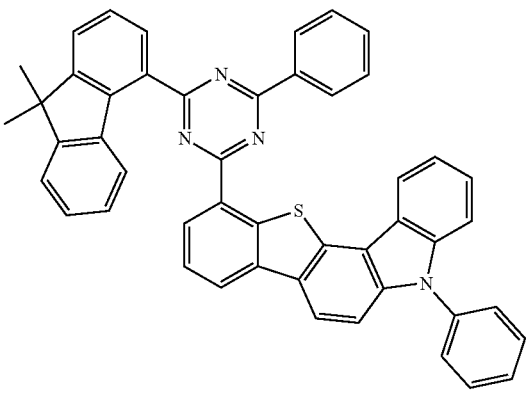

[B-113]
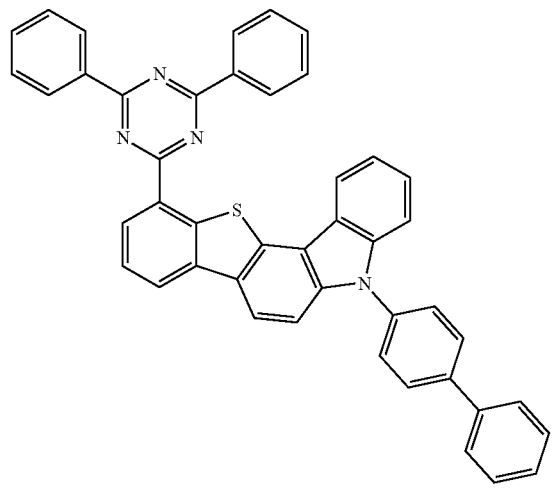
[B-114]
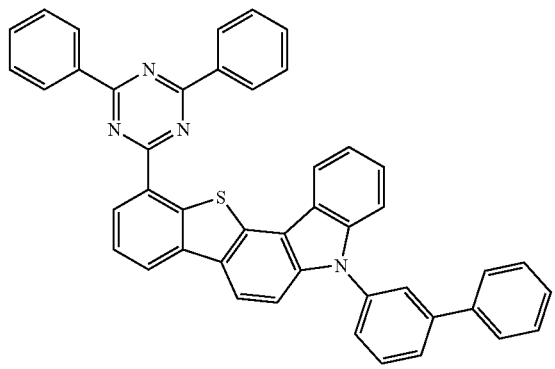
[B-115]
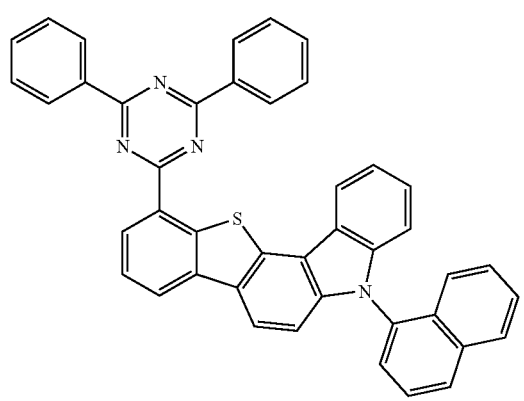
[B-116]
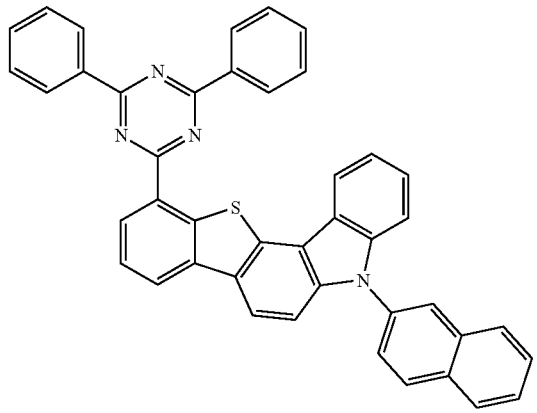
[B-117]
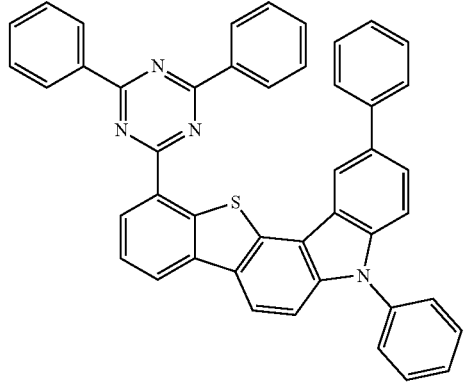
[B-118]
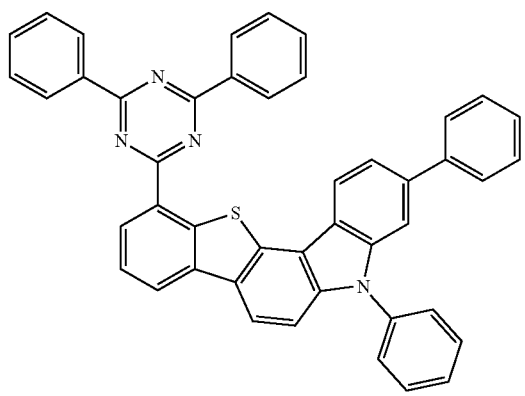

[B-119]
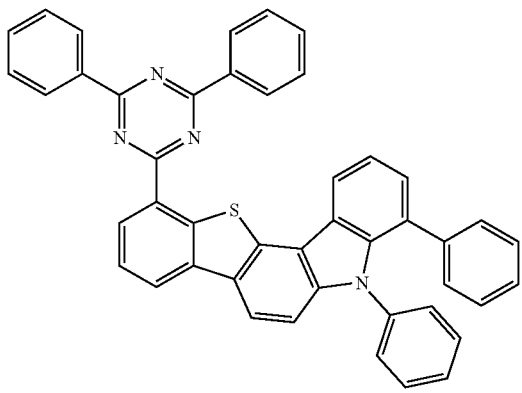
[B-120]
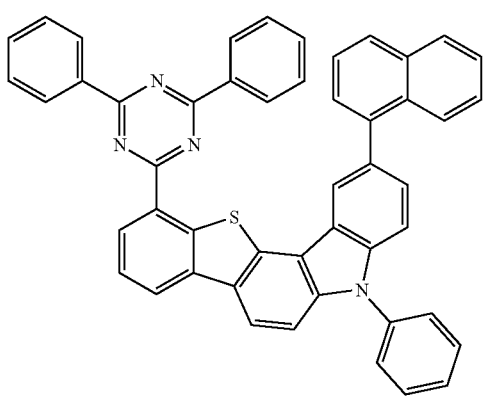
[B-121]
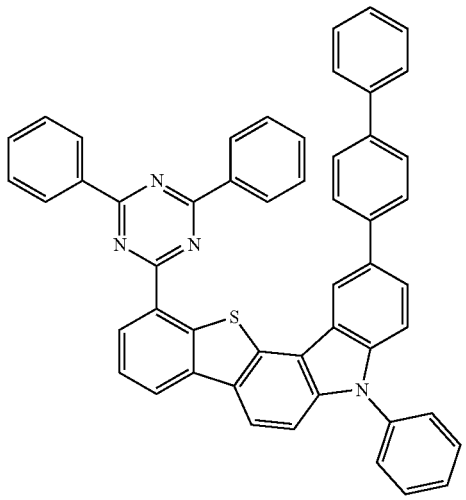
[B-122]
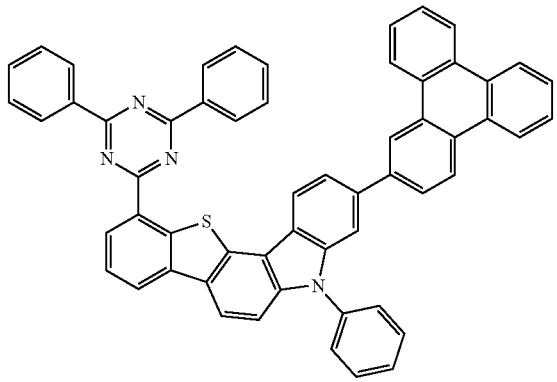
[B-123]
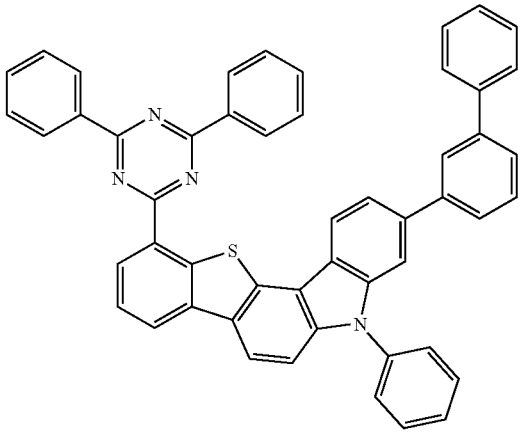
[B-124]
[B-125]
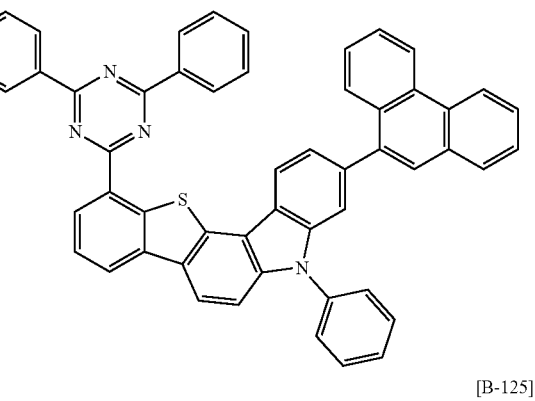

[B-126]
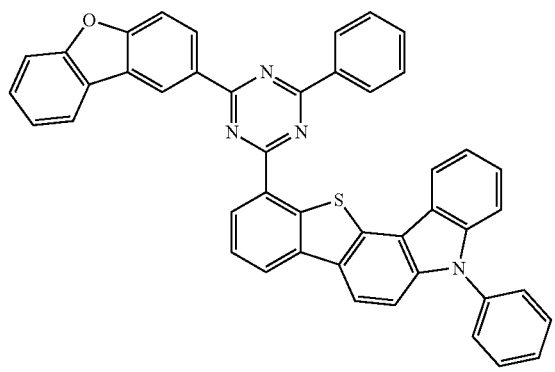
[B-129]
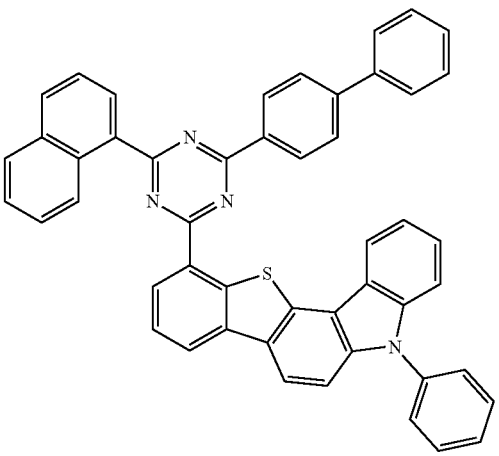
[B-127]
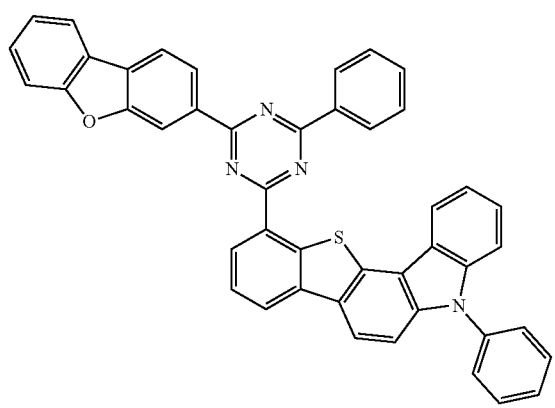
[B-130]
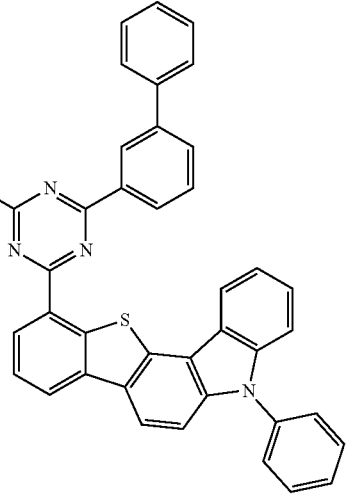
[B-128]
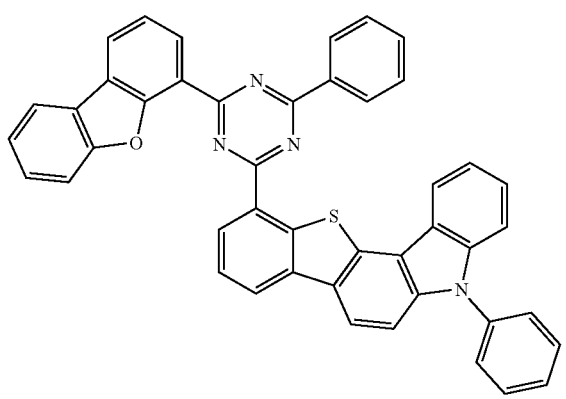
[B-131]
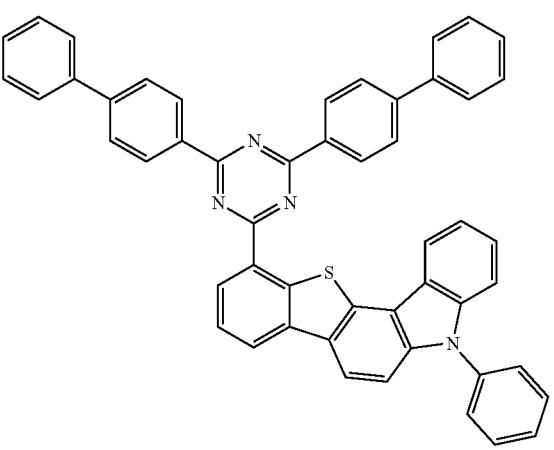

[B-132]
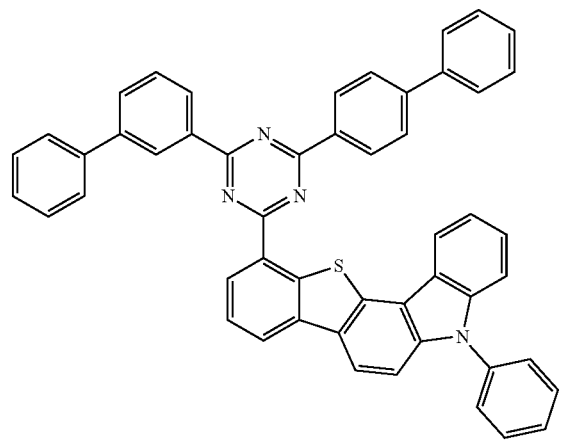
[B-133]
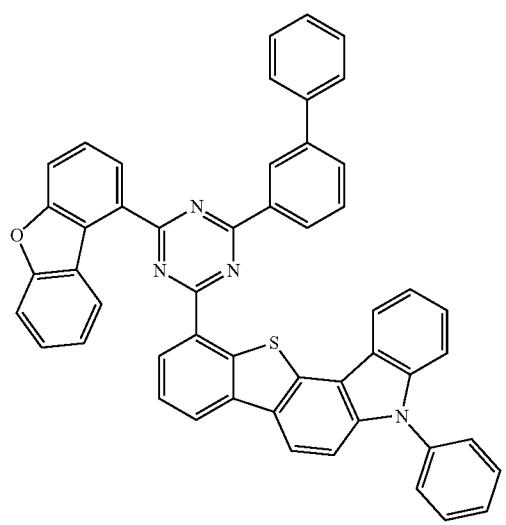
[B-135]
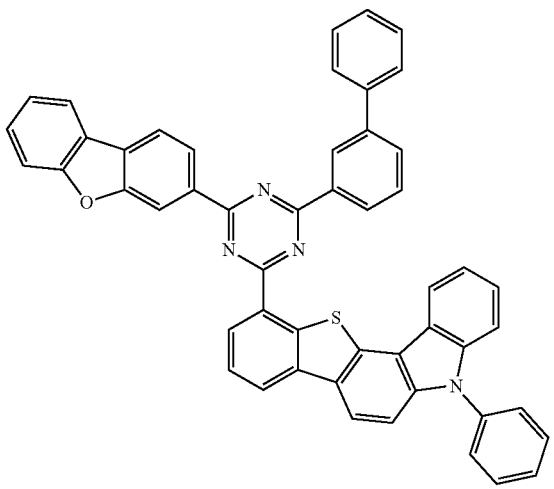
[B-136]
[B-134]
[B-137]
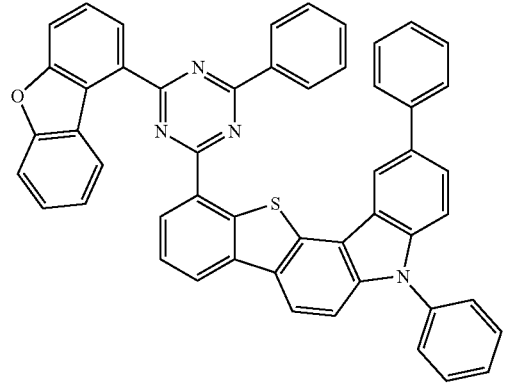

[B-138]
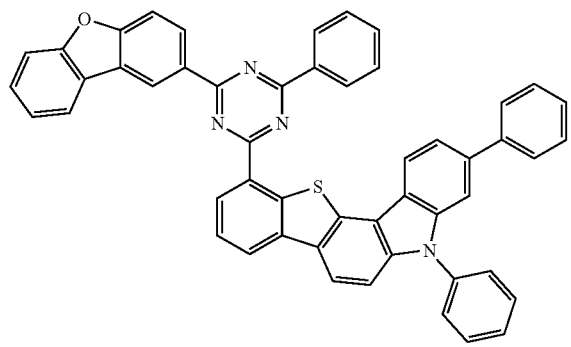
[B-139]
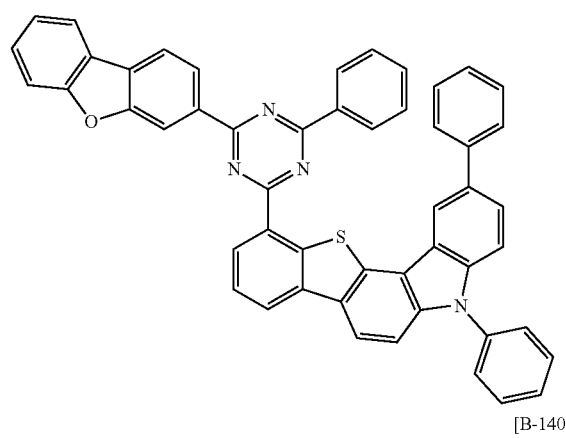
[B-140]
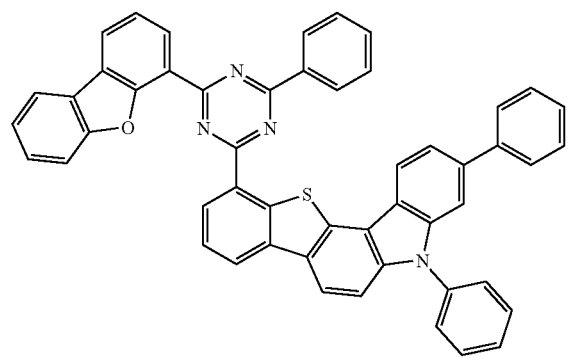
[B-141]
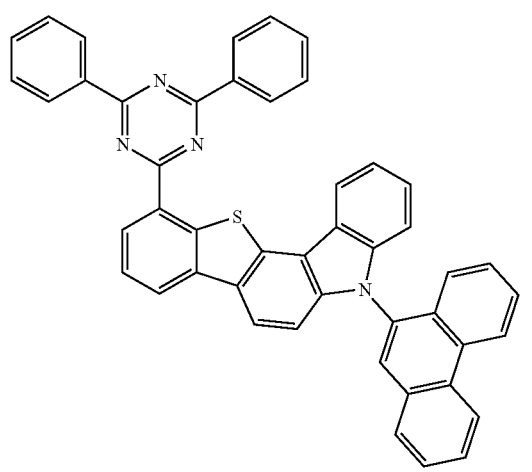
[B-142]
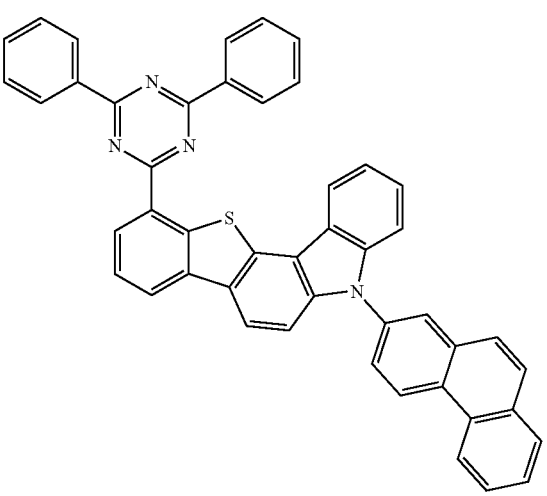
[B-143]
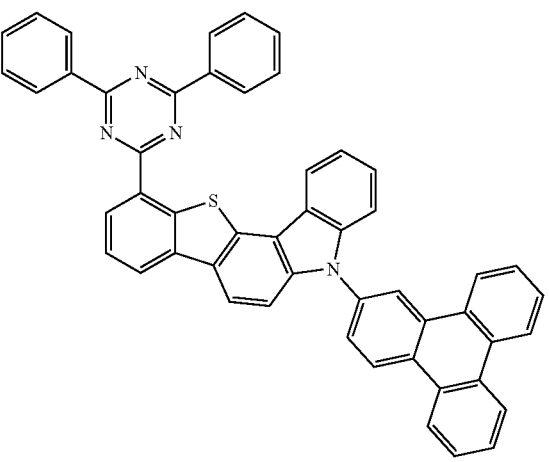
[B-144]
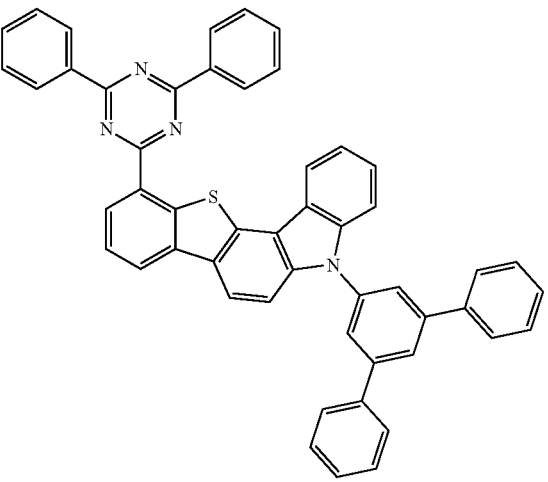

[B-145]
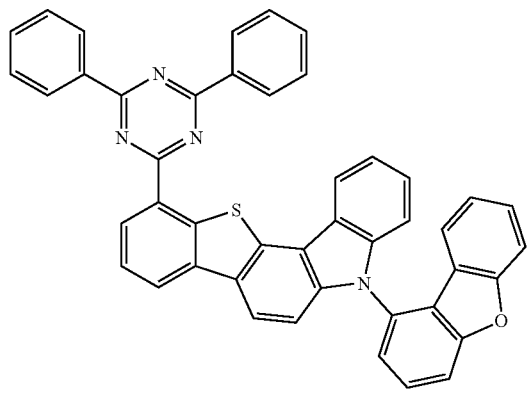
[B-146]
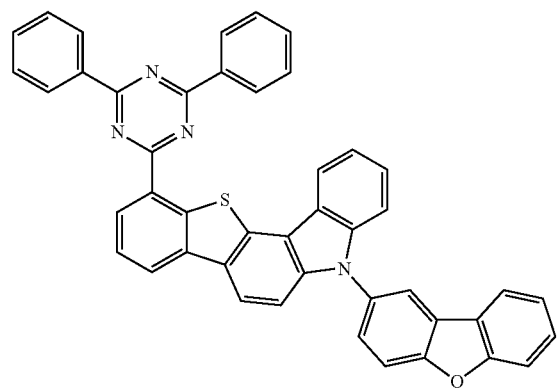
[B-147]
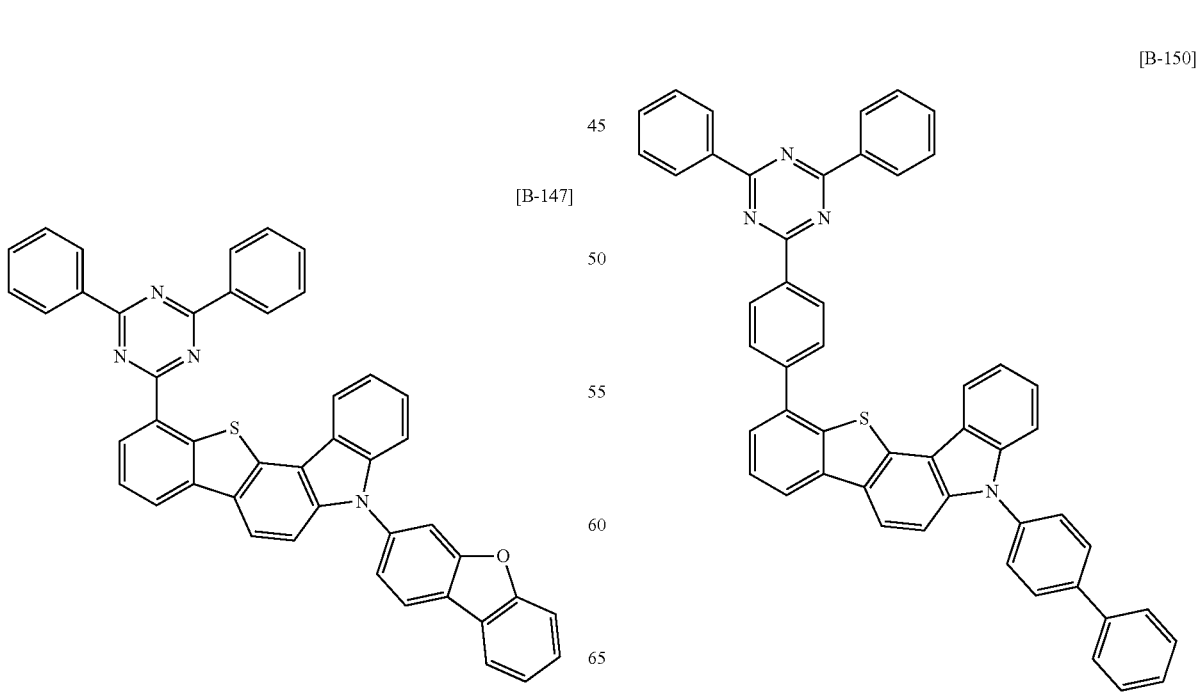
[B-148]
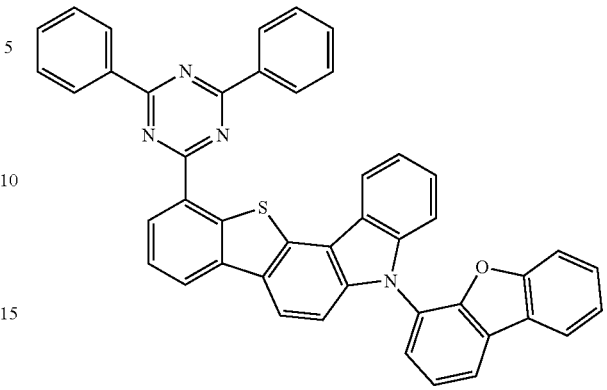
[B-149]
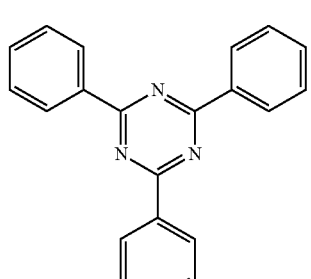
[B-150]
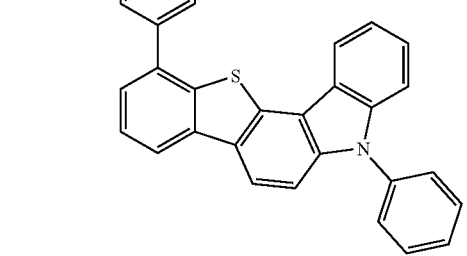

-continued
[B-151]
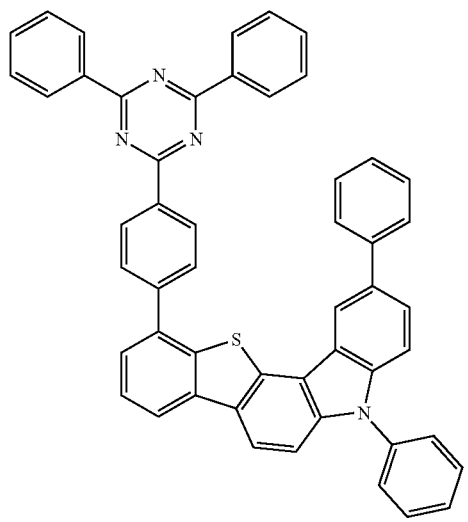
[B-152]
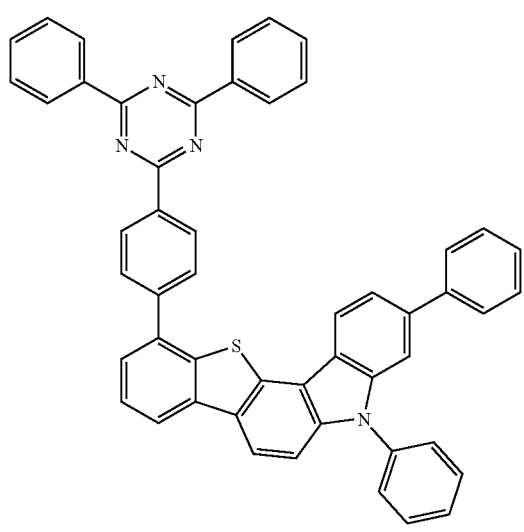
[B-153]
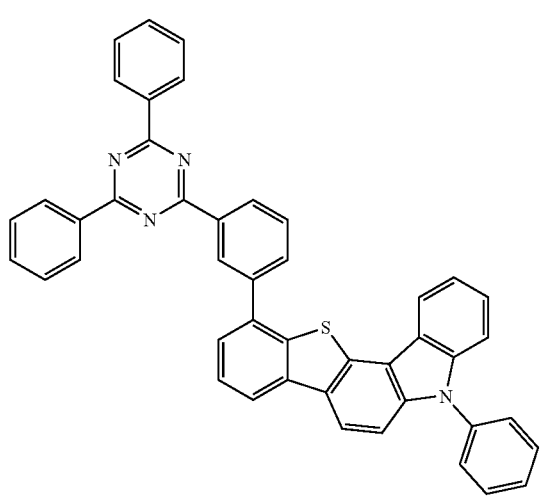
-continued
[B-154]
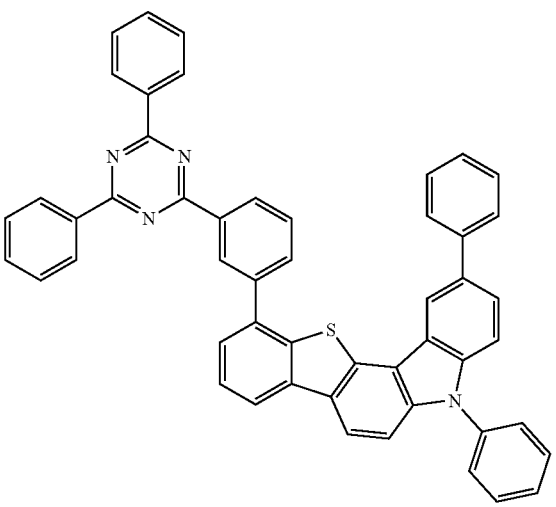
[B-155]
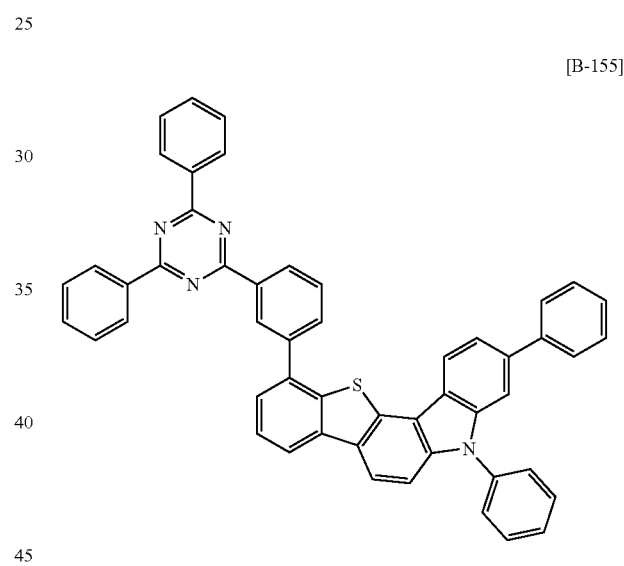
[B-156]
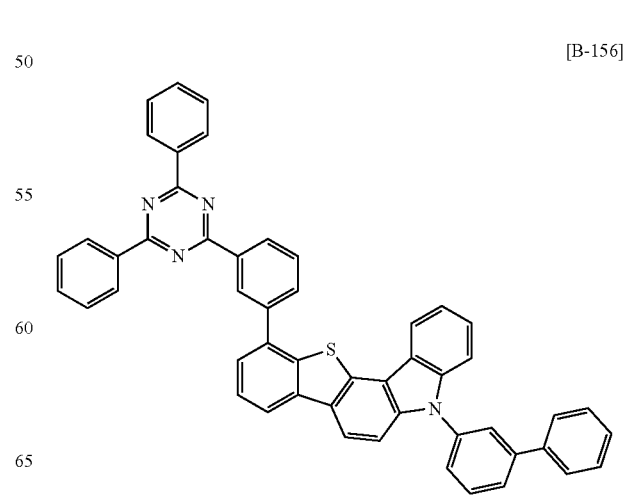

[B-157]
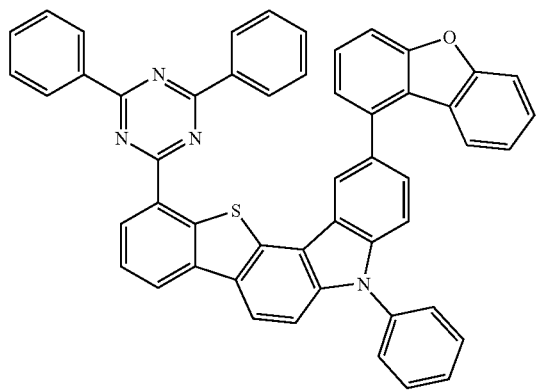
[B-160]
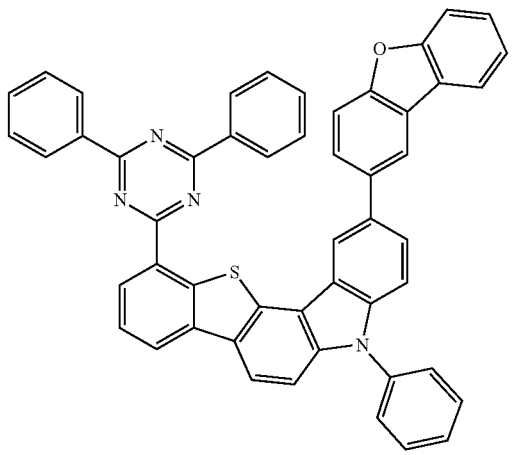
[B-158]
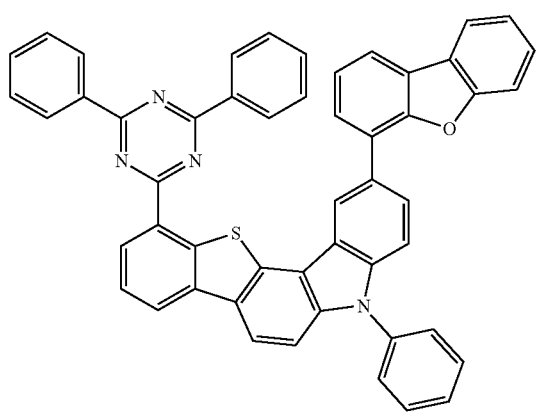
[B-161]
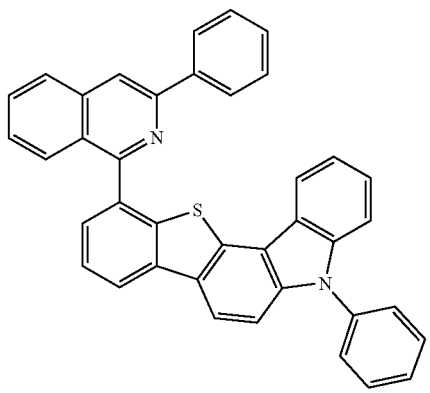
[B-159]
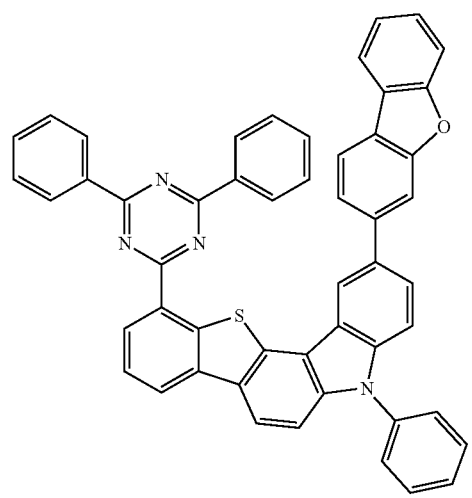
[B-162]
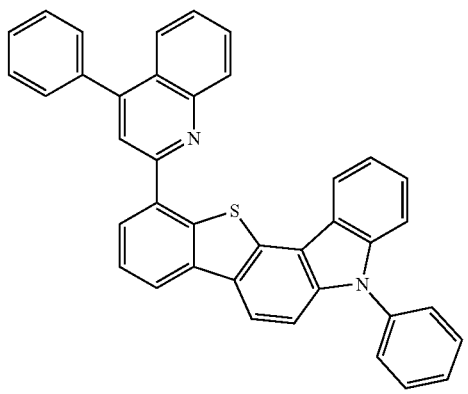

[B-163]
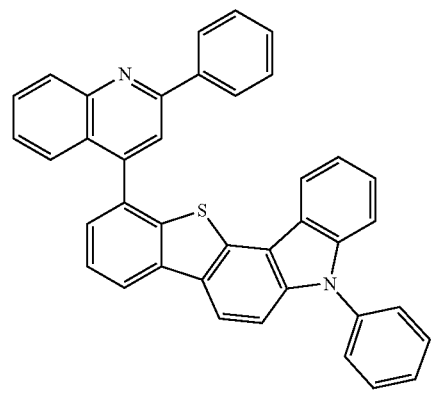
[B-164]
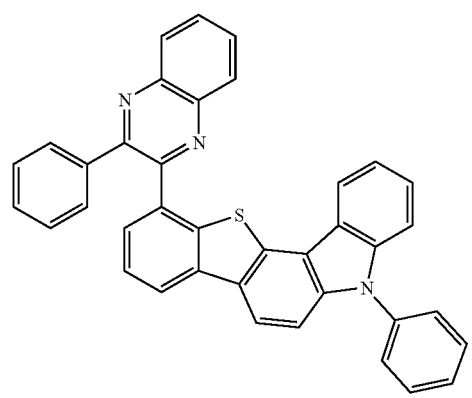
[B-165]
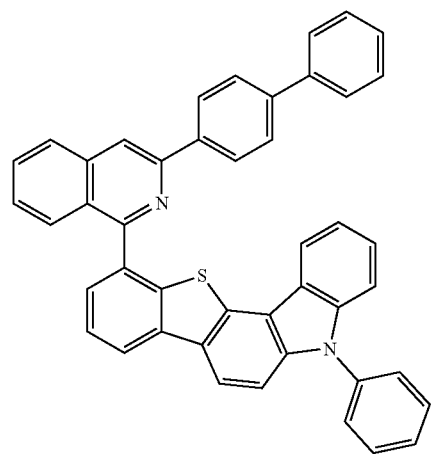
[B-166]
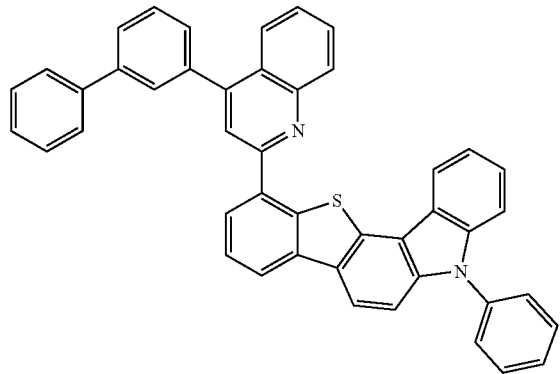
[B-167]
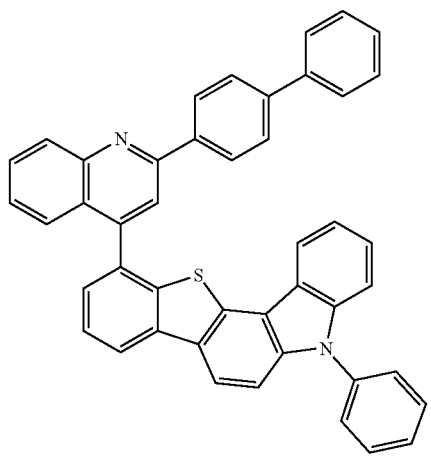
[B-168]
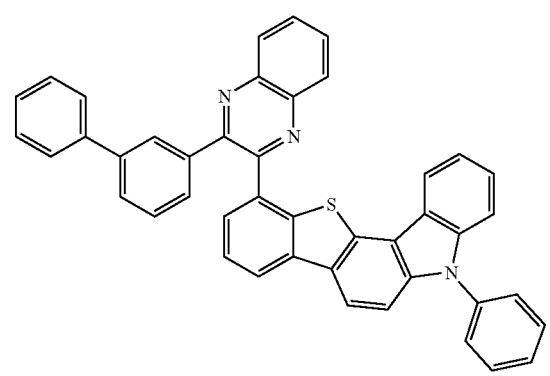
[B-169]
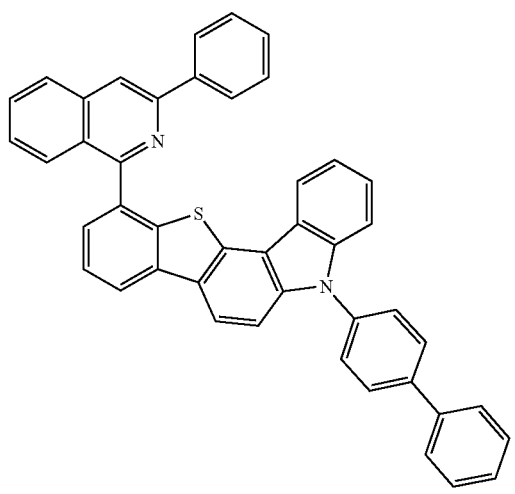

-continued
[B-170]
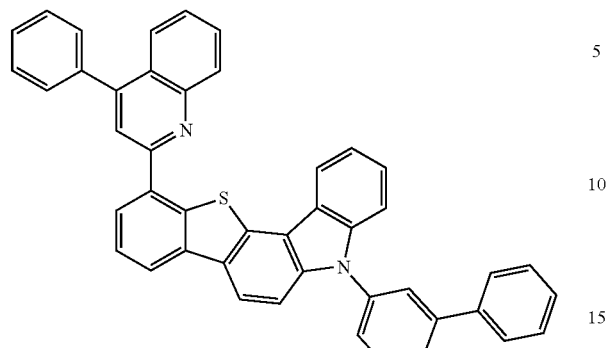
[B-171]
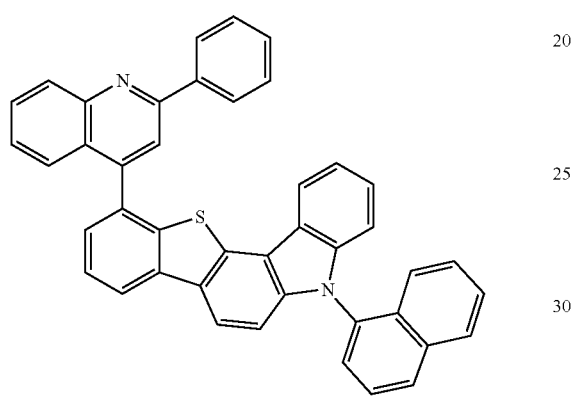
[B-172]
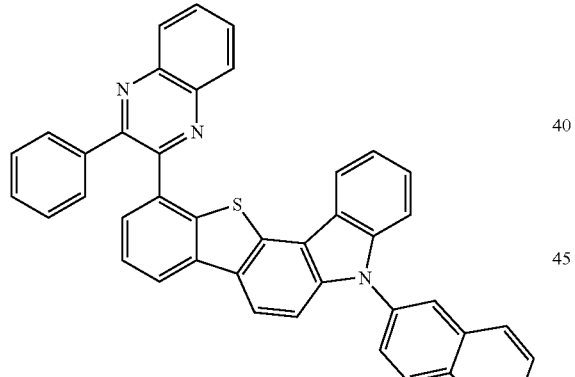
[B-173]
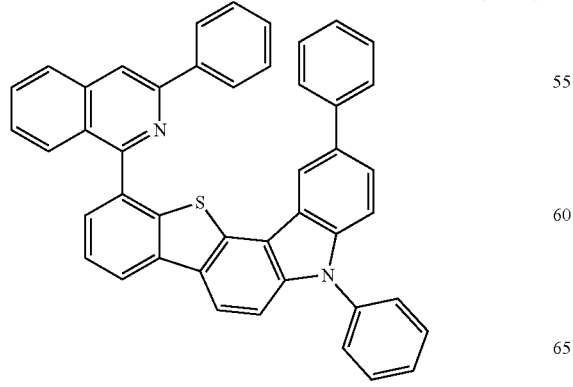
-continued
[B-174]
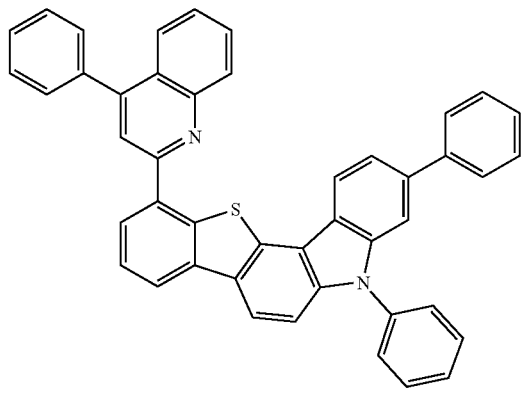
[B-175]
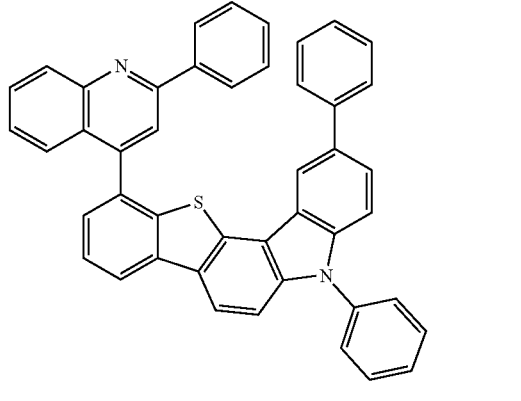
[B-176]
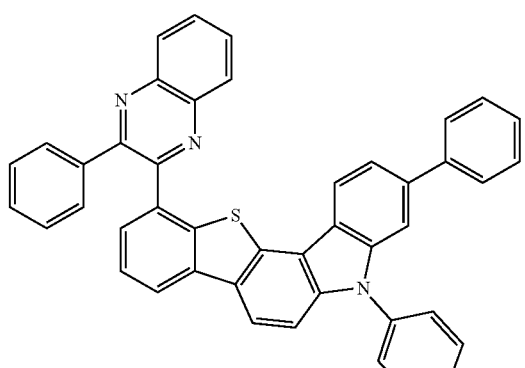
[B-177]
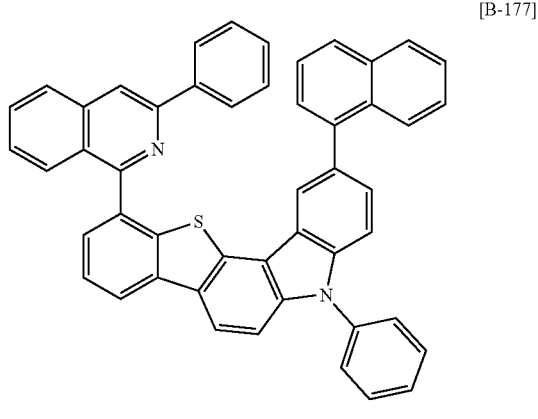

[B-178]
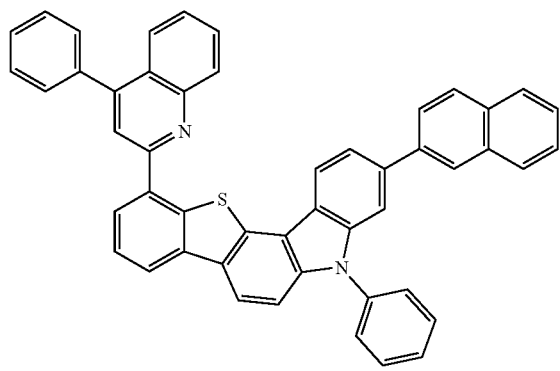
[B-179]
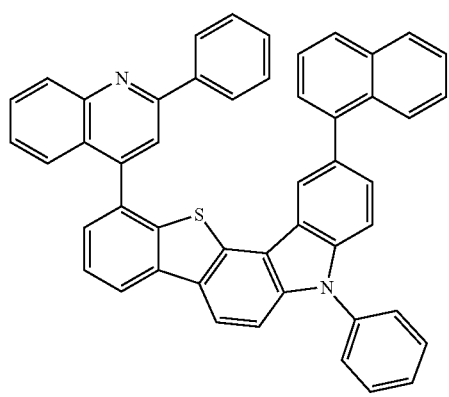
[B-180]
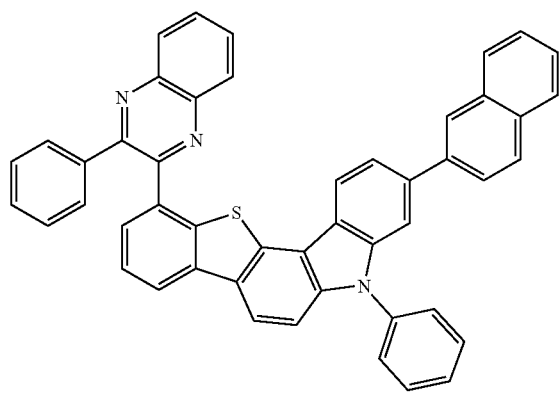
[B-181]
[B-182]
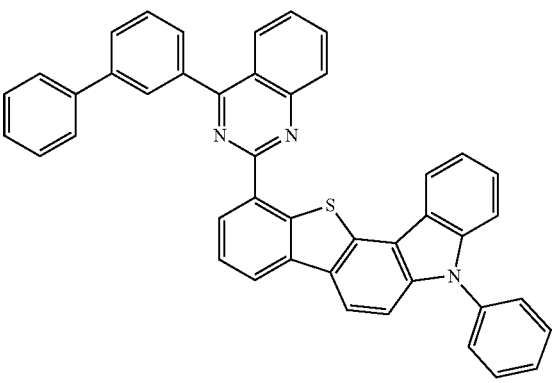
[B-183]
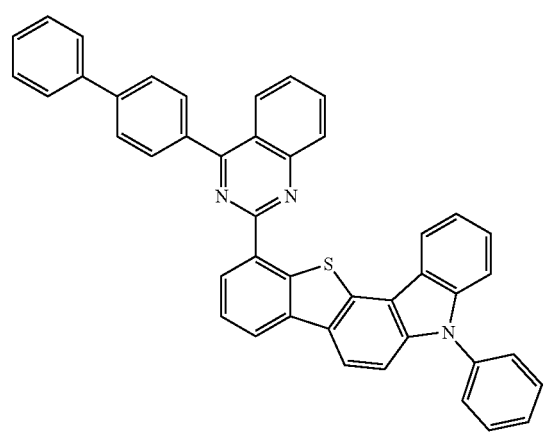
[B-184]
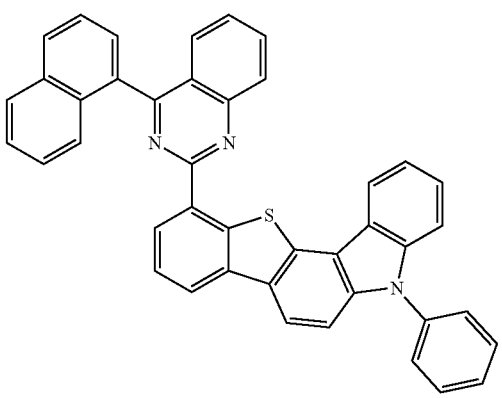

[B-185]
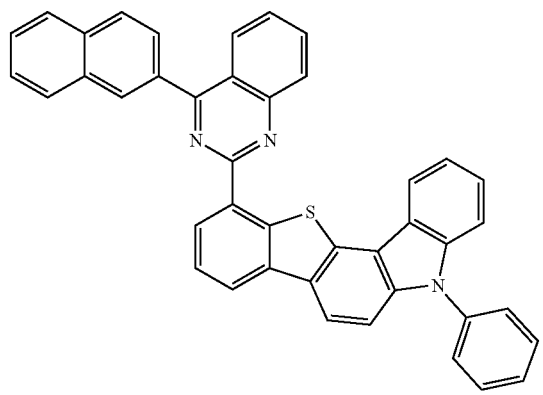
[B-188]
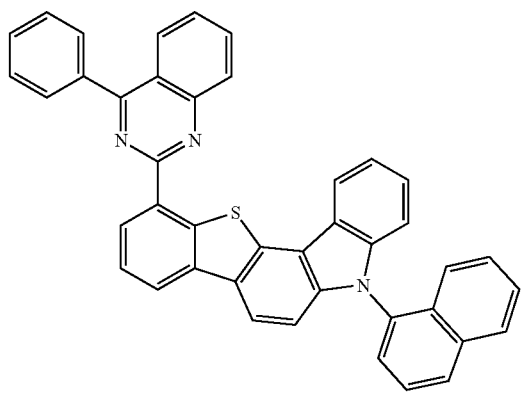
[B-186]
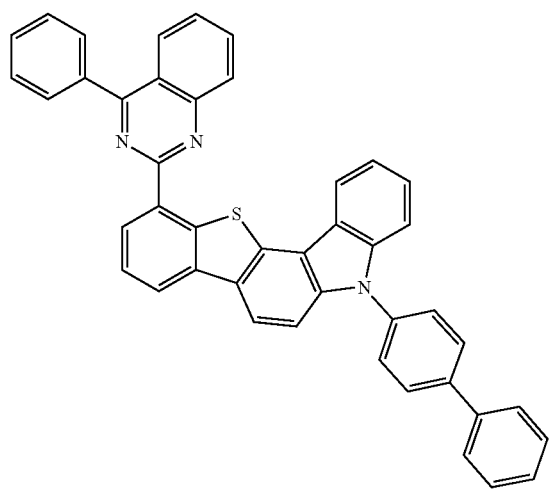
[B-189]
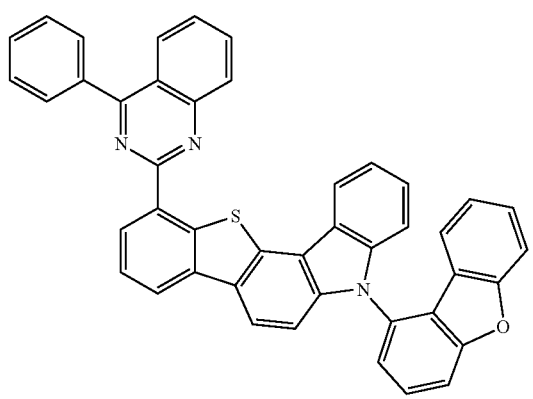
[B-187]
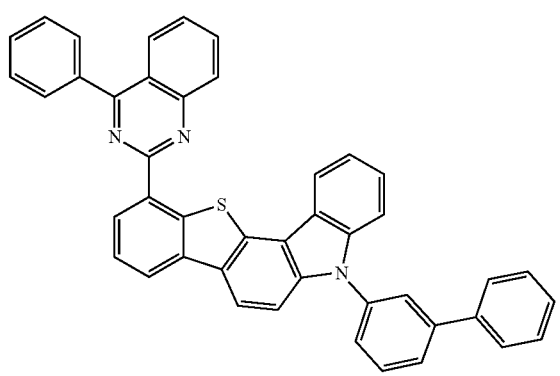
[B-190]
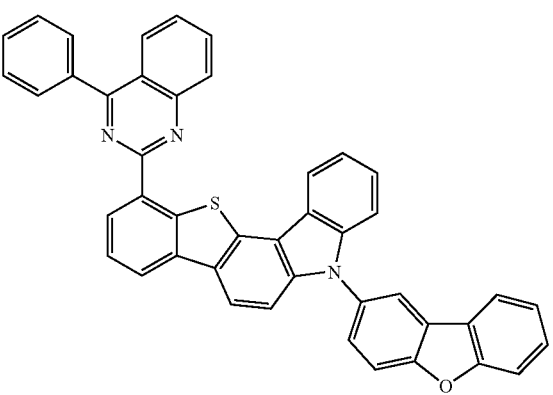

[B-191]
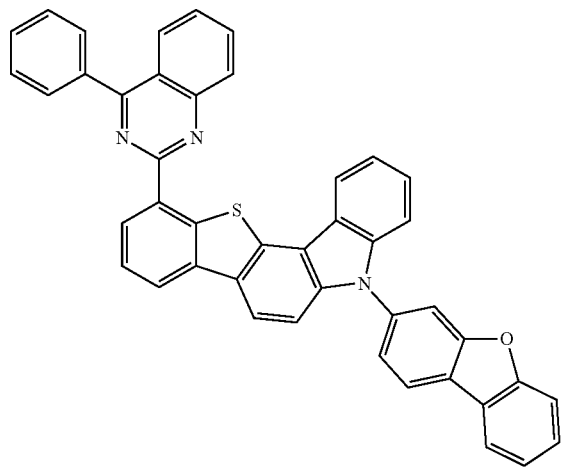
[B-192]
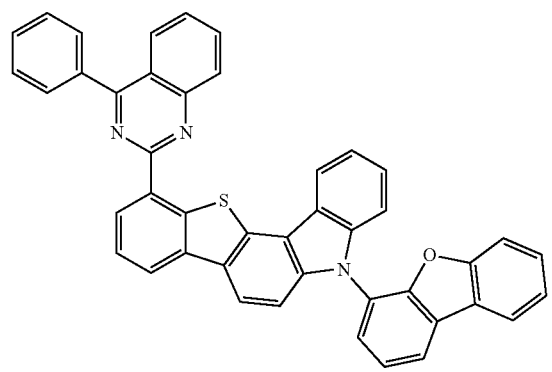
[B-193]
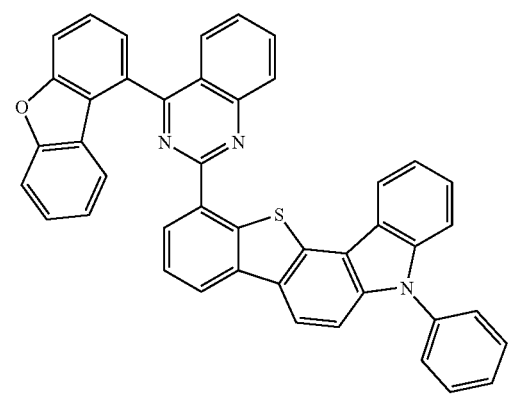
[B-194]
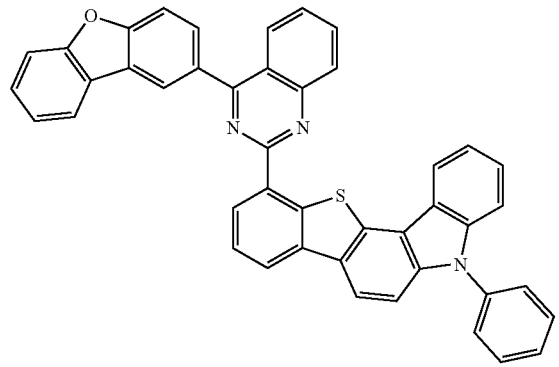
[B-195]
[B-196]
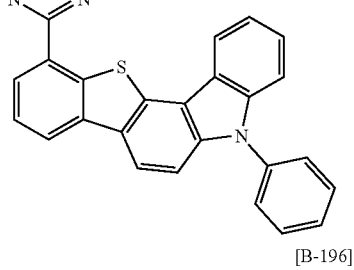
[B-197]
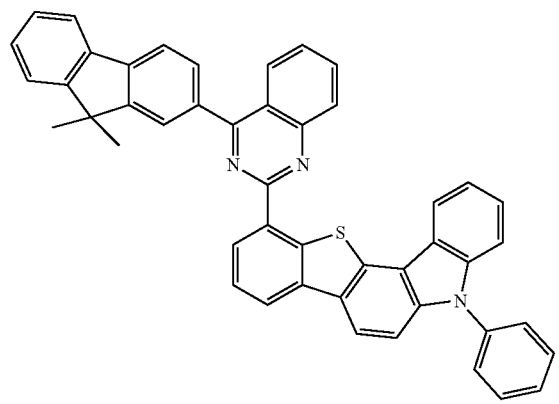

[B-198]
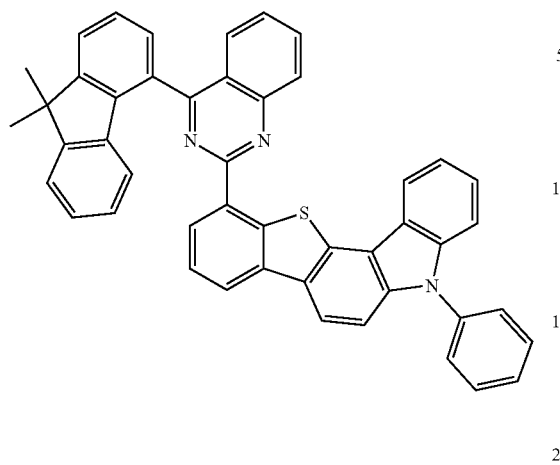
[B-199]
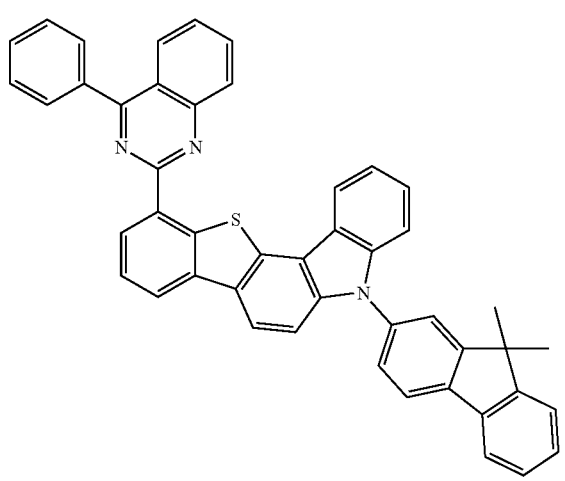
[B-200]
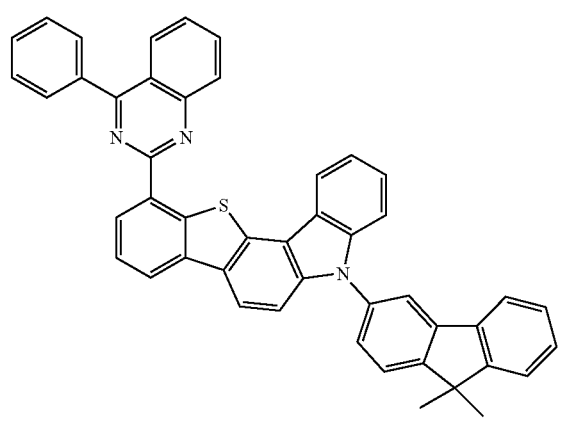
[B-201]
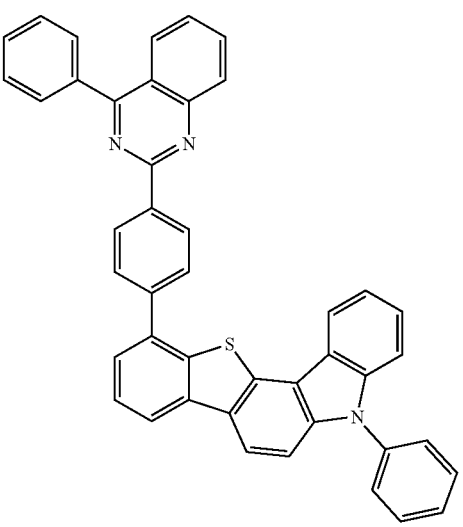
[B-202]
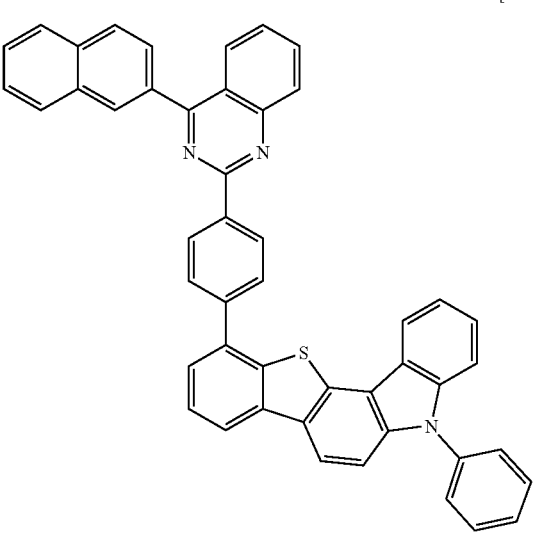
[B-203]
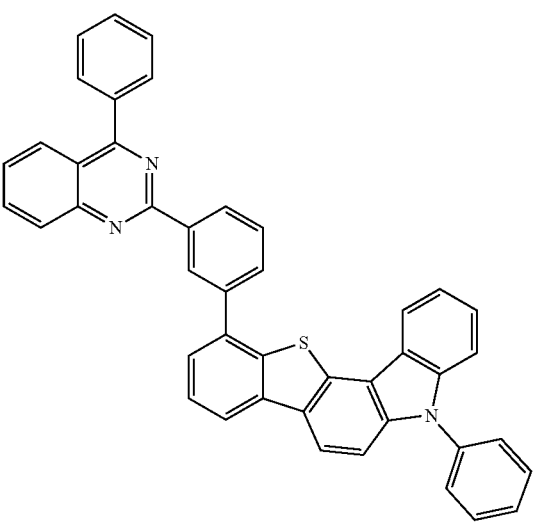

[B-204]
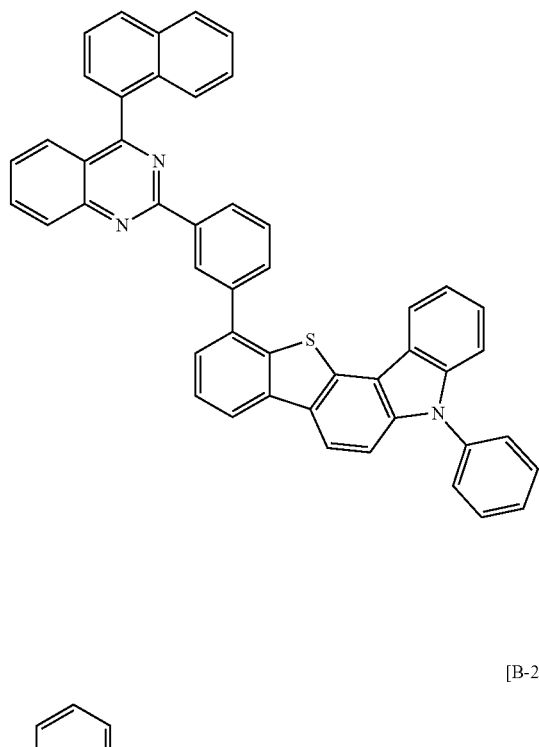

[B-205]
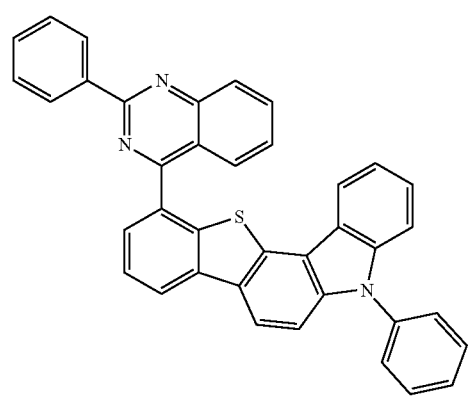

[B-206]
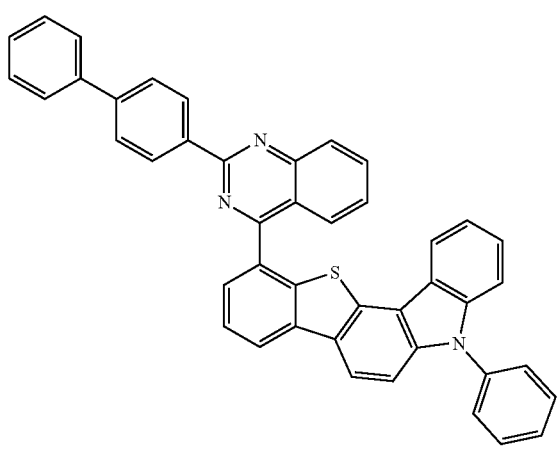

[B-207]
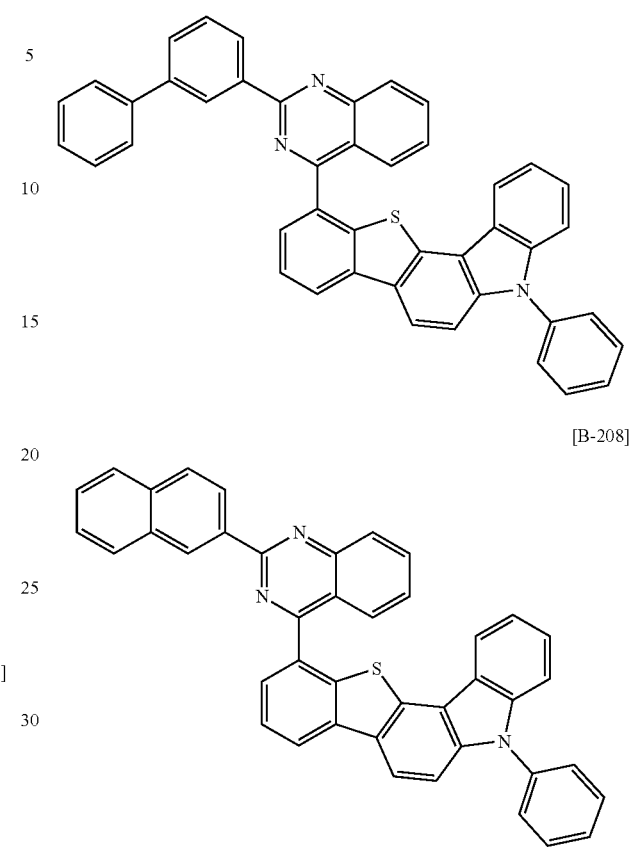

[B-208]

In an example embodiment of the present invention, second compound for an organic optoelectronic diode which is applied to an organic light emitting diode along with the aforementioned first compound for an organic optoelectronic diode as a form of a composition may be represented by Chemical Formula 2.

$Z^2$ and $Z^3$ of Chemical Formula 2 may independently be a substituted or unsubstituted C6 to C20 aryl group, for example a substituted or unsubstituted phenyl group, a substituted or unsubstituted biphenyl group, a substituted or unsubstituted terphenyl group, or a substituted or unsubstituted naphthyl group.

In an example embodiment of the present invention, m of Chemical Formula 2 may be an integer of 0 or 1 and for example Chemical Formula 2 may be selected from structures of Group II.

[Group II]

C-1
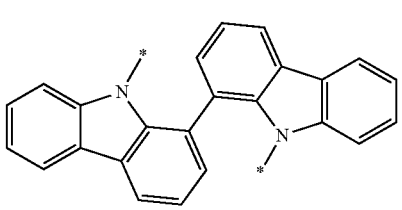

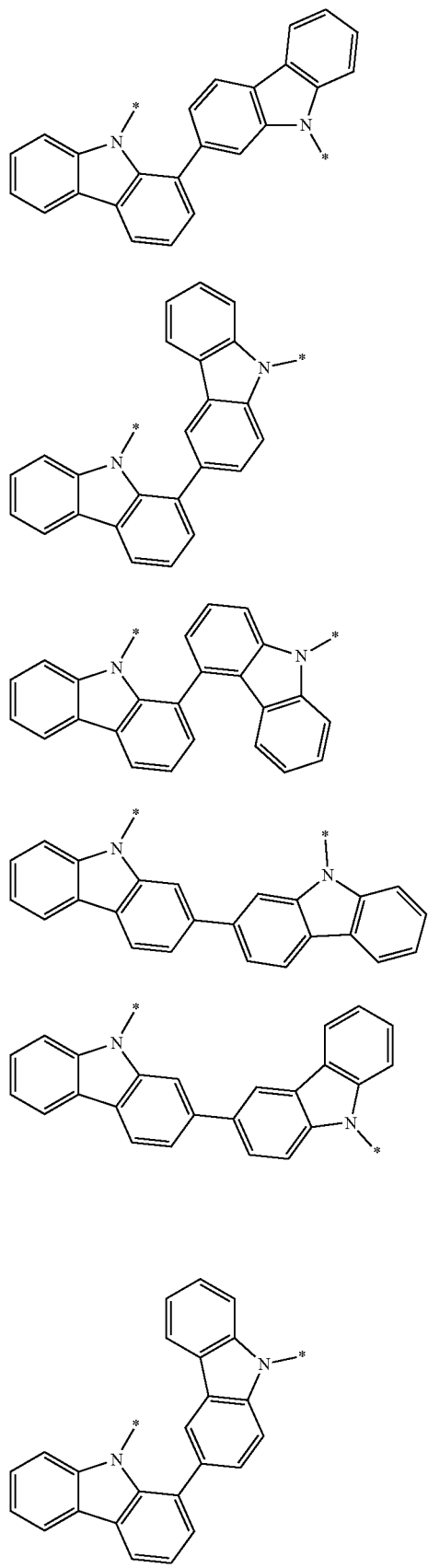
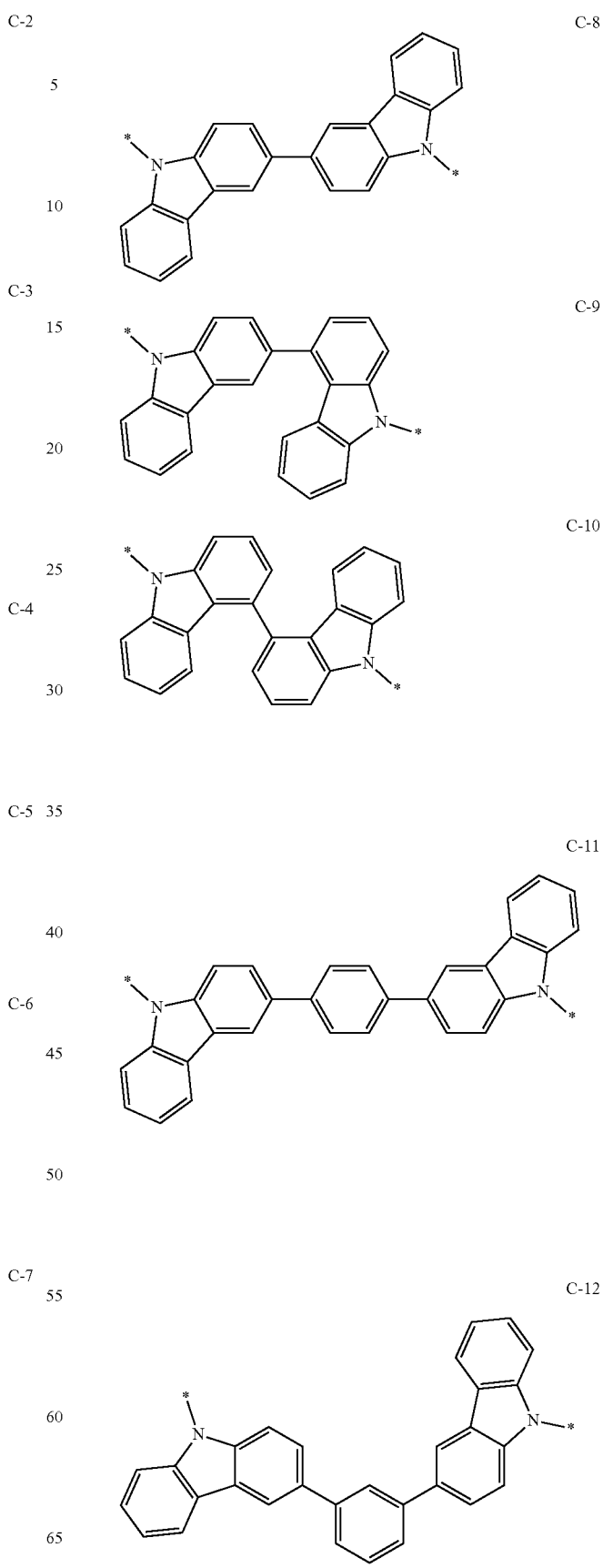

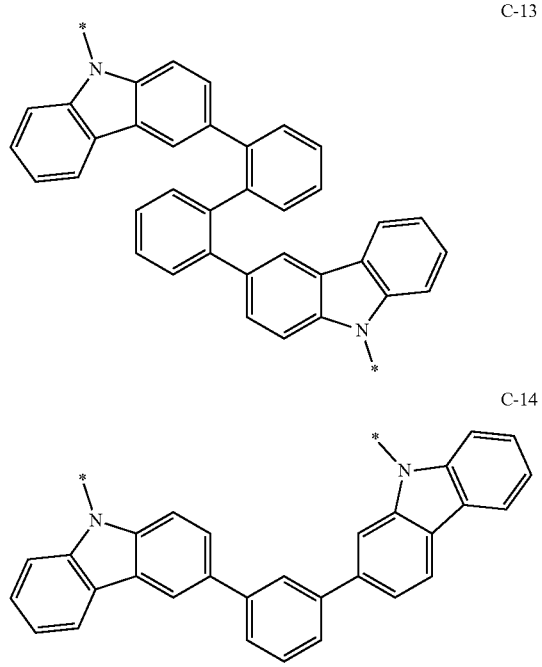
C-13
C-14
C-15
C-16
C-17
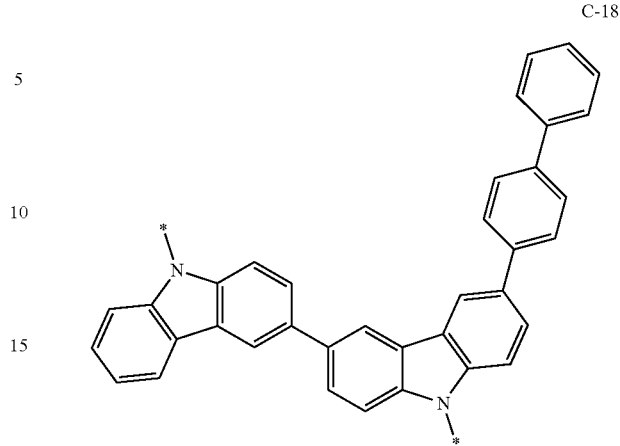
C-18
In Group II, * is each linking point with $Y^2$ and $Y^3$.
In a specific example embodiment of the present invention, Chemical Formula 2 may be one of structures of Group II, and *-$Y^2$—$Z^2$ and *-$Y^3$—$Z^3$ may independently be one of substituents of Group III.
[Group III]
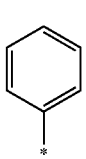
B-1
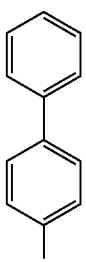
B-2
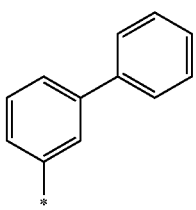
B-3
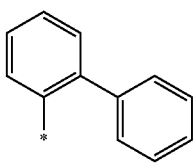
B-4
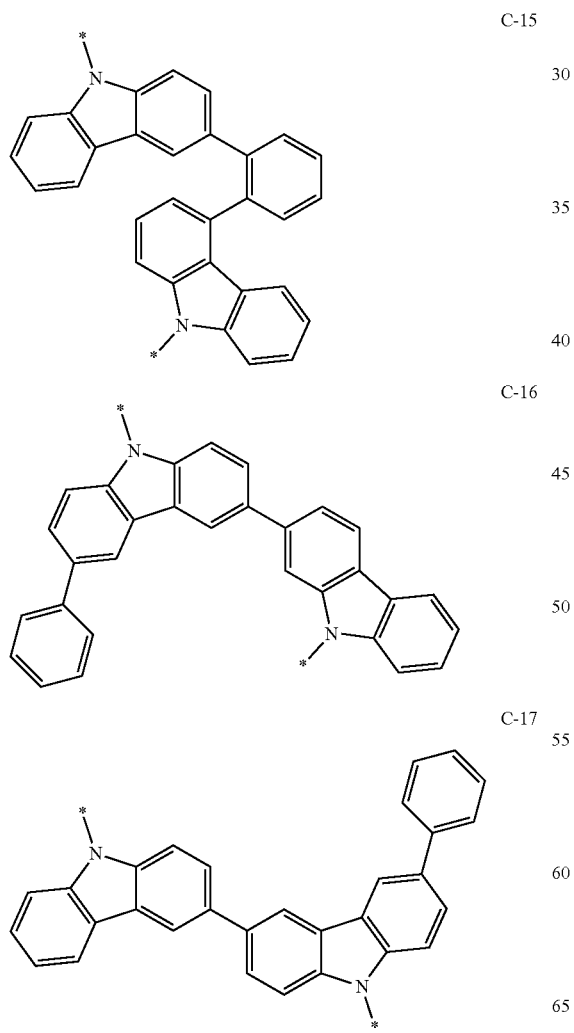

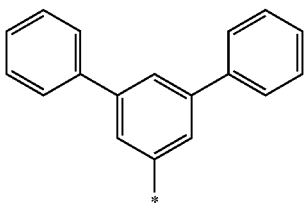
B-5

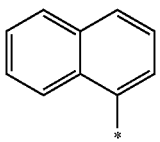
B-6

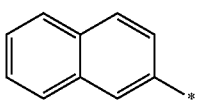
B-7

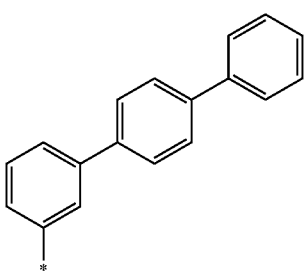
B-8

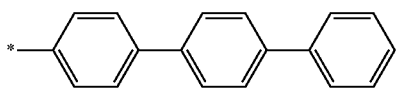
B-9

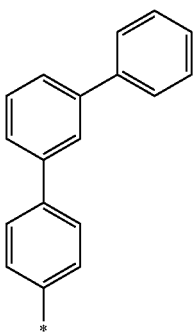
B-10

In Group III, * is a point at which it is linked with N of carbazole.

In a more specific example embodiment of the present invention, m of Chemical Formula 2 may be 0, and for example, Chemical Formula 2 may be represented by C-6 or C-8 of Group II, and in a the most specific example embodiment, Chemical Formula 2 may be C-8 of Group II.

In the most specific example embodiment of the present invention, Chemical Formula 2 may be represented by C-8 of Group II and *-$Y^2$—$Z^2$ and *-$Y^3$—$Z^3$ may independently be selected from B-1 to B-4 of Group III.

On the other hand, in an example embodiment of the present invention $R^5$ to $R^{10}$ of Chemical Formula 2 may independently be hydrogen, deuterium, or a substituted or unsubstituted C6 to C30 aryl group, more specifically $R^5$ to $R^{10}$ of Chemical Formula 2 may independently be hydrogen, deuterium, a substituted or unsubstituted phenyl group, or a substituted or unsubstituted naphthyl group, for example, $R^5$ to $R^{10}$ of Chemical Formula 2 may be all hydrogen; one of $R^5$ to $R^7$ of Chemical Formula 2 may be a phenyl group or a naphthyl group and $R^8$ to $R^{10}$ may be all hydrogen; or one of $R^5$ to $R^7$ of Chemical Formula 2 may be all hydrogen and one of $R^8$ to $R^{10}$ of Chemical Formula 2 may be a phenyl group or a naphthyl group; or one of $R^5$ to $R^7$ of Chemical Formula 2 may be a phenyl group or a naphthyl group and one of $R^8$ to $R^{10}$ of Chemical Formula 2 may be a phenyl group or a naphthyl group.

The aforementioned second compound for an organic optoelectronic diode represented by Chemical Formula 2 may be for example selected from compounds of Group 2, but is not limited thereto.

[Group 2]

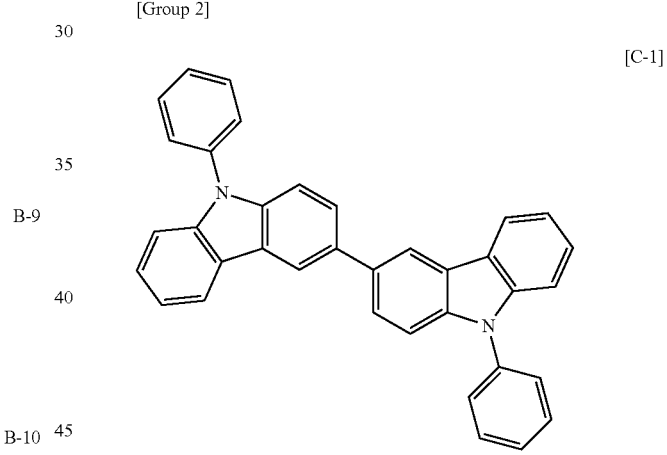
[C-1]

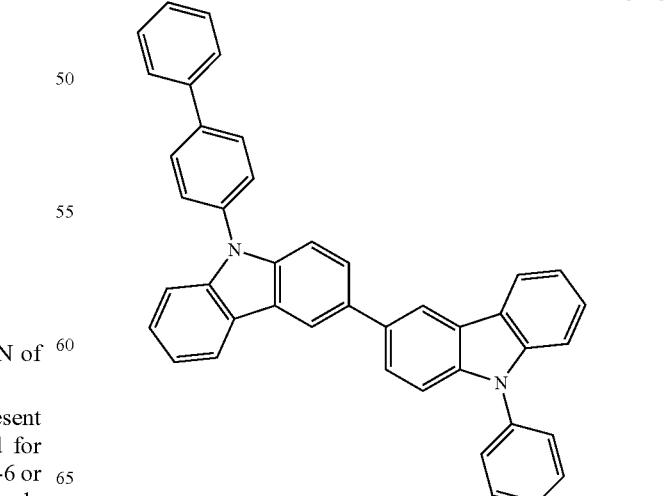
[C-2]

[C-3]
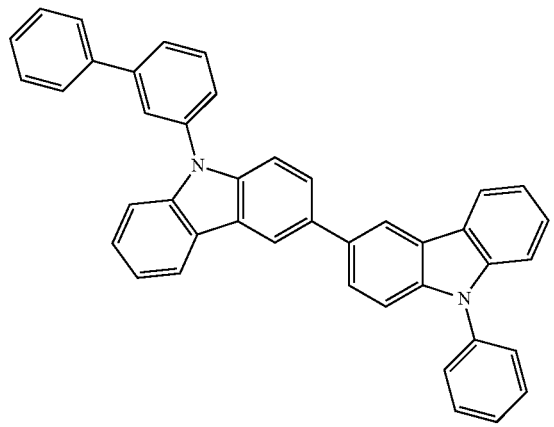
[C-4]
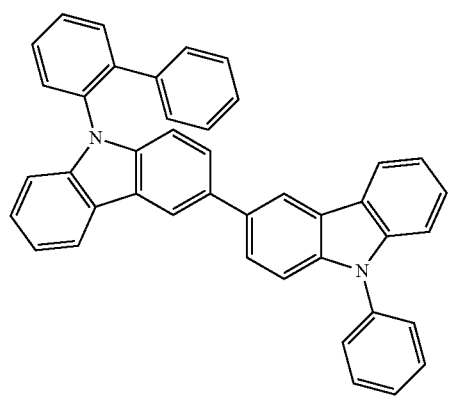
[C-5]
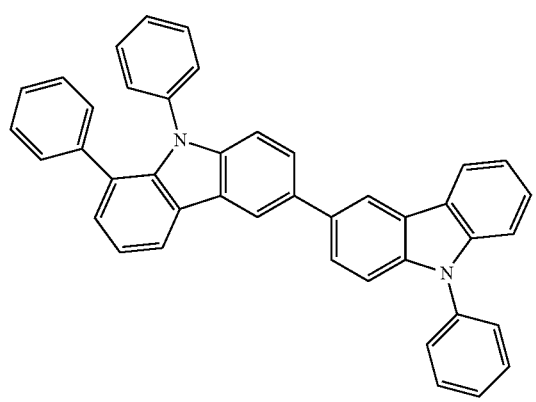
[C-6]
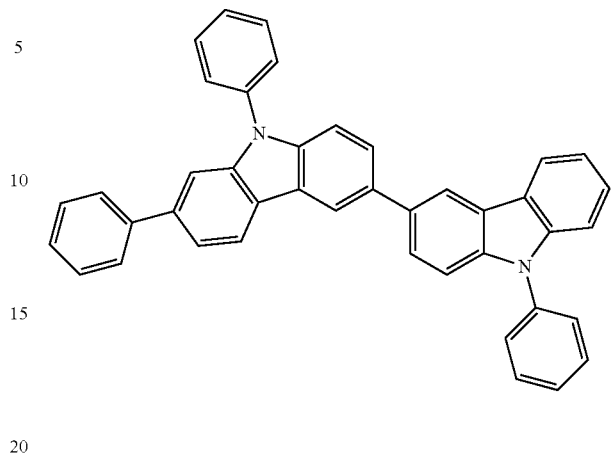
[C-7]
[C-8]
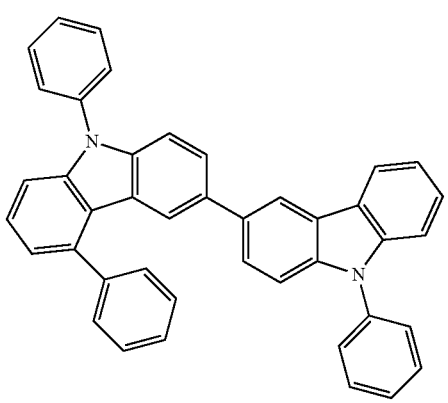

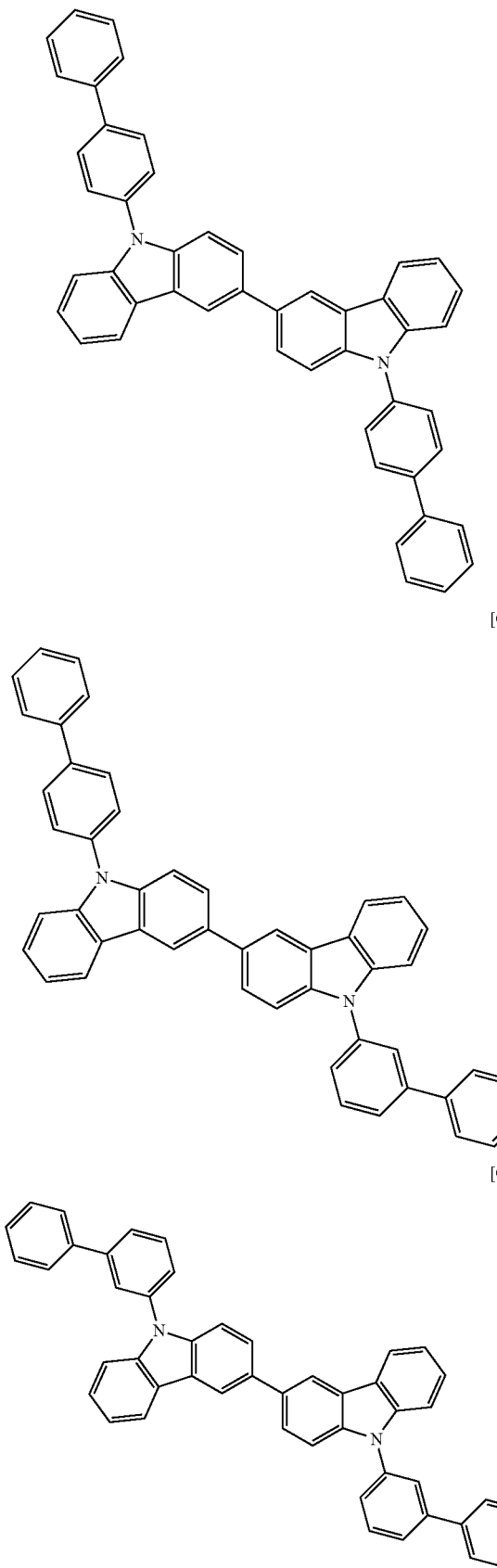
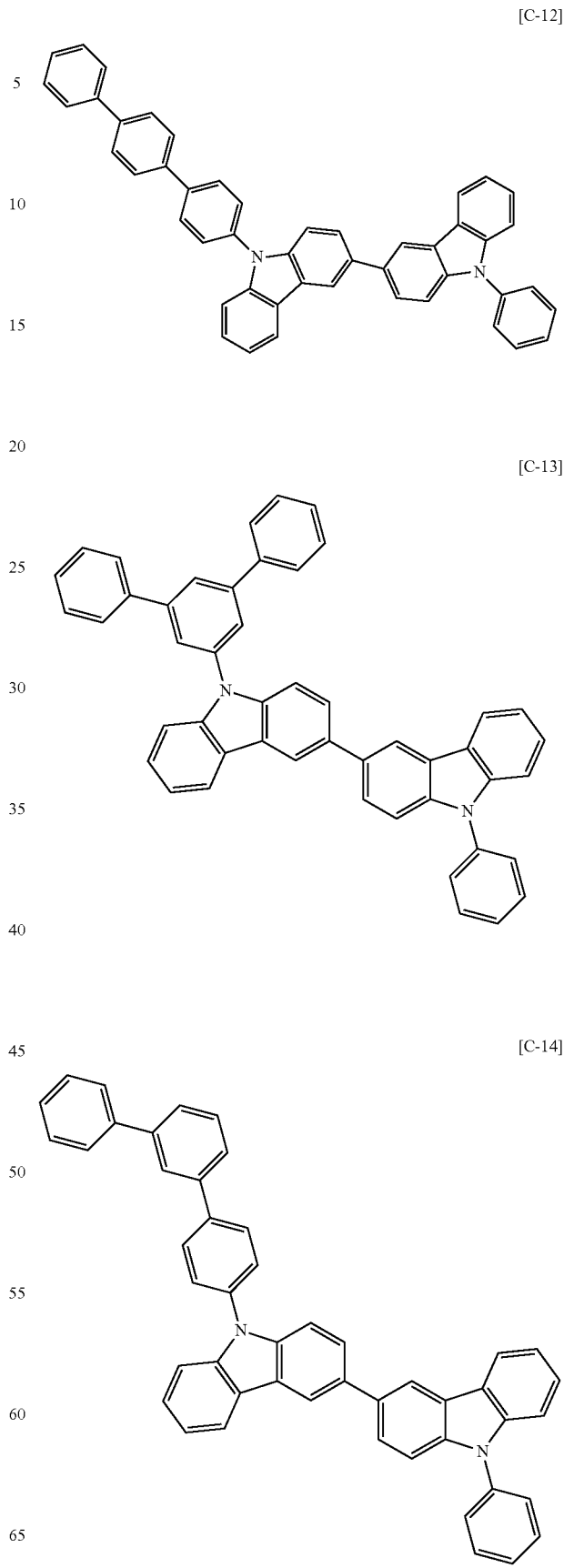

[C-15]
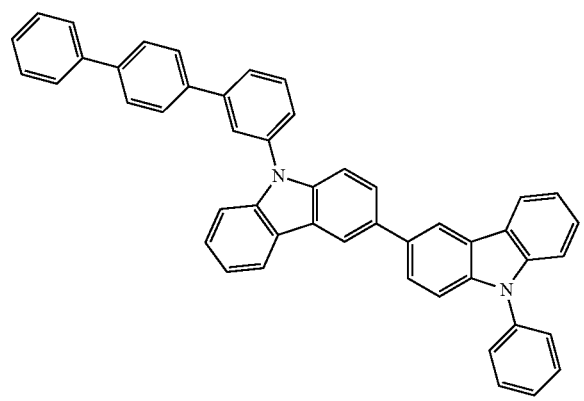
[C-16]
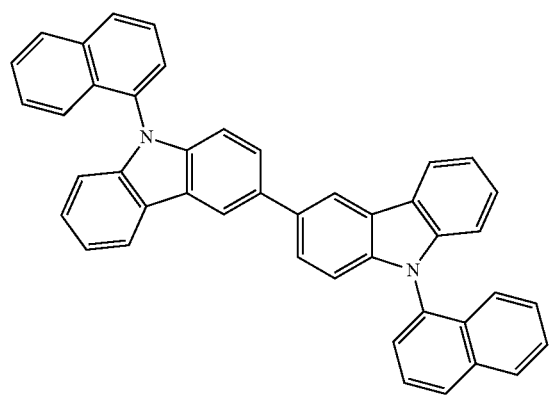
[C-17]
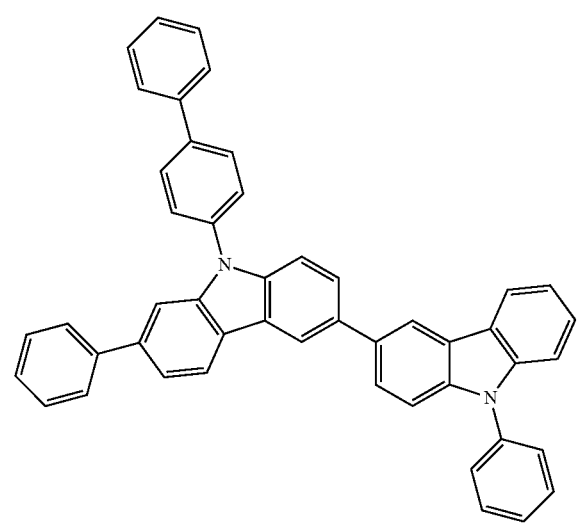
[C-18]
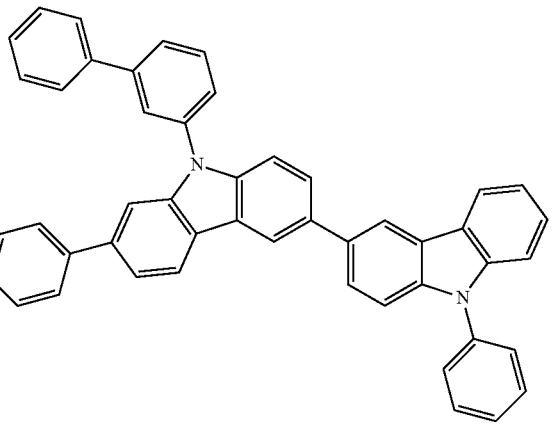
[C-19]
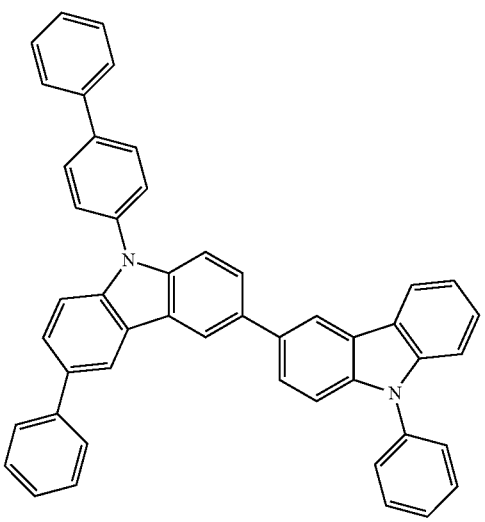
[C-20]
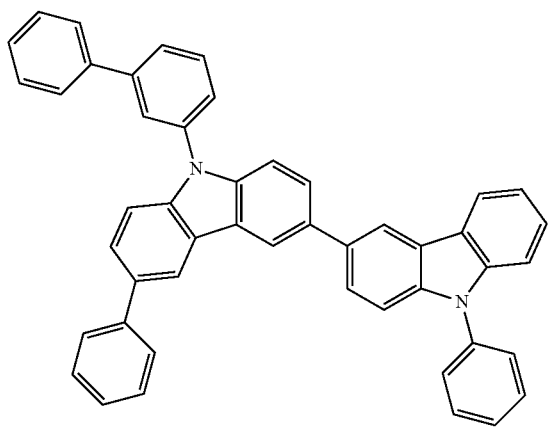

[C-21]
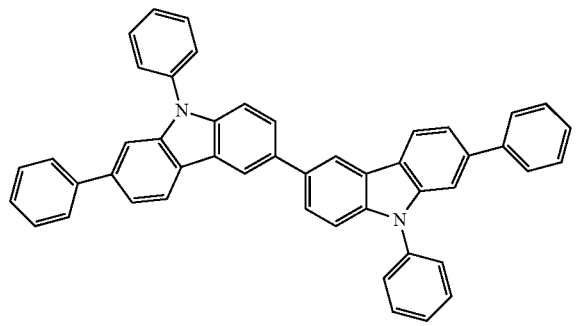
[C-22]
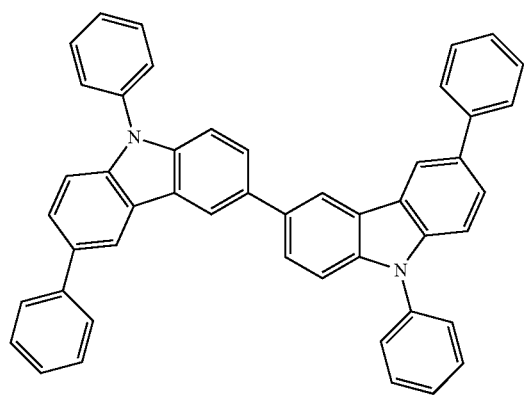
[C-23]
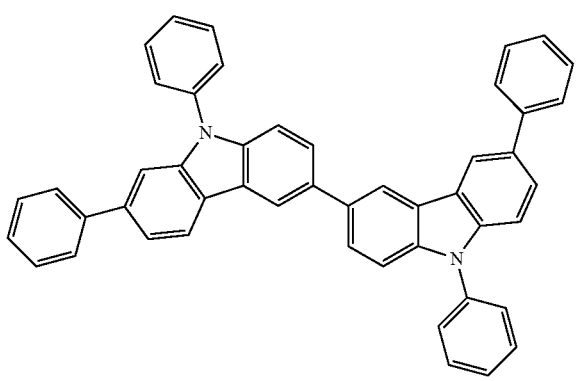
[C-24]
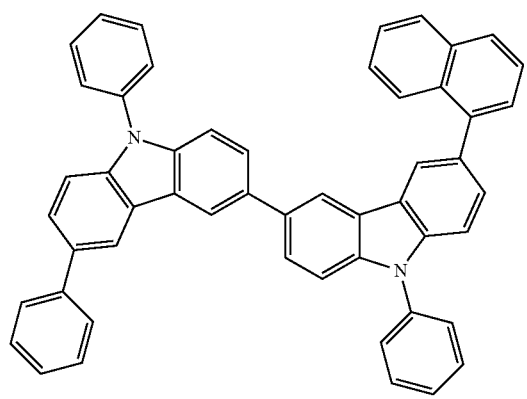
[C-25]
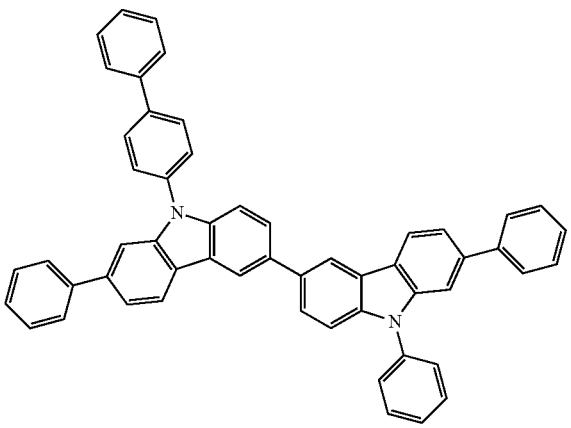
[C-26]
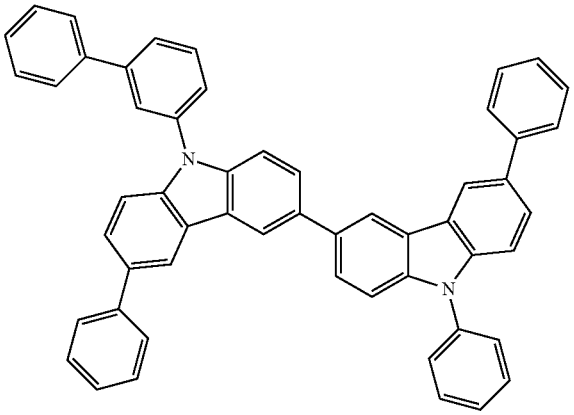
[C-27]
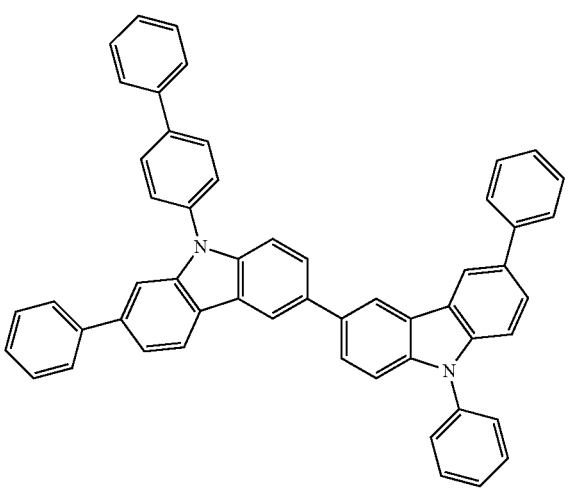

-continued
[C-28]
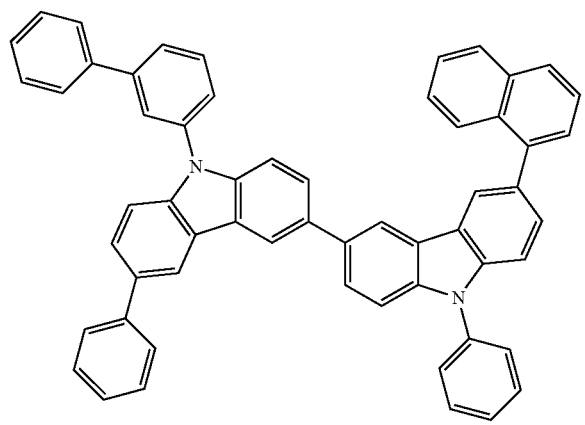
[C-29]
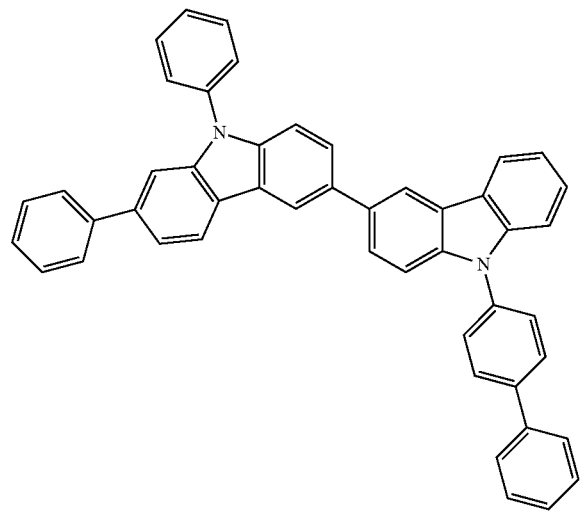
[C-30]
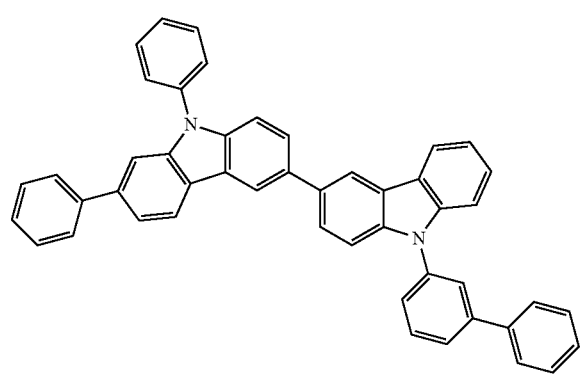
[C-31]
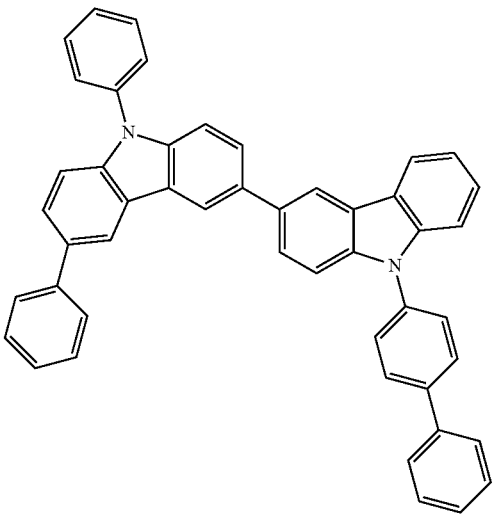
[C-32]
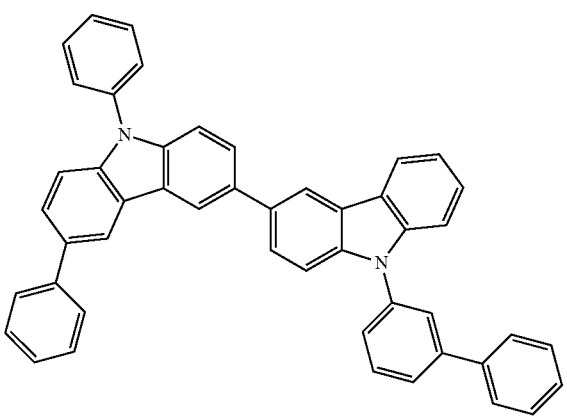
[C-33]
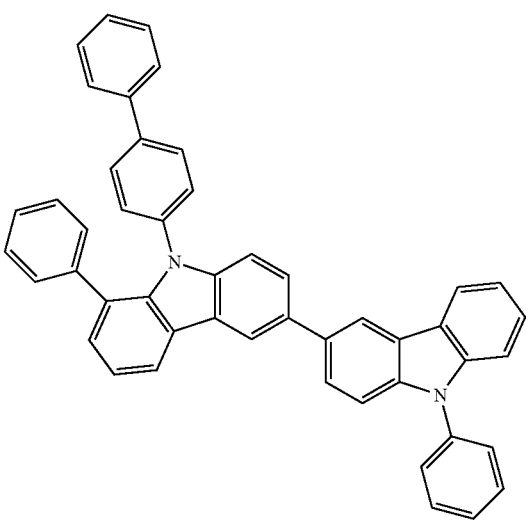

[C-34]
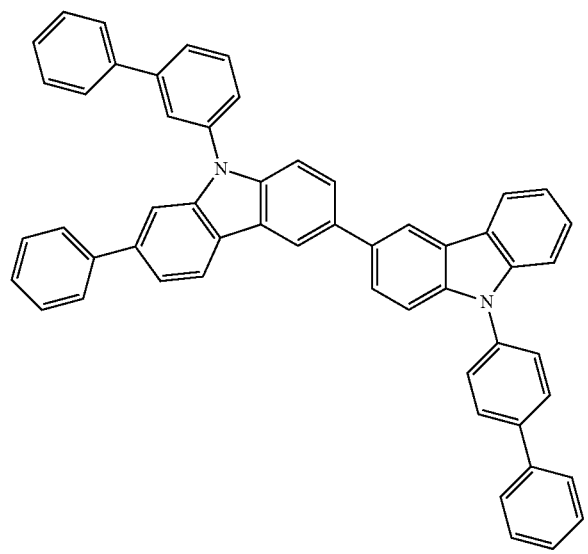
[C-35]
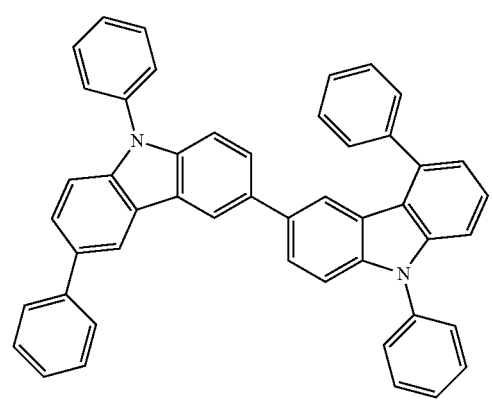
[C-36]
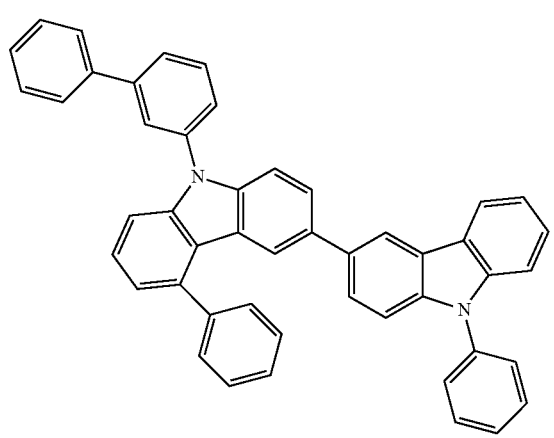
[C-37]
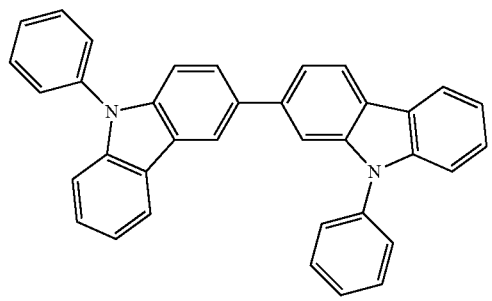
[C-38]
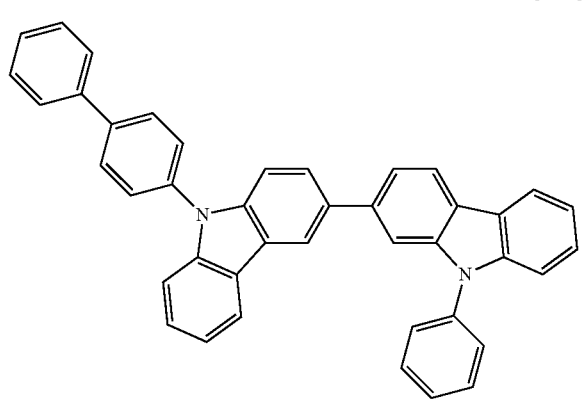
[C-39]
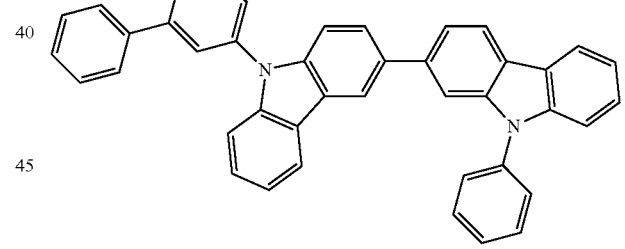
[C-40]
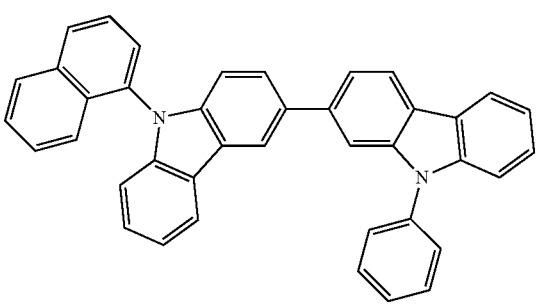

[C-41]
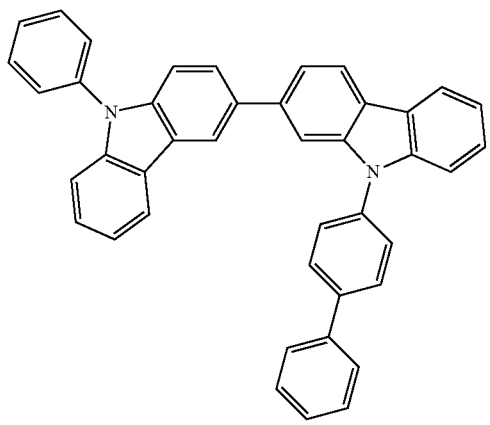
[C-45]
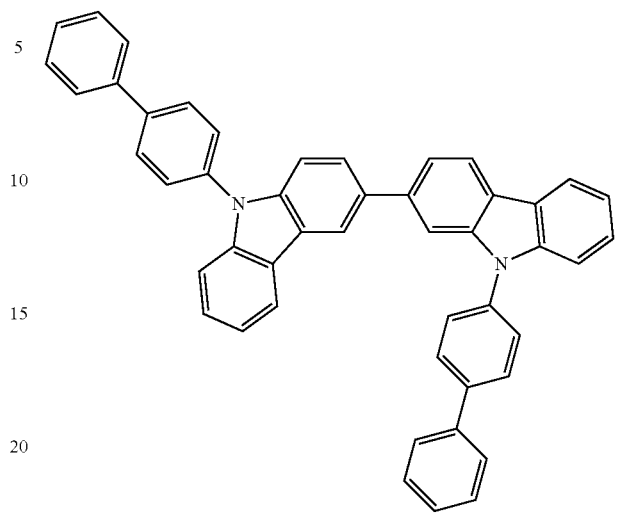
[C-42]
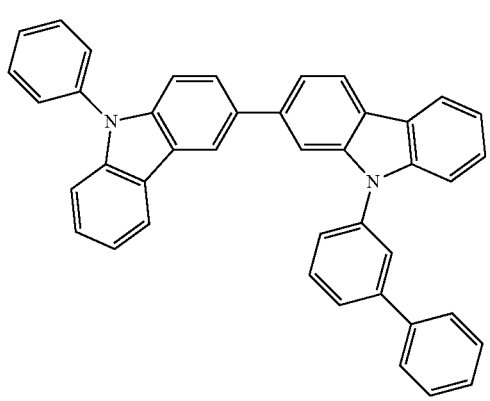
[C-46]
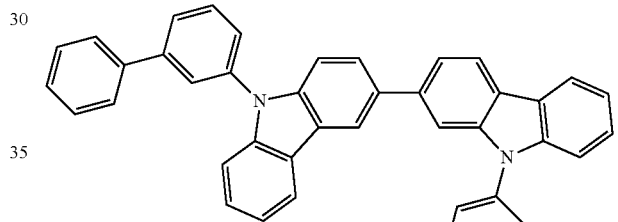
[C-43]
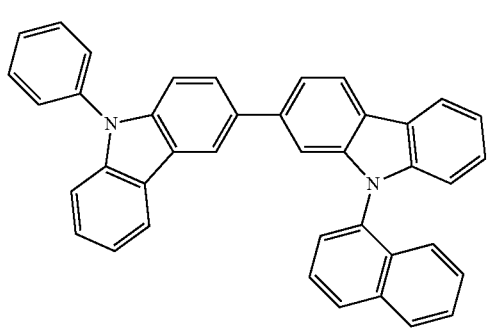
[C-47]
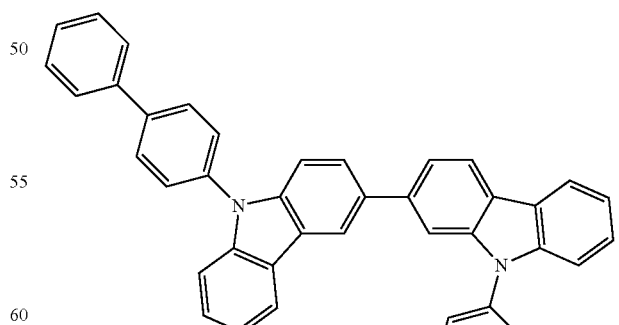
[C-44]
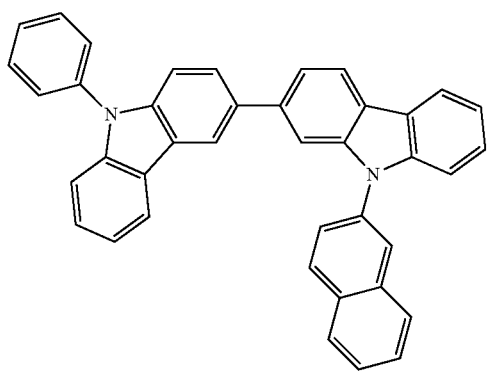

[C-48]
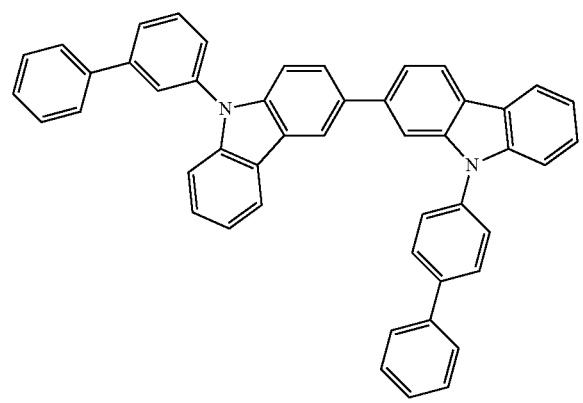
[C-49]
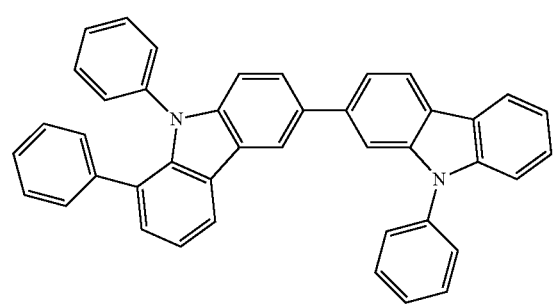
[C-50]
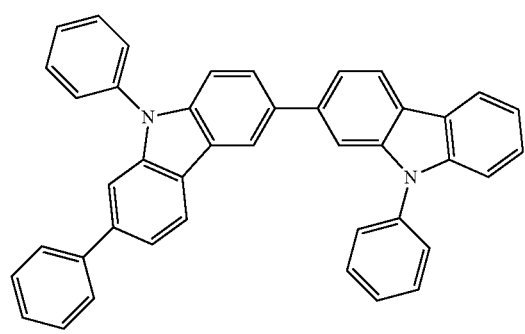
[C-51]
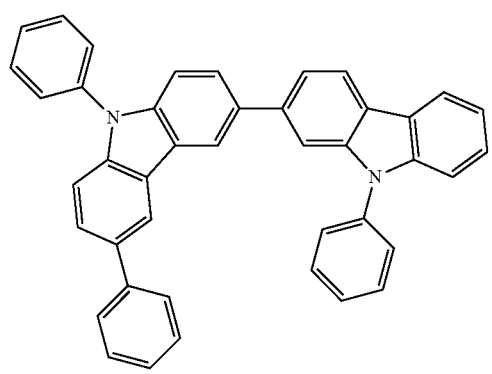
[C-52]
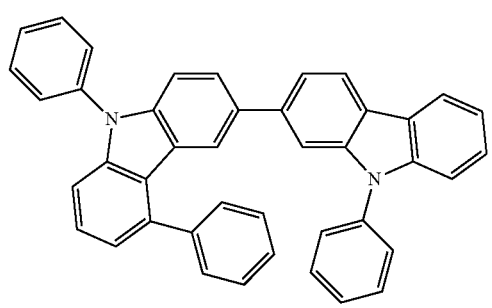
[C-53]
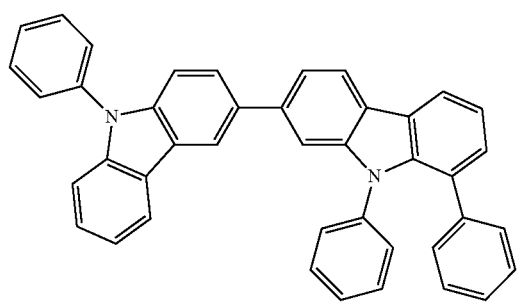
[C-54]
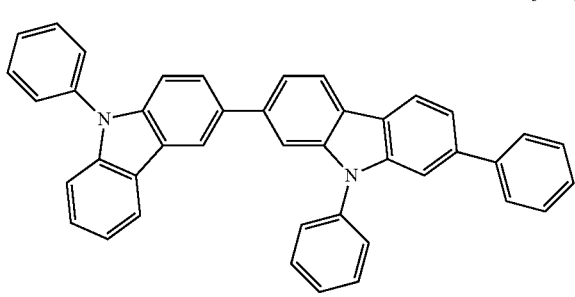
[C-55]
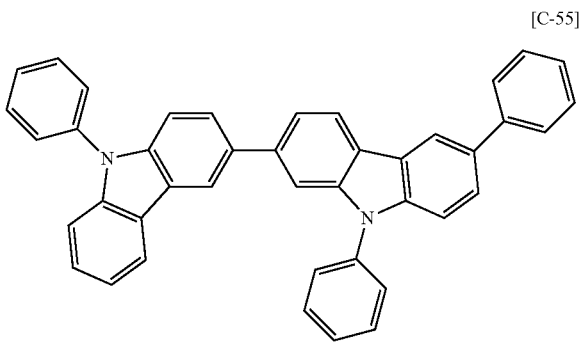

-continued

[C-56]

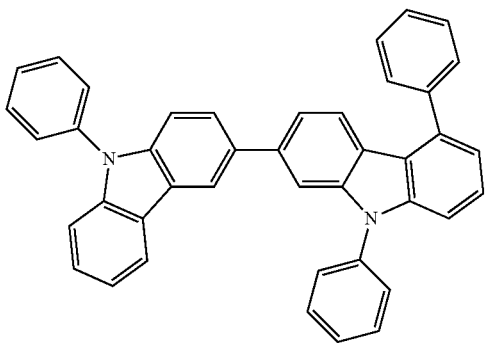

The second compound for the organic optoelectronic diode may increase charge mobility and stability and greatly improve luminance efficiency and life-span characteristics, when used with the first compound for the organic optoelectronic diode in a light emitting layer. In addition, the charge mobility may be adjusted by controlling a ratio between the second compound for the organic optoelectronic diode and the first compound for the organic optoelectronic diode.

For example, they may be included in a weight ratio of about 1:9 to 9:1, specifically about 2:8 to 8:2, about 3:7 to 7:3, about 4:6 to 6:4, or about 5:5, and for example the first compound for the organic optoelectronic diode and the second compound for the organic optoelectronic diode may be included in a range of about 3:7. Within the ranges, efficiency and life-span may be improved simultaneously.

The composition may include at least one organic compound in addition to the aforementioned first compound for the organic optoelectronic diode and second compound for the organic optoelectronic diode.

The composition for the organic optoelectronic diode may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$L_2MX$ [Chemical Formula Z]

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

Another embodiment provides a compound for an organic optoelectronic diode represented by Chemical Formula 1-1. The compound for the organic optoelectronic diode represented by Chemical Formula 1-1 is the same as described above.

Hereinafter, an organic optoelectronic diode including the aforementioned composition for the organic optoelectronic diode is described.

The organic optoelectronic diode according to another embodiment includes an anode and a cathode facing each other and at least one organic layer disposed between the anode and the cathode, wherein the organic layer includes the aforementioned composition for the organic optoelectronic diode.

For example, the organic layer may include a light emitting layer, and the light emitting layer may include the composition for the organic optoelectronic diode of the present invention.

Specifically, the composition for the organic optoelectronic diode may be included as a host, for example a green host or a red host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the composition for the organic optoelectronic diode.

The organic optoelectronic diode may be any element to convert electrical energy into photoenergy and vice versa without particular limitation, and may be, for example an organic optoelectronic diode, an organic light emitting diode, an organic solar cell, and an organic photo conductor drum.

Herein, an organic light emitting diode as one example of an organic optoelectronic diode is described referring to drawings.

FIGS. 1 and 2 are cross-sectional views of an organic light emitting diode according to embodiments.

Referring to FIG. 1, an organic optoelectronic diode 100 according to an embodiment includes an anode 120 and a cathode 110 facing each other and an organic layer 105 disposed between the anode 120 and cathode 110.

The anode 120 may be made of a conductor having a large work function to help hole injection and may be for example made of a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or SnO$_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO$_2$/Al, LiF/Ca, LiF/Al, and BaF$_2$/Ca, but is not limited thereto.

The organic layer 105 includes a light emitting layer 130 including the aforementioned composition for the organic optoelectronic diode.

FIG. 2 is a cross-sectional view showing an organic light emitting diode according to another embodiment.

Referring to FIG. 2, an organic light emitting diode 200 further include a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The composition for the organic optoelectronic diode of the present invention may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The aforementioned organic light emitting diode may be applied to an organic light emitting diode display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there in no particular comment or were synthesized by known methods.

Preparation of Compound for Organic Optoelectronic Diode

The compound as one specific examples of the present invention was synthesized through the following steps.

First Compound for Organic Optoelectronic Diode

Synthesis Example 1: Synthesis of Intermediate M-1

Reaction Scheme 1

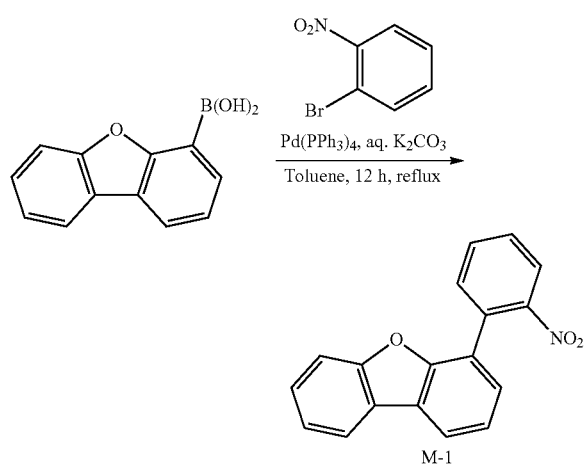

20 g (94.3 mmol) of 4-dibenzofuranboronic acid and 19.05 g (94.3 mmol) of 2-bromonitro-benzene were put in a round-bottomed flask, 313 ml of toluene was added thereto to dissolve them, and 117 ml of an aqueous solution prepared by dissolving 19.5 g (141.5 mmol) of potassium carbonate was added thereto and then, stirred. Subsequently, 1.09 g (0.94 mmol) of tetrakistriphenyl phosphine palladium was added thereto and then, refluxed and stirred under a nitrogen atmosphere for 12 hours. When a reaction was complete, an extraction solution obtained by performing extraction with ethylacetate was dried with magnesium sulfate and filtered, and a filtrate therefrom was concentrated under a reduced pressure. A product therefrom was purified through silica gel column chromatography with n-hexane/dichloromethane (a volume ratio of 7:3) to obtain 25.4 g of Intermediate M-1 as a target compound (a yield=93%).

LC-Mass (theoretical value: 289.07 g/mol, measured value: M+1=290.16 g/mol)

Synthesis Example 2: Synthesis of Intermediate M-2

Reaction Scheme 2

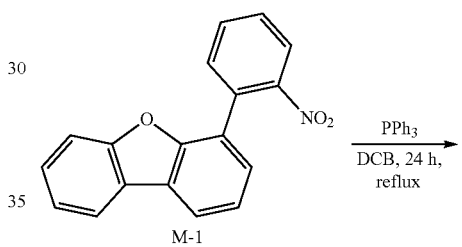

25 g (86.4 mmol) of Intermediate M-1 and 45.3 g (173 mmol) of triphenylphosphine were put in a round-bottomed flask, and 260 ml of dichlorobenzene was added thereto to dissolve them and then, stirred under a nitrogen atmosphere for 24 hours at 170° C. When a reaction was complete, an extraction solution obtained by performing an extraction with toluene and distilled water was dried with magnesium sulfate and filtered, and then, a filtrate therefrom was concentrated under a reduced pressure. A product therefrom was purified through silica gel column chromatography with n-hexane/dichloromethane (a volume ratio of 7:3) to obtain 16.7 g of Intermediate M-2 as a target compound (a yield=75%).

LC-Mass (theoretical value: 257.08 g/mol, measured value: M+1=258.21 g/mol)

Synthesis Example 3: Synthesis of Intermediate M-3

Reaction Scheme 3

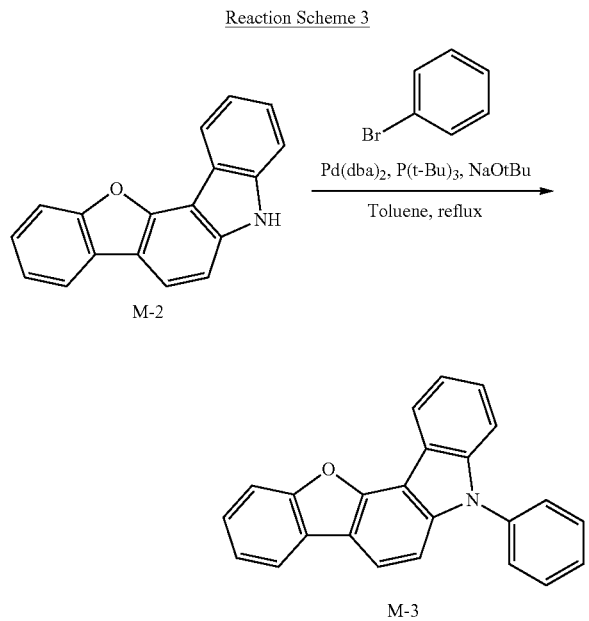

16 g (62.2 mmol) of Intermediate M-2, 14.6 g (93.3 mmol) of bromobenzene, 9.0 g (93.3 mmol) of sodium t-butoxide were put in a round-bottomed flask, and 190 ml of toluene was added thereto to dissolve them. Subsequently, 1.07 g (1.87 mmol) of Pd(dba)₂ and 1.13 g (5.60 mmol) of tri-tertiary-butylphosphine were sequentially added thereto and then, refluxed and stirred under a nitrogen atmosphere for 12 hours. When a reaction was complete, after performing an extraction with toluene and distilled water, an organic layer therefrom was dried with magnesium sulfate and filtered, and a filtrate therefrom was concentrated under a reduced pressure. A product therefrom was purified through silica gel column chromatography with n-hexane/dichloromethane (a volume ratio of 8:2) to obtain 17.6 g of M-3 (a yield=85%) as a target compound.

LC-Mass (theoretical value: 333.12 g/mol, measured value: M+1=334.16 g/mol)

Synthesis Example 4: Synthesis of Intermediate M-4

Reaction Scheme 4

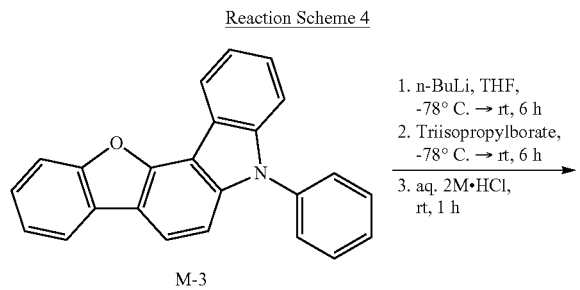

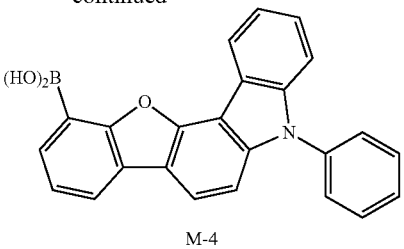

21.1 g (63.3 mmol) of M-3 was added to 190 ml of anhydrous tetrahydrofuran in a round-bottomed flask which was heated and dried under a reduced pressure and then, dissolved therein and cooled down to −20° C. and stirred under a nitrogen atmosphere. Subsequently, 31 ml (76 mmol) of a 2.5 M n-butyllithium normal hexane solution was slowly added thereto and stirred at room temperature under a nitrogen atmosphere for 6 hours. The reaction solution was cooled down to −20° C., and 14.3 g (76 mmol) of triisopropylborate was slowly added thereto and then, stirred at room temperature under a nitrogen atmosphere for 6 hours. The reaction solution was cooled down to 0° C., an amount of distilled water was added thereto to complete a reaction, 114 ml of a 2.0 M hydrochloric acid aqueous solution was added thereto, an extraction solution obtained by using diethylether was dried with magnesium sulfate and filtered, and a filtrate therefrom was concentrated under a reduced pressure. The residue was dissolved in acetone, and n-hexane was added thereto for recrystallization. A solid produced therein was filtered under a reduced pressure to obtain 17.0 g of Intermediate M-4 as a target compound (a yield=71%).

LC-Mass (theoretical value: 377.12 g/mol, measured value: M+1=378.15 g/mol)

Synthesis Example 5: Synthesis of Intermediate M-5

Reaction Scheme 5

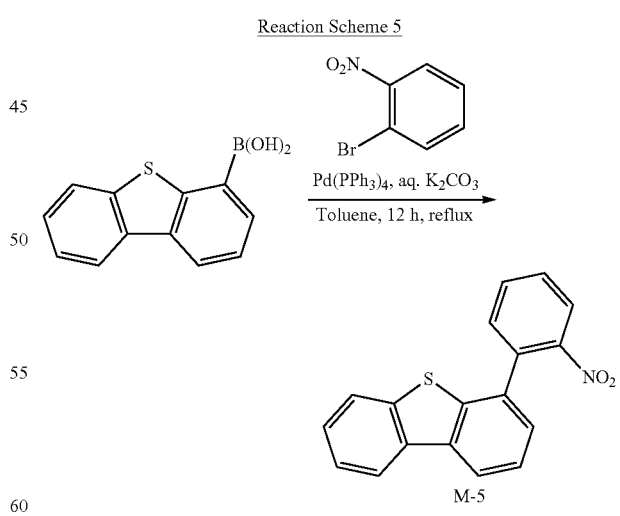

27.4 g of Intermediate M-5 (a yield=95%) was obtained according to the same method as Synthesis Example 1 by using 21.5 g (94.3 mmol) of 4-dibenzothiopheneboronic acid instead of 4-dibenzofuran boronic acid.

LC-Mass (theoretical value: 305.05 g/mol, measured value: M+1=306.29 g/mol)

Synthesis Example 6: Synthesis of Intermediate M-6

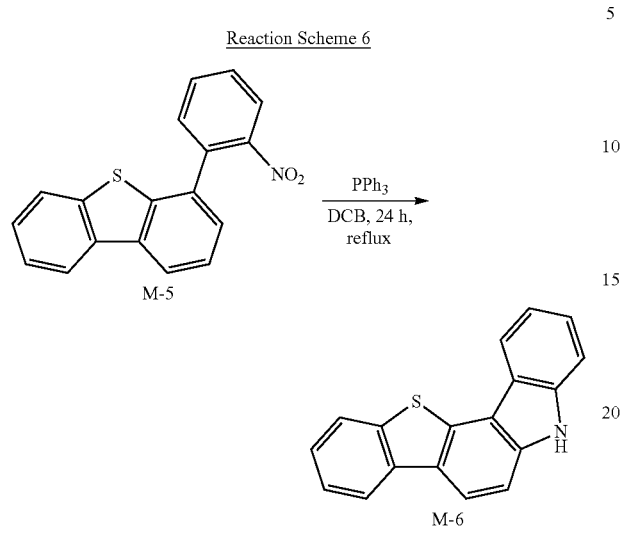

17.5 g of Intermediate M-6 as a target compound (a yield=74%) was obtained according to the same method as Synthesis Example 2 by using 26.4 g (86.4 mmol) of Intermediate M-5 instead of Intermediate M-1.

LC-Mass (theoretical value: 273.06 g/mol, measured value: M+1=274.19 g/mol)

Synthesis Example 7: Synthesis of Intermediate M-7

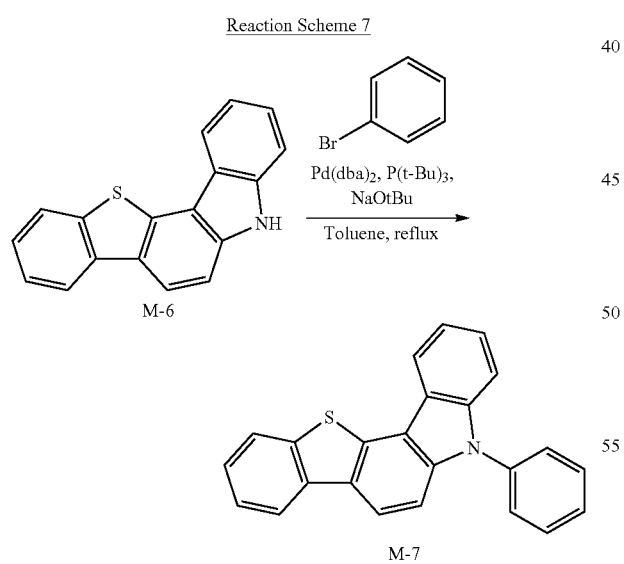

18 g of M-7 as a target compound was obtained according to the same method as Synthesis Example 3 by using 17 g (62.2 mmol) of Intermediate M-6 instead of Intermediate M-2 (a yield=83%).

LC-Mass (theoretical value: 349.09 g/mol, measured value: M+1=350.13 g/mol)

Synthesis Example 8: Synthesis of Intermediate M-8

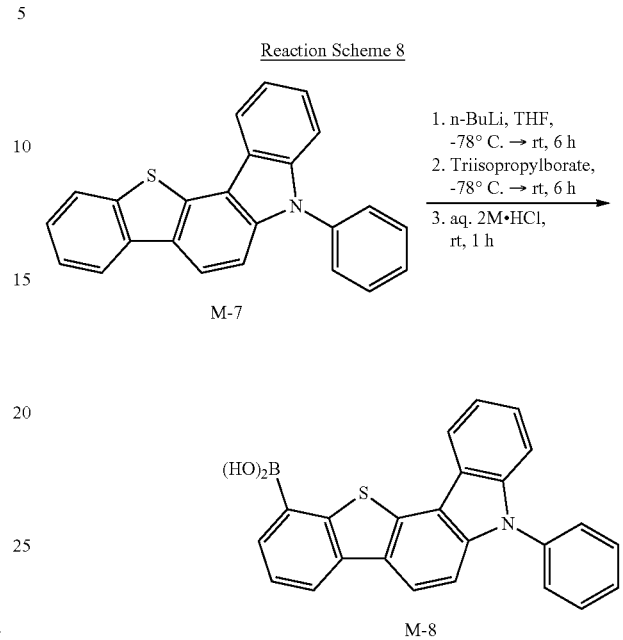

18.4 g of Intermediate M-8 as a target compound was obtained according to the same method as Synthesis Example 4 by using 22.1 g (63.3 mmol) of Intermediate M-7 instead of Intermediate M-3 (a yield=74%).

LC-Mass (theoretical value: 393.10 g/mol, measured value: M+1=394.21 g/mol)

Synthesis Example 9: Synthesis of Compound A-101

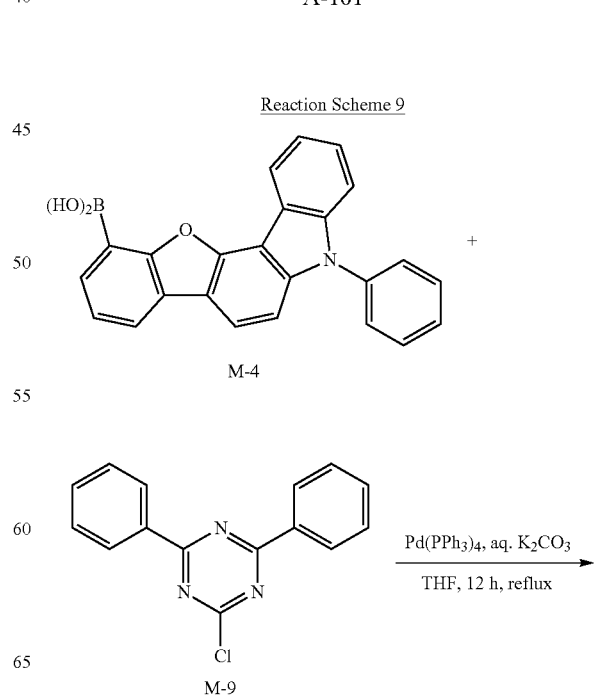

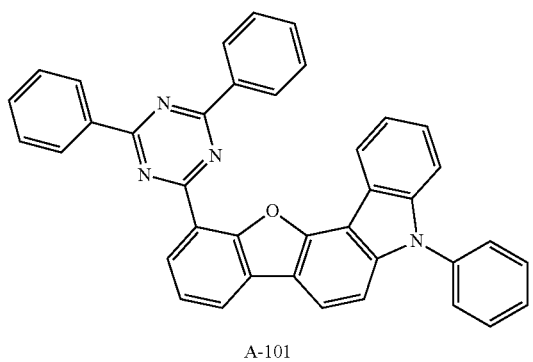

A-101

10 g (26.5 mmol) of Intermediate M-4 and 7.1 g (26.5 mmol) of Intermediate M-9 were put in a round-bottomed flask, 133 ml of tetrahydrofuran was added thereto to dissolve them, and 55 ml of an aqueous solution obtained by dissolving 5.5 g (39.8 mmol) of potassium carbonate was added thereto and then, stirred. Subsequently, 0.31 g (0.265 mmol) of tetrakistriphenyl phosphine palladium was added thereto and then, refluxed and stirred under a nitrogen atmosphere for 12 hours. When a reaction was complete, the reactant was filtered and then, washed with distilled water. A product therefrom was dissolved in xylene and filtered through a silica gel pad, and a filtrate therefrom was concentrated under a reduced pressure and recrystallized with xylene to obtain 13.8 g of A-101 as a target compound (a yield=92%).

LC-Mass (theoretical value: 564.20 g/mol, measured value: M+1=565.16 g/mol)

Synthesis Example 10: Synthesis of Compound A-103

Reaction Scheme 10

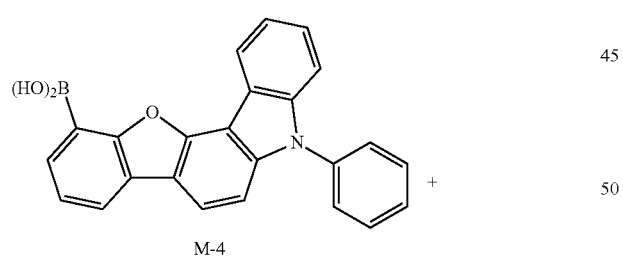

M-4

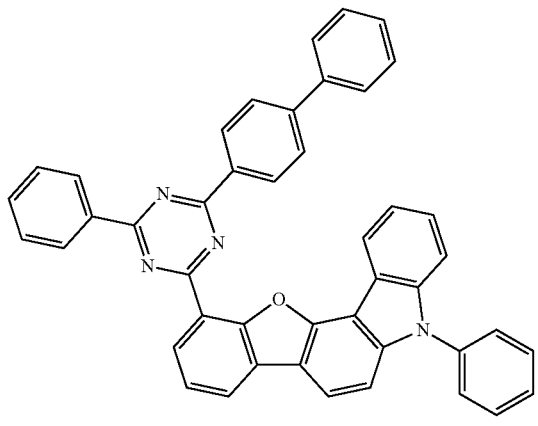

A-103

15.1 g of A-103 as a target compound (a yield=89%) was obtained according to the same method as Synthesis Example 9 except that 9.1 g (26.5 mmol) of Intermediate M-10 was used instead of Intermediate M-9.

LC-Mass (theoretical value: 640.23 g/mol, measured value: M+1=641.41 g/mol)

Synthesis Example 11: Synthesis of Compound A-153

Reaction Scheme 11

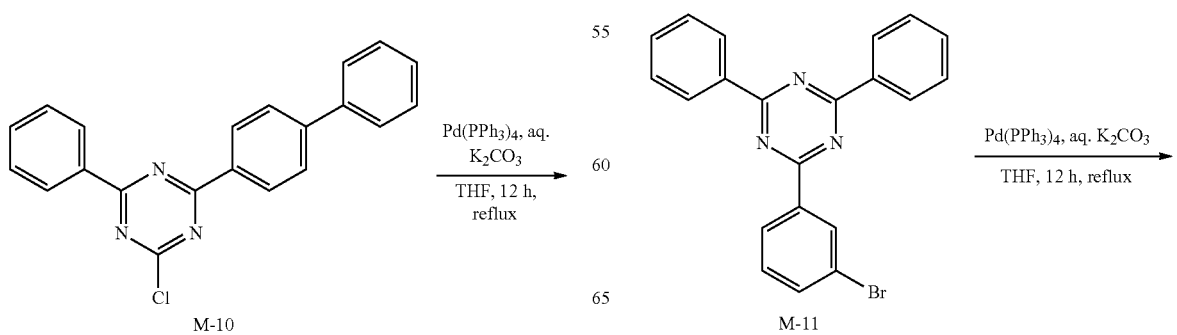

M-4

M-10

M-11

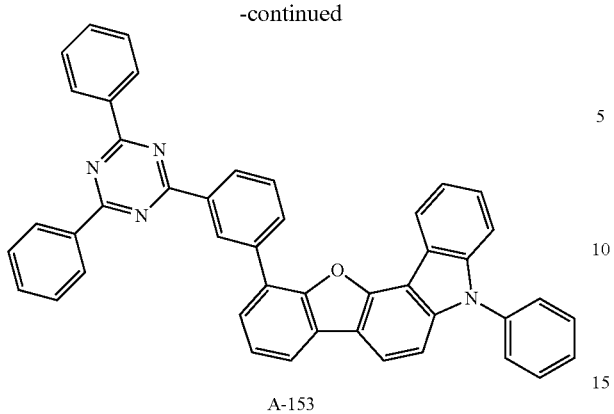

A-153

15.3 g of A-153 as a target compound (a yield=90%) was obtained according to the same method as Synthesis Example 9 except that 10.3 g (26.5 mmol) of Intermediate M-11 was used instead of Intermediate M-9.

LC-Mass (theoretical value: 640.23 g/mol, measured value: M+1=641.31 g/mol)

Synthesis Example 12: Synthesis of Compound A-183

Reaction Scheme 12

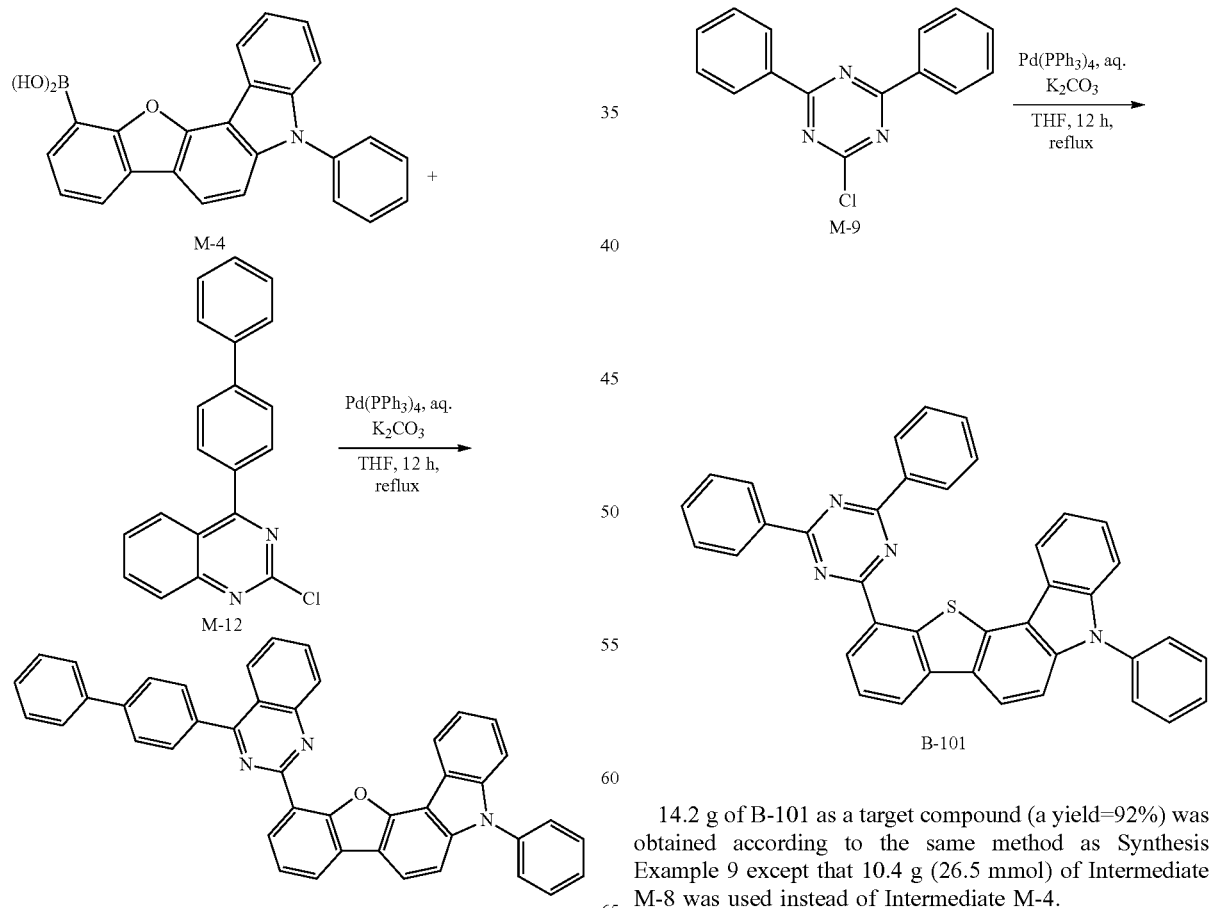

A-183

15.0 g of A-183 as a target compound (a yield=92%) was obtained according to the same method as Synthesis Example 9 except that 8.4 g (26.5 mmol) of Intermediate M-12 was used instead of Intermediate M-9.

LC-Mass (theoretical value: 613.22 g/mol, measured value: M+1=614.39 g/mol)

Synthesis Example 13: Synthesis of Compound B-101

Reaction Scheme 13

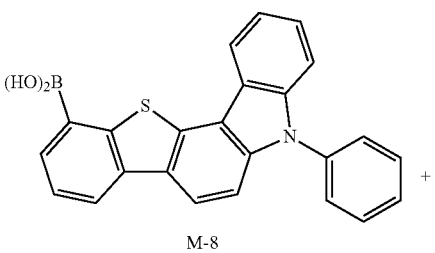

B-101

14.2 g of B-101 as a target compound (a yield=92%) was obtained according to the same method as Synthesis Example 9 except that 10.4 g (26.5 mmol) of Intermediate M-8 was used instead of Intermediate M-4.

LC-Mass (theoretical value: 580.17 g/mol, measured value: M+1=581.51 g/mol)

Synthesis Example 14: Synthesis of Compound B-181

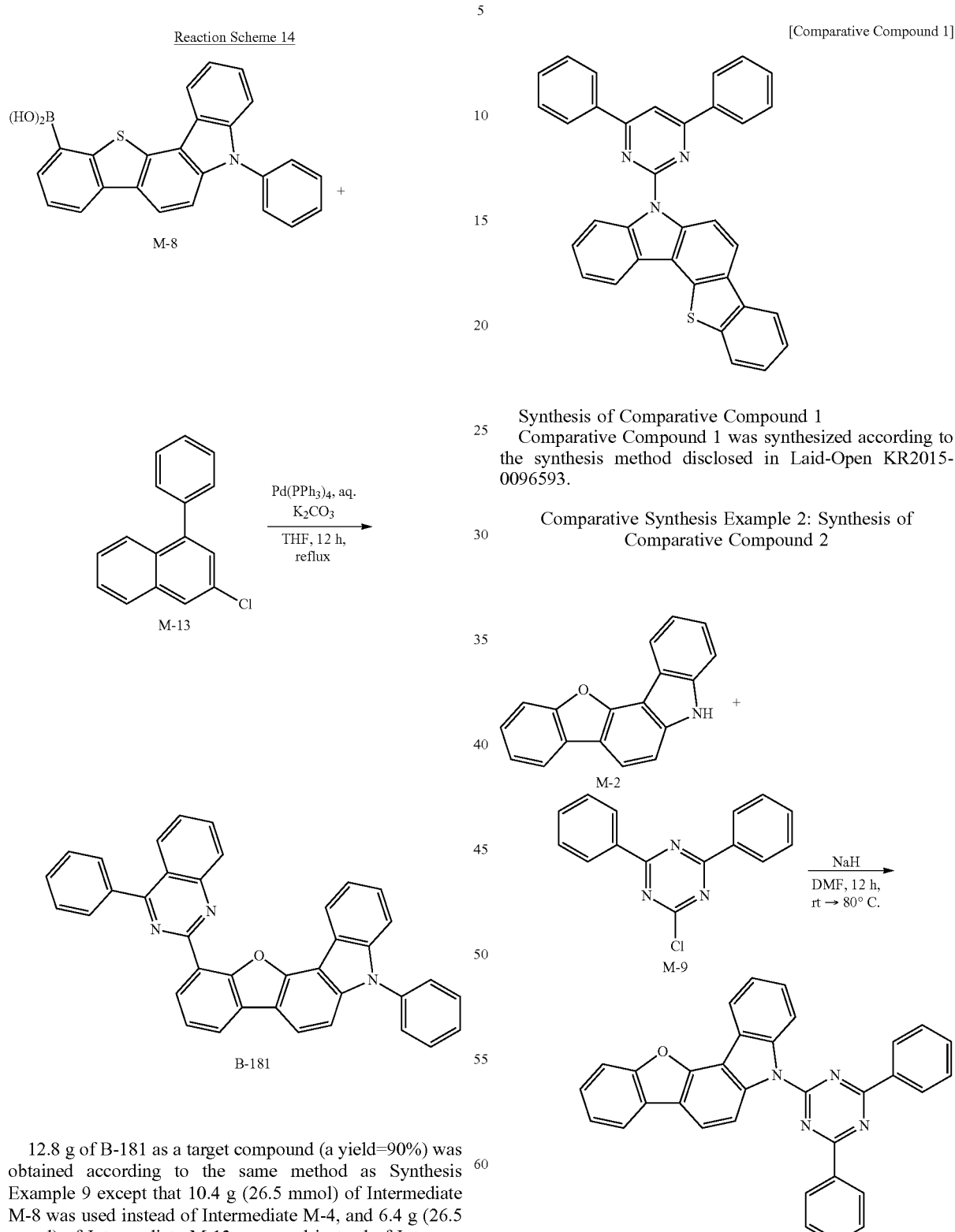

12.8 g of B-181 as a target compound (a yield=90%) was obtained according to the same method as Synthesis Example 9 except that 10.4 g (26.5 mmol) of Intermediate M-8 was used instead of Intermediate M-4, and 6.4 g (26.5 mmol) of Intermediate M-13 was used instead of Intermediate M-9.

LC-Mass (theoretical value: 537.18 g/mol, measured value: M+1=538.31 g/mol)

Comparative Synthesis Example 1: Synthesis of Comparative Compound 1

Synthesis of Comparative Compound 1

Comparative Compound 1 was synthesized according to the synthesis method disclosed in Laid-Open KR2015-0096593.

Comparative Synthesis Example 2: Synthesis of Comparative Compound 2

0.48 g (20.0 mmol) of sodium hydride and 100 ml of dimethyl formamide were put in a round-bottomed flask and then, stirred at room temperature under nitrogen. Subsequently, 5.1 g (20.0 mmol) of Intermediate M-2 was added thereto and then, stirred at room temperature for 30 minutes. Then, 5.4 g (20.0 mmol) of Intermediate M-9 was added thereto and then, stirred at 80° C. for 12 hours. When a reaction was complete, methanol and distilled water were added to the reactant and then, stirred at 0° C., and the reactant was filtered and then, washed with distilled water. A product therefrom was dissolved in xylene and filtered through a silica gel pad, and then, a filtrate therefrom was concentrated under a reduced pressure and recrystallized in xylene to obtain 8.3 g of Comparative Compound 2 as a target compound (a yield=85%).

LC-Mass (theoretical value: 488.16 g/mol, measured value: M+1=489.32 g/mol)

Synthesis of Second Compound for Organic Optoelectronic Diode

Synthesis Example 15: Synthesis of Compound C-1

Reaction Scheme 15

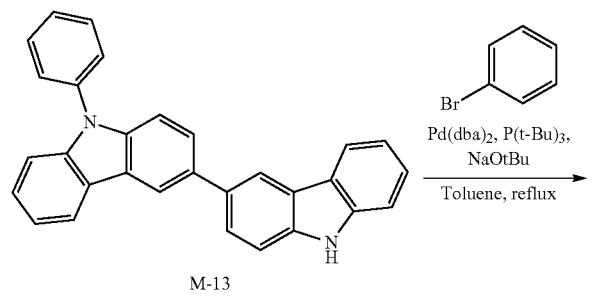

M-13

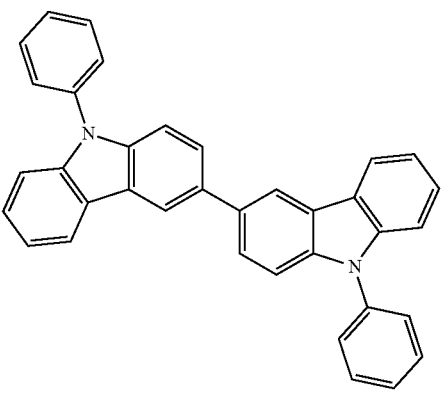

C-1

12.7 g (31.1 mmol) of Intermediate M-13, 7.3 g (46.6 mmol) of bromobenzene, and 4.5 g (46.6 mmol) of sodium t-butoxide were put in a round-bottomed flask, and 190 ml of toluene was added thereto to dissolve them. Subsequently, 0.54 g (0.94 mmol) of Pd(dba)₂ and 0.57 g (2.8 mmol) of tri-tertiary-butylphosphine were sequentially added thereto and then, refluxed and stirred under a nitrogen atmosphere for 12 hours. When a reaction was complete, after performing an extraction with toluene and distilled water, an organic layer therefrom was dried with magnesium sulfate and filtered, and a filtrate therefrom was concentrated under a reduced pressure. A product therefrom was purified through silica gel column chromatography with n-hexane/dichloromethane (a volume ratio of 7:3) to obtain 13.6 g (a yield=90%) of C-1 as a target compound.

LC-Mass (theoretical value: 484.19 g/mol, measured value: M+1=485.24 g/mol)

Synthesis Example 16: Synthesis of Compound C-2

Reaction Scheme 16

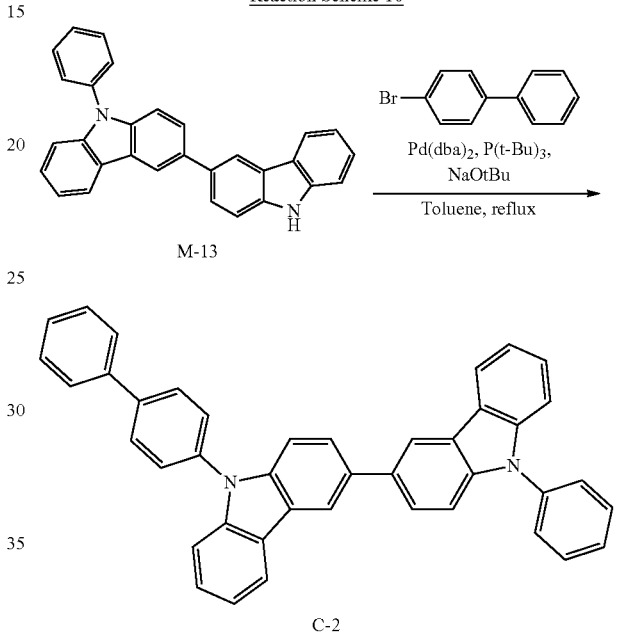

C-2

15.9 g (a yield=91%) of C-2 as a target compound was obtained according to the same method as Synthesis Example 15 except that 10.9 g (46.6 mmol) of 4-bromobiphenyl was used instead of the bromobenzene.

LC-Mass (theoretical value: 560.23 g/mol, measured value: M+1=561.49 g/mol)

Synthesis Example 17: Synthesis of Compound C-10

Reaction Scheme 17

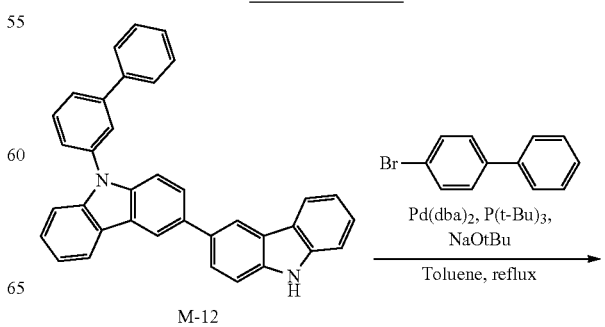

M-12

-continued

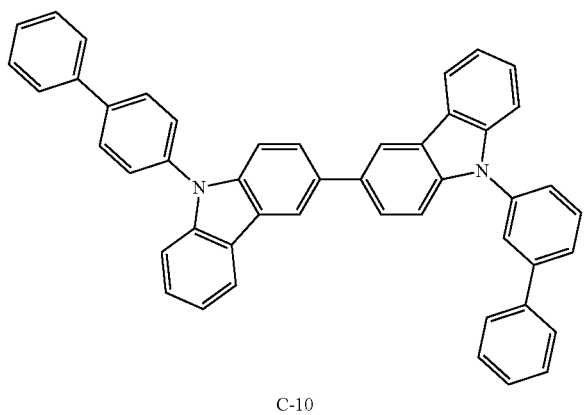

C-10

17.6 g of C-10 as a target compound (a yield=89%) was obtained according to the same method as Synthesis Example 15 except that 15.1 g (31.1 mmol) of intermediate M-14 was used instead of Intermediate M-13, and 10.9 g (46.6 mmol) of 4-bromobiphenyl was used instead of the bromobenzene.

LC-Mass (theoretical value: 636.26 g/mol, measured value: M+1=637.51 g/mol)

Manufacture of Organic Light Emitting Diode

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light emitting layer was formed on the hole transport layer by vacuum-depositing Compound A-101 of Synthesis Example 9 and Compound C-1 of Synthesis Example 15 simultaneously as hosts and 10 wt % of tris(2-phenylpyridine)iridium (III) [Ir(ppy)$_3$] as a dopant. Herein, Compound A-1 and Compound B-1 were used in a 3:7 ratio and their ratios of the following examples were separately described. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer structure, and specifically A structure of ITO/Compound A (700 Å)/Compound B (50 Å)/Compound C (1020 Å)/EML [Compound A-101: Compound C-1:Ir(ppy)3=27 wt %:63 wt %:10 wt %] (400 Å)/Compound D:Liq (300 Å)/Liq (15 Å)/A1 (1200 Å).

Compound A: N4,N4'-diphenyl-N4,N4'-bis(9-phenyl-9H-carbazol-3-yl)biphenyl-4,4'-diamine, Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine, and Compound D: 8-(4-(4,6-di(naphthalen-2-yl)-1,3,5-triazin-2-yl)phenyl)quinolone.

Examples 2 to 4

Diodes according to Examples 2 to 4 were respectively manufactured according to the same method as Example 1 by using Compound A-101, Compound A-103, and Compound B-101 alone as shown in Table 1, respectively.

Examples 5 to 9

Diodes according to Example 5 to Example 9 were respectively manufactured according to the same method as Example 1 by using the first host and second hosts as shown in Table 2, respectively.

Comparative Examples 1 and 2

Diodes according to Comparative Example 1 and Comparative Example 2 were respectively manufactured according to the same method as Example 1 by using Comparative Compound 1 and Comparative Compound 2 alone as shown in Table 1, respectively.

Comparative Examples 3 and 4

Diodes according to Comparative Example 3 and Comparative Example 4 were respectively manufactured according to the same method as Example 1 by using Comparative Compound 1 and Comparative Compound 2 alone instead of Compound A-101 of Example 1 as shown in Table 2, respectively.

Evaluation

Luminous efficiency and driving voltages of each organic light emitting diode according to Examples Example 1 to Example 9 and Comparative Example 1 to Comparative Example 4 were evaluated. Specific measurement methods are as follows, and the results are shown in Tables 1 and 2.

(1) Measurement of Current Density Change Depending on Voltage Change

The obtained organic light emitting diodes were measured regarding a current value flowing in the unit diode, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltages of the organic light emitting diodes were increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-span

T90 life-spans of the organic light emitting diodes according to Examples 1 to 12 and Comparative Examples 1 to 7 were measured as a time when their luminance decreased to 90% relative to the initial luminance (cd/m$^2$) after emitting light with 5000 cd/m$^2$ as the initial luminance (cd/m$^2$) and measuring their luminance decrease depending on a time with a Polanonix life-span measurement system.

TABLE 1

Only Host Diode

| | Host | Color | Efficiency Cd/A | Driving (Vd) | Life-span T90 |
|---|---|---|---|---|---|
| Example 2 | Compound A-101 | green | 43 | 4.8 | 100 |
| Example 3 | Compound A-103 | green | 45 | 4.6 | 120 |
| Example 4 | Compound B-101 | green | 43 | 4.9 | 95 |
| Comparative Example 1 | Comparative Compound 1 | green | 31 | 5.6 | 70 |
| Comparative Example 2 | Comparative Compound 2 | green | 39 | 5.0 | 85 |

Referring to Table 1, as for a single host, when Examples 2 to 4 were compared with Comparative Examples 1 and 2, Examples 2 to 4, wherein triazine electron transporting substituents were linked with dibenzofuran or dibenzothiophene, exhibited higher efficiency, a lower driving, and a longer life-span than Comparative Examples 1 to 2, wherein the triazine electron transporting substituents were linked with carbazole nitrogen.

TABLE 2

Mixed Host Diode Effect

| | First host | Second host | First host + Second host ratio | Color | Efficiency Cd/A | Life-span (T90) | Driving (Vd) |
|---|---|---|---|---|---|---|---|
| Example 1 | Compound A-101 | Compound C-1 | 3:7 | green | 45 | 300 | 4.3 |
| Example 5 | Compound A-103 | Compound C-1 | 3:7 | green | 51 | 360 | 4.1 |
| Example 6 | Compound A-153 | Compound C-1 | 3:7 | green | 47 | 350 | 4.2 |
| Example 7 | Compound B-101 | Compound C-1 | 3:7 | green | 46 | 300 | 4.4 |
| Example 8 | Compound A-103 | Compound C-2 | 3:7 | green | 51 | 380 | 4.0 |
| Example 9 | Compound A-103 | Compound C-10 | 3:7 | green | 52 | 400 | 4.0 |
| Comparative Example 3 | Comparative Compound 1 | Compound C-1 | 3:7 | green | 39 | 180 | 5.1 |
| Comparative Example 4 | Comparative Compound 2 | Compound C-1 | 3:7 | green | 43 | 280 | 4.5 |

Referring to Table 2, when the first host and the second host were used according to the present invention, Example 1 and Examples 5 to 9, wherein electron-transporting substituents like triazine were linked with dibenzofuran or dibenzothiophene, exhibited higher efficiency, a lower driving, and a longer life-span than Comparative Examples using a mixed host of the same second host.

When the electron transporting group such as triazine was linked with a dibenzofuran or dibenzothiophene moiety of indolodibenzofuran or indolodibenzothiophene, LUMO of the electron transporting group such as triazine expanded up to the dibenzofuran or dibenzothiophene moiety and stabilized electrons, and accordingly, the low driving, and long life-span effects were expected to be obtained.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS 100, 200: organic light emitting diode
105: organic layer
110: cathode
120: anode
130: light emitting layer
140: hole auxiliary layer

The invention claimed is:

1. A composition for an organic optoelectronic diode, comprising
a first compound for an organic optoelectronic diode represented by Chemical Formula 1; and
a second compound for an organic optoelectronic diode represented by Chemical Formula 2:

[Chemical Formula 1]

[Chemical Formula 2]

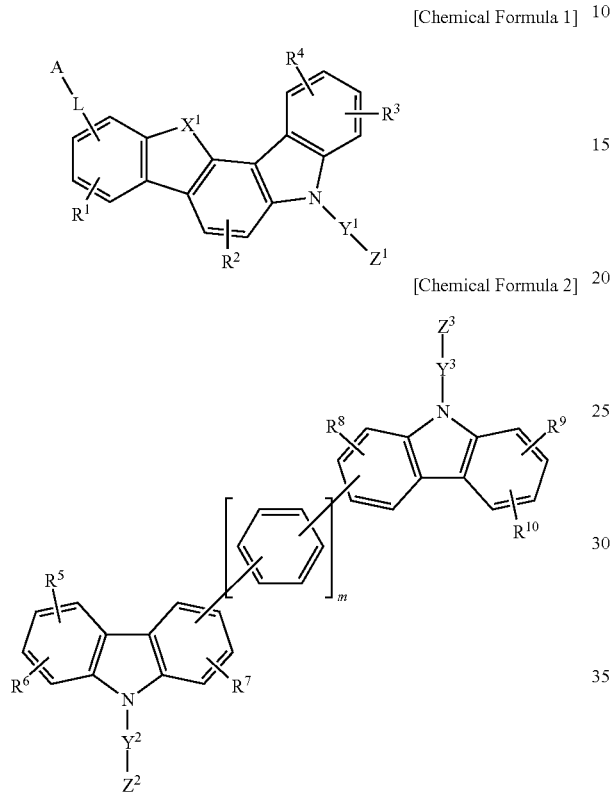

wherein, in Chemical Formula 1 and Chemical Formula 2,
$X^1$ is O or S,
A is a substituted or unsubstituted pyridinyl group, a substituted or unsubstituted pyrimidinyl group, a substituted or unsubstituted triazinyl group, a substituted or unsubstituted benzimidazolyl group, a substituted or unsubstituted pyrazinyl group, a substituted or unsubstituted quinolinyl group, a substituted or unsubstituted isoquinolinyl group, a substituted or unsubstituted quinoxalinyl group, or a substituted or unsubstituted quinazolinyl group,
L and $Y^1$ to $Y^3$ are independently a single bond, a substituted or unsubstituted C6 to C30 arylene group, or a substituted or unsubstituted C2 to C30 heteroarylene group,
$Z^1$ to $Z^3$ are independently a substituted or unsubstituted C6 to C30 aryl group or a substituted or unsubstituted C2 to C30 heterocyclic group,
$R^1$ to $R^{10}$ are independently hydrogen, deuterium, a substituted or unsubstituted C1 to C10 alkyl group, a substituted or unsubstituted C6 to C30 aryl group, or a substituted or unsubstituted C2 to C30 heterocyclic group, and
m is one of integers of 0 to 2.

2. The composition for the organic optoelectronic diode of claim 1, wherein A is a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinoxalinyl group, or a substituted or unsubstituted quinazolinyl group.

3. The composition for the organic optoelectronic diode of claim 1, wherein A is one of substituents of Group I:

[Group I]

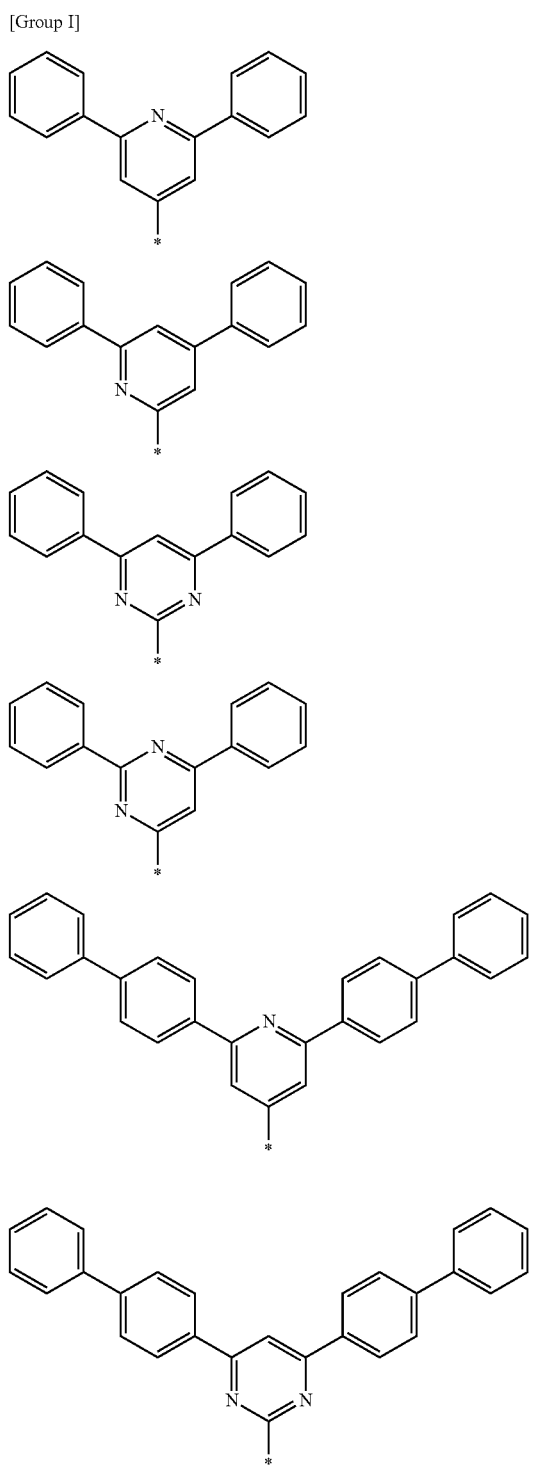

203
-continued
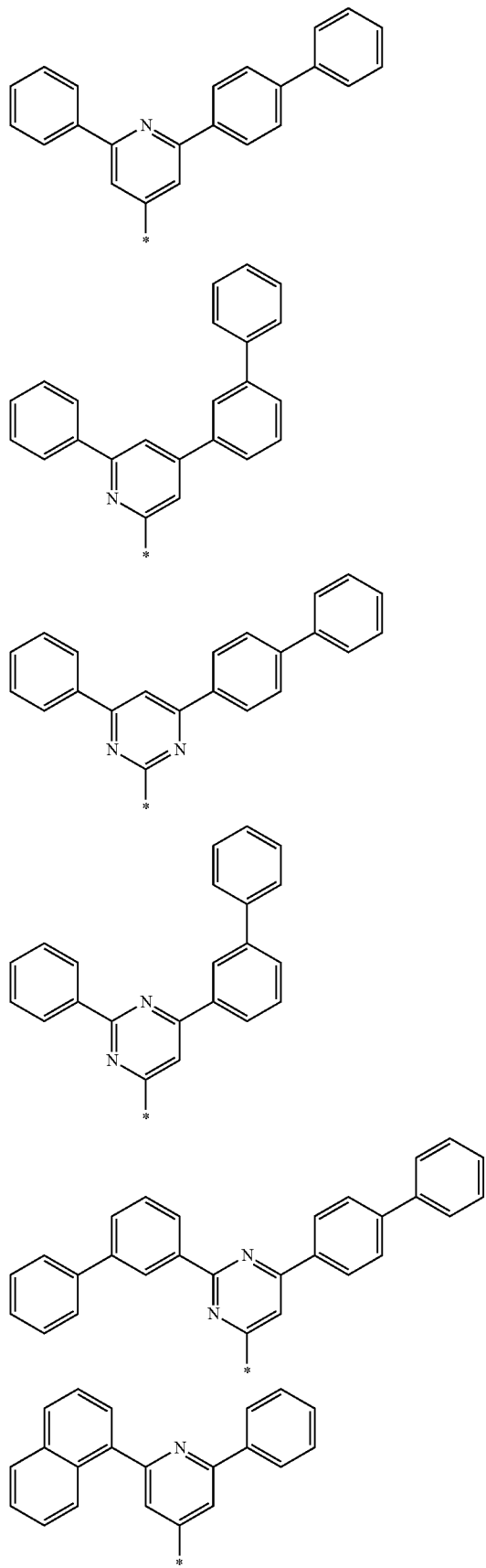
204
-continued
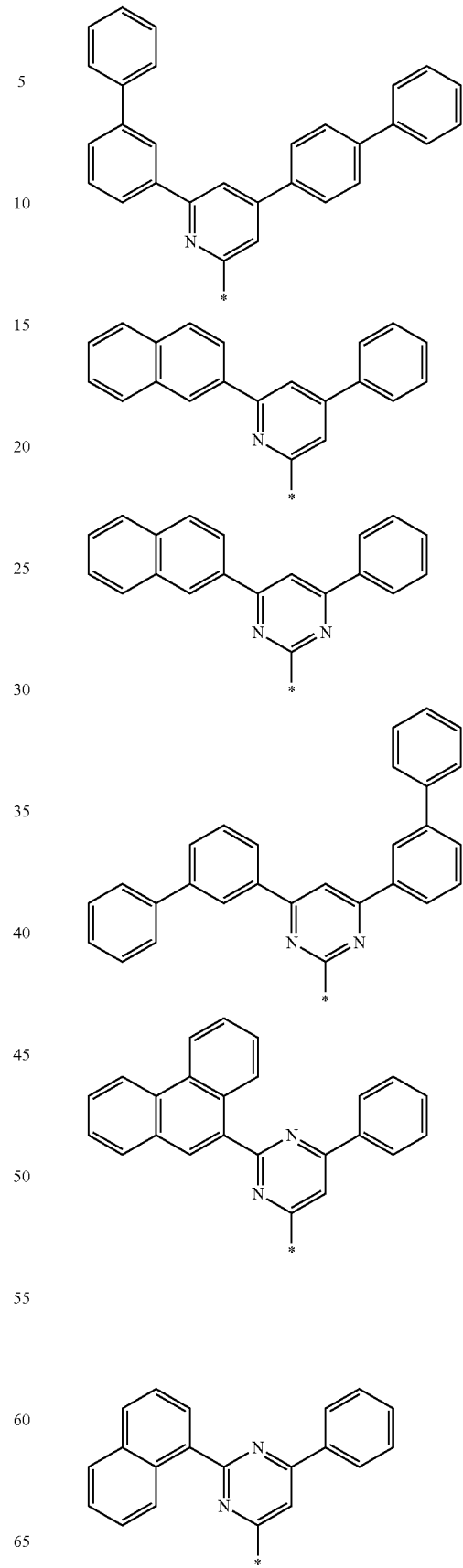

205
-continued
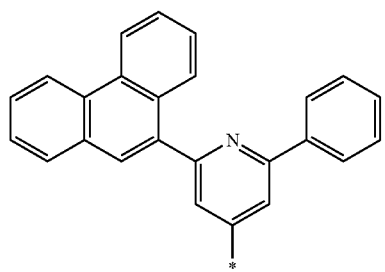
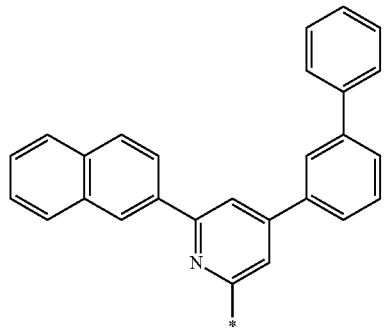
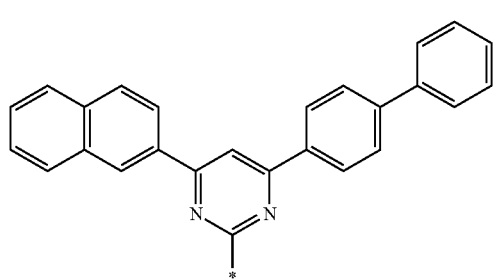
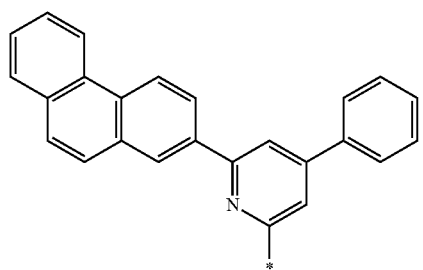
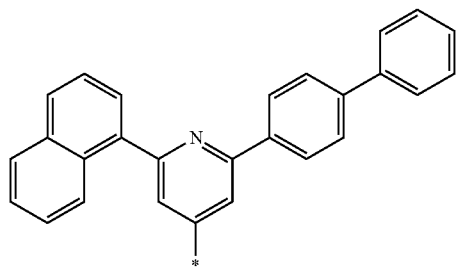
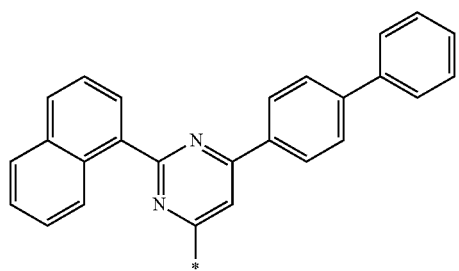
206
-continued
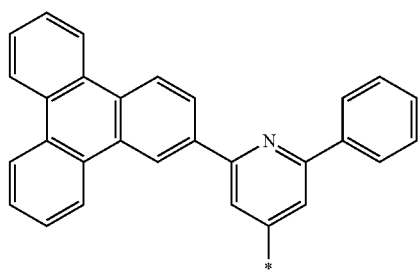
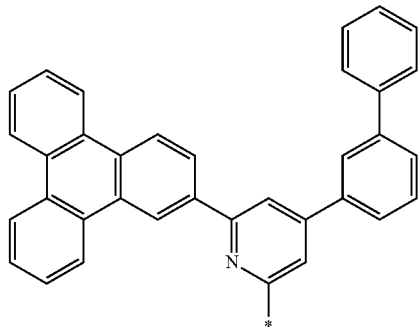
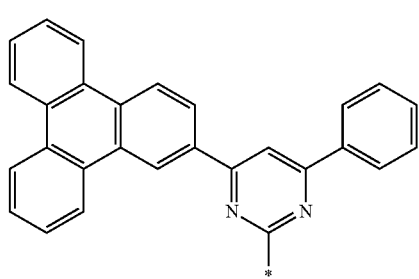
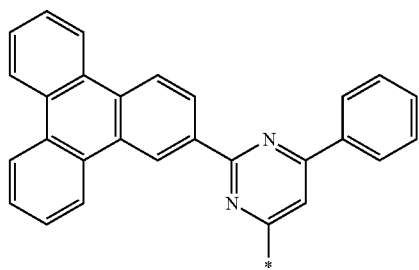
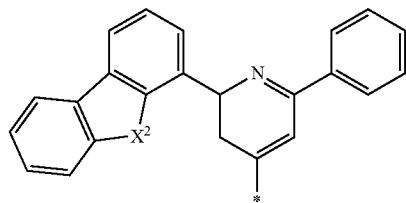
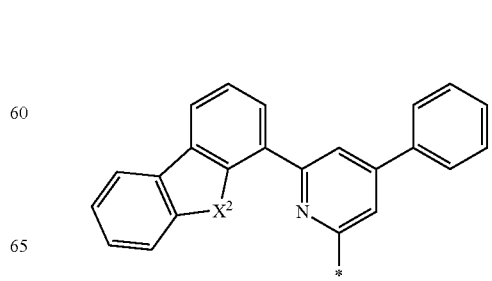

207
-continued
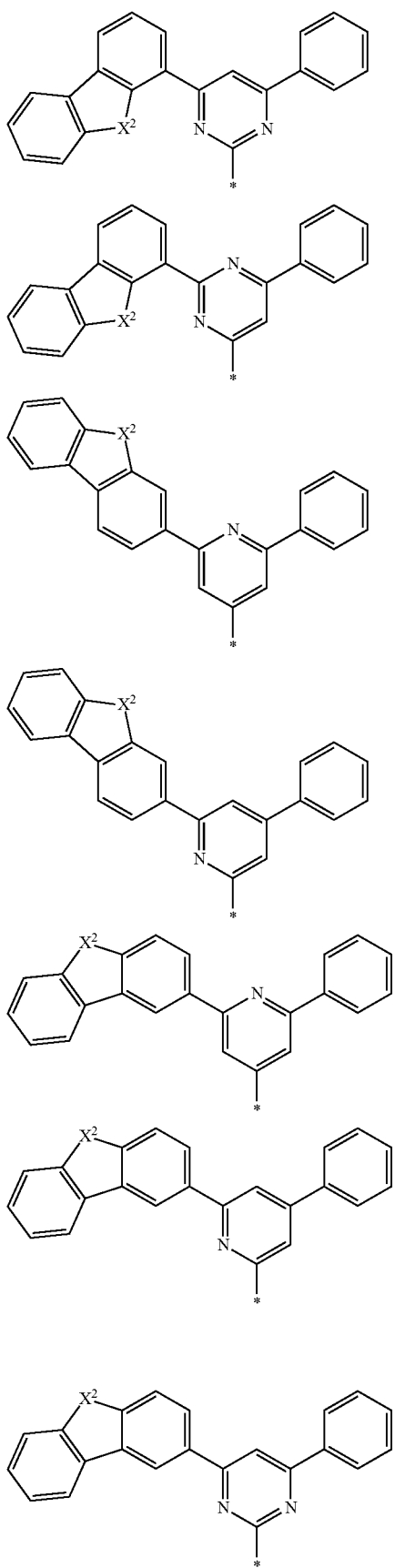
208
-continued
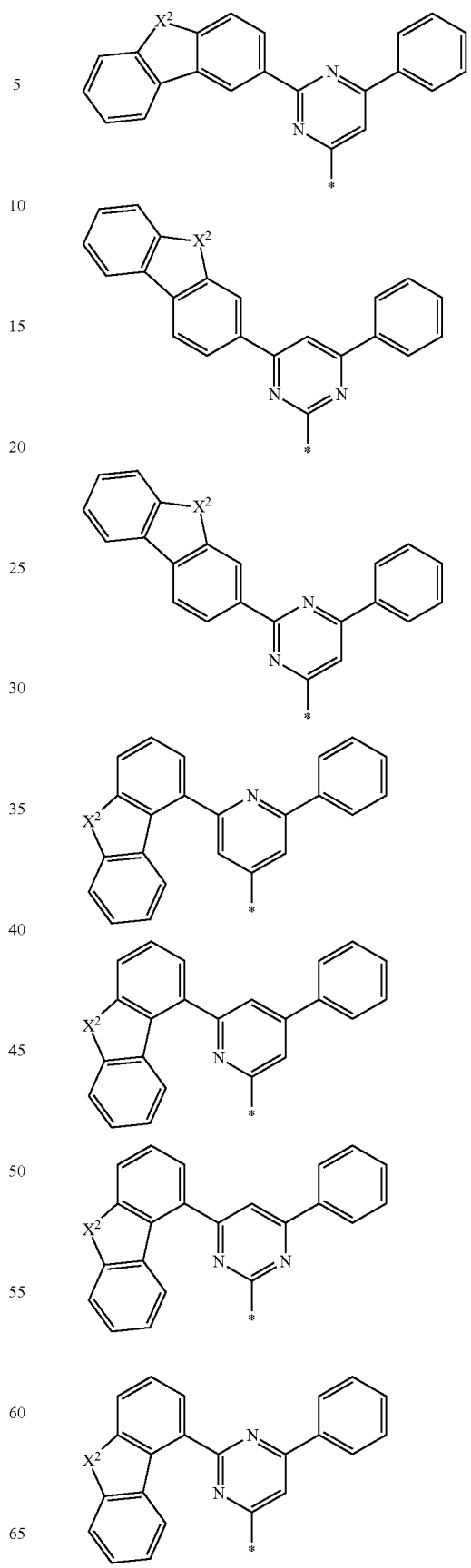

209
-continued
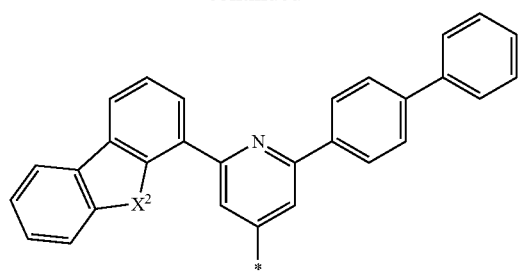
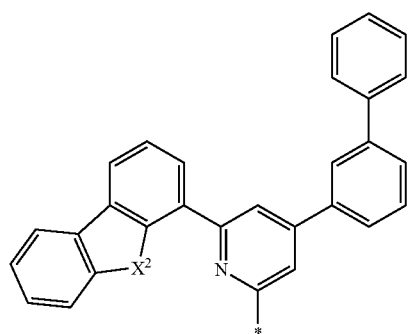
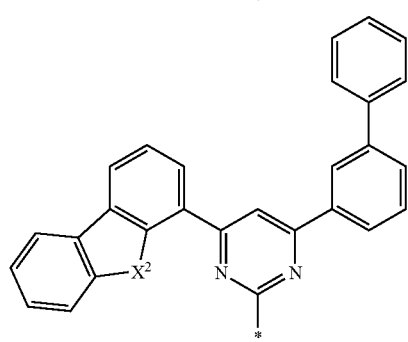
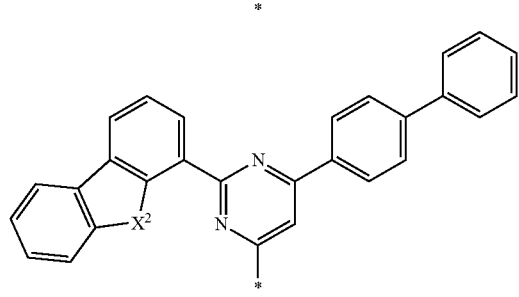
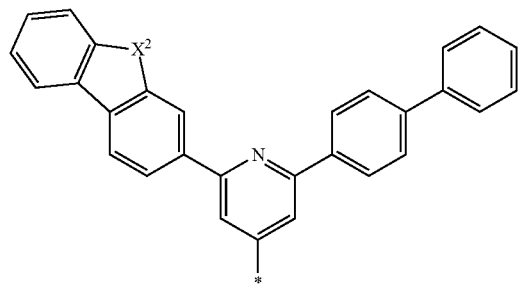
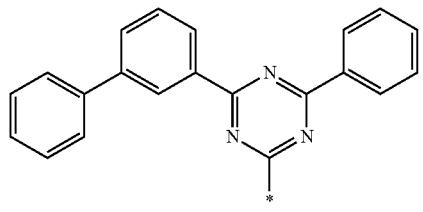
210
-continued
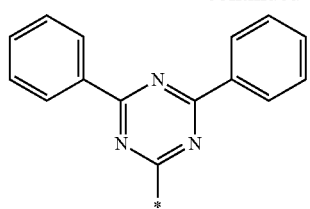
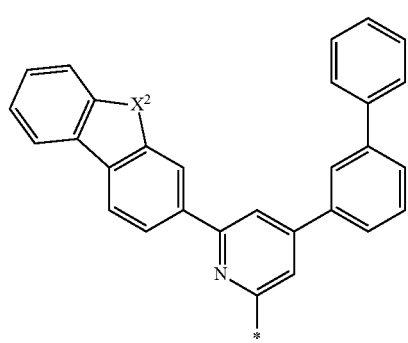
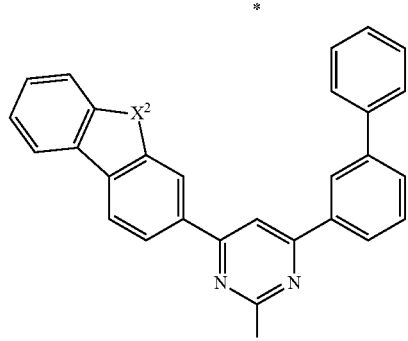
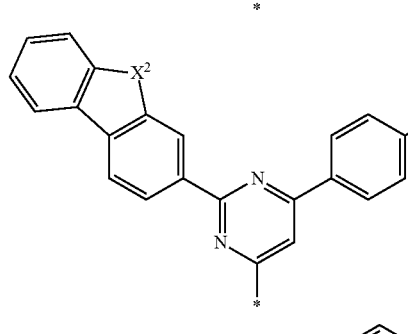
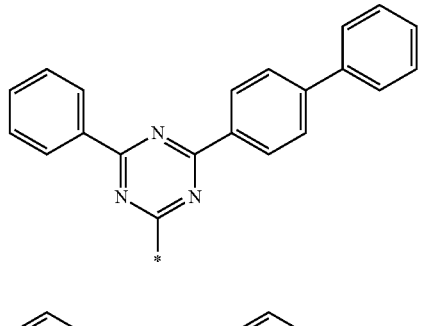
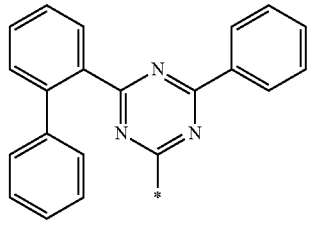

211
-continued
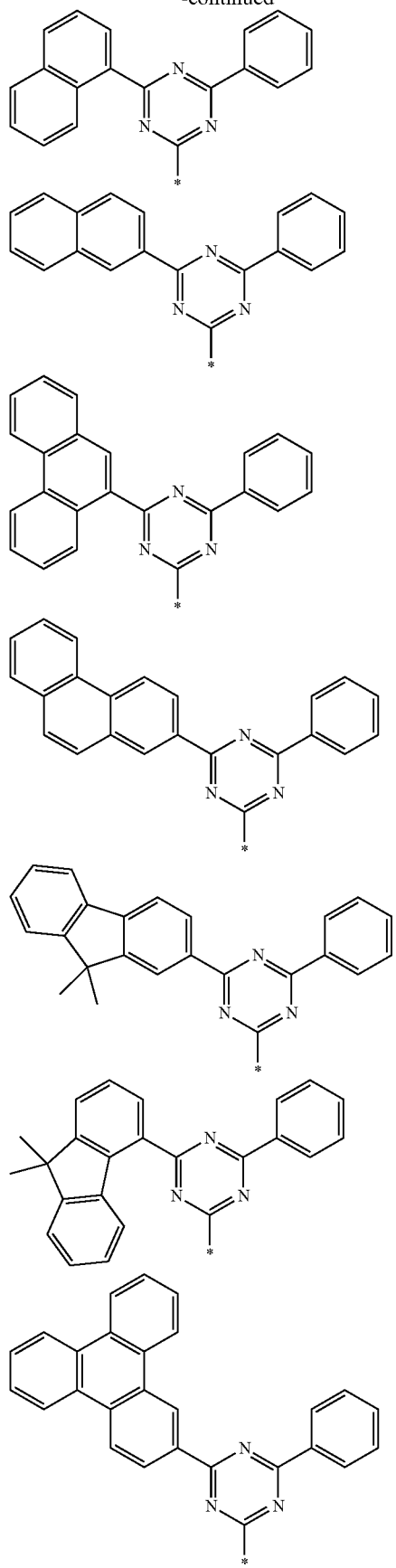
212
-continued
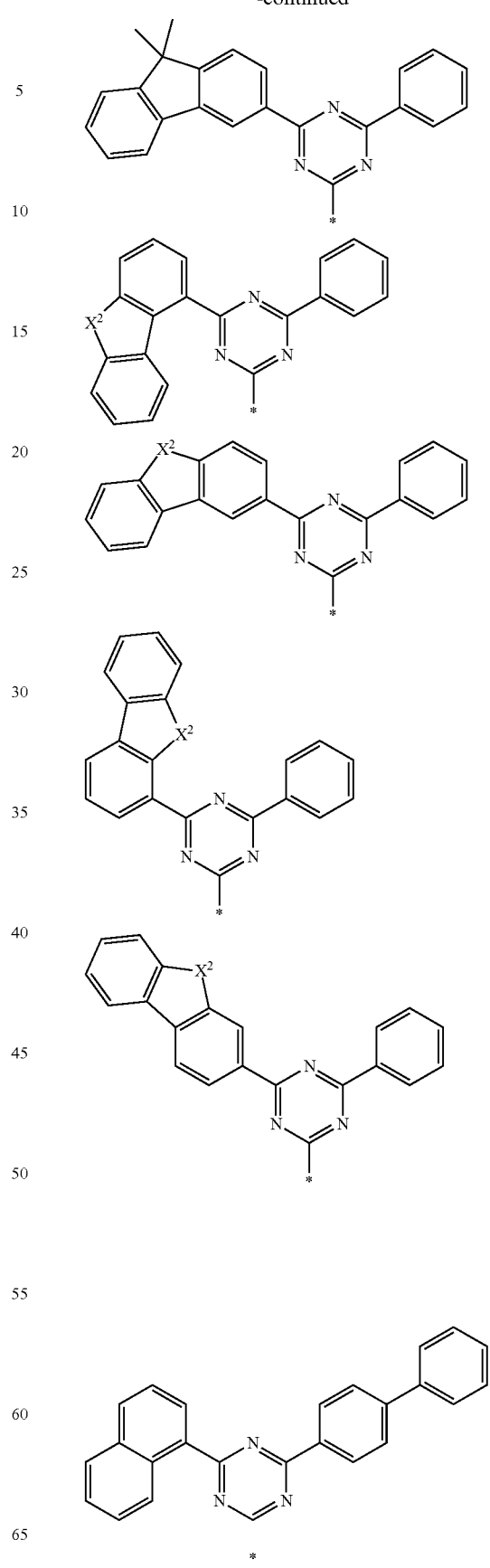

213
-continued
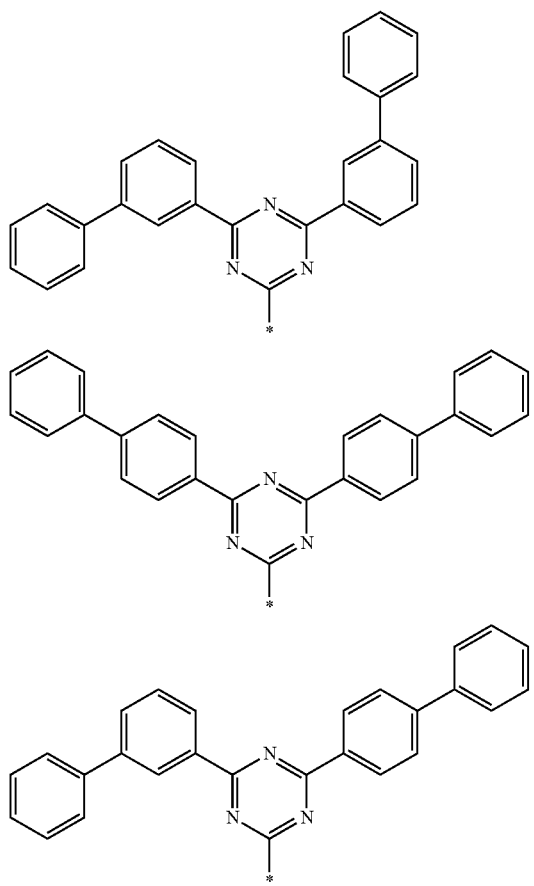
214
-continued
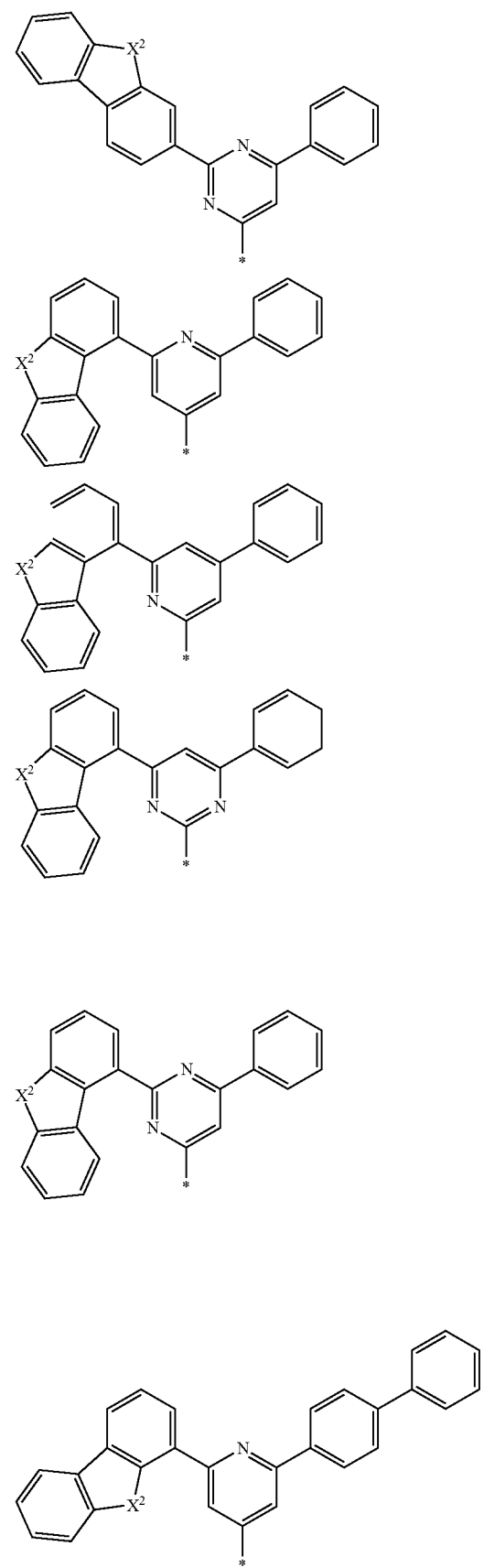

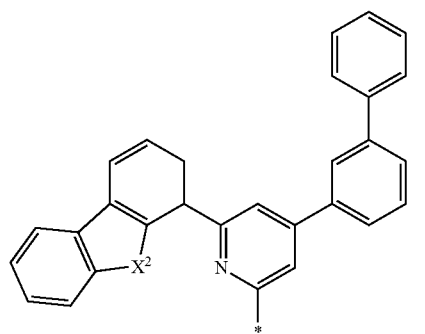
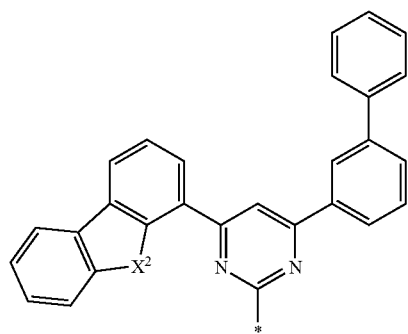
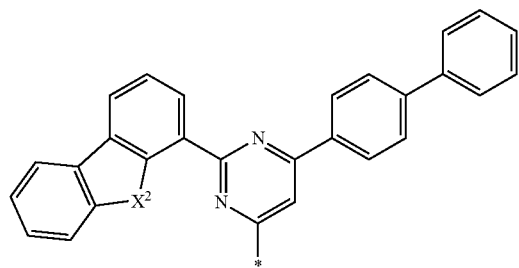
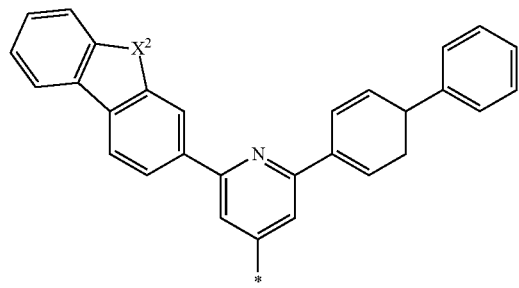
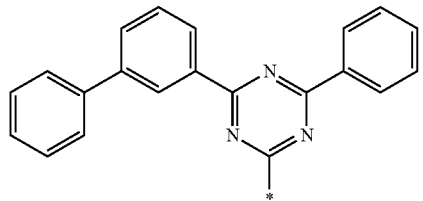
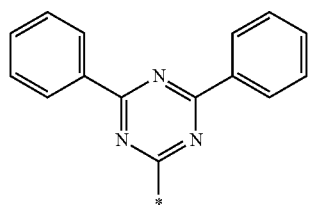
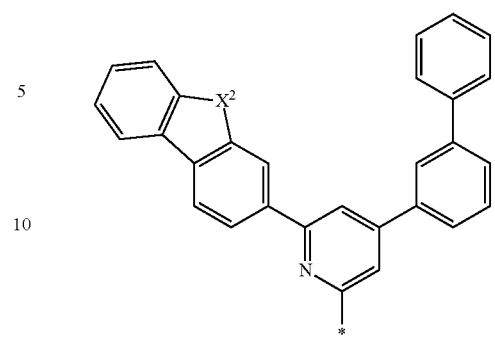
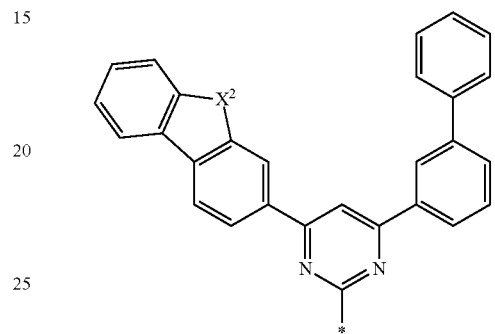
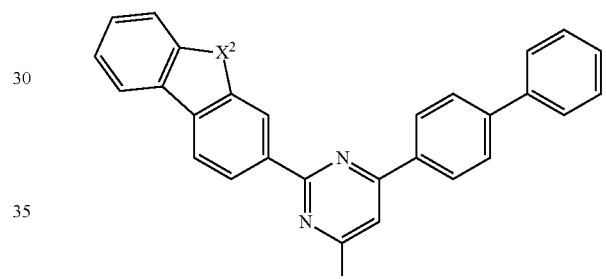
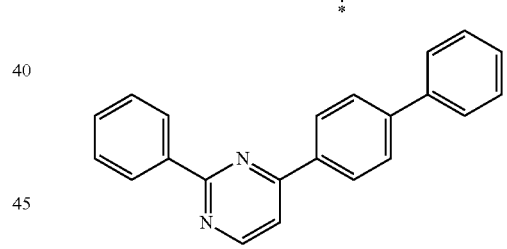
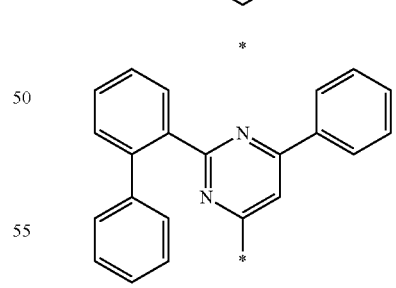
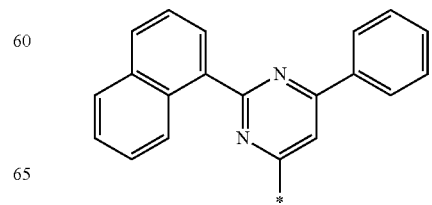

217
-continued
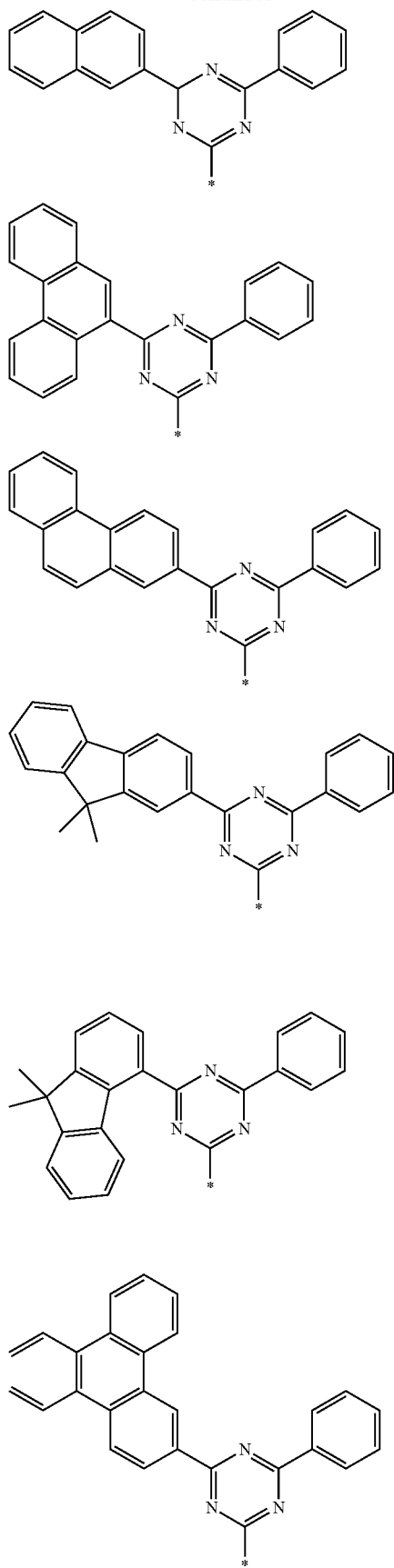
218
-continued
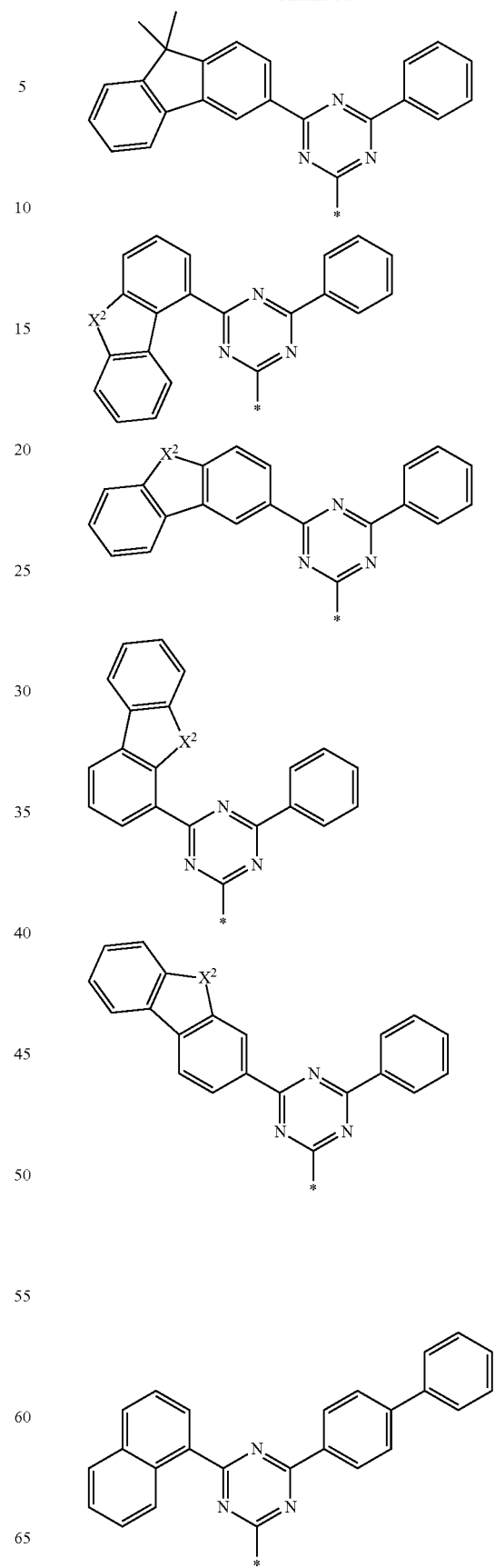

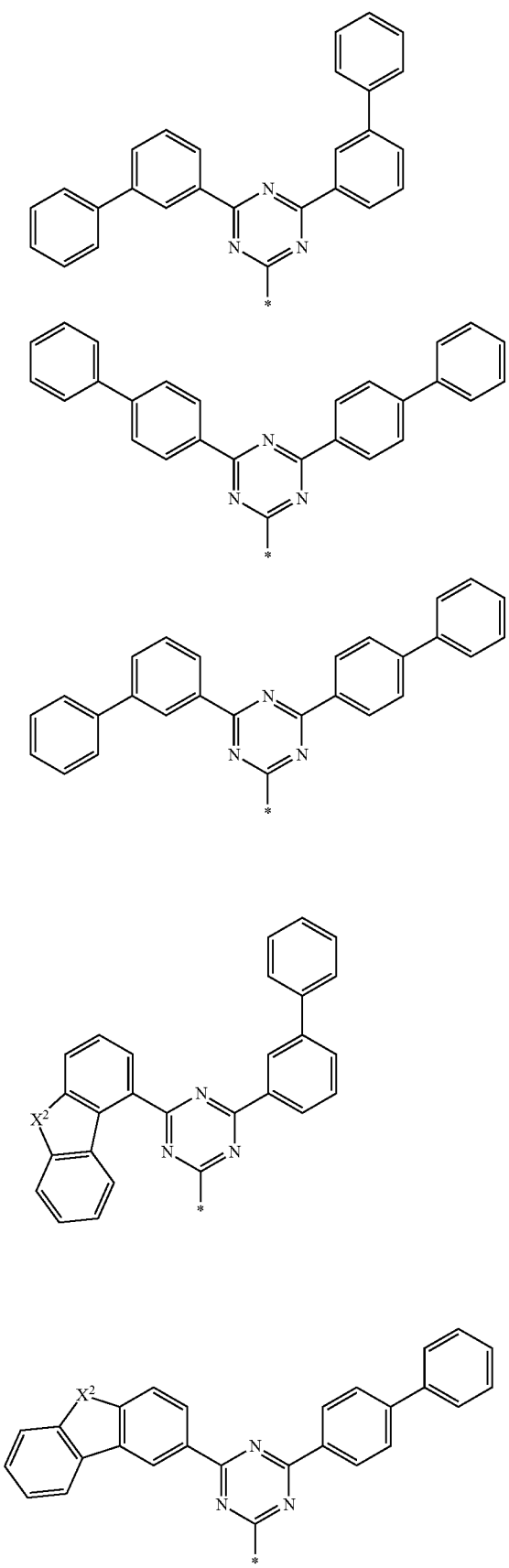
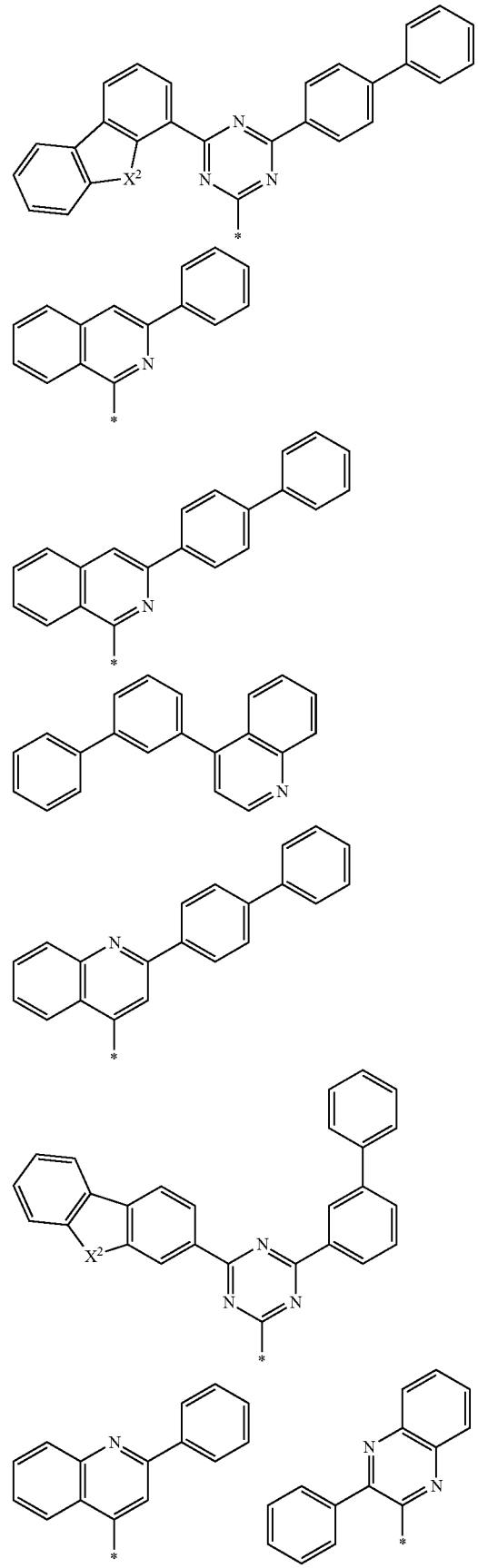

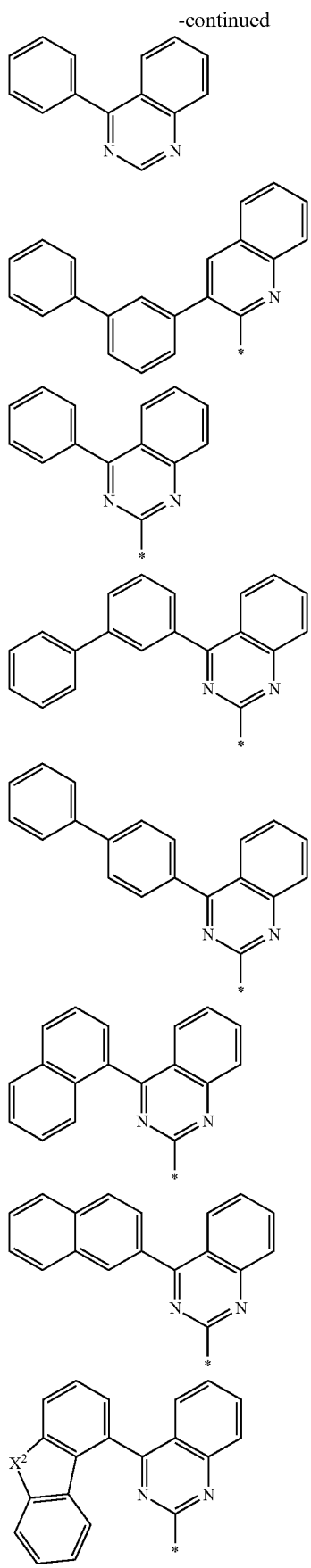
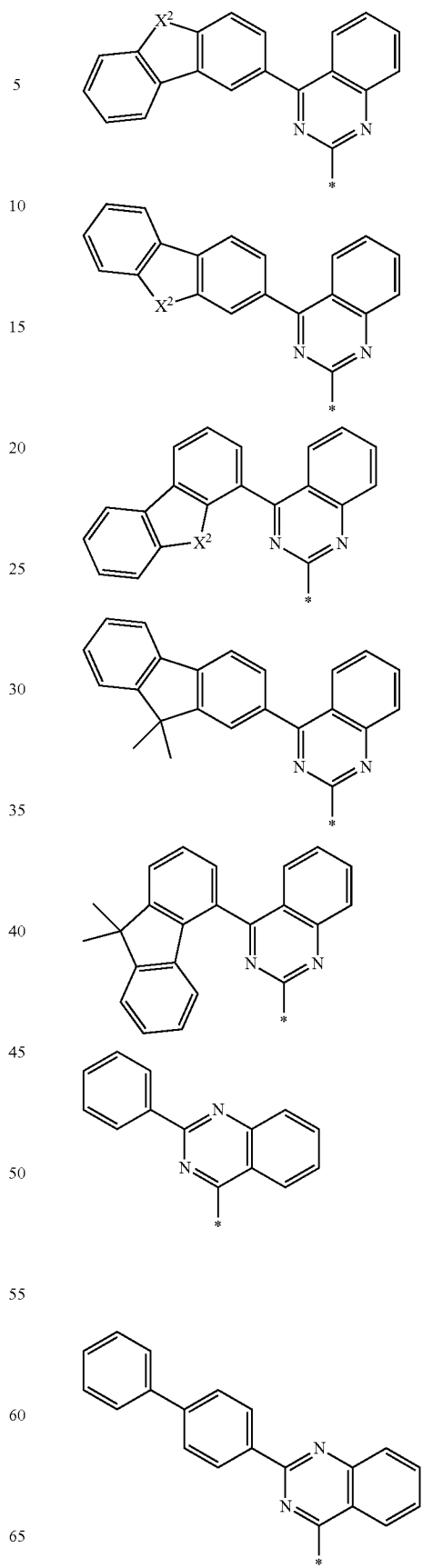

-continued

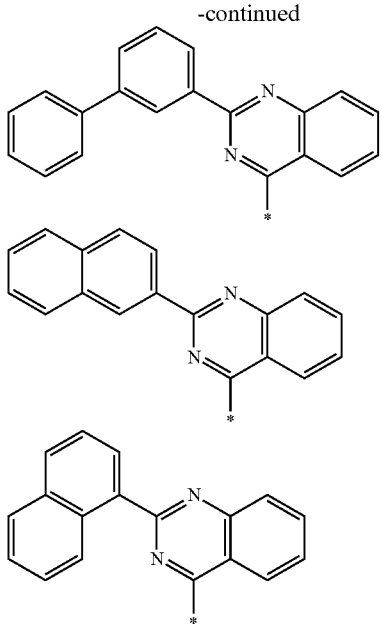

wherein, in Group I,
X² is O or S, and
is a linking point with L.

4. The composition for the organic optoelectronic diode of claim 1, wherein Z¹ is a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted dibenzofuranyl group, or a substituted or unsubstituted dibenzothiophenyl group.

5. The composition for the organic optoelectronic diode of claim 1, wherein Z² and Z³ are independently a substituted or unsubstituted phenyl group, a substituted or unsubstituted biphenyl group, a substituted or unsubstituted terphenyl group, or a substituted or unsubstituted naphthyl group.

6. The composition for the organic optoelectronic diode of claim 1, wherein Chemical Formula 1 is represented by Chemical Formula 1-1:

[Chemical Formula 1-1]

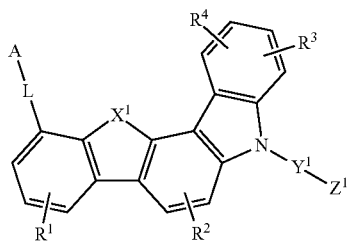

wherein, in Chemical Formula 1-1,
X¹ is O or S,
A is a substituted or unsubstituted pyridinyl group, a substituted or unsubstituted pyrimidinyl group, a substituted or unsubstituted triazinyl group, a substituted or unsubstituted benzimidazolyl group, a substituted or unsubstituted pyrazinyl group, a substituted or unsubstituted quinolinyl group, a substituted or unsubstituted isoquinolinyl group, a substituted or unsubstituted quinoxalinyl group, or a substituted or unsubstituted quinazolinyl group, L is a single bond or a C6 to C30 arylene group, Y¹ is a single bond, a substituted or unsubstituted C6 to C30 arylene group, or a substituted or unsubstituted C2 to C30 heteroarylene group, Z¹ is a substituted or unsubstituted C6 to C30 aryl group or a substituted or unsubstituted C2 to C30 heterocyclic group, and R¹ to R⁴ are independently hydrogen, deuterium, C1 to C10 alkyl group, a substituted or unsubstituted C6 to C30 aryl group, or a substituted or unsubstituted C2 to C30 heterocyclic group.

7. The composition for the organic optoelectronic diode of claim 1, wherein

Chemical Formula 2 is one of structures of Group II, and
*-Y²—Z² and *—Y³—Z³ are independently one of substituents of Group III,

[Group II]

C-1
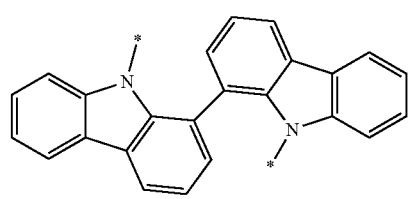

C-2
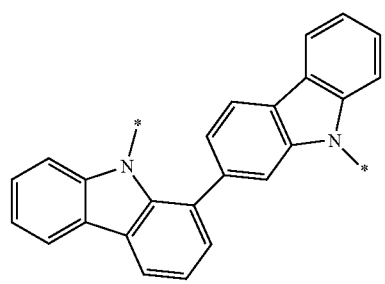

C-3
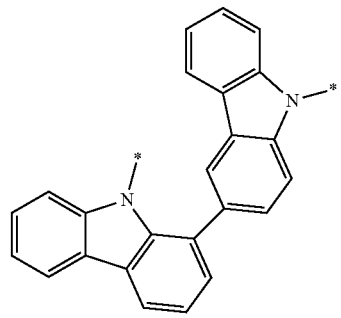

C-4
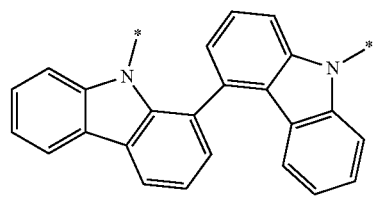

C-5
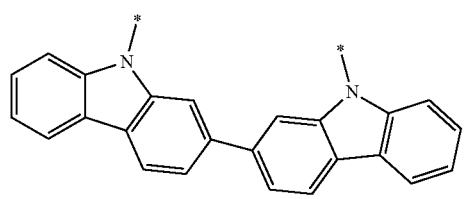
C-6
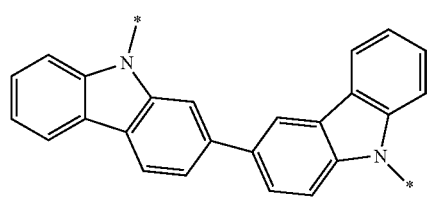
C-7
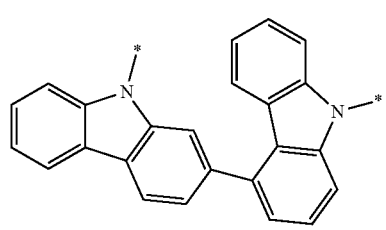
C-8
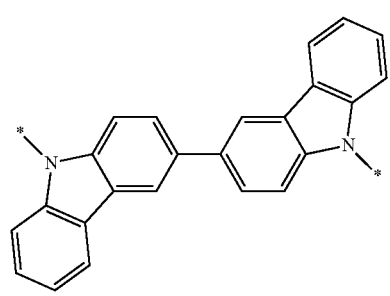
C-9
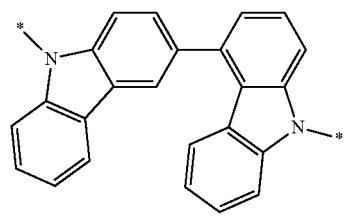
C-10
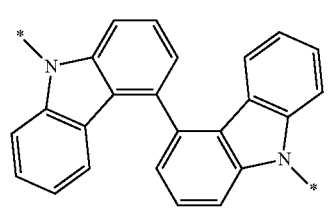
C-11
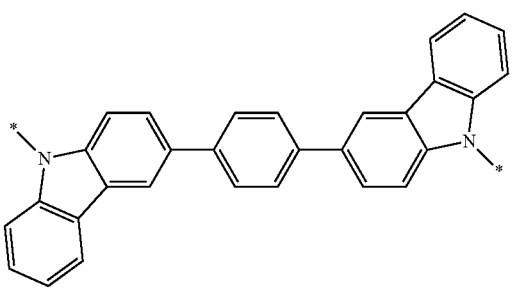
C-12
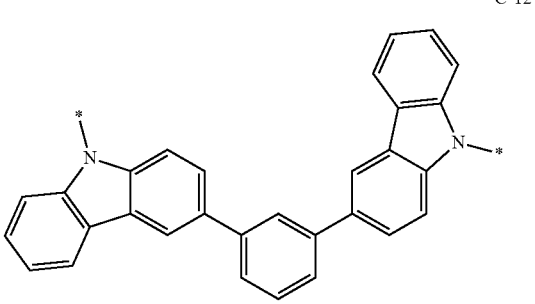
C-13
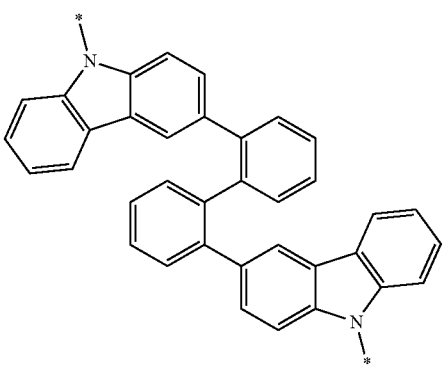
C-14
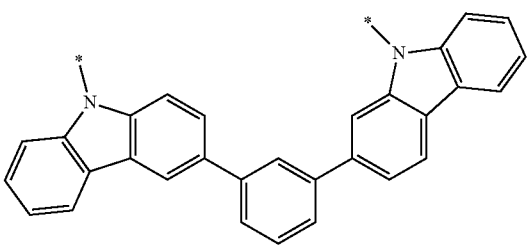
C-15
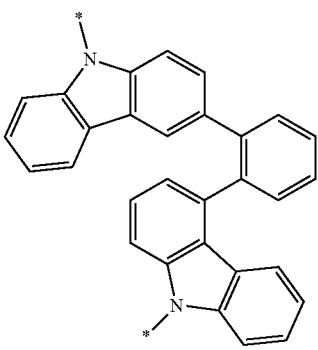

C-16
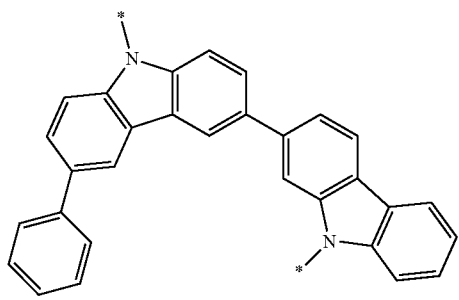
B-3
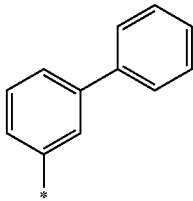
C-17
B-4
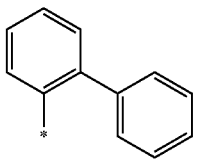
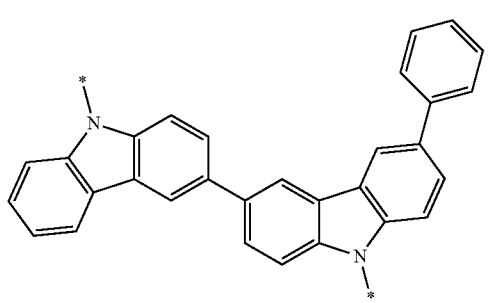
B-5
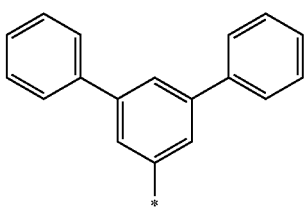
C-18
B-6
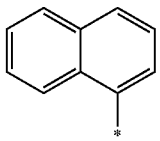
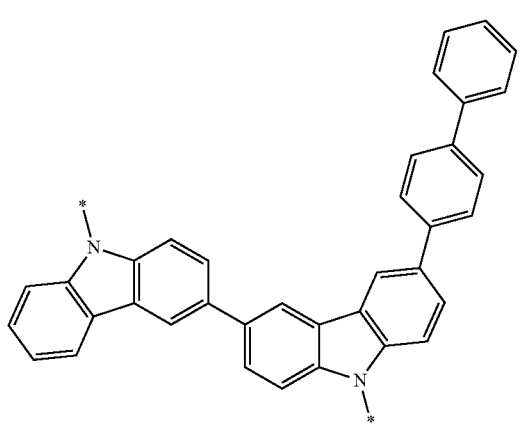
B-7
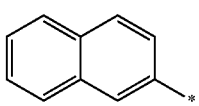
[Group III]
B-1
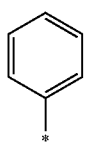
B-8
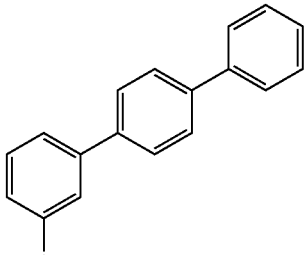
B-2
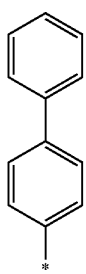
B-9
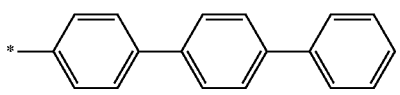

B-10

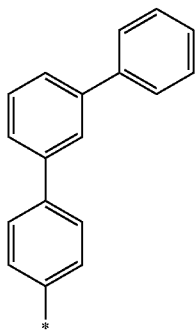

wherein, in Group II and Group III, * is a linking point.

8. The composition for the organic optoelectronic diode of claim 7, wherein
Chemical Formula 2 is represented by C-8 of Group II, and
—$Y^2$—$Z^2$ and *-$Y^3$—$Z^3$ are independently selected from the group consisting of B-1 to B-4.

9. An organic optoelectronic diode comprising
an anode and a cathode facing each other, and
at least one organic layer disposed between the anode and the cathode,
wherein the organic layer comprises the composition for the organic optoelectronic diode of claim 1.

10. The organic optoelectronic diode of claim 9, wherein
the organic layer comprises a light emitting layer, and
the light emitting layer comprises the composition for the organic optoelectronic diode.

11. The organic optoelectronic diode of claim 10, wherein the composition for the organic optoelectronic diode is included in the light emitting layer as a host.

12. A display device comprising the organic optoelectronic diode of claim 9.

13. The composition for the organic optoelectronic diode of claim 1, wherein:
the first compound is Compound A-101, and
the second compound is Compound C-1,

[A-101]

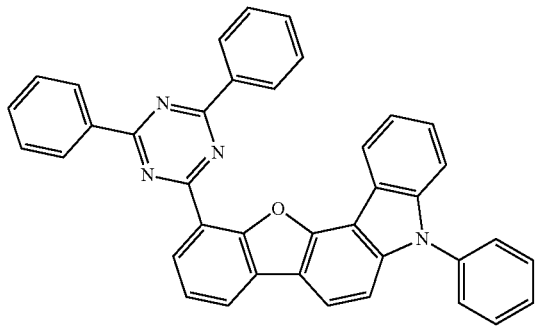

[C-1]

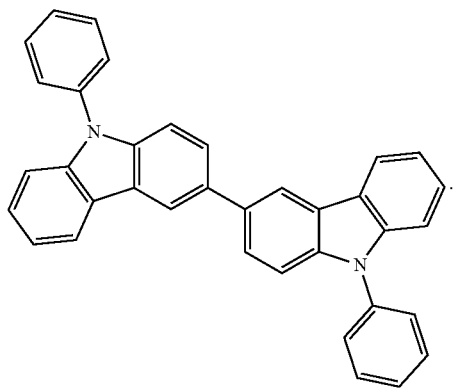

* * * * *